(12) United States Patent
Glunz et al.

(10) Patent No.: US 11,078,197 B2
(45) Date of Patent: Aug. 3, 2021

(54) 5-MEMBERED AND BICYCLIC HETEROCYCLIC AMIDES AS INHIBITORS OF ROCK

(71) Applicant: BRISTOL-MYERS SQUIBB COMPANY, Princeton, NJ (US)

(72) Inventors: Peter W. Glunz, Yardley, PA (US); Vladimir Ladziata, Ewing, NJ (US); Indawati De Lucca, Pennington, NJ (US); George O. Tora, Langhorne, PA (US); Tarun Kumar Maishal, Bangalore (IN); Raghuram Tangirala, Bengaluru (IN); Kamalraj Thiyagarajan, Vellore (IN)

(73) Assignee: Bristol-Myers Squibb Company, Princeton, NJ (US)

( * ) Notice: Subject to any disclaimer, the term of this patent is extended or adjusted under 35 U.S.C. 154(b) by 3 days.

(21) Appl. No.: 16/629,717

(22) PCT Filed: Jul. 11, 2018

(86) PCT No.: PCT/US2018/041573
§ 371 (c)(1),
(2) Date: Jan. 9, 2020

(87) PCT Pub. No.: WO2019/014308
PCT Pub. Date: Jan. 17, 2019

(65) Prior Publication Data
US 2021/0147406 A1    May 20, 2021

Related U.S. Application Data

(60) Provisional application No. 62/531,563, filed on Jul. 12, 2017.

(51) Int. Cl.
| | | |
|---|---|---|
| *C07D 417/12* | (2006.01) |
| *C07D 401/14* | (2006.01) |
| *C07D 403/12* | (2006.01) |
| *C07D 417/14* | (2006.01) |
| *C07D 471/04* | (2006.01) |
| *C07D 491/052* | (2006.01) |
| *C07D 495/04* | (2006.01) |
| *C07D 519/00* | (2006.01) |

(52) U.S. Cl.
CPC ......... *C07D 417/12* (2013.01); *C07D 401/14* (2013.01); *C07D 403/12* (2013.01); *C07D 417/14* (2013.01); *C07D 471/04* (2013.01); *C07D 491/052* (2013.01); *C07D 495/04* (2013.01); *C07D 519/00* (2013.01)

(58) Field of Classification Search
CPC .. C07D 417/12; C07D 401/14; C07D 403/12; C07D 417/14; C07D 471/04; C07D 491/052; C07D 495/04; C07D 519/00
USPC ..................................... 514/210.16
See application file for complete search history.

(56) References Cited

FOREIGN PATENT DOCUMENTS

| | | |
|---|---|---|
| WO | WO2010032875 A2 | 3/2010 |
| WO | WO2014113620 A2 | 7/2014 |
| WO | WO2014134388 A1 | 9/2014 |
| WO | WO2014134391 A1 | 9/2014 |
| WO | WO2015002915 A1 | 1/2015 |
| WO | WO2015002926 A1 | 1/2015 |
| WO | WO2016010950 A1 | 1/2016 |
| WO | WO2016028971 A1 | 2/2016 |
| WO | WO2016112236 A1 | 7/2016 |
| WO | WO2016144936 A1 | 9/2016 |
| WO | WO2017123860 A1 | 7/2017 |
| WO | WO2017205709 A1 | 11/2017 |
| WO | WO2018009622 A1 | 1/2018 |
| WO | WO2018009625 A1 | 1/2018 |
| WO | WO2018009627 A1 | 1/2018 |
| WO | WO2018102325 A1 | 6/2018 |
| WO | WO2019014300 A1 | 1/2019 |
| WO | WO2019014303 A1 | 1/2019 |
| WO | WO2019014304 A1 | 1/2019 |
| WO | WO2019089868 A1 | 5/2019 |

*Primary Examiner* — Kristin A Vajda
(74) *Attorney, Agent, or Firm* — Hong Liu

(57) ABSTRACT

The present invention provides compounds of Formula (I): or stereoisomers, tautomers, or pharmaceutically-acceptable salts thereof wherein all the variables are as defined herein. These compounds are selective ROCK inhibitors. This invention also relates to pharmaceutical compositions comprising these compounds and methods of treating cardiovascular, smooth muscle, oncologic, neuropathologic, autoimmune, fibrotic, and/or inflammatory disorders using the same.

16 Claims, No Drawings
Specification includes a Sequence Listing.

5-MEMBERED AND BICYCLIC HETEROCYCLIC AMIDES AS INHIBITORS OF ROCK

CROSS REFERENCE TO RELATED APPLICATIONS

This application is a 371 application of PCT/US2018/041573 filed Jul. 11, 2018, which is entitled to priority pursuant to 35 U.S.C. § 119(e) to U.S. provisional patent application No. 62/531,563, filed Jul. 12, 2017, which is incorporated herein in its entirety.

FIELD OF THE INVENTION

The present invention relates generally to novel 5-membered and bicyclic heterocyclic amides and their analogues thereof, which are inhibitors of Rho kinases, compositions containing them, and methods of using them, for example, for the treatment or prophylaxis of disorders associated with aberrant Rho kinase activity.

BACKGROUND OF THE INVENTION

Rho-Kinase (ROCK) is a member of the serine-threonine protein kinase family. ROCK exists in two isoforms, ROCK1 and ROCK2 (Ishizaki, T. et al., *EMBO J.*, 15:1885-1893 (1996)). ROCK has been identified as an effector molecule of RhoA, a small GTP-binding protein (G protein) that plays a key role in multiple cellular signaling pathways. ROCK and RhoA are ubiquitously expressed across tissues. The RhoA/ROCK signaling pathway is involved in a number of cellular functions, such as ACTIN® organization, cell adhesion, cell migration, and cytokinesis (Riento, K. et al., *Nat. Rev. Mol. Cell Biol.*, 4:446-456 (2003)). It is also directly involved in regulating smooth muscle contraction (Somlyo, A. P., *Nature*, 389:908-911 (1997)). Upon activation of its receptor, RhoA is activated, and, in turn, it activates ROCK. Activated ROCK phosphorylates the myosin-binding subunit of myosin light chain phosphatase, which inhibits activity of the phosphatase and leads to contraction. Contraction of the smooth muscle in the vasculature increases blood pressure, leading to hypertension.

There is considerable evidence in the literature that the Rho A/ROCK signaling pathway plays an important role in signal transduction initiated by several vasoactive factors, for example angiotensin II (Yamakawa, T. et al., *Hypertension*, 35:313-318 (2000)), urotension II (Sauzeau, V. et al., *Circ. Res.*, 88:1102-1104 (2001)), endothelin-1 (Tangkijvanich, P. et al., *Hepatology*, 33:74-80 (2001)), serotonin (Shimokawa, H., *Jpn. Circ. J.*, 64:1-12 (2000)), norepinephrine (Martinez, M. C. et al., *Am. Physiol.*, 279:H1228-H1238 (2000)) and platelet-derived growth factor (PDGF) (Kishi, H. et al., *J. Biochem.*, 128:719-722 (2000)). Many of these factors are implicated in the pathogenesis of cardiovascular disease.

Additional studies in the literature, some using the known ROCK inhibitors fasudil (Asano, T. et al., *J. Pharmacol. Exp. Ther.*, 241:1033-1040 (1987)) or Y-27632 (Uehata, M. et al., *Nature*, 389:990-994 (1997)) further illustrate the link between ROCK and cardiovascular disease. For example, ROCK expression and activity have been shown to be elevated in spontaneously hypertensive rats, suggesting a link to the development of hypertension in these animals (Mukai, Y. et al., *FASEB J.*, 15:1062-1064 (2001)). The ROCK inhibitor Y-27632 (Uehata, M. et al., *Nature*, ibid) was shown to significantly decrease blood pressure in three rat models of hypertension, including the spontaneously hypertensive rat, renal hypertensive rat and deoxycortisone acetate salt hypertensive rat models, while having only a minor effect on blood pressure in control rats. This reinforces the link between ROCK and hypertension.

Other studies suggest a link between ROCK and atherosclerosis. For example, gene transfer of a dominant negative form of ROCK suppressed neointimal formation following balloon injury in porcine femoral arteries (Eto, Y. et al., *Am. J. Physiol. Heart Circ. Physiol.*, 278:H1744-H1750 (2000)). In a similar model, ROCK inhibitor Y-27632 also inhibited neointimal formation in rats (Sawada, N. et al., *Circulation*, 101:2030-2033 (2000)). In a porcine model of IL-1 beta-induced coronary stenosis, long term treatment with the ROCK inhibitor fasudil was shown to progressively reduce coronary stenosis, as well as promote a regression of coronary constrictive remodeling (Shimokawa, H. et al., *Cardiovasc. Res.*, 51:169-177 (2001)).

Additional investigations suggest that a ROCK inhibitor would be useful in treating other cardiovascular diseases. For example, in a rat stroke model, fasudil was shown to reduce both the infarct size and neurologic deficit (Toshima, Y., *Stroke*, 31:2245-2250 (2000)). The ROCK inhibitor Y-27632 was shown to improve ventricular hypertrophy, fibrosis and function in a model of congestive heart failure in Dahl salt-sensitive rats (Kobayashi, N. et al., *Cardiovasc. Res.*, 55:757-767 (2002)).

Other animal or clinical studies have implicated ROCK in additional diseases including coronary vasospasm (Shimokawa, H. et al., *Cardlovasc. Res.*, 43:1029-1039 (1999)), cerebral vasospasm (Sato, M. et al., *Circ. Res.*, 87:195-200 (2000)), ischemia/reperfusion injury (Yada, T. et al., *J. Am. Coll. Cardiol.*, 45:599-607 (2005)), pulmonary hypertension (Fukumoto, Y. et al., *Heart*, 91:391-392 (2005)), angina (Shimokawa, H. et al., *J. Cardiovasc. Pharmacol.*, 39:319-327 (2002)), renal disease (Satoh, S. et al., *Eur. J. Pharmacol.*, 455:169-174 (2002)) and erectile dysfunction (Gonzalez-Cadavid, N. F. et al., *Endocrine*, 23:167-176 (2004)).

In another study, it has been demonstrated that inhibition of the RhoA/ROCK signaling pathway allows formation of multiple competing lamellipodia that disrupt the productive migration of monocytes (Worthylake, R. A. et al., *J. Biol. Chem.*, 278:13578-13584 (2003)). It has also been reported that small molecule inhibitors of Rho Kinase are capable of inhibiting MCP-1 mediated chemotaxis in vitro (Iijima, H., *Bioorg. Med Chem.*, 15:1022-1033 (2007)). Due to the dependence of immune cell migration upon the RhoA/ROCK signaling pathway one would anticipate inhibition of Rho Kinase should also provide benefit for diseases such as rheumatoid arthritis, psoriasis, and inflammatory bowel disease.

The above studies provide evidence for a link between ROCK and cardiovascular diseases including hypertension, atherosclerosis, restenosis, stroke, heart failure, coronary vasospasm, cerebral vasospasm, ischemia/reperfusion injury, pulmonary hypertension and angina, as well as renal disease and erectile dysfunction. Given the demonstrated effect of ROCK on smooth muscle, ROCK inhibitors may also be useful in other diseases involving smooth muscle hyper-reactivity, including asthma and glaucoma (Shimokawa, H. et al., *Arterioscler. Thromb. Vasc. Biol.*, 25:1767-1775 (2005)). Furthermore, Rho-kinase has been indicated as a drug target for the treatment of various other diseases, including airway inflammation and hyperresponsiveness (Henry, P. J. et al., *Pulm. Pharmacol Ther.*, 18:67-74 (2005)), cancer (Rattan, R. et al., *J. Neurosci. Res.*, 83:243-255 (2006); Lepley, D. et al., *Cancer Res.*, 65:3788-3795 (2005)), fibrotic diseases (Jiang, C. et al., *Int. J Mol. Sci.*, 13:8293-8307 (2012); Zhou, L. et al., *Am. J Nephrol*, 34:468-475 (2011)), as well as neurological disorders, such as spinal-cord injury, Alzheimer's disease, multiple sclerosis, stroke and neuropathic pain (Mueller, B. K. et al., *Nat. Rev. Drug Disc.*, 4:387-398 (2005); Sun, X. et al., *J. Neuroimmunol.*, 180:126-134 (2006)).

There remains an unmet medical need for new drugs to treat cardiovascular disease. In the 2012 update of Heart Disease and Stroke Statistics from the American Heart Association (*Circulation*, 125:e2-e220 (2012)), it was reported that cardiovascular disease accounted for 32.8% of all deaths in the U.S., with coronary heart disease accounting for ~1 in 6 deaths overall in the U.S. Contributing to these numbers, it was found that ~33.5% of the adult U.S. population was hypertensive, and it was estimated that in 2010-6.6 million U.S. adults would have heart failure. Therefore, despite the number of medications available to treat cardiovascular diseases (CVD), including diuretics, beta blockers, angiotensin converting enzyme inhibitors, angiotensin blockers and calcium channel blockers, CVD remains poorly controlled or resistant to current medication for many patients.

Although there are many reports of ROCK inhibitors under investigation (see, for example, US 2012/0122842 A1, US 2010/0041645 A1, US 2008/0161297 A1, and Hu, E. et al., *Exp. Opin. Ther. Targets*, 9:715-736 (2005), and WO2014/113620, WO 2014/134388, WO 2014/134391, WO2015/002915, WO2015/002926, WO2016/010950, WO2016/028971, WO2016/112236, and WO2016/144936, of which the later nine references are assigned to the present applicant), fasudil is the only marketed ROCK inhibitor at this time. An i.v. formulation was approved in Japan for treatment of cerebral vasospasm. There remains a need for new therapeutics, including ROCK inhibitors, for the treatment of cardiovascular diseases, cancer, neurological diseases, renal diseases, fibrotic diseases, bronchial asthma, erectile dysfunction, and glaucoma.

SUMMARY OF THE INVENTION

The present invention provides novel 5-membered and bicyclic heterocyclic amindes, their analogues, including stereoisomers, enantiomers, diastereoisomers, tautomers, pharmaceutically-acceptable salts, or solvates thereof, which are useful as selective inhibitors of Rho kinases.

The present invention also provides processes and intermediates for making the compounds of the present invention.

The present invention also provides pharmaceutical compositions comprising a pharmaceutically acceptable carrier and at least one of the compounds of the present invention or stereoisomers, enantiomers, diastereoisomers, tautomers, pharmaceutically-acceptable salts, or solvates thereof.

The compounds of the invention may be used in the treatment and/or prophylaxis of conditions associated with aberrant ROCK activity.

The compounds of the present invention may be used in therapy.

The compounds of the present invention may be used for the manufacture of a medicament for the treatment and/or prophylaxis of a condition associated with aberrant ROCK activity.

In another aspect, the present invention is directed to a method of treating a cardiovascular or related disease which method comprises administering to a patient in need of such treatment a compound of the present invention as described above.

Examples of such diseases that may be treated include, for example, hypertension, atherosclerosis, restenosis, stroke, heart failure, renal failure, coronary artery disease, peripheral artery disease, coronary vasospasm, cerebral vasospasm, ischemia/reperfusion injury, pulmonary hypertension, angina, erectile dysfunction and renal disease.

In another aspect, the present invention is directed to a method of treating diseases involving smooth muscle hyper reactivity including asthma, erectile dysfunction and glaucoma, which method comprises administering to a patient in need of such treatment a compound of the present invention as described above.

In another aspect, the present invention is directed to a method of treating diseases mediated at least partially by Rho kinase including fibrotic diseases, oncology, spinal-cord injury, Alzheimer's disease, multiple sclerosis, stroke, neuropathic pain, rheumatoid arthritis, psoriasis and inflammatory bowel disease, which method comprises administering to a patient in need of such treatment a compound of the present invention as described above.

In yet additional aspects, the present invention is directed at pharmaceutical compositions comprising the above-mentioned compounds, processes for preparing the above-mentioned compounds and intermediates used in these processes.

The compounds of the invention can be used alone, in combination with other compounds of the present invention, or in combination with one or more, preferably one to two other agent(s).

These and other features of the invention will be set forth in expanded form as the disclosure continues.

DETAILED DESCRIPTION OF THE INVENTION

I. Compounds of the Invention

In one aspect, the present invention provides, inter alia, compounds of Formula (I):

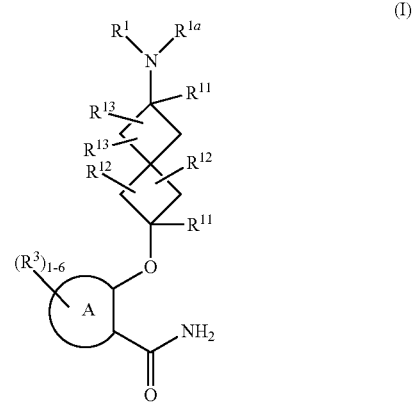

or stereoisomers, enantiomers, diastereoisomers, tautomers, pharmaceutically-acceptable salts, sovates, or prodrugs thereof, wherein:

Ring A is selected from a 5-membered heteroaryl comprising carbon atoms and 1-4 heteroatoms selected from N, O, and S, and a bicyclic heterocycle;

$R^1$ is selected from H and $C_{1-4}$ alkyl;

$R^{1a}$ is $C(O)R^4$; or $R^1$ and $R^{1a}$ are taken together with the nitrogen atom to which they are attached to form a ring of Formula (Ia);

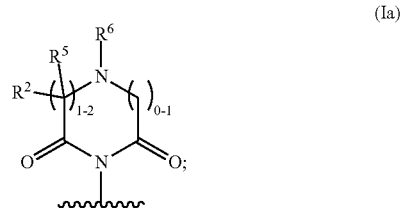

$R^2$ is selected from H, $C_{1-7}$alkyl, $C_{2-7}$alkenyl, $C_{2-7}$ alkynyl, $-(CR^{10}R^{10})_nC_{3-10}$ carbocycle and $-(CR^{10}R^{10})_n$-4- to 15-membered heterocycle comprising carbon atoms and 1-4 heteroatoms selected from N, $NR^8$, O, and $S(O)_p$, wherein said alkyl, alkenyl, alkynyl, carbocycle, and heterocycle are substituted with 1-4 $R^7$;

$R^3$, at each occurrence, is independently selected from H, halogen, $C_{1-6}$ alkyl, $C_{2-6}$ alkenyl, $C_{1-4}$ alkoxy, $C_{1-4}$ alkylthio, $C_{1-4}$ haloalkyl, $-CH_2OH$, $-OCH_2F$, $-OCHF_2$, $-OCF_3$, CN, $-NH_2$, $-NH(C_{1-4}$ alkyl), $-N(C_{1-4}$ alkyl$)_2$, $-CO_2H$, $-CH_2CO_2H$, $-CO_2(C_{1-4}$ alkyl), $-CO(C_{1-4}$ alkyl), $-CH_2NH_2$, $-CONH_2$, $-CONH(C_{1-4}$ alkyl), $-CON(C_{1-4}$ alkyl$)_2$, $-OCH_2CO_2H$, $-NHCO(C_{1-4}$ alkyl), $-NHCO_2(C_{1-4}$ alkyl), $-NHSO_2(C_{1-4}$ alkyl), $-SO_2NH_2$, $-C(=NH)NH_2$, a carbocycle, and a heterocycle, wherein said alkyl, alkenyl, alkoxy, alkylthio, haloalkyl, carbocycle, and heterocycle are substituted with 0-4 $R^9$;

$R^4$ is selected from $-(CR^{10}R^{10})_nC_{3-10}$ carbocycle and $-(CR^{10}R^{11})_n$-4- to 15-membered heterocycle comprising carbon atoms and 1-4 heteroatoms selected from N, $NR^8$, O, and $S(O)_p$; wherein said carbocycle, and heterocycle are substituted with 1-4 $R^7$;

$R^5$ is H; or $R^2$ and $R^5$ are taken together to form =O; or $R^2$ and $R^5$ are taken together with the carbon atom, to which they are both attached, to form a carbocycle or heterocycle wherein said carbocycle and heterocycle are substituted with 1-4 $R^7$;

$R^6$ is selected from H, $C_{1-4}$ alkyl, $-(CR^{10}R^{10})_nC_{3-10}$ carbocycle and $-(CR^{10}R^{10})_n$-4- to 15-membered heterocycle comprising carbon atoms and 1-4 heteroatoms selected from N, $NR^8$, O, and $S(O)_p$, wherein said alkyl, alkenyl, carbocycle, and heterocycle are substituted with 1-4 $R^7$; provided that $R^2$, $R^5$, and $R^6$ are not all H;

$R^7$, at each occurrence, is independently selected from H, =O, $NO_2$, halogen, $C_{1-7}$ alkyl, $C_{2-4}$ alkenyl, $C_{2-4}$ alkynyl, $C_{1-4}$ alkoxy, CN, OH, $CHF_2$, $CF_3$, $-(CH_2)_n-CO_2H$, $-(CH_2)_n-CO_2(C_{1-4}$ alkyl), $-(CH_2)_n-NR^8R^8$, $-NHCOH$, $-NHCO(C_{1-4}$ alkyl), $-NHCOCF_3$, $-NHCO_2(C_{1-4}$ alkyl), $-NHCO_2(CH_2)_2O(C_{1-4}$ alkyl), $-NHCO_2(CH_2)_3O(C_{1-4}$ alkyl), $-NHCO_2(CH_2)_2OH$, $-NHCO_2(CH_2)_2NH_2$, $-NHCO_2(CH_2)_2N(C_{1-4}$ alkyl$)_2$, $-NHCO_2CH_2CO_2H$, $-CH_2NHCO_2(C_{1-4}$ alkyl), $-NHC(O)NR^8R^8$, $-NHSO_2(C_{1-4}$ alkyl), $-S(O)_p(C_{1-4}$ alkyl), $-SO_2NH_2$, $-SO_2NH(C_{1-4}$ alkyl), $-SO_2N(C_{1-4}$ alkyl$)_2$, $-SO_2NH(CH_2)_2OH$, $-SO_2NH(CH)_2O(C_{1-4}$ alkyl), $-(CH_2)_n-CONR^8R^8$, $-O(CH_2)_n$-carbocycle, $-O(CH_2)_n$-heterocycle, $-NHCO$-carbocycle, $-NHCO$-heterocycle, $-(CH_2)_n$-carbocycle, and $-(CH_2)_n$-heterocycle comprising carbon atoms and 1-4 heteroatoms selected from N, $NR^8$, O, and $S(O)_p$, wherein said alkyl, alkenyl, alkynyl, alkoxy, carbocycle, and heterocycle are substituted with 0-4 $R^9$;

$R^8$, at each occurrence, is independently selected from H, $C_{1-6}$ alkyl, $C_{2-4}$ alkenyl, $C_{2-4}$ alkynyl, $-(CH_2)_n-C(O)C_{1-4}$alkyl, $-(CH_2)_n-C(O)$carbocycle, $-(CH_2)_n-C(O)$heterocycle, $-(CH_2)_n-C(O)NR^aR^a$, $-(CH_2)-NR^aC(O)C_{1-4}$alkyl, $-(CH_2)_n-C(O)OC_{1-4}$alkyl, $-(CH_2)_n-C(O)C_{1-4}$alkyl, $-(CH_2)_n-C(O)O$-carbocycle, $-(CH_2)_n-C(O)O$-heterocycle, $-(CH_2)_n-SO_2$alkyl, $-(CH_2)_n$SO_2carbocycle, $-(CH_2)_n-SO_2$heterocycle, $-(CH_2)_n-SO_2NR^aR^a$, $-(CH_2)_n$-carbocycle, and $-(CH_2)_n$-heterocycle, wherein said alkyl, carbocycle, and heterocycle are substituted with 0-4 $R^9$;

alternatively, $R^8$ and $R^8$ are taken together with the nitrogen atom to which they are attached to form a 4- to 10-membered heterocycle substituted with 0-4 $R^9$;

$R^9$, at each occurrence, is independently selected from halogen, OH, =O, CN, $NO_2$, $C_{1-4}$ alkyl, $C_{1-4}$ alkoxy, $CO(C_{1-4}$ alkyl), $CO_2H$, $CO_2(C_{1-4}$ alkyl), $-(CHR^{10})_nNR^aR^a$, $S(O)_p(C_{1-4}$ alkyl), $-(CHR^{10})_nCONR^aR^a$, $-(CHR^{10})_nNR^4CO(C_{1-4}$ alkyl), $-(CHR^{10})_nO-CONR^a$ $(CH_2)_nC_2R^a$, $S(O)_pC_{1-4}$alkyl, $S(O)NR^aR^a$, $-O(CHR^{10})_n$carbocycle, $-O(CHR^{10})_n$heterocycle, $-O(CHR^{10})_nNR^aR^a$, and $-(CR^{10}R^{10})_n$-4- to 10-membered heterocycle, wherein said alkyl, alkoxy, carbocycle, and heterocycle are substituted with 0-4 $R^b$;

$R^{10}$, at each occurrence, is independently selected from H and $C_{1-4}$ alkyl;

$R^{11}$ is independently selected from H and $C_{1-3}$ alkyl optionally substituted with halogen, $C_{1-4}$ alkoxy, OH, CN, $-CO_2H$, $-CO_2(C_{1-4}$ alkyl), $-CO(C_{1-4}$ alkyl), $-CONH_2$, $-CONH(C_{1-4}$ alkyl), and $-CON(C_{1-4}$ alkyl$)_2$;

$R^{12}$ and $R^{13}$ are independently selected from H, OH, $-OC_{1-3}$alkyl substituted with 0-4 $R^d$, $C_{1-3}$ alkyl with substituted with 0-4 $R^d$;

$R^a$, at each occurrence, is independently selected from H, $C_{1-4}$ alkyl, $-(CH_2)_nOH$, $CO(C_{1-4}$ alkyl), $COCF_3$, $CO_2(C_{1-4}$ alkyl), $-CONH_2$, $-CONH-C_{1-4}$ alkylene-$CO_2(C_{1-4}$ alkyl), $C_{1-4}$ alkylene-$CO_2(C_{1-4}$ alkyl), $R^c$, $CO_2R^c$, and $CONHR^c$; alternatively, $R^a$ and $R^a$ are taken together with the nitrogen atom to which they are attached to form a 4- to 10-membered heterocycle, wherein said alkyl, alkylene, and heterocycle are substituted with 0-4 $R^b$;

$R^b$, at each occurrence, is independently selected from =O, OH, halogen, CA alkyl, $C_{1-4}$ alkoxy, $OCF_3$, $OC(O)C_{1-4}$ alkyl, $NH_2$, $NO_2$, $N(C_{1-4}$ alkyl$)_2$, $CO(C_{1-4}$ alkyl), $CO(C_{1-4}$ haloalkyl), $CO_2H$, $CO_2(C_{1-4}$ alkyl), $CONH_2$, $-CONH(C_{1-4}$ alkyl), $-CON(C_{1-4}$ alkyl$)_2$, $-CONH-C_{1-4}$ alkylene-O$(C_{1-4}$ alkyl), $-CONH-C_{1-4}$ alkylene-NH$(C_{1-4}$ alkyl), $-CONH-C_{1-4}$ alkylene-N$(C_{1-4}$ alkyl$)_2$, $-C_{1-4}$ alkylene-O-P(O)(OH)$_2$, $-NHCO_2(C_{1-4}$ alkyl), $-R^c$, $COR^c$, $CO_2R^c$, and $CONHR^c$, wherein said alkyl and alkoxy are substituted with $R^d$;

$R^c$, at each occurrence, is independently selected from $-(CH_2)_nC_{3-6}$ cycloalkyl, $-(CH_2)_n$-phenyl, and $-(CH_2)_n$-5- to 6-membered heterocycle containing carbon atoms and 1-4 heteroatoms selected from the group consisting of: N, NH, N$(C_{1-4}$ alkyl), O, and $S(O)_p$; wherein each ring moiety is substituted with 0-2 $R^d$;

$R^d$, at each occurrence, is independently selected from =O, halogen, OH, $C_{1-4}$ alkyl, $NH_2$, $NH(C_{1-4}$ alkyl), $N(C_{1-4}$ alkyl$)_2$, $C_{1-4}$ alkoxy, and $-NHCO(C_{1-4}$ alkyl);

n, at each occurrence, is independently selected from 0, 1, 2, 3, and 4; and p, at each occurrence, is independently selected from 0, 1, and 2.

In another aspect, the present invention provides compounds of Formula (II):

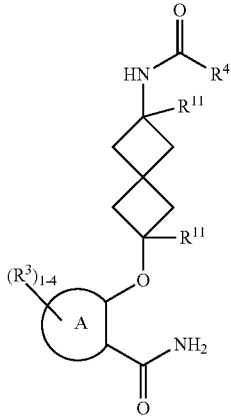
(II)

or stereoisomers, enantiomers, diastereoisomers, tautomers, pharmaceutically-acceptable salts, sovates, or prodrugs thereof, wherein:

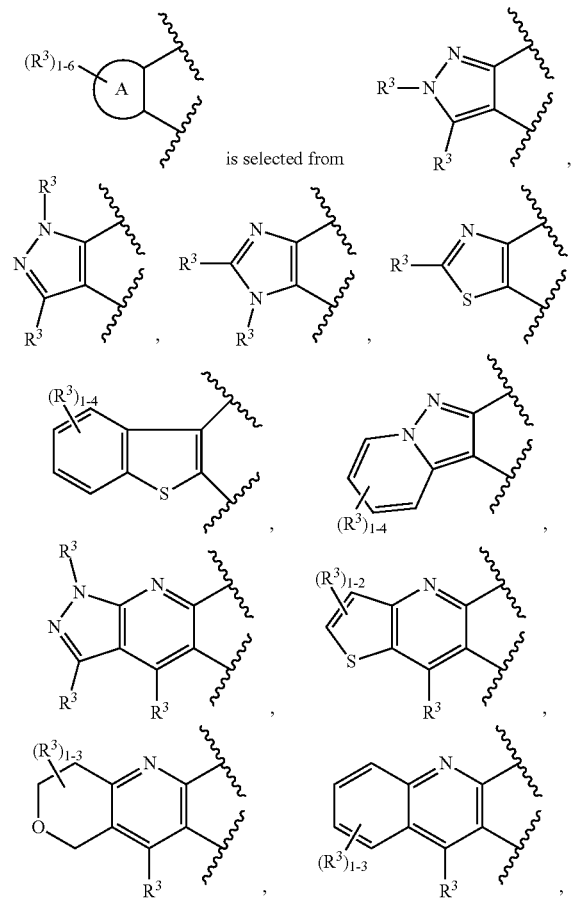

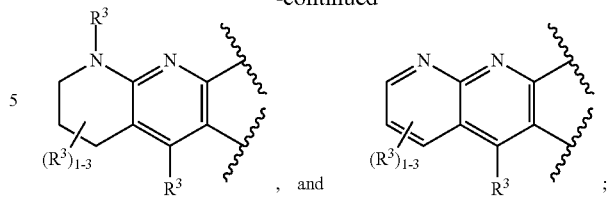

$R^3$, at each occurrence, is independently selected from H, halogen, $C_{1-6}$ alkyl, $C_{2-6}$ alkenyl, $C_{1-4}$ alkoxy, $C_{1-4}$ alkylthio, $C_{1-4}$ haloalkyl, —$CH_2OH$, —$OCH_2F$, —$OCHF_2$, —$OCF_3$, CN, —$NH_2$, —NH($C_{1-4}$ alkyl), —N($C_{1-4}$ alkyl)$_2$, —$CO_2H$, —$CH_2CO_2H$, —$CO_2(C_{1-4}$ alkyl), —CO($C_{1-4}$ alkyl), —$CH_2NH_2$, —$CONH_2$, —CONH($C_{1-4}$ alkyl), —CON($C_{1-4}$ alkyl)$_2$, —$OCH_2CO_2H$, —NHCO($C_{1-4}$ alkyl), —$NHCO_2$ ($C_{1-4}$ alkyl), —$NHSO_2(C_{1-4}$ alkyl), —$SO_2NH_2$, —C(=NH) $NH_2$, a carbocycle, and a heterocycle, wherein said alkyl, alkenyl, alkoxy, alkylthio, haloalkyl, carbocycle, and heterocycle are substituted with 0-4 $R^9$;

$R^4$ is selected from $C_{3-10}$ carbocycle and 4- to 15-membered heterocycle comprising carbon atoms and 1-4 heteroatoms selected from N, $NR^8$, O, and $S(O)_p$; wherein said carbocycle, and heterocycle are substituted with 1-4 $R^7$;

$R^7$, at each occurrence, is independently selected from H, =O, $NO_2$, halogen, $C_{1-7}$ alkyl, $C_{2-4}$ alkenyl, $C_{2-4}$ alkynyl, $C_{1-4}$ alkoxy, CN, OH, $CHF_2$, $CF_3$, —$(CH_2)_n$—$CO_2H$, —$(CH_2)_n$—$CO_2(C_{1-4}$ alkyl), —$(CH_2)_n$—$NR^8R^8$, —NHCOH, —NHCO($C_{1-4}$ alkyl), —$NHCOCF_3$, —$NHCO_2$ ($C_{1-4}$ alkyl), —$NHCO_2(CH_2)_2O(C_{1-4}$ alkyl), —$NHCO_2$ $(CH_2)_3O(C_{1-4}$ alkyl), —$NHCO_2(CH_2)_2OH$, —$NHCO_2$ $(CH_2)_2NH_2$, —$NHCO_2(CH_2)_2N(C_{1-4}$ alkyl)$_2$, —$NHCO_2CH_2CO_2H$, —$CH_2NHCO_2(C_{1-4}$ alkyl), —NHC (O)$NR^8R^8$, —$NHSO_2(C_{1-4}$ alkyl), —$S(O)_p(C_{1-4}$ alkyl), —$SO_2NH_2$, —$SO_2NH(C_{1-4}$ alkyl), —$SO_2N(C_{1-4}$ alkyl)$_2$, —$SO_2NH(CH_2)_2OH$, —$SO_2NH(CH2)_2O(C_{1-4}$ alkyl), —$(CH_2)_n$—$CONR^8R^8$, —$O(CH_2)_n$-carbocycle, —$O(CH_2)_n$-heterocycle, —NHCO-carbocycle, —NHCO-heterocycle, —$(CH_2)_n$-carbocycle, and —$(CH_2)_n$-heterocycle comprising carbon atoms and 1-4 heteroatoms selected from N, $NR^8$, O, and $S(O)_p$, wherein said alkyl, alkenyl, alkynyl, alkoxy, carbocycle, and heterocycle are substituted with 0-4 $R^9$;

$R^8$, at each occurrence, is independently selected from H, $C_{1-6}$ alkyl, $C_{2-4}$ alkenyl, $C_{2-4}$ alkynyl, —$(CH_2)_n$—C(O)$C_{1-4}$alkyl, —$(CH_2)_n$—C(O)carbocycle, —$(CH_2)_n$—C(O)heterocycle, —$(CH_2)_n$—C(O)$NR^aR^a$, —$(CH_2)_n$—$NR^aC(O)$ $C_{1-4}$alkyl, —$(CH_2)_n$—C(O)O$C_{1-4}$alkyl, —$(CH_2)_n$—C(O) $C_{1-4}$alkyl, —$(CH_2)$—C(O)O-carbocycle, —$(CH_2)_n$—C(O) O-heterocycle, —$(CH_2)_n$—$SO_2$alkyl, —$(CH_2)$ $SO_2$carbocycle, —$(CH_2)_n$—$SO_2$heterocycle, —$(CH_2)_n$—$SO_2NR^aR^a$, —$(CH_2)_n$-carbocycle, and —$(CH_2)_n$-heterocycle, wherein said alkyl, alkenyl, alkynyl, carbocycle, and heterocycle are substituted with 0-4 $R^9$;

alternatively, $R^8$ and $R^8$ are taken together with the nitrogen atom to which they are attached to form a 4- to 10-membered heterocycle substituted with 0-4 $R^9$;

$R^9$, at each occurrence, is independently selected from halogen, OH, =O, CN, $NO_2$, $C_{1-4}$ alkyl, $C_{1-4}$ alkoxy, CO($C_{1-4}$ alkyl), $CO_2H$, $CO_2(C_{1-4}$ alkyl), —$(CHR^{10})NR^aR^a$, $S(O)_p(C_{1-4}$ alkyl), —$(CHR^{10})_n$CONR$^aR^a$, —$(CHR^{10})_n$NRCO($C_{1-4}$ alkyl), —$(CHR^{10})_n$OCONR$^a$ $(CH_2)_nCO_2R^8$, $S(O)_pC_{1-4}$alkyl, $S(O)_pNR^aR^a$, —$O(CHR^{10})_n$carbocycle, —$O(CHR^{10})_n$heterocycle, —$O(CHR^{10})_nNR^aR^a$, and —$(CR^{10}R^{10})_n$-4- to 10-membered heterocycle, wherein said alkyl, alkoxy, carbocycle, and heterocycle are substituted with 0-4 $R^b$;

$R^{10}$, at each occurrence, is independently selected from H and $C_{1-4}$ alkyl;

$R^{11}$ is independently selected from H and $C_{1-3}$ alkyl optionally substituted with halogen, $C_{1-4}$ alkoxy, OH, and CN;

$R^a$, at each occurrence, is independently selected from H, $C_{1-4}$ alkyl, —$(CH_2)_n$OH, $CO(C_{1-4}$ alkyl), $COCF_3$, $CO_2(C_{1-4}$ alkyl), —$CONH_2$, —CONH—$C_{1-4}$ alkylene-$CO_2(C_{1-4}$ alkyl), $C_{1-4}$ alkylene-$CO_2(C_{1-4}$ alkyl), $R^c$, $CO_2R^c$, and $CONHR^c$; alternatively, $R^a$ and $R^a$ are taken together with the nitrogen atom to which they are attached to form a 4- to 10-membered heterocycle, wherein said alkyl, alkylene, and heterocycle are substituted with 0-4 $R^b$;

$R^b$, at each occurrence, is independently selected from =O, OH, halogen, $C_{1-4}$ alkyl, $C_{1-4}$ alkoxy, $OCF_3$, $OC(O)C_{1-4}$ alkyl, $NH_2$, $NO_2$, $N(C_{1-4}$ alkyl)$_2$, $CO(C_{1-4}$ alkyl), $CO(C_{1-4}$ haloalkyl), $CO_2H$, $CO_2(C_{1-4}$ alkyl), $CONH_2$, —$CONH(C_{1-4}$ alkyl), —$CON(C_{1-4}$ alkyl)$_2$, —CONH—$C_{1-4}$alkylene-$O(C_{1-4}$ alkyl), —CONH—$C_{1-4}$ alkylene-N$(C_{1-4}$ alkyl)$_2$, —$NHCO_2(C_{1-4}$ alkyl), —R, $COR^c$, $CO_2R^c$, and $CONHR^c$, wherein said alkyl and alkoxy are substituted with $R^d$;

$R^c$, at each occurrence, is independently selected from —$(CH_2)_n$—$C_{3-6}$ cycloalkyl, —$(CH_2)_n$-phenyl, and —$(CH_2)_n$-5- to 6-membered heterocycle containing carbon atoms and 1-4 heteroatoms selected from the group consisting of: N, NH, $N(C_{1-4}$ alkyl), O, and $S(O)_p$; wherein each ring moiety is substituted with 0-2 $R^d$;

$R^d$, at each occurrence, is independently selected from =O, halogen, OH, $C_{1-4}$ alkyl, $NH_2$, $NH(C_{1-4}$ alkyl), $N(C_{1-4}$ alkyl)$_2$, $C_{1-4}$ alkoxy, and —$NHCO(C_{1-4}$ alkyl);

n, at each occurrence, is independently selected from 0, 1, 2, 3, and 4; and p, at each occurrence, is independently selected from 0, 1, and 2.

In another aspect, the present invention provides compounds of Formula (II) or stereoisomers, enantiomers, diastereoisomers, tautomers, pharmaceutically-acceptable salts, sovates, or prodrugs, wherein:

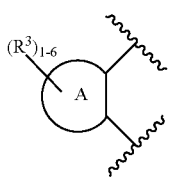

is selected from

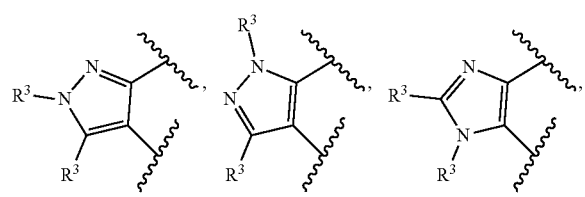

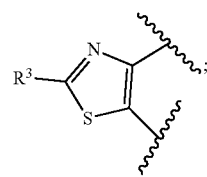

$R^3$, at each occurrence, is independently selected from H, $C_{1-4}$ alkyl, a carbocycle, and a heterocycle, wherein said alkyl, carbocycle, and heterocycle are substituted with 0-4 $R^9$;

$R^4$ is selected from

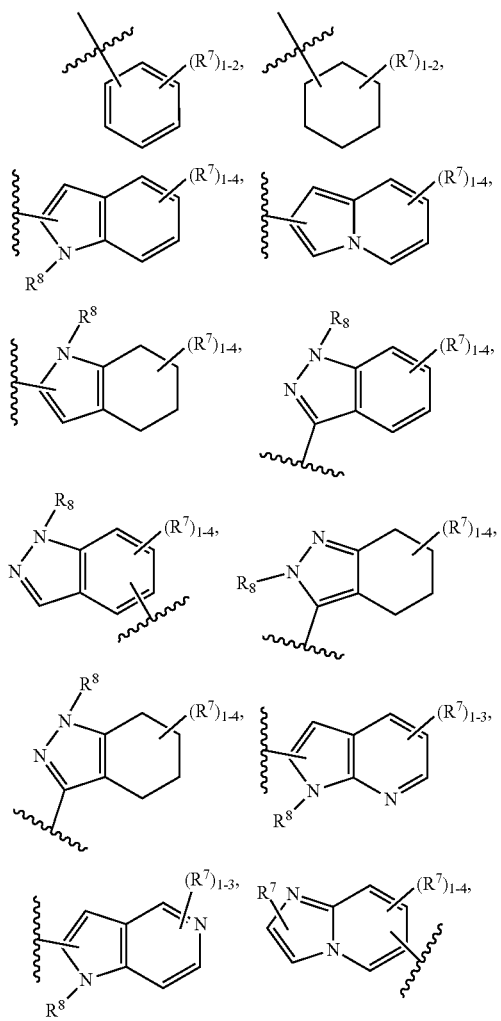

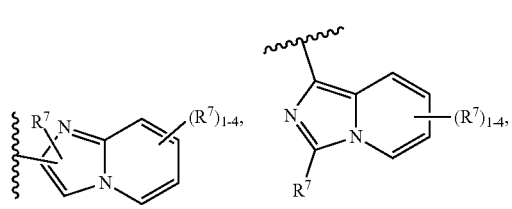

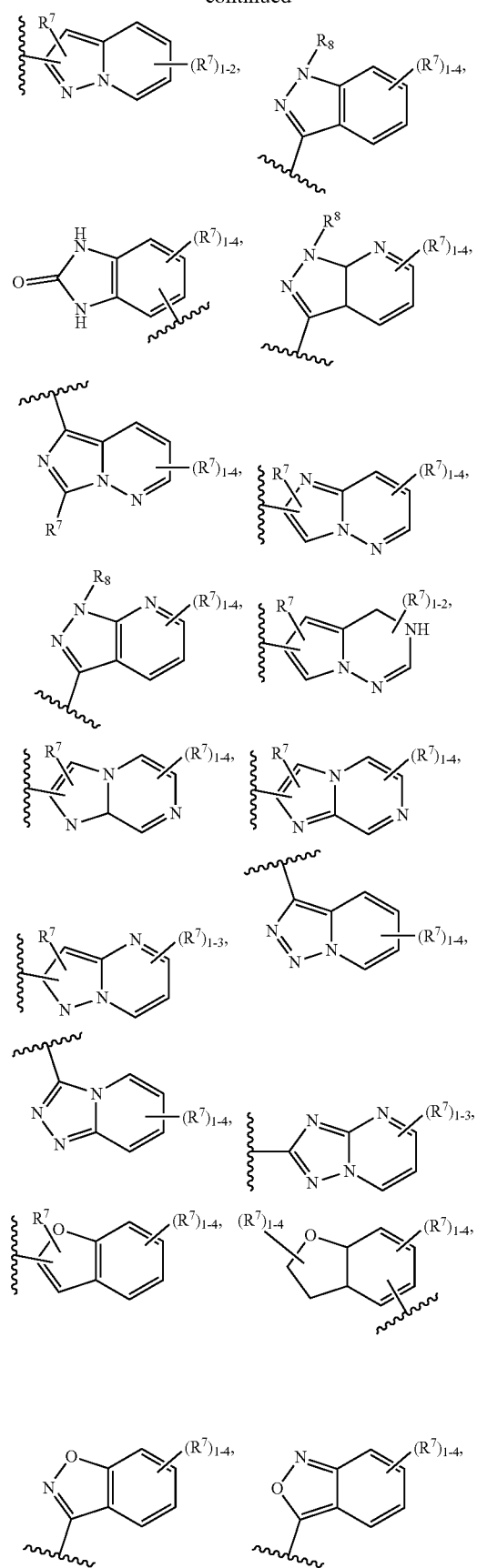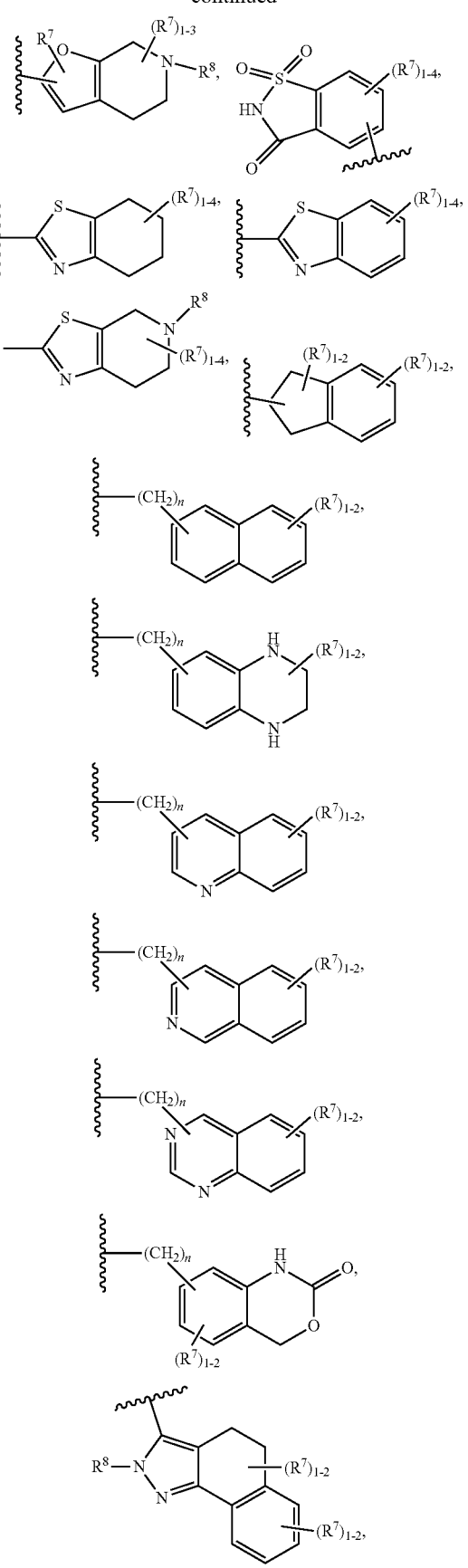

-continued

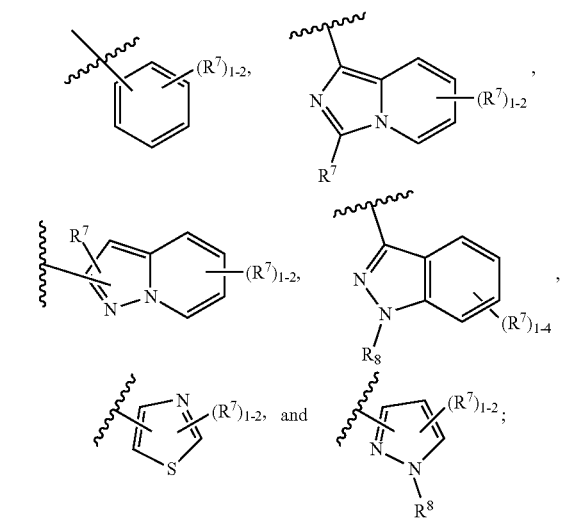

R⁷, at each occurrence, is independently selected from H, =O, NO₂, halogen, $C_{1-4}$ alkyl, $C_{1-4}$ alkoxy, CN, OH, CF₃, —(CH₂)ₙ—CO₂H, —(CH₂)ₙ—CO₂($C_{1-4}$ alkyl), —(CH₂)ₙ—NR⁸R⁸, —NHCO($C_{1-4}$ alkyl), —NHCOCF₃, —NHCO₂($C_{1-4}$ alkyl), —NHCO₂(CH₂)₂O($C_{1-4}$ alkyl), —NHCO₂(CH₂)₃O($C_{1-4}$ alkyl), —NHCO₂(CH₂)₂OH, —NHCO₂(CH₂)₂NH₂, —NHCO₂(CH₂)₂N($C_{1-4}$ alkyl)₂, —NHCO₂CH₂CO₂H, —CH₂NHCO₂($C_{1-4}$ alkyl), —NHC(O)NRgRO, —NHSO₂($C_{1-4}$ alkyl), —S(O)₂($C_{1-4}$ alkyl), —SO₂NH₂, —SO₂NH($C_{1-4}$ alkyl), —SO₂N($C_{1-4}$ alkyl)₂, —SO₂NH(CH₂)₂OH, —SO₂NH(CH₂)₂O($C_{1-4}$ alkyl), —(CH₂)ₙ—CONR⁸R⁸, —O(CH₂)ₙ-carbocycle, —O(CH₂)ₙ-heterocycle, —NHCO-carbocycle, —NHCO-heterocycle, —SO₂N($C_{1-4}$ alkyl)₂-carbocycle, —SO₂N($C_{1-4}$ alkyl)-heterocycle comprising carbon atoms and 1-4 heteroatoms selected from N, NR⁸, O, and S(O)ₚ, (CH₂)ₙ-carbocycle, and —(CH₂)ₙ-heterocycle comprising carbon atoms and 1-4 heteroatoms selected from N, NR⁸, O, and S(O)ₚ, wherein said alkyl, alkoxy, carbocycle, and heterocycle are substituted with 0-4 R⁹;

R⁸, at each occurrence, is independently selected from H, $C_{1-4}$ alkyl, C(O)$C_{1-4}$alkyl, C(O)carbocycle, C(O)heterocycle, —(CH₂)ₙ—C(O)NRᵃRᵃ, C(O)O$C_{1-4}$alkyl, C(O)O-carbocycle, C(O)O-heterocycle, SO₂alkyl, SO₂carbocycle, SO₂heterocycle, SO₂NRᵃRᵃ, —(CH₂)ₙ-carbocycle, and —(CH₂)ₙ-heterocycle, wherein said alkyl, carbocycle, and heterocycle are substituted with 0-4 R⁹;

alternatively, R⁸ and R⁸ are taken together with the nitrogen atom to which they are attached to form a 4- to 10-membered heterocycle substituted with 0-4 R⁹;

R⁹, at each occurrence, is independently selected from halogen, OH, =O, CN, NO₂, CHF₂, CF₃, $C_{1-4}$ alkyl, $C_{1-4}$ alkoxy, CH₂OH, CO₂H, CO₂($C_{1-4}$ alkyl), CONH₂, —(CH₂)ₙNRᵃRᵃ, —(CH₂)ₙCONRᵃRᵃ, —(CH₂)ₙNHCO($C_{1-4}$ alkyl), —S(O)₂($C_{1-4}$ alkyl), —S(O)₂($C_{1-4}$ alkyl), —O(CH₂)ₙheterocycle, —O(CH₂)₂₋₄NRᵃRᵃ, and —(CH₂)ₙ-4- to 10-membered heterocycle, wherein said alkyl, alkoxy, carbocycle, and heterocycle are substituted with 0-4 Rᵇ;

Rᵃ, at each occurrence, is independently selected from H and C alkyl; alternatively, Rᵃ and Rᵃ are taken together with the nitrogen atom to which they are attached to form a 4- to 10-membered heterocycle, wherein said alkyl, alkylene, and heterocycle are substituted with 0-4 Rᵇ; and Rᵇ, at each occurrence, is independently selected from =O, halogen, $C_{1-4}$ alkyl, $C_{1-4}$ alkoxy, OCF₃, NH₂, NO₂, N(C alkyl)₂, CO($C_{1-4}$ alkyl), CO($C_{1-4}$haloalkyl), CO₂($C_{1-4}$ alkyl), CONH₂, —CONH($C_{1-4}$ alkyl), —CON($C_{1-4}$ alkyl)₂, —CONH—$C_{1-4}$ alkylene-O($C_{1-4}$alkyl), —CONH—$C_{1-4}$ alkylene-N($C_{1-4}$ alkyl)₂, and —NHCO₂($C_{1-4}$ alkyl); other variables are as defined in Formula (II) above.

In another aspect, the present invention provides compounds of Formula (II) or stereoisomers, enantiomers, diastereoisomers, tautomers, pharmaceutically-acceptable salts, sovates, or prodrugs, wherein:

R³, at each occurrence, is independently selected from H, $C_{1-4}$ alkyl, phenyl, $C_{3-6}$ cycloalkyl, and a heterocycle, wherein said alkyl, phenyl, cycloalkyl, and heterocycle are substituted with 0-4 R⁹;

R⁴ is selected from

R⁷, at each occurrence, is independently selected from H, halogen, $C_{1-7}$ alkyl, $C_{1-7}$ alkoxy, —NR⁸R⁸, $C_{3-6}$ cycloalkyl, phenyl, and —(CH₂)ₙ-heterocycle comprising carbon atoms and 1-4 heteroatoms selected from N, NR⁸, O, and S(O)ₚ, wherein said alkyl, alkoxy, cycloalkyl phneyl, and heterocycle are substituted with 0-4 R⁹;

R⁸, at each occurrence, is independently selected from H, $C_{1-4}$ alkyl, —(CH₂)ₙ—$C_{3-6}$ cycloalkyl, —(CH₂)ₙ-phenyl, and —(CH₂)ₙ-heterocycle, wherein said alkyl, cycloalkyl, phenyl, and heterocycle are substituted with 0-4 R⁹;

alternatively, R⁸ and R⁸ are taken together with the nitrogen atom to which they are attached to form a heterocycle selected from,

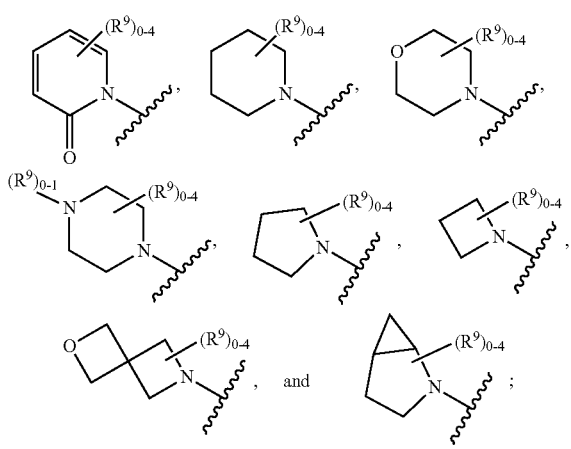

$R^9$, at each occurrence, is independently selected from F, Cl, OH, =O, CN, $C_{1-4}$ alkyl, $C_{1-4}$ alkoxy, —$(CH_2)_nNR^aR^a$, —$(CH_2)_nCONR^aR^a$, $C_{3-6}$ cycloalkyl, and a 4- to 10-membered heterocycle, wherein said alkyl, alkoxy, cycloalkyl, and heterocycle are substituted with 0-4 $R^b$;

$R^a$, at each occurrence, is independently selected from H, $C_{1-4}$ alkyl, —$(CH_2)OH$, $CO(C_{1-4}$ alkyl), $COCF_3$, $C_2(C_{1-4}$ alkyl), —$CONH_2$, —CONH—$C_{1-4}$ alkylene-$CO_2(C_{1-4}$ alkyl), and $C_{1-4}$ alkylene-$CO_2(C_{1-4}$ alkyl); and $R^b$, at each occurrence, is independently selected from halogen, OH, $C_{1-4}$ alkyl, $C_{1-4}$ alkoxy, $OCF_3$, $NH_2$, $NO_2$, $N(C_{1-4}$ alkyl)$_2$, $CO(C_{1-4}$ alkyl), $CO(C_{1-4}$ haloalkyl), $CO_2(C_{1-4}$ alkyl), $CONH_2$, —$CONH(C_{1-4}$ alkyl), —$CON(C_{1-4}$ alkyl)$_2$, —CONH—$C_{1-4}$ alkylene-O($C_{1-4}$ alkyl), —CONH—$C_{1-4}$ alkylene-N($C_{1-4}$ alkyl)$_2$, and —$NHC_2(C_{1-4}$ alkyl); other variables are as defined in Formula (II) above.

In another aspect, the present invention provides compounds of Formula (II) or stereoisomers, enantiomers, diastereoisomers, tautomers, pharmaceutically-acceptable salts, sovates, or prodrugs, wherein:

$R^3$, at each occurrence, is independently selected from H, $C_{1-4}$ alkyl, phenyl, $C_{3-6}$ cycloalkyl, and a heterocycle, wherein said alkyl, phenyl, cycloalkyl, and heterocycle are substituted with 0-4 $R^9$; $R^4$ is selected from

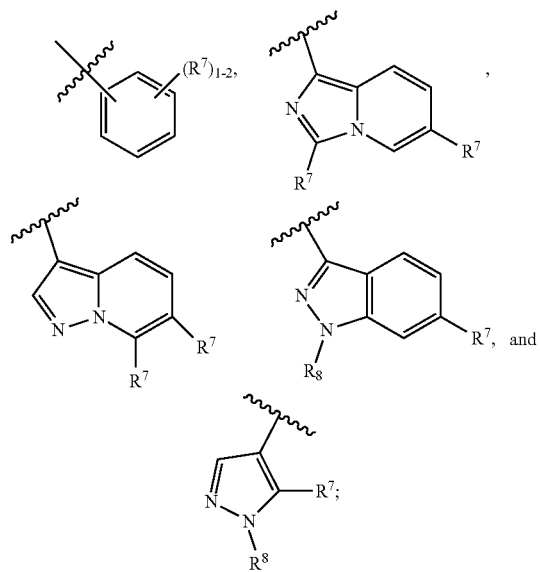

$R^7$, at each occurrence, is independently selected from H, halogen, CN, $C_{1-7}$ alkyl, $C_{1-7}$ alkoxy, —$NR^8R^8$, $C_{3-6}$ cycloalkyl, phenyl, and —$(CH_2)_n$-heterocycle comprising carbon atoms and 1-4 heteroatoms selected from N, $NR^8$, O, and $S(O)_p$, wherein said alkyl, alkoxy, cycloalkyl phenyl, and heterocycle are substituted with 0-4 $R^9$;

$R^8$, at each occurrence, is independently selected from H, $C_{1-4}$ alkyl, —$(CH_2)_n$-$C_{3-6}$ cycloalkyl, —$(CH_2)_n$-phenyl, and —$(CH_2)_n$heterocycle, wherein said alkyl, cycloalkyl, phenyl, and heterocycle are substituted with 0-4 $R^9$;

alternatively, $R^8$ and $R^8$ are taken together with the nitrogen atom to which they are attached to form a heterocycle selected from

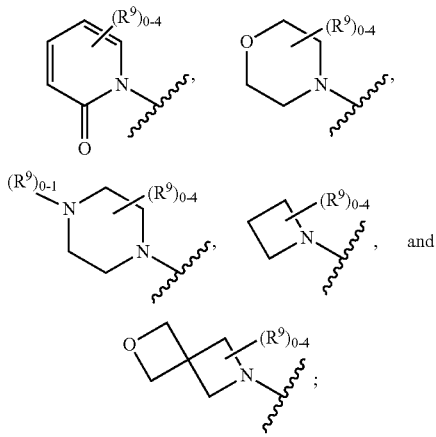

$R^9$, at each occurrence, is independently selected from F, Cl, OH, =O, CN, $C_{1-4}$ alkyl, $C_{1-4}$ alkoxy, —$(CH_2)_nNR^aR^a$, —$(CH_2)_nCONR^aR^a$, $C_{3-6}$ cycloalkyl, and a 4- to 10-membered heterocycle, wherein said alkyl, alkoxy, cycloalkyl, and heterocycle are substituted with 0-4 $R^b$;

$R^a$, at each occurrence, is independently selected from H, $C_{1-4}$ alkyl, —$(CH_2)_nOH$, $CO(C_{1-4}$ alkyl), $COCF_3$, $CO_2(C_{1-4}$ alkyl), —$CONH_2$, —CONH—$C_{1-4}$ alkylene-$CO_2(C_{1-4}$ alkyl), and $C_{1-4}$ alkylene-$CO_2(C_{1-4}$alkyl); and $R^b$, at each occurrence, is independently selected from halogen, OH, $C_{1-4}$ alkyl, $C_{1-4}$ alkoxy, $OCF_3$, $NH_2$, $NO_2$, $N(C_{1-4}$ alkyl)$_2$, $CO(C_{1-4}$ alkyl), $CO(C_{1-4}$ haloalkyl), $CO_2(C_{1-4}$ alkyl), $CONH_2$, —$CONH(C_{1-4}$ alkyl), —$CON(C_{1-4}$ alkyl)$_2$, —CONH—$C_{1-4}$ alkylene-O($C_{1-4}$ alkyl), —CONH—$C_{1-4}$ alkylene-N($C_{1-4}$ alkyl)$_2$, and —$NHC_2(C_{1-4}$ alkyl); other variables are as defined in Formula (II) above.

In another aspect, the present invention provides compounds of Formula (II) or stereoisomers, enantiomers, diastereoisomers, tautomers, pharmaceutically-acceptable salts, sovates, or prodrugs, wherein:

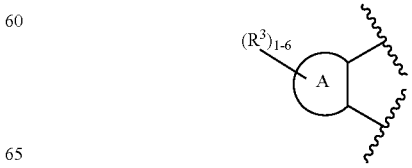

is selected from

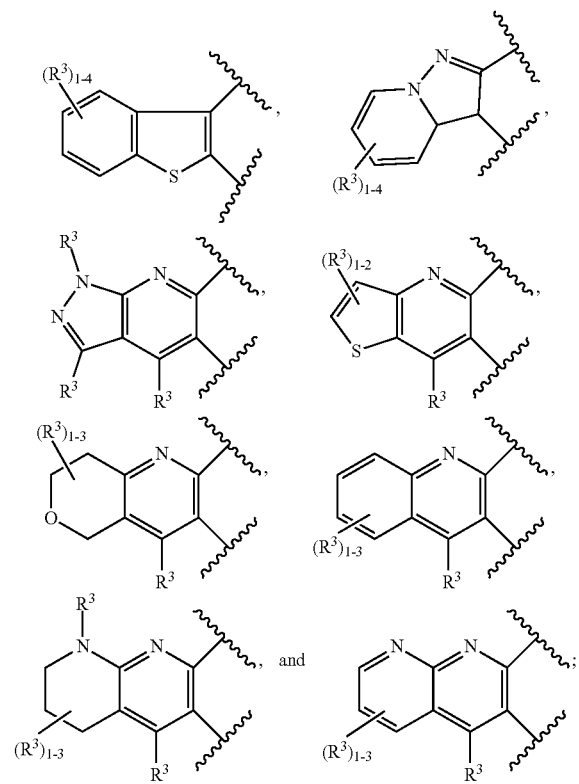

R³, at each occurrence, is independently selected from H and C$_{1-4}$ alkyl;

R⁴ is selected from

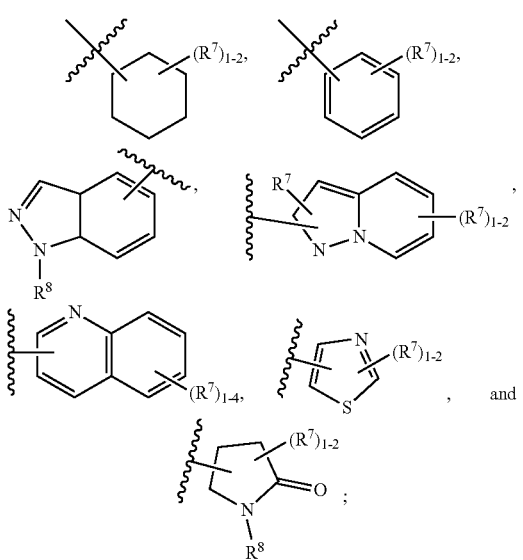

R⁷, at each occurrence, is independently selected from H, halogen, CN, C$_{1-4}$ alkyl, C$_{1-4}$ alkoxy, —NR⁸R⁸, C$_{3-6}$ cycloalkyl, phenyl, and —(CH$_2$)$_n$-heterocycle comprising carbon atoms and 1-4 heteroatoms selected from N, NR⁸, O, and S(O)$_p$, wherein said alkyl, alkoxy, cycloalkyl phneyl, and heterocycle are substituted with 0-4 R⁹;

R⁸, at each occurrence, is independently selected from H, C$_{1-4}$ alkyl, —(CH$_2$)$_n$-phenyl, and —(CH$_2$)$_n$-heterocycle, wherein said alkyl, phenyl, and heterocycle are substituted with 0-4 R⁹;

R⁹, at each occurrence, is independently selected from F, Cl, OH, =O, CN, 14 alkyl, C$_{1-4}$ alkoxy, —(CH$_2$)$_n$NR$^a$R$^a$, —(CH$_2$)$_n$CONR$^a$R$^a$, C$_{3-6}$ cycloalkyl, and a 4- to 10-membered heterocycle, wherein said alkyl, alkoxy, cycloalkyl, and heterocycle are substituted with 0-4 R$^b$;

R$^a$, at each occurrence, is independently selected from H, C$_{1-4}$ alkyl, —(CH$_2$)$_n$OH, CO(C$_{1-4}$ alkyl), COCF$_3$, CO$_2$(C$_{1-4}$ alkyl), —CONH$_2$, —CONH—C$_{1-4}$ alkylene-CO$_2$(C$_{1-4}$ alkyl), and C$_{1-4}$ alkylene-CO$_2$(C$_{1-4}$ alkyl); and R$^b$, at each occurrence, is independently selected from halogen, C$_{1-4}$ alkyl, C$_{1-4}$ alkoxy, OCF$_3$, NH$_2$, NO$_2$, and N(C$_{1-4}$ alky)$_2$;

other variables are as defined in Formula (II) above.

In another aspect, the present invention provides compounds of Formula (II) or stereoisomers, enantiomers, diastereoisomers, tautomers, pharmaceutically-acceptable salts, sovates, or prodrugs, wherein:

R⁴ is selected from

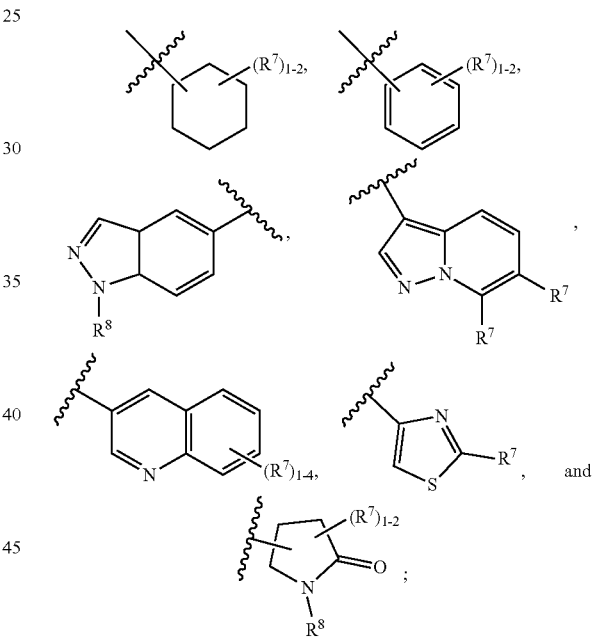

R⁷, at each occurrence, is independently selected from H, halogen, C$_{1-4}$ alkyl, C$_{1-4}$ alkoxy, —NR⁸R⁸, C$_{3-6}$ cycloalkyl, phenyl, and —(CH$_2$)$_n$-heterocycle comprising carbon atoms and 1-4 heteroatoms selected from N, NR⁸, O, and S(O)$_p$, wherein said alkyl, alkoxy, cycloalkyl phneyl, and heterocycle are substituted with 0-4 R⁹;

R⁸, at each occurrence, is independently selected from H, C$_{1-4}$ alkyl, —(CH$_2$)$_n$—C$_{3-6}$ cycloalkyl, —(CH$_2$)$_n$-phenyl, and —(CH$_2$)$_n$-heterocycle, wherein said alkyl, cycloalkyl, phenyl, and heterocycle are substituted with 0-4 R⁹;

R⁹, at each occurrence, is independently selected from F, Cl, OH, =O, CN, C$_{1-4}$ alkyl, C$_{1-4}$ alkoxy, —(CH$_2$)$_n$NR$^a$R$^a$, —(CH$_2$)CONR$^a$R$^a$, C$_{3-6}$ cycloalkyl, and a 4- to 10-membered heterocycle, wherein said alkyl, alkoxy, cycloalkyl, and heterocycle are substituted with 0-4 R$^b$;

R$^a$, at each occurrence, is independently selected from H, C$_{1-4}$ alkyl, —(CH$_2$)$_n$OH, CO(C$_{1-4}$ alkyl), COCF$_3$, CO$_2$(C$_{1-4}$ alkyl), —CONH$_2$, —CONH—C$_{1-4}$ alkylene-CO$_2$(C$_{1-4}$ alkyl), and C$_{1-4}$ alkylene-CO$_2$(C$_{1-4}$ alkyl); and R$^b$, at each occurrence, is independently selected from halogen, C$_{1-4}$ alkyl, C$_{1-4}$ alkoxy, OCF$_3$, NH$_2$, NO$_2$, N(C$_{1-4}$ alkyl)$_2$, CO(C$_{1-4}$ alkyl), CO(C$_{1-4}$ haloalkyl), CO$_2$(C$_{1-4}$ alkyl), CONH$_2$, —CONH(C$_{1-4}$ alkyl), —CON(CA alkyl)$_2$, —CONH—C$_{1-4}$ alkylene-O(C$_{1-4}$ alkyl), —CONH—C$_{1-4}$ alkylene-N(C$_{1-4}$ alkyl)$_2$, and —NHCO$_2$(C$_{1-4}$ alkyl);

other variables are as defined in Formula (II) above.

In another aspect, the present invention provides compounds of Formula (III):

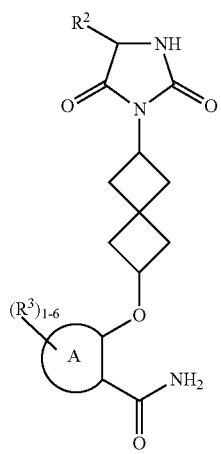

(III)

or stereoisomers, enantiomers, diastereoisomers, tautomers, pharmaceutically-acceptable salts, sovates, or prodrugs thereof, wherein:

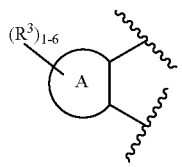

is selected from

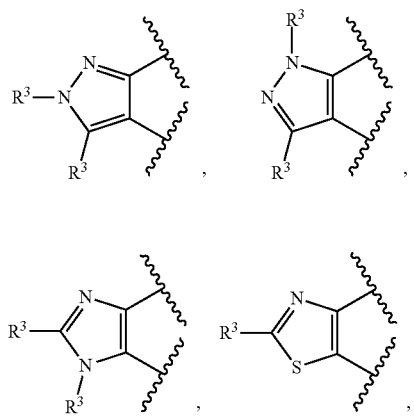

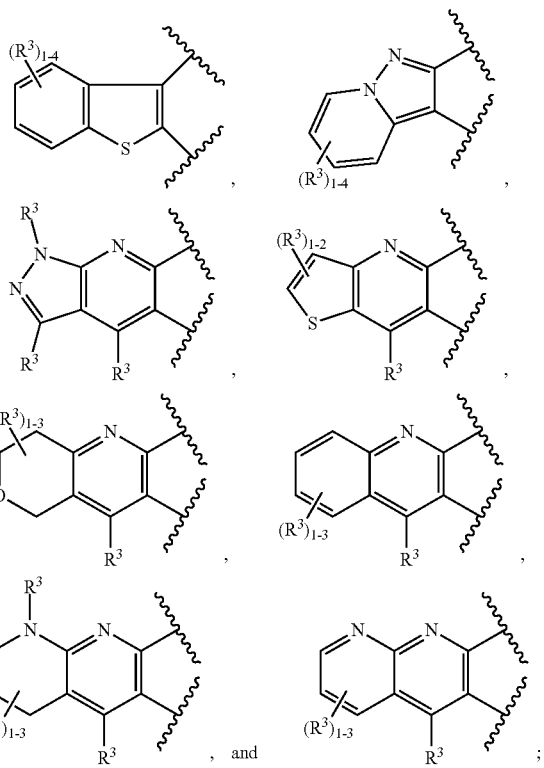

R$^2$ is selected from C$_{1-4}$ alkyl, —(CH$_2$)$_{0-1}$-phenyl and —(CH$_2$) 4-6-membered heteroaryl comprising carbon atoms and 1-2 heteroatoms selected from N, O, and S(O)$_p$, wherein said alkyl, phenyl, and heteroaryl are substituted with 1-4 R$^7$;

R$^3$, at each occurrence, is independently selected from H, C$_{1-4}$ alkyl, and cyclopropyl; and R$^7$, at each occurrence, is independently selected from H, C$_{1-4}$ alkyl, $_{1-4}$ alkoxy, CN, OH, CHF$_2$, and CF$_3$.

In another aspect, the present invention provides compounds of Formula (IV):

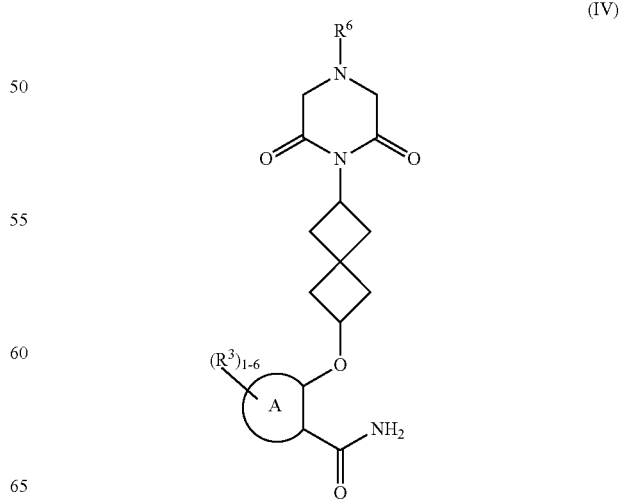

(IV)

or stereoisomers, enantiomers, diastereoisomers, tautomers, pharmaceutically-acceptable salts, sovates, or prodrugs thereof, wherein:

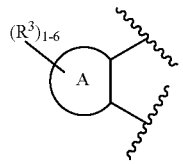

is selected from

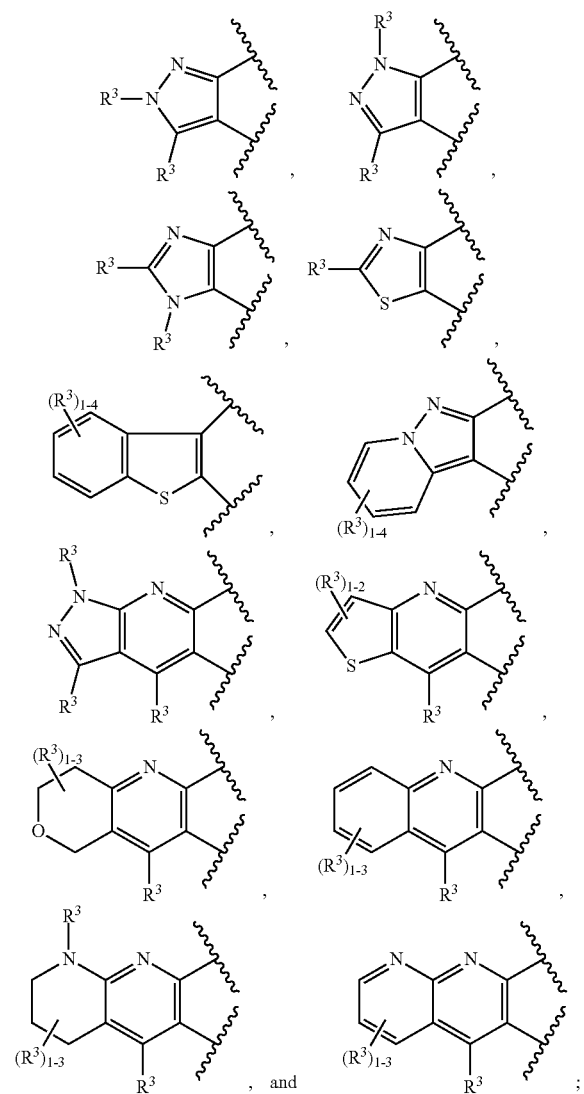

, and

;

$R^3$, at each occurrence, is independently selected from H, $C_{1-4}$ alkyl, and cyclopropyl; and $R^6$ is selected from $C_{1-4}$ alkyl, —$(CH_2)_{0-1}$-phenyl and —$(CH_2)$ 4-6-membered heteroaryl comprising carbon atoms and 1-2 heteroatoms selected from N, O, and $S(O)_p$.

In another aspect, the present invention provides a compound selected from any subset list of compounds exemplified in the present application.

In another aspect, the present invention provides compounds of Formula (II) or stereoisomers, enantiomers, diastereoisomers, tautomers, pharmaceutically-acceptable salts, sovates, or prodrugs, wherein:

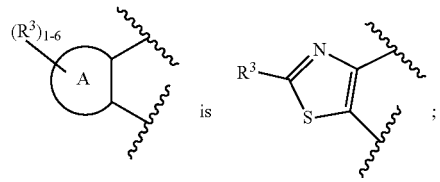

is

;

$R^3$ is $C_{1-4}$ alkoxy;

$R^4$ is selected from

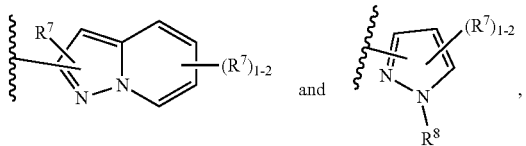

and

, $R^7$, at each occurrence, is independently selected from H, halogen, $C_{1-4}$ alkyl, $C_{1-4}$ alkoxy, CN, and OH, wherein said alkyl and alkoxy are substituted with 0-4 $R^9$;

$R^8$ is selected from 6-membered aryl and 6-membered heterocycle, wherein said aryl and heterocyle are substituted with 0-4 $R^9$;

$R^9$, at each occurrence, is independently selected from halogen, OH, CN, $CHF_2$, and $CF_3$.

In another aspect, the present invention provides compounds of Formula (II) or stereoisomers, enantiomers, diastereoisomers, tautomers, pharmaceutically-acceptable salts, sovates, or prodrugs, wherein:

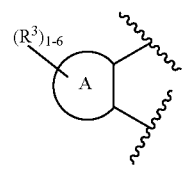

is selected from

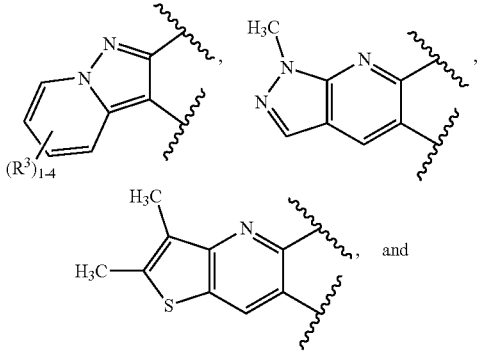

, and

-continued

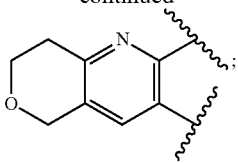

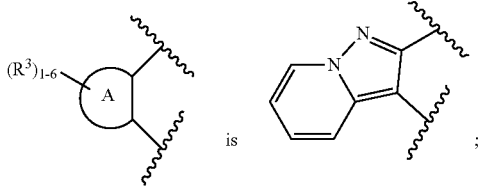
is $R^3$, at each occurrence, is independently selected from H, halogen, $C_{1-6}$ alkyl, $C_{1-4}$ alkoxy, a carbocycle, and a heterocycle, wherein said alkyl, alkoxy, carbocycle, and heterocycle are substituted with 0-4 $R^9$;

$R^4$ is selected from

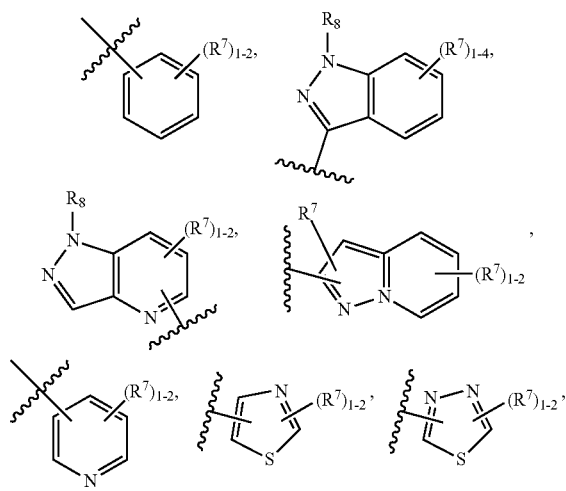

$R^7$, at each occurrence, is independently selected from H, $C_{1-3}$ alkyl, $C_{1-4}$ alkoxy, $NHR^8$, and a carbocycle, wherein said alkyl, alkoxy, and carbocycle are substituted with 0-4 $R^9$;

$R^8$, at each occurrence, is independently selected from H, $C_{1-6}$ alkyl, a carbocycle, and a heterocycle, wherein said alkyl, carbocycle, and heterocycle are substituted with 0-4 $R^9$;

$R^9$, at each occurrence, is independently selected from halogen, OH, CN, $C_{1-4}$ alkyl, $S(O)_p C_{1-4}$alkyl, -4- to 10-membered heterocycle, wherein said alkyl and heterocycle are substituted with 0-4 $R^9$;

$R^a$, at each occurrence, is independently selected from H and $C_{1-4}$ alkyl substituted with 0-4 $R^b$;

$R^b$, at each occurrence, is independently selected from halogen and $C_{1-4}$ alkylsubstituted with 0-2 $R^d$;

$R^d$ is halogen; and p, at each occurrence, is independently selected from 0, 1, and 2.

In another aspect, the present invention provides compounds of Formula (III) or stereoisomers, enantiomers, diastereoisomers, tautomers, pharmaceutically-acceptable salts, sovates, or prodrugs, wherein:

$R^2$ is $C_{1-4}$ alkyl substituted with 1-4 $R^7$;

$R^7$, at each occurrence, is independently selected from H, OH, $CHF_2$, and $CF_3$.

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention as showin in Formula (I), (II), (III), or (IV).

For example, in one non-limiting embodiment,

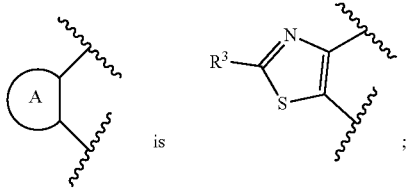
is selected from

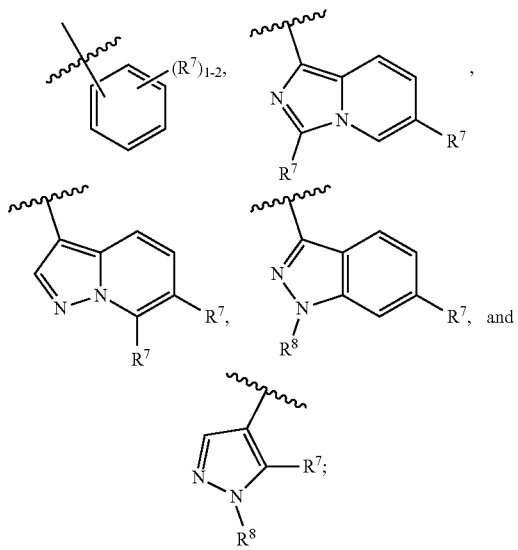

$R^3$ is selected from H, $C_{1-4}$ alkyl, cyclopropyl, and phenyl; $R^7$, at each occurrence, is independently selected from H, halogen, CN, $C_{1-7}$ alkyl, $C_{1-7}$ alkoxy, $—NR^8R^8$, $C_{3-6}$ cycloalkyl, phenyl, and $—(CH_2)_n$-heterocycle comprising carbon atoms and 1-4 heteroatoms selected from N, $NR^8$, O, and $S(O)_p$, wherein said alkyl, alkoxy, cycloalkyl, phneyl, and heterocycle are substituted with 0-4 $R^9$; $R^8$, at each occurrence, is independently selected from H, $C_{1-4}$ alkyl, —(CH$_2$)$_n$—C$_{3-6}$ cycloalkyl, —(CH$_2$)$_n$-phenyl, and —(CH$_2$)$_n$-heterocycle, wherein said alkyl, cycloalkyl, phenyl, and heterocycle are substituted with 0-4 R$^9$; R$^9$, at each occurrence, is independently selected from F, Cl, OH, =O, CN, C$_{1-4}$ alkyl, C$_{1-4}$ alkoxy, —(CH$_2$)$_n$NR$^a$R$^a$, —(CH$_2$)$_n$CONR$^a$R$^a$, C$_{3-6}$ cycloalkyl, and a 4- to 10-membered heterocycle, wherein said alkyl, alkoxy, cycloalkyl, and heterocycle are substituted with 0-4 R$^b$.

In another non-limiting embodiment,

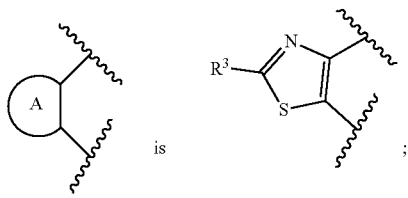

R$^4$ is selected from,

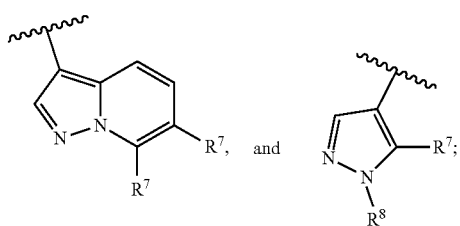

R$^3$ is C$_{1-3}$ alkoxy; R$^7$, at each occurrence, is independently selected from H, C$_{1-7}$ alkyl and C$_{1-7}$ alkoxy, wherein said alkyl and alkoxy, are substituted with 0-4 R$^9$; R$^8$ is selected from H, phenyl, and pyridyl, wherein said phenyl and pyridyl are substituted with 0-4 R$^9$; R$^9$, at each occurrence, is independently selected from F, Cl, OH, and C$_{1-4}$ alkyl substituted with 0-2 R$^b$, and R$^b$ is halogen.

In another non-limiting embodiment,

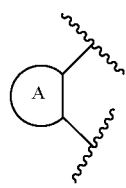

is selected from

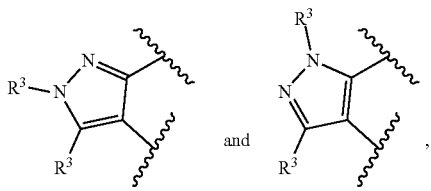

R$^3$ is selected from H, C$_{1-4}$ alkyl (optionally substituted with F, alkoxy, NR$^a$R$^a$), cyclopropyl, phenyl (optionally substitetuted with CN); —(CH$_2$)$_{0-1}$-heterocycle; R$^4$ is selected from

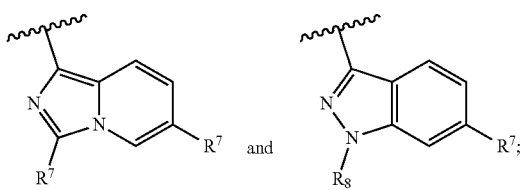

R$^3$ is selected from H, C$_{1-4}$ alkyl (optionally substituted with F, alkoxy, NR$^a$R$^a$), CH$_2$NR and cyclopropyl, phenyl (optionally substitetuted with CN); R$^7$, at each occurrence, is independently selected from H, halogen, CN, C$_{1-7}$ alkyl, C$_{1-7}$ alkoxy, —NR$^8$R$^8$, C$_{3-6}$ cycloalkyl, phenyl, and —(CH$_2$)$_n$-heterocycle comprising carbon atoms and 1-4 heteroatoms selected from N, NR$^8$, O, and S(O)$_p$, wherein said alkyl, alkoxy, cycloalkyl phneyl, and heterocycle are substituted with 0-4 R$^9$; R$^8$, at each occurrence, is independently selected from H, C$_{1-4}$ alkyl, —(CH$_2$)$_n$—C$_{3-6}$ cycloalkyl, —(CH$_2$)$_n$-phenyl, and —(CH$_2$)$_n$-heterocycle, wherein said alkyl, cycloalkyl, phenyl, and heterocycle are substituted with 0-4 R$^9$; R$^9$, at each occurrence, is independently selected from F, Cl, OH, =O, CN, C$_{1-4}$ alkyl, 1-4 alkoxy, —(CH$_2$)$_n$NR$^a$R$^a$, —(CH$_2$)$_n$CONR$^a$R$^a$, C$_{3-6}$ cycloalkyl, and a 4- to 10-membered heterocycle, wherein said alkyl, alkoxy, cycloalkyl, and heterocycle are substituted with 0-4 R$^b$;

In another non-limiting embodiment,

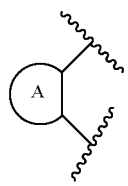

is selected from

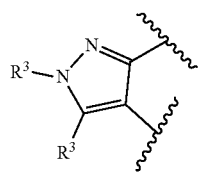

and

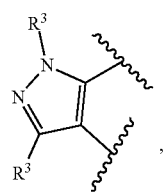

R³ is selected from H, C₁₋₄ alkyl (optionally substituted with F, alkoxy, NRᵃRᵃ), cyclopropyl, phenyl (optionally substituted with CN); —(CH₂)₀₋₁-heterocycle; R⁴ is

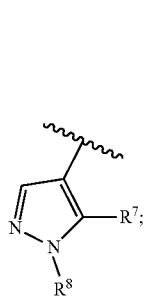

R⁷ is selected from H and C₁₋₇ alkyl; R⁸ is selected from phenyl and pyridyl, each is optionally substituted with F, Cl, OH, CN, C₁₋₄ alkyl, and C₁₋₄ alkoxy.

In another non-limiting embodiment,

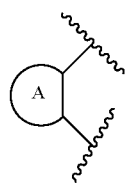

is selected from

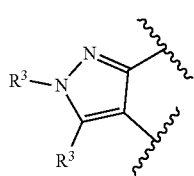

and

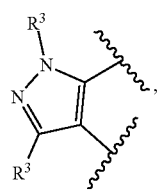

R³ is selected from H, C₁₋₄ alkyl, cyclopropyl, phenyl, —(CH₂)₀₋₁-heterocycle; R⁴ is

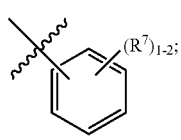

In another non-limiting embodiment,

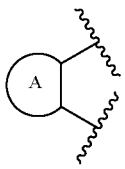

is selected from

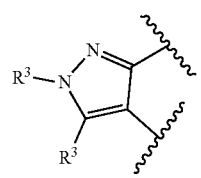

and

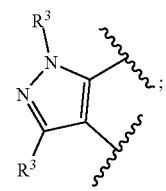

R³ is selected from H, C₁₋₄ alkyl (optionally substituted with F, alkoxy, NRᵃRᵃ), cyclopropyl, phenyl (optionally substituted with CN); —(CH₂)₀₋₁-heterocycle; R⁴ is

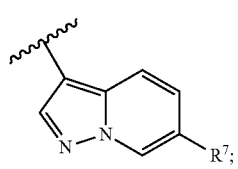

R⁷ is —NR⁸R⁸, wherein R⁸ and R⁸ are taken together to form

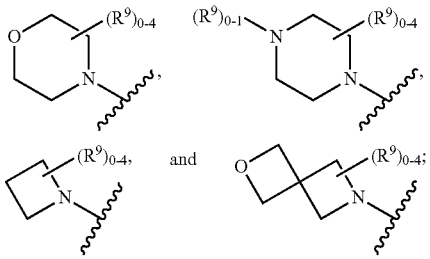

R⁹, at each occurrence, is independently selected from F, Cl, OH, =O, CN, C₁₋₄ alkyl optionally substituted with F, Cl, and OH.

In another non-limiting embodiment,

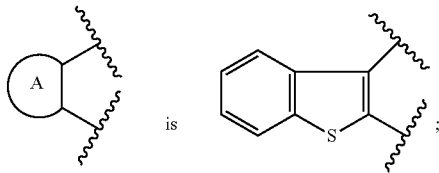 is 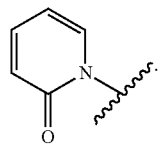

R⁴ is selected from

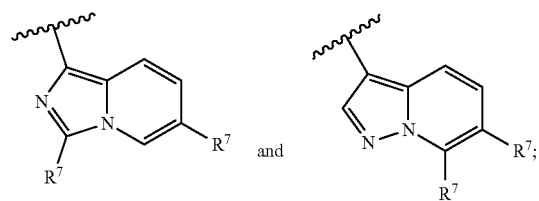

R⁷, at each occurrence, is independently selected from H, F, Cl, Br, $C_{1-7}$ alkyl (optionally substituted with F), $C_{1-4}$ alkoxy (optionally substituted with OH), —NR⁸R⁸, wherein R⁸ and R⁸ are taken together to form

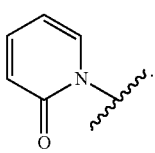 [SMILES: *n1ccccc1=O]

In another non-limiting embodiment,

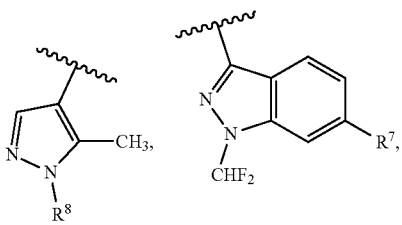

R⁴ is selected from

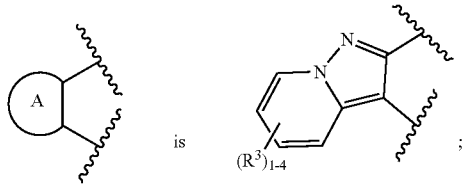

R⁷, at each occurrence, is independently selected from H, F, Cl, Br, $C_{1-7}$ alkyl (optionally substituted with F), $C_{1-7}$ alkoxy (optionally substituted with OH), —NR⁸R⁸, wherein R⁸ and R⁸ are taken together to form

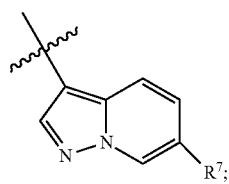

In another non-limiting embodiment is

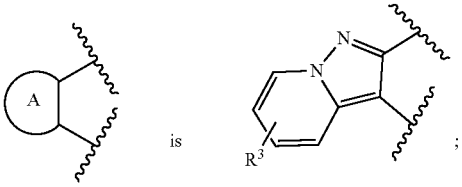

R³ is selected from H, F, $C_{1-2}$ alkyl (optionally substituted with 1-3 F), $C_{1-2}$ alkoxy, phenyl, and pyridyl optionally substitetuted with F; R⁴ is selected fromd

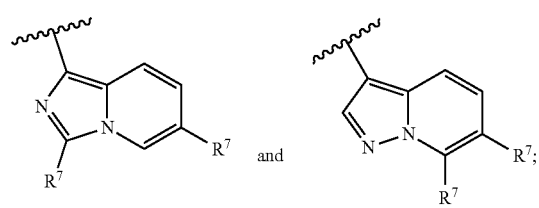

and

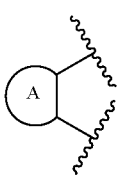

R⁷, at each occurrence, is independently selected from H, $C_{1-7}$ alkyl and $C_{1-7}$ alkoxy, wherein said alkyl and alkoxy, are substituted with 0-4 R⁹; R⁸ is selected from H, phenyl, and pyridyl, wherein said phenyl and pyridyl are substituted with 0-4 R⁹; R⁹, at each occurrence, is independently selected from F, Cl, OH, and $C_{1-4}$ alkyl substituted with 0-4 $R^b$, and $R^b$ is halogen.

In another non-limiting embodiment,

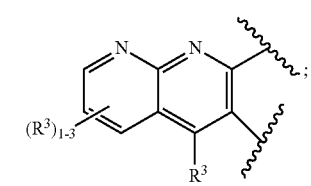

R⁴ is selected from

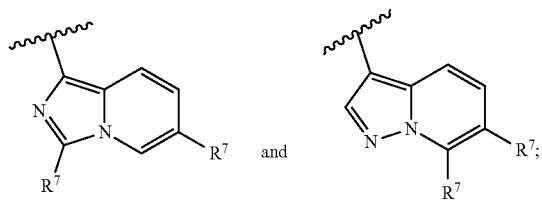 and

R⁷, at each occurrence, is independently selected from H, F, Cl, Br, C₁₋₇ alkyl (optionally substituted with F), C₁₋₇ alkoxy (optionally alkoxy substituted with OH), —NR⁸R⁸, wherein R⁸ and R⁸ are taken together to form

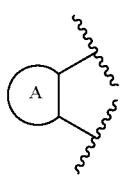.

In another non-limiting embodiment,

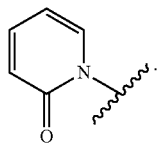 is 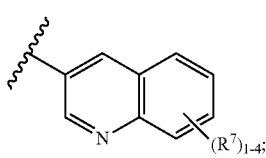 ;

R⁴ is selected from

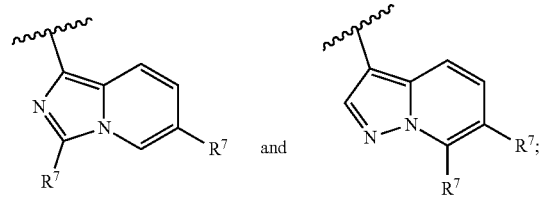 and

R⁷, at each occurrence, is independently selected from H, F, Cl, Br, C₁₋₇ alkyl (optionally substituted with F), C₁₋₇ alkoxy (optionally substituted with OH).

In another non-limiting embodiment,

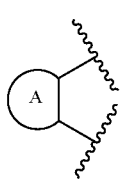 is 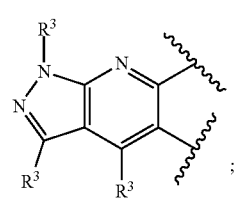 ;

R³ is selected from H and C₁₋₄ alkyl; R⁴ is selected from

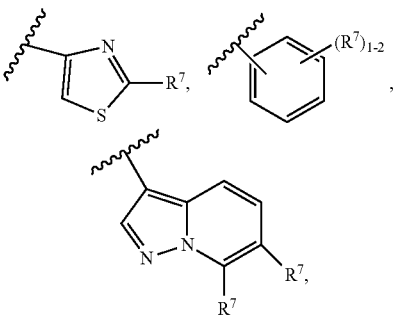

and

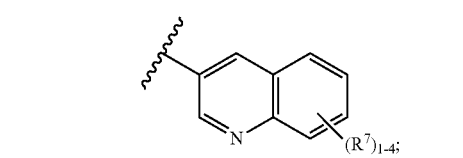

R⁷, at each occurrence, is independently selected from H, CN, C₁₋₇ alkoxy (optionally substituted with OH), and pyridyl.

In another non-limiting embodiment,

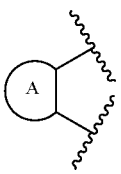 is 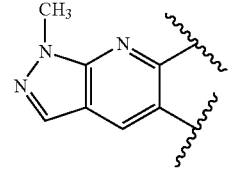 ;

R⁴ is selected from

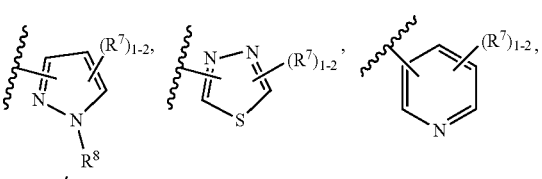

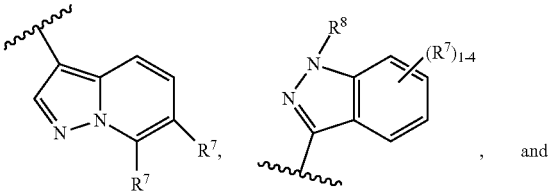, and

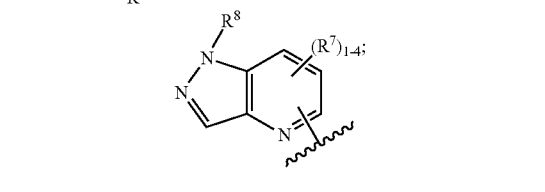

R⁷, at each occurrence, is independently selected from H, CN, C₁₋₄ alkyl, C₁₋₄ alkoxy (optionally substituted with OH), $C_{3-6}$cycloalkyl, phenyl (optionally substituted with F, Cl, $CF_3$, $SO_2C_{1-4}$alkyl), and pyridyl (optionally substituted with $CH_2OH$); $R^8$ is selected from H, $CHF_2$, $CH_2CHF_2$, phenyl (optionally substituted with CN, $SO_2C_{1-2}$alkyl, pyrazole optionally substituted with methyl, ethyl, and $CHF_2$).

In another non-limiting embodiment,

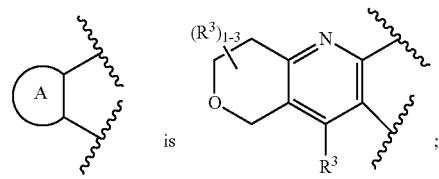

$R^3$ is selected from H and $C_{1-4}$ alkyl; $R^4$ is selected from

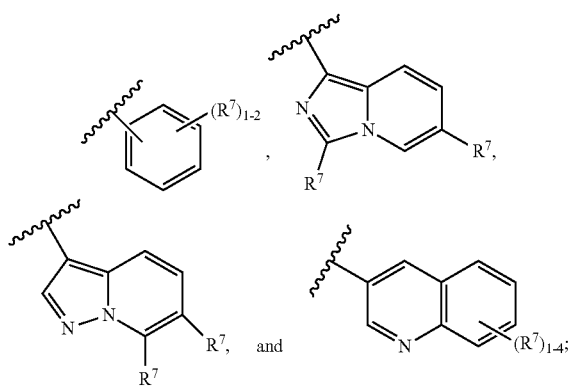

$R^7$, at each occurrence, is independently selected from H, F, Cl, Br, CN, $C_{1-7}$ alkyl (optionally substituted with F and CN), and $C_{1-7}$ alkoxy (optionally substituted with OH).

In another non-limiting embodiment,

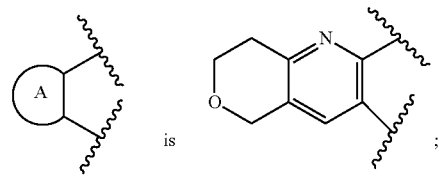

$R^4$ is selected from

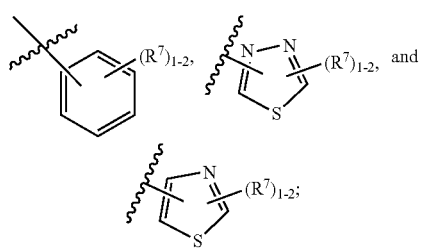

$R^7$, at each occurrence, is independently selected from H, $NHR^8$, $C_{1-3}$ alkyl, and $C_{1-3}$ alkoxy optionally substituted with F; $R^8$ is independently selected from H and $C_{1-3}$ alkyl optionally substituted with F and OH;

In another non-limiting embodiment,

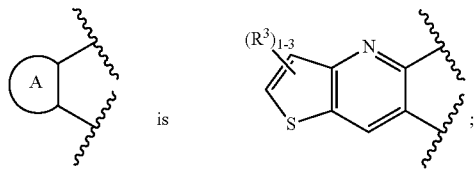

$R^3$ is selected from H and $C_{1-4}$ alkyl; $R^4$ is selected from

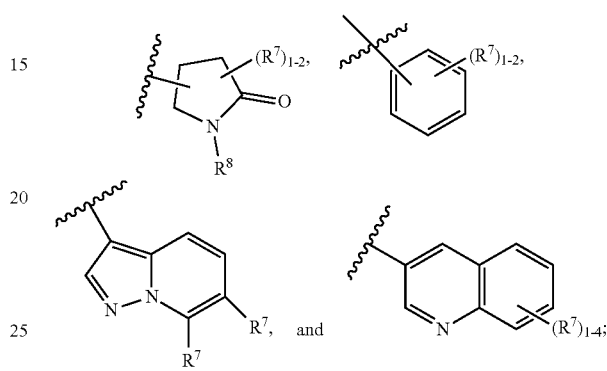

$R^7$, at each occurrence, is independently selected from H, F, Cl, Br, CN, $C_{1-7}$ alkyl (optionally substituted with F), and $C_{1-7}$ alkoxy (optionally substituted with OH); and $R^8$ is —$(CH_2)_{0-1}$-phenyl.

In another non-limiting embodiment

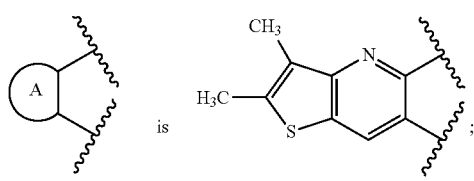

$R^4$ is selected from

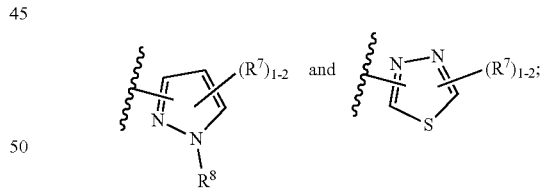

$R^7$ is selected from H, $C_{1-3}$ alkyl, and $NHR^8$; and $R^8$ is selected from H, $C_{1-4}$ alkyl, and phenyl optionaly subsitued with 1-2 F.

In another non-limiting embodiment,

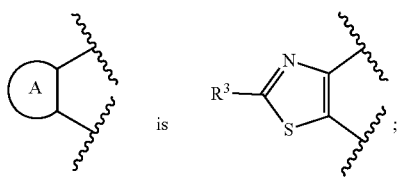

$R^3$ is selected from H, $C_{1-4}$ alkyl, and cyclopropyl

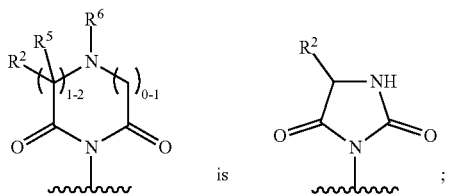
is
;

$R^2$ is selected from —$(CH_2)_{1-2}$—$C_{3-6}$cycloalkyl (optionally substituted with F), —$(CH_2)_{1-2}$-phenyl, —$(CH_2)_{1-2}$-heterocycle (optionally substituted with $C_{1-4}$ alkyl), $C_{1-6}$ alkyl (optionally substituted with F, OH, $C_{1-4}$ alkoxy (optionally substituted with F), $NHCO_2(C_{1-4}$alkyl), $SC_{1-4}$alkyl, $S(O)_2NH_2$, $OCH_2$-phenyl), $C_{2-4}$ alkenyl, and $C_{2-4}$ alkynyl.

In another non-limiting embodiment,

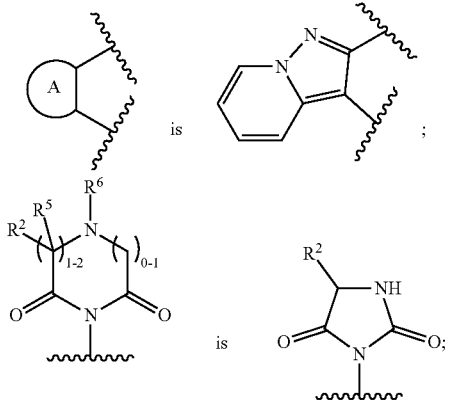
is
;
is
;

$R^2$ is selected from $C_{1-6}$alkyl optionally substituted with 1-3 F.

In another non-limiting embodiment,

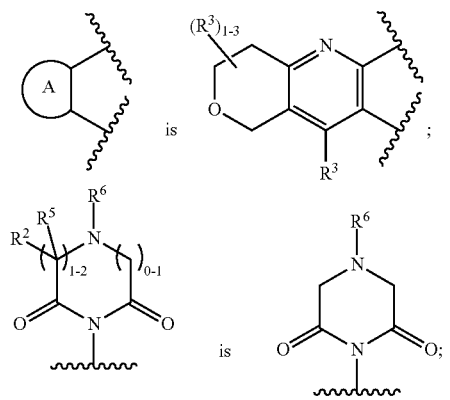
is
;
is
;

$R^2$ is selected from —$(CH_2)_{1-2}$—$C_{3-6}$cycloalkyl (optionally substituted with F), —$(CH_2)_{0-2}$-phenyl, —$(CH_2)_{1-2}$-heterocycle (optionally substituted with $C_{1-4}$ alkyl), $C_{1-4}$ alkyl (optionally substituted with F, OH, $C_{1-4}$ alkoxy (optionally substituted with F), $NHCO_2(C_{1-4}$alkyl), $SC_{1-4}$alkyl, $S(O)_2NH_2$, $OCH_2$-phenyl), $C_{2-4}$alkenyl, and $C_{2-4}$ alkynyl.

In another non-limiting embodiment,

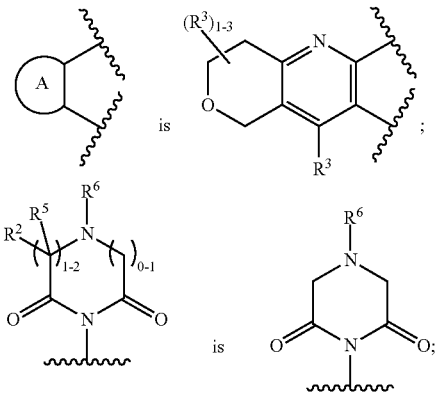
is
;
is
;

$R^6$ is selected from —$(CH_2)_{1-2}$—$C_{3-6}$cycloalkyl and —$(CH_2)_{1-2}$-phenyl.

In another embodiment, the compounds of the present invention have ROCK $IC_{50}$ values ≤10 μM.

In another embodiment, the compounds of the present invention have ROCK $IC_{50}$ values ≤1 μM.

In another embodiment, the compounds of the present invention have ROCK $IC_{50}$ values ≤0.1 μM.

In another embodiment, the compounds of the present invention have ROCK $IC_{50}$ values ≤0.05 μM.

In another embodiment, the compounds of the present invention have ROCK $IC_{50}$ values ≤0.01 μM.

II. Other Embodiments of the Invention

In another embodiment, the present invention provides a composition comprising at least one of the compounds of the present invention or a stereoisomer, a tautomer, a pharmaceutically-acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically-acceptable salt, or a solvate, thereof.

In another embodiment, the present invention provides a pharmaceutical composition, comprising: a pharmaceutically acceptable carrier and a therapeutically effective amount of at least one of the compounds of the present invention or a stereoisomer, a tautomer, a pharmaceutically-acceptable salt, or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition further comprising additional therapeutic agent(s).

In another embodiment, the present invention provides a method for the treatment and/or prophylaxis of a condition associated with aberrant ROCK activity comprising administering to a patient in need of such treatment and/or prophylaxis a therapeutically effective amount of at least one of the compounds of the present invention or a stereoisomer, a tautomer, a pharmaceutically-acceptable salt, or a solvate thereof. As used herein, the term "patient" encompasses all mammalian species.

In another embodiment, the present invention provides compounds according to the present invention for use as a medicament.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" is the protective treatment of a disease state to reduce and/or minimize the risk and/or reduction in the risk of recurrence of a disease state by administering to a patient a therapeutically effective amount of at least one of the compounds of the present invention or a or a stereoisomer, a tautomer, a pharmaceutically-acceptable salt, or a solvate thereof. Patients may be selected for prophylaxis therapy based on factors that are known to increase risk of suffering a clinical disease state compared to the general population. For prophylaxis treatment, conditions of the clinical disease state may or may not be presented yet. "Prophylaxis" treatment can be divided into (a) primary prophylaxis and (b) secondary prophylaxis. Primary prophylaxis is defined as treatment to reduce or minimize the risk of a disease state in a patient that has not yet presented with a clinical disease state, whereas secondary prophylaxis is defined as minimizing or reducing the risk of a recurrence or second occurrence of the same or similar clinical disease state.

As used herein, "prevention" cover the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population.

In another embodiment, the present invention provides a combined preparation of a compound of the present invention and additional therapeutic agent(s) for simultaneous, separate or sequential use in therapy.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms.

The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The term "stereoisomer" refers to isomers of identical constitution that differ in the arrangement of their atoms in space. Enantiomers and diastereomers are examples of stereoisomers. The term "enantiomer" refers to one of a pair of molecular species that are mirror images of each other and are not superimposable. The term "diastereomer" refers to stereoisomers that are not mirror images. The term "racemate" or "racemic mixture" refers to a composition composed of equimolar quantities of two enantiomeric species, wherein the composition is devoid of optical activity.

The symbols "R" and "S" represent the configuration of substituents around a chiral carbon atom(s). The symbols "aR" and "aS" represent the configuration of substituents around a molecule that contains an axis of chirality. The isomeric descriptors "R", "S", "aR" and "aS" are used as described herein for indicating atom configuration(s) relative to a core molecule and are intended to be used as defined in the literature (IUPAC Recommendations 1996, *Pure and Applied Chemistry*, 68:2193-2222 (1996)).

The term "chiral" refers to the structural characteristic of a molecule that makes it impossible to superimpose it on its mirror image. The term "homochiral" refers to a state of enantiomeric purity. The term "optical activity" refers to the degree to which a homochiral molecule or nonracemic mixture of chiral molecules rotates a plane of polarized light.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_1$-$C_6$ alkyl" denotes alkyl having 1 to 6 carbon atoms.

Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and iso-propoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro (F), chloro (Cl), bromo (Br), and iodo (I). "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups, including mono-, bi- or poly-cyclic ring systems. "$C_3$ to $C_7$ cycloalkyl" or "3-7 cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle" or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic hydrocarbon ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclootane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

As used herein, the term "bicyclic spiro carbocycle" refers to 5- to 20-membered polycyclic hydrocarbon group with rings connected through one common carbon atom (called as spiro atom), wherein one or more rings may contain one or more double bonds, but none of the rings has a completely conjugated pi-electron system. Preferably a bicyclic spiro carbocycle is 6 to 14 membered, more preferably is 7 to 10 membered. Bicyclic spiro carbocycle may be 4-membered/4-membered, 4-membered/5-membered, 4-membered/6-membered, 5-membered/5-membered, or 5-membered/6-membered spiro ring.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., *Hawley's Condensed Chemical Dictionary*, 13th Edition, John Wiley & Sons, Inc., New York (1997). "$C_6$ or $C_{10}$ aryl" or "$C_{6-10}$aryl" refers to phenyl and naphthyl. Unless otherwise specified, "aryl", "$C_6$ or $C_{10}$ aryl" or "$C_{6-10}$ aryl" or "aromatic residue" may be unsubstituted or substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

The term "benzyl", as used herein, refers to a methyl group on which one of the hydrogen atoms is replaced by a phenyl group, wherein said phenyl group may optionally be substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2$, and $CO_2CH_3$.

As used herein, the term "heterocycle" or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and S(O)$_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted.

The nitrogen atom is substituted or unsubstituted (i.e., N or NR wherein R is H or another substituent, if defined). The nitrogen and sulfur heteroatoms may optionally be oxidized (i.e., N→O and S(O)$_p$, wherein p is 0, 1 or 2).

Bridged rings are also included in the definition of heterocycle. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring.

When a ring is bridged, the substituents recited for the ring may also be present on the bridge.

The term "counterion" is used to represent a negatively charged species such as chloride, bromide, hydroxide, acetate, and sulfate.

When a dotted ring is used within a ring structure, this indicates that the ring structure may be saturated, partially saturated or unsaturated.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically-acceptable salts" refer to derivatives of the disclosed compounds wherein the parent compound is modified by making acid or base salts thereof. Examples of pharmaceutically-acceptable salts include, but are not limited to, mineral or organic acid salts of basic groups such as amines; and alkali or organic salts of acidic groups such as carboxylic acids. The pharmaceutically-acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically-acceptable salts of the present invention can be synthesized from the parent compound that contains a basic or acidic moiety by conventional chemical methods. Generally, such salts can be prepared by reacting the fre acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, Pa. (1990), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology,* 112:309-396, Academic Press (1985);

b) Bundgaard, H., Chapter 5, "Design and Application of Prodrugs", *A Textbook of Drug Design and Development,* pp. 113-191, Krosgaard-Larsen, P. et al., eds., Harwood Academic Publishers (1991);

c) Bundgaard, H., *Adv. Drug Deliv. Rev.,* 8:1-38 (1992);

d) Bundgaard, H. et al., *J. Pharm. Sci.,* 77:285 (1988); and e) Kakeya, N. et al., *Chem. Pharm. Bull.,* 32:692 (1984).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice,* The Royal Society of Chemistry, Cambridge, UK (1994); Testa, B. et al., *Hydrolysis in Drug and Prodrug Metabolism, Chemistry, Biochemistry and Enzymology,* VCHA and Wiley-VCH, Zurich, Switzerland (2003); Wermuth, C. G., ed., *The Practice of Medicinal Chemistry,* Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Deuterium has one proton and one neutron in its nucleus and that has twice the mass of ordinary hydrogen. Deuterium can be represented by symbols such as "$^2$H" or "D". The term "deuterated" herein, by itself or used to modify a compound or group, refers to replacement of one or more hydrogen atom(s), which is attached to carbon(s), with a deuterium atom. Isotopes of carbon include $^{13}$C and $^{14}$C.

Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain an N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "saturated" for saturated, "MW" for molecular weight, "nip" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "S" for delta, "s" for singlet, "d" for doublet, "t" for triplet, "q" for quartet, "m" for multiplet, "br" for broad, "Hz" for hertz, and "a", "p", "R", "S", "E", and "Z" are stereochemical designations familiar to one skilled in the art.

Me Methyl
Et Ethyl
Pr Propyl
i-Pr Isopropyl
Bu Butyl
i-Bu Isobutyl
t-Bu tert-butyl
Ph Phenyl
Bn Benzyl
Boc tert-butyloxycarbonyl
AcOH or HOAc acetic acid
$AlCl_3$ aluminum chloride
AIBN Azobisisobutyronitrile
$BBr_3$ boron tribromide
$BCl_3$ boron trichloride
BEMP 2-tert-butylimino-2-diethylamino-1,3-dimethylperhydro-1,3,2-diazaphosphorine
BOP reagent benzotriazol-1-yloxytris(dimethylamino)phosphonium hexafluorophosphate
Burgess reagent 1-methoxy-N-triethylammoniosulfonyl-methanimidate
CBz Carbobenzyloxy
$CH_2Cl$ Dichloromethane
$CH_3CN$ or ACN Acetonitrile
$CDCl_3$ deutero-chloroform
$CHCl_3$ Chloroform
mCPBA or m-CPBA meta-chloroperbenzoic acid
$Cs_2CO_3$ cesium carbonate
$Cu(OAc)_2$ copper (II) acetate
$Cy_2NMe$ N-cyclohexyl-N-methylcyclohexanamine
DBU 1,8-diazabicyclo[5.4.0]undec-7-ene
DCE 1,2 dichloroethane
DCM Dichloromethane
DEA Diethylamine
DEAD diethyl azodicarboxylate
Dess-Martin 1,1,1-tris(acetyloxy)-1,1-dihydro-1,2-beniziodoxol-3-(1H)-one
DIAD diisopropyl azodicarboxylate
DIC or DIPCDI Diisopropylcarbodiimide
DIEA, DIPEA or Diisopropylethylamine Hunig's base
DMAP 4-dimethylaminopyridine
DME 1,2-dimethoxyethane
DMF dimethyl formamide
DMSO dimethyl sulfoxide
cDNA complimentary DNA
Dppp (R)-(+)-1,2-bis(diphenylphosphino)propane
DuPhos (+)-1,2-bis((2S,5S)-2,5-diethylphospholano)benzene
EDC N-(3-dimthylaminopropyl)-N'-ethylcarbodiimide
EDCI N-(3-dimthylaminopropyl)-N'-ethylcarbodiimide hydrochloride
EDTA ethylenediaminetetraacetic acid
(S,S)-EtDuPhosRh(I) (+)-1,2-bis((2S,5S)-2,5-diethylphospholano)benzene(1,5-cyclooctadiene)rhodium(I) trifluoromethanesulfonate
$Et_3N$ or TEA triethylamine
EtOAc ethyl acetate
$Et_2O$ diethyl ether
EtOH Ethanol
GMF glass microfiber filter
Grubbs (II) (1,3-bis(2,4,6-trimethylphenyl)-2-imidazolidinylidene)dichloro (phenylmethylene)(triycyclohexylphosphine)ruthenium
HCl hydrochloric acid
HATU O-(7-azabenzotriazol-1-yl)-N,N,N',N'-tetramethyluronium hexafluorophosphate
HEPES 4-(2-hydroxyethyl)piperaxine-1-ethanesulfonic acid
Hex Hexane
HOBt or HOBT 1-hydroxybenzotriazole
$H_2SO_4$ sulfuric acid
$K_2CO_3$ potassium carbonate
KOAc potassium acetate
$K_3PO_4$ potassium phosphate
LAH lithium aluminum hydride
LG leaving group
LiOH lithium hydroxide
MeOH Methanol
$MgSO_4$ magnesium sulfate
MsOH or MSA methylsulfonic acid NaCl sodium chloride
NaH sodium hydride
NaHCO3 sodium bicarbonate
Na$_2$CO$_3$ sodium carbonate
NaOH sodium hydroxide
Na$_2$SO$_3$ sodium sulfite
Na$_2$SO$_4$ sodium sulfate
NBS N-bromosuccinimide
NCS N-chlorosuccinimide
NH$_3$ Ammonia
NH$_4$Cl ammonium chloride
NH$_4$OH ammonium hydroxide
OTf triflate or trifluoromethanesulfonate
Pd$_2$(dba)$_3$ tris(dibenzylideneacetone)dipalladium(O)
Pd(OAc)$_2$ palladium(II) acetate
Pd/C palladium on carbon
Pd(dppf)Cl$_2$ [1,1'-bis(diphenylphosphino)-ferrocene]dichloropalladium(II)
Ph$_3$PCl$_2$ triphenylphosphine dichloride
PG protecting group
POCl$_3$ phosphorus oxychloride
i-PrOH or IPA Isopropanol
PS Polystyrene
SEM-Cl 2-(trimethysilyl)ethoxymethyl chloride
SiO$_2$ silica oxide
SnCh tin(II) chloride
TBAI tetra-n-butylammonium iodide
TMA trimethylamine
TFA trifluoroacetic acid
THE Tetrahydrofuran
TMSCHN2 trimethylsilyldiazomethane
T3P® propane phosphonic acid anhydride
TRIS tris (hydroxymethyl) aminomethane The compounds of the present invention can be prepared in a number of ways known to one skilled in the art of organic synthesis.

IV. Biology

In Vitro Assays

The effectiveness of compounds of the present invention as ROCK inhibitors can be determined in a 30 μL assay containing 20 mM HEPES, pH 7.5, 20 mM MgCl$_2$, 0.015% Brij-35.4 mM DTT, 5 μM ATP and 1.5 μM peptide substrate (FITC-AHA-AKRRRLSSLRA-OH) (SEQ ID NO. 1). Compounds were dissolved in DMSO so that the final concentration of DMSO was <2%, and the reaction was initiated with Rho kinase variants. After incubation, the reaction was terminated by the addition of EDTA and the phosphorylated and non-phosphorylated peptides separated using a LABCHIP®3000 Reader (Caliper Life Sciences). Controls consisted of assays that did not contain compound, and backgrounds consisted of assays that contained enzyme and substrate but had EDTA from the beginning of the reaction to inhibit kinase activity. Compounds were tested in dose-response format, and the inhibition of kinase activity was calculated at each concentration of compound. The inhibition data were fit using a curve-fitting program to determine the IC$_{50}$; i.e., the concentration of compound required to inhibit 50% of kinase activity.

Representative Examples were tested in the ROCK2 assay described above and found having ROCK2 inhibitory activity. Their ROCK2 inhibitory activity (IC$_{50}$ values) of ≤3 μM (3000 nM) was observed and shown in Table A below.

TABLE A

| Example No. | ROCK2 Activity IC$_{50}$ |
|---|---|
| 1 | 42.7 |
| 2 | 20.0 |
| 3 | 68.8 |
| 4 | 20.1 |
| 5 | 52.6 |
| 6 | 25.6 |
| 7 | 4.8 |
| 8 | 5.4 |
| 9 | 349.0 |
| 10 | 27.4 |
| 11 | 23.3 |
| 12 | 40.1 |
| 13 | 575.8 |
| 14 | 14.1 |
| 15 | 12.5 |
| 16 | 136.7 |
| 17 | 18.5 |
| 18 | 13.4 |
| 19 | 10.5 |
| 20 | 6.8 |
| 21 | 18.9 |
| 22 | 7.0 |
| 23 | 77.7 |
| 24 | 1,479.4 |
| 25 | 6.4 |
| 26 | 25.4 |
| 27 | 13.8 |
| 28 | 551.1 |
| 29 | 254.0 |
| 30 | 7.7 |
| 31 | 73.3 |
| 32 | 29.9 |
| 33 | 347.4 |
| 34 | 17.2 |
| 35 | 202.0 |
| 36 | 22.4 |
| 37 | 259.3 |
| 38 | 426.1 |
| 39 | 2,404.7 |
| 40 | 136.5 |
| 41 | 55.6 |
| 42 | 13.7 |
| 43 | 119.0 |
| 44 | 25.2 |
| 45 | 25.0 |
| 46 | 359.4 |
| 47 | 113.1 |
| 48 | 685.3 |
| 49 | 449.9 |
| 50 | 322.2 |
| 51 | 44.8 |
| 52 | 33.9 |
| 53 | 22.0 |
| 54 | 253.0 |
| 55 | 78.3 |
| 56 | 53.2 |
| 57 | 15.9 |
| 58 | 203.8 |
| 59 | 5.3 |
| 60 | 35.5 |
| 61 | 55.5 |
| 62 | 11.6 |
| 63 | 6.1 |
| 64 | 11.4 |
| 65 | 141.4 |
| 66 | 225.2 |
| 67 | 142.0 |
| 68 | 108.0 |
| 69 | 4.5 |
| 70 | 45.4 |
| 71 | 8.7 |
| 73 | 1,157.8 |
| 75 | 26.7 |
| 76 | 6.8 |
| 77 | 633.9 |
| 78 | 3,100.9 |
| 79 | 22.2 |

TABLE A-continued

| Example No. | ROCK2 Activity IC$_{50}$ |
|---|---|
| 80 | 2,340.0 |
| 81 | 323.2 |
| 82 | 20 |
| 83 | 9.7 |
| 84 | 2.2 |
| 85 | 144.3 |
| 86 | 85.9 |
| 87 | 156.2 |
| 88 | 35.0 |
| 89 | 716.4 |
| 90 | 114.3 |
| 91 | 330.5 |
| 92 | 190.7 |
| 93 | 1,457.1 |
| 94 | 39 |
| 95 | 79.0 |
| 96 | 125.6 |
| 97 | 12 |
| 98 | 25.7 |
| 99 | 67.1 |
| 100 | 36.6 |
| 101 | 6 |
| 102 | 8 |
| 103 | 5 |
| 104 | 2,041.4 |
| 105 | 132.5 |
| 106 | 587.2 |
| 107 | 1,832.9 |
| 108 | 1,869.4 |
| 109 | 329.9 |
| 110 | 12.2 |
| 111 | 105.9 |
| 112 | 205.1 |
| 113 | 53.1 |
| 114 | 115.0 |
| 115 | 31.2 |
| 116 | 71.6 |
| 117 | 58.7 |
| 118 | 639.0 |
| 119 | 351.4 |
| 120 | 804.7 |
| 121 | 18.3 |
| 122 | 116.8 |
| 123 | 241.3 |
| 124 | 90.4 |
| 125 | 316.3 |
| 126 | 46.4 |
| 127 | 112.8 |
| 128 | 83.2 |
| 129 | 702.3 |
| 130 | 611.1 |
| 131 | 1171.0 |
| 132 | 222.6 |
| 133 | 20.2 |
| 134 | 143.1 |
| 135 | 390.3 |
| 136 | 112.4 |
| 137 | 150.2 |
| 138 | 22.0 |
| 139 | 207.7 |
| 140 | 62.1 |
| 141 | 203.5 |
| 142 | 60.3 |
| 143 | 108.7 |
| 144 | 366.6 |
| 145 | 111.0 |
| 146 | 5.2 |
| 147 | 2.9 |
| 148 | 52.7 |
| 149 | 14.5 |
| 150 | 7.1 |
| 151 | 13.6 |
| 152 | 6.3 |
| 153 | 0.8 |
| 154 | 2.3 |
| 155 | 2.7 |
| 156 | 4.3 |
| 157 | 10.9 |
| 158 | 4.6 |
| 159 | 1.1 |
| 160 | 1.6 |
| 161 | 223.4 |
| 162 | 162.0 |

V. Pharmaceutical Compositions, Formulations and Combinations

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the patient to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmacetical Sciences*, 18th Edition (1990).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the disorder.

By way of general guidance, the daily oral dosage of each active ingredient, when used for the indicated effects, will range between about 0.001 to about 1000 mg/kg of body weight, preferably between about 0.01 to about 100 mg/kg of body weight per day, and most preferably between about 0.1 to about 20 mg/kg/day. Intravenously, the most preferred doses will range from about 0.001 to about 10 mg/kg/minute during a constant rate infusion. Compounds of this invention may be administered in a single daily dose, or the total daily dosage may be administered in divided doses of two, three, or four times daily.

Compounds of this invention can also be administered by parenteral administration (e.g., intra-venous, intra-arterial, intramuscularly, or subcutaneously. When administered intra-venous or intra-arterial, the dose can be given continuously or intermittent. Furthermore, formulation can be developed for intramuscularly and subcutaneous delivery that ensure a gradual release of the active pharmaceutical ingredient.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 1000 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the inhibition of ROCK. Such compounds may be provided in a commercial kit, for example, for use in pharmaceutical research involving ROCK. For example, a compound of the present invention could be used as a reference in an assay to compare its known activity to a compound with an unknown activity. This would ensure the experimentor that the assay was being performed properly and provide a basis for comparison, especially if the test compound was a derivative of the reference compound. When developing new assays or protocols, compounds according to the present invention could be used to test their effectiveness.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically-acceptable salt form thereof; and, (c) a package insert stating that the pharmaceutical composition can be used for the treatment of a cardiovascular and/or inflammatory disorder (as defined previously). In another embodiment, the package insert states that the pharmaceutical composition can be used in combination (as defined previously) with a second therapeutic agent to treat cardiovascular and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof. The following Examples have been prepared, isolated and characterized using the methods disclosed herein.

VI. General Synthesis Including Schemes

The compounds of the present invention may be synthesized by methods available to those skilled in the art of organic chemistry (Maffrand, J. P. et al., *Heterocycles*, 16(1):35-37 (1981)). General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds.

Examples of compounds of the present invention prepared by methods described in the general schemes are given in the intermediates and examples section set out hereinafter. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diastereoselectivity of transformations, providing enantio-enriched products upon cleavage of the chiral auxiliary.

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al., (*Protective Groups in Organic ynthesis*, 4th Edition, Wiley-Interscience (2006)).

Scheme 1

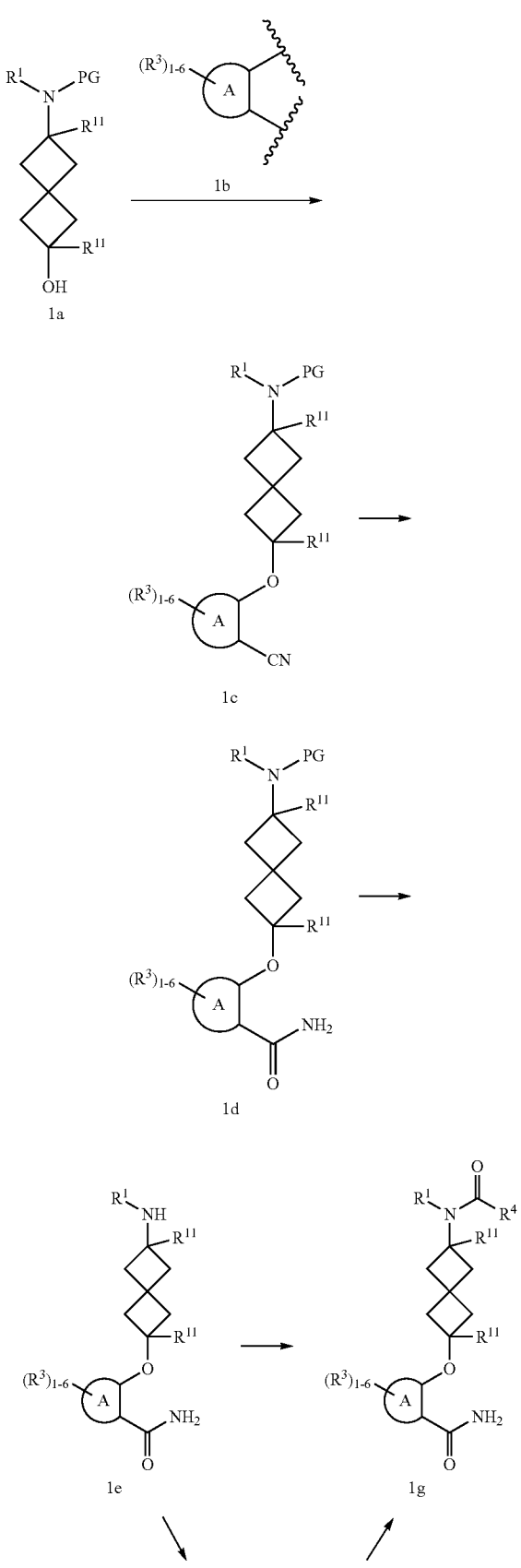

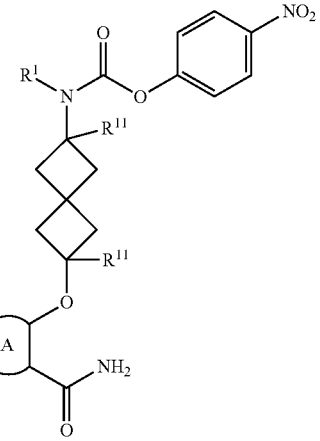

Scheme 1 shows the synthesis of compound 1g from spiroheptane alcohol 1a and heteroaryl nitrile 1b. Spiroheptane alcohol 1a and heteroaryl nitrile 1b are either commercially available or can be prepared by known methods. Treatment of alcohol 1a with a base such as NaH, followed by addition to heteroaryl nitrile 1b, where X is a leaving group such as F, Cl, Br or mesylate. Alternatively, coupling between 1a and 1b (when X=OH) can be accomplished via a Mitsunobu reaction, using reagents such as triphenylphosphine and DIAD. When $R_6$=H, reaction with an electrophilic reagent in the presence of base affords product 1c, where $R_6$ is an alkyl or substituted alkyl group. $R_6$ may be further derivatized after installation into 1c or in subsequent compounds. Nitrile intermediate 1e can be converted to the primary amide 1d via treatment with $K_2CO_3$/MgO and $H_2O_2$. Removal of a protecting group (PG) on 1d, via appropriate means based upon the particular protecting group, affords amine 1e. When $R_6$=H, reductive amination with an appropriate ketone or aldehyde using a reagent such as $NaBH_3CN$ or $Na(OAc)_3BH$ affords product 1e, where $R_6$ is an alkyl or substituted alkyl group. $R_6$ may be further derivatized after installation into 1e or in subsequent compounds. Amine 1e is converted directly to 1g (amide, carbamate, or urea) by treatment with appropriate reagents. Amides can be formed via coupling of carboxylic acids, using a coupling reagent such as BOP, T3P or HATU, or via reaction with an acid chloride. Carbamates can be prepared via reaction with a chloroformate reagent and a base such as TEA or DIEA. Ureas may be formed via treatment with an isocyanate. Alternatively, reaction of amine 1e with 4-nitrophenyl chloroformate affords carbamate 1f. Treatment of 1f with an alcohol in the presence of base affords the carbamate product 1g. Treatment of 1f with an amine in the presence of base affords the urea product 1g.

Scheme 2

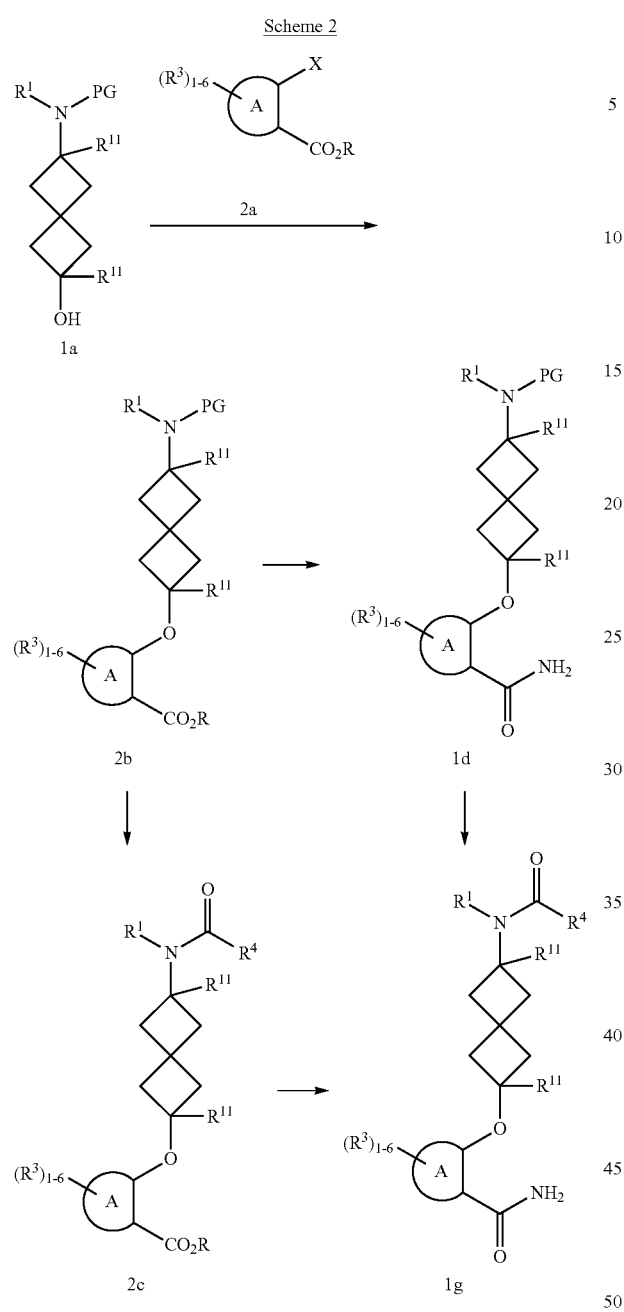

amine, which is converted to 2c (amide, carbamate, or urea) by treatment with appropriate reagents, as in Scheme 1. Ester 2c can be converted to amide 1g as described above for the conversion of 2b to 1d.

Scheme 3

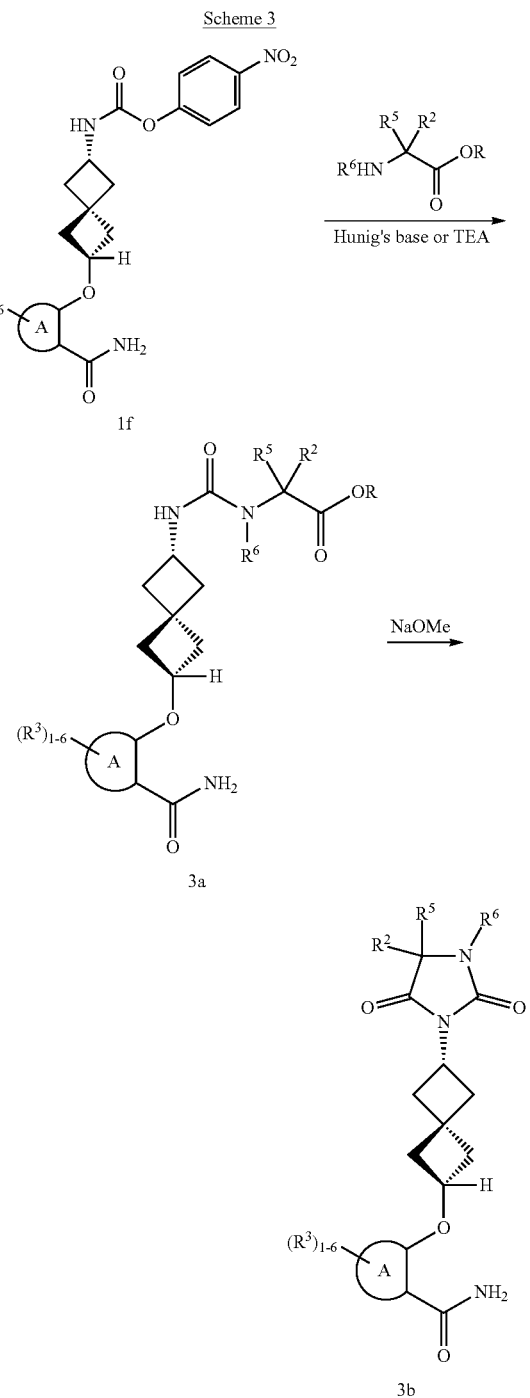

Scheme 2 shows the synthesis of compound 1g from spiroheptane alcohol 1a and heteroaryl ester 2a. Spiroheptane alcohol 1a and heteroaryl ester 2a are either commercially available or can be prepared by known methods. Treatment of alcohol 1a with a base such as NaH, followed by addition to heteroaryl ester 2a, where X is a leaving group such as F, Cl, Br or mesylate. Alternatively, coupling between 1a and 2a (when X=OH) can be accomplished via a Mitsunobu reaction, using reagents such as triphenylphosphine and DIAD, Ester 2b can then be converted to amide 1d, either directly by treatment with ammonia, or stepwise via saponification with LiOH and subsequent amide formation with ammonia and a coupling reagent such as BOP. 1d is converted to 1g, as shown in Scheme 1. Alternatively, Removal of a protecting group (PG) on 1d, via appropriate means based upon the particular protecting group, affords an Scheme 1 shows the synthesis of hydantoin 3b from carbamate if. Carbamate if can be treated with amino acid esters (where R=Me, Et and $R_3$=H, alkyl, aryl; either commercially available or prepared by known methods) to afford urea 3a. Urea 3a can then be cyclized to hydantoin 3b by treatment with NaOMe.

Purification of intermediates and final products was carried out via either normal or reverse phase chromatography. Normal phase chromatography was carried out using pre-packed SiO$_2$ cartridges eluting with either gradients of hexanes and EtOAc, DCM and MeOH unless otherwise indicated. Reverse phase preparative HPLC was carried out using C18 columns eluting with gradients of Solvent A (90% water, 10% MeOH, 0.1% TFA) and Solvent B (10% water, 90% MeOH, 0.1% TFA, UV 220 nm) or with gradients of Solvent A (90% water, 10% CH$_3$CN, 0.1% TFA) and Solvent B (10% water, 90% CH$_3$CN, 0.1% TFA, UV 220 nm) or with gradients of Solvent A (98% water, 2% CH$_3$CN, 0.05% TFA) and Solvent B (98% CH$_3$CN, 2% water, 0.05% TFA, UV 220 nm)(or) Sunfire Prep C18 OBD 5 u 30×100 mm, 25 min gradient from 0-100% B. A=H$_2$O/CH$_3$CN/TFA 90:10:0.1. B=CH$_3$CN/H$_2$O/TFA 90:10:0.1

Unless otherwise stated, analysis of final products was carried out by reverse phase analytical HPLC.

Method A: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

Method B: Waters Acquity UPLC BEH C18, 2.1×50 mm, 1.7-μm particles; Mobile Phase A: 5:95 acetonitrile: water with 0.1% TFA; Mobile Phase B: 95:5 acetonitrile:water with 0.1% TFA; Temperature: 50° C.; Gradient: 0-100% B over 3 minutes, then a 0.75-minute hold at 100% B; Flow: 1.11 m/min.

Method C: SunFire C18 column (3.5 μm, 3.0×150 mm). Gradient elution (1.0 mL/min) from 10-100% Solvent B over 10 min and then 100% Solvent B for 5 min. Solvent A is (95% water, 5% acetonitrile, 0.05% TFA) and Solvent B is (5% water, 95% acetonitrile, 0.05% TFA, UV 220 nm).

Method D: XBridge Phenyl column (3.5 μm, 3.0×150 mm). Gradient elution (1.0 mL/min) from 10-100% Solvent B over 10 min and then 100% Solvent B for 5 min. Solvent A is (95% water, 5% acetonitrile, 0.05% TFA) and Solvent B is (5% water, 95% acetonitrile, 0.05% TFA, UV 220 nm).

Method E. Phenomenex Luna C18 (2 μm 2.0×30 mm). Gradient elution (1.0 mL/min) from 0-100% Solvent B over 2 min and then 100% Solvent B for 1 min. Solvent A is (90% water, 10% MeOH, 0.1% TFA) and Solvent B is (10% water, 90% MeOH, 0.1% TFA, UV 220 mu).

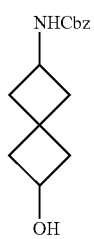

Intermediate 1A. Preparation of Benzyl (6-oxospiro[3.3]heptan-2-yl)carbamate.

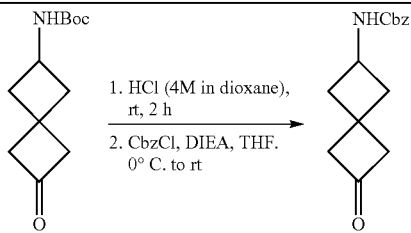

Commercially available tert-butyl (6-oxospiro[3.3]heptan-2-yl)carbamate (0.150 g, 0.666 mmol) was dissolved in HCl (4 M in dioxane) (5.0 mL, 20 mmol). After stirring for 2 h, the reaction mixture was concentrated under reduced pressure, and co-evaporated with Et$_2$O (4×10 mL), and further dried under high vacuum. The deprotected aminospiroketone, HCl salt was suspended in anhydrous THF (5 mL) and cooled to 0° C. Cbz-Cl (0.105 mL, 0.732 mmol) was then added dropwise, followed by immediate addition of DIEA (0.291 mL, 1.66 mmol). The reaction mixture was stirred at 0° C. for 30 min, then ice bath was removed, and the reaction mixture was stirred at rt. After 1 h, the reaction mixture was quenched by the addition of MeOH (0.5 mL), concentrated under reduced pressure and the residue was purified normal phase chromatography to give benzyl (6-oxospiro[3.3]heptan-2-yl)carbamate (0.15 g, 89% yield) as a colorless syrup. MS (ESI) m/z: 260.1 (M+H)$^+$. $^1$H NMR (500 MHz, CDCl$_3$) δ ppm 7.36 (s, 5H), 5.10 (s, 2H), 4.95 (br s, 1H), 4.31-4.15 (m, 1H), 3.14 (br d, J=2.9 Hz, 2H), 3.09-3.04 (m, 2H), 2.71-2.50 (m, 2H), 2.27-2.13 (m, 2H).

Intermediate 1.

Intermediate 1.

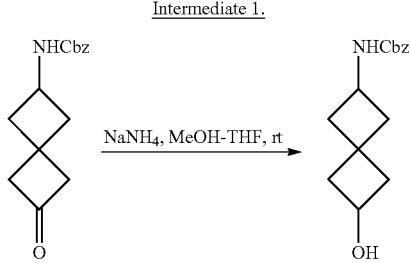 [SMILES: O=C1CC2(C1)CC(NC(=O)OCc1ccccc1)C2 ; O=C(NC1CC2(CC(O)C2)C1)OCc1ccccc1]

Benzyl (6-oxospiro[3.3]heptan-2-yl)carbamate (0.153 g, 0.590 mmol) was dissolved in anhydrous THF (3 mL)/MeOH (3 mL) and cooled to 0° C. NaBH$_4$ (0.033 g, 0.89 mmol) was added in one portion and stirred at 0° C. for 30 min before allowing the reaction mixture to warm to rt. After an additional 30 min, the reaction mixture was quenched by the addition of saturated NH$_4$Cl (1 mL). The organic solvents were removed by concentrating under reduced pressure. The resulting residue was dissolved in EtOAc (50 mL) and treated with saturated NH$_4$Cl (25 mL). After 5 min, the organic phase was separated, washed with brine (25 mL), dried over Na$_2$SO$_4$, filtered, and concentrated under reduced pressure to afford benzyl (6-hydroxyspiro[3.3]heptan-2-yl) carbamate (0.154 g, 0.589 mmol, 100% yield) as a white solid. The material was used in the next step without further purification. MS (ESI) m/z: 262.1 (M+H)$^+$. $^1$H NMR (500

MHz, CDCl₃) δ ppm 7.27 (s, 5H), 5.10-4.95 (m, 2H), 4.08-3.95 (m, 1H), 3.74 (br s, 3H), 2.47-2.13 (m, 4H), 1.94-1.70 (m, 4H).

Intermediate 2. Preparation of benzyl ((aR)-6-hydroxyspiro[3.3]heptan-2-ylcarbamate Intermediate 3. Preparation of benzyl((aS)-6-hydroxyspiro[3.3]heptan-2-yl)carbamate.

Intermediate 3. Preparation of benzyl ((aS)-6-hydroxyspiro[3.3]heptan-2-yl)carbamate.

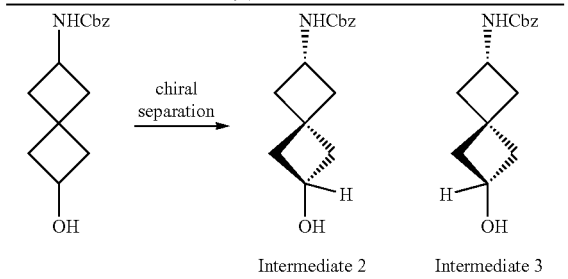

Intermediate 2       Intermediate 3

Intermediate 1 (100 mg, 0.383 mmol) was subjected to chiral prep HPLC (Instrument: PIC Solution Prep SFC; column: Chiralpak IF, 30×250 mm, 5 micron; Mobile Phase: 15% MeOH+0.1% DEA/85% CO₂; Flow Conditions: 85 mL/min, 150 Bar, 40° C.; Detector Wavelength: 220 nm) to afford Intermediate 2 (48 mg, 48% yield), followed by Intermediate 3 (47 mg, 47% yield), both as off-white solids.

Intermediate 2: MS (ESI) m/z: 262.0 (M+H)⁺. ¹H NMR (500 MHz, CDCl₃) δ ppm 7.35 (s, 5H), 5.08 (br s, 2H), 4.82 (br s, 1H), 4.20 (quin, J=7.2 Hz, 1H), 4.10 (br d, J=7.4 Hz, 1H), 2.47 (br d, J=4.4 Hz, 1H), 2.44-2.33 (m, 2H), 2.31-2.24 (m, 1H), 1.99-1.80 (m, 4H).

Intermediate 3: MS (ESI) m/z: 262.0 (M+H)⁺. ¹H NMR (500 MHz, CDCl₃) δ ppm 7.35 (s, 5H), 5.08 (br s, 2H), 4.81 (br s, 1H), 4.20 (quin, J=7.1 Hz, 1H), 4.10 (br d, J=8.0 Hz, 1H), 2.53-2.44 (m, 1H), 2.43-2.32 (m, 2H), 2.29 (dt, J=11.6, 6.1 Hz, 1H), 1.99-1.79 (m, 4H)

Intermediate 4. Preparation of 6-(2-Hydroxy-2-methylpropoxy)pyrazolo-[1,5-a]pyridine-3-carboxylic acid.

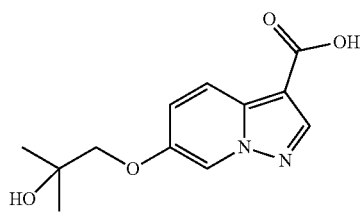 [SMILES: CC(C)(O)COc1ccc2c(C(=O)O)cnn2c1]

Ethyl 6-hydroxypyrazolo[1,5-a]pyridine-3-carboxylate (0.250 g, 1.21 mmol) was suspended in MeCN (10 mL), then 2,2-dimethyloxirane (1.62-mL, 18.2 mmol), K₂CO₃ (0.67 g, 4.9 mmol) and water (0.667 mL) were added. The reaction mixture was stirred under microwave irradiation at 120° C. for 30 min. The reaction mixture was concentrated under reduced pressure, the residue was dissolved in MeOH (4.5 mL)/THF (4.5 mL), and LiOH (1 M aq.)(3.64 mL, 3.64 mmol) was added. The reaction mixture was stirred under microwave irradiation at 120° C. for 15 min. Solvent was removed under reduced pressure, and the residue was purified by reverse phase HPLC to afford Intermediate 4 (0.19 g, 61% yield) as a white solid. MS (ESI) m/z: 251.0 (M+H)⁺. ¹H NMR (500 MHz, DMSO-d6) δ ppm 8.55 (d, J=1.7 Hz, 1H), 8.28 (s, 1H), 7.96 (d, J=9.4 Hz, 1H), 7.38 (dd, J=9.6, 2.2 Hz, 1H), 3.82 (s, 2H), 1.22 (s, 6H).

Intermediate 5. Preparation of Methyl 6-(benzyloxy)-7-bromopyrazolo[5-a]pyridine-3-carboxylate.

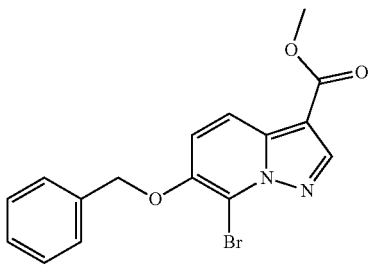 [SMILES: COC(=O)c1cnn2c(Br)c(OCc3ccccc3)ccc12]

TFA (30 mL) was placed in the round-bottom flask equipped with a magnetic stirrer and the reaction mixture was cooled to 0° C. under Ar. tert-Butyl (mesitylsulfonyl) oxycarbamate (6.34 g, 20.0 mmol) was added portion wise over 5 min, and the reaction mixture was stirred at 0° C. for 1 h under Ar. The reaction mixture was then quenched by the addition of ice water (100 mL), and a white precipitate formed. The reaction mixture was diluted with cold water (150 mL), the solid was filtered off, and was washed with cold water until pH7.0. The obtained solid was dissolved in DCM (75 mL), and was stirred with Na₂SO₄ at 0° C. for 15 min to remove residual water. Na₂SO₄ was removed by filtration, and the DCM solution was added to a cooled (ice bath) solution of 3-(benzyloxy)-2-bromopyridine (4.41 g, 16.1 mmol) in DCM (25 mL). The reaction mixture was stirred at 0° C. for 2 h. The ice bath was removed and the reaction mixture was allowed to reach rt and was stirred at this temperature for 1 h. Solvent was removed under reduced pressure. The residue was dissolved in DMF (100 mL), then methyl propiolate (2.86 mL, 32.1 mmol) and K₂CO₃ (6.66 g, 48.2 mmol) were added sequentially. The resulting suspension was stirred at rt for 16 h. The reaction mixture was diluted with EtOAc (500 mL), washed with water (3×250 mL), brine (250 mL), dried (Na₂SO₄) and filtered. The residue was purified by flash chromatography to give Intermediate 5 (0.88 g, 15% yield) as an off-white solid. MS (ESI) m/z: 360.8 (M+H)⁺. ¹H NMR (300 MHz, CDCl₃) δ ppm 8.45 (s, 1H), 8.15 (d, J=9.6 Hz, 1H), 7.48-7.16 (m, 6H), 5.24 (s, 2H), 3.91 (s, 3H).

Intermediate 6. Preparation of 7-Cyclonronyl-6-(2-hydroxy-2-methylpropoxy)pyrazolo[1,5-a]pyridine-3-carboxylic acid.

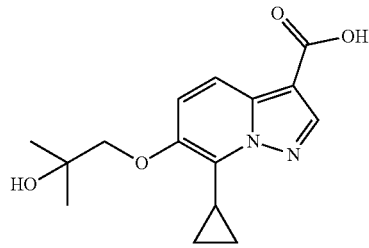

Intermediate 6A. Preparation of Methyl 6-(benzyloxy)-7-cyclopropyl-pyrazolo[1,5-a]pyridine-3-carboxylate

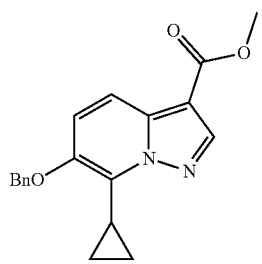 [SMILES: COC(=O)c1cnn2c(C3CC3)c(OCc3ccccc3)ccc12]

Intermediate 5 (350 mg, 0.969 mmol), cyclopropylboronic acid (333 mg, 3.88 mmol), palladium(II) acetate (11.0 mg, 0.0480 mmol), tricyclohexylphosphonium tetrafluoroborate (35.7 mg, 0.0970 mmol) and phosphoric acid, potassium salt (617 mg, 2.91 mmol) were placed in a pressure vial, and the reaction mixture was degassed (3×Ar/vacuum). Toluene (10 mL) and water (0.2 mL) were added, and the reaction mixture was degassed again. The vial was capped and the reaction mixture was heated to 100° C. for 16 h. The solvent volume was reduced under reduced pressure, and the residue was purified by flash chromatography to give Intermediate 6A (280 mg, 89% yield) as a white solid. MS (ESI) m/z: 323.0 (M+H)$^+$. 1H NMR (500 MHz, DMSO-d6) δ ppm 8.38 (s, 1H), 7.98 (d, J=9.4 Hz, 1H), 7.46-7.38 (m, 4H), 7.37-7.33 (m, 1), 7.30 (d, J=9.6 Hz, 1H), 5.11 (s, 2H), 3.89 (s, 3H), 2.49 (tt, J=8.7, 5.6 Hz, 1H), 1.46-1.41 (m, 2H), 1.17-1.11 (m, 2H).

Intermediate 6B. Preparation of Methyl 7-cyclopropyl-6-hydroxypyrazolo-[l,5-a]pyridine-3-carboxylate.

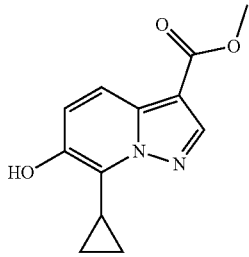 [SMILES: COC(=O)c1cnn2c(C3CC3)c(O)ccc12]

Intermediate 6A (150 mg, 0.465 mmol) was dissolved in THF (4 mL)/MeOH (4 mL), and TEA (0.324 mL, 2.33 mmol) were added. The reaction mixture was degassed (3× vacuum/Ar), then palladium on carbon (10 wt %) (49.5 mg, 0.0470 mmol) was added. The reaction mixture was degassed again, and stirred under hydrogen atmosphere (1 atm; balloon) for 1 h. Pd—C was filtered off using a membrane filter, and the filtrate was concentrated under reduced pressure to afford Intermediate 6B (100 mg, 95% yield) as a white solid. MS (ESI) m/z: 233.1 (M+H)$^+$. $^1$H NMR (500 MHz, DMSO-d6) δ ppm 9.74 (br s, 1H), 8.32 (s, 1H), 7.81 (d, J=9.4 Hz, 1H), 7.30 (d, J=9.4 Hz, 1H), 3.79 (s, 3H), 2.48-2.44 (m, 1H), 1.44-1.37 (m, 2H), 1.06-0.98 (m, 2H).

Intermediate 6

Intermediate 6B (0.050 g, 0.22 mmol) was suspended in MeCN (2.0 mL), then 2,2-dimethyloxirane (0.288 mL, 3.23 mmol), K$_2$CO$_3$ (0.119 g, 0.861 mmol) and water (0.133 mL) were added. The reaction mixture was stirred under microwave irradiation at 120° C. for 30 min. The reaction mixture was concentrated under reduced pressure, the residue was dissolved in MeOH (1 mL)/THF (1 mL), and LiOH (1 M aq.) (0.646 mL, 0.646 mmol) was added. The reaction mixture was stirred under microwave irradiation at 120° C. for 15 min. Solvent was removed under reduced pressure and the residue was purified by reverse phase HPLC to afford Intermediate 6 (0.037 g, 59% yield) as a white solid. MS (ESI) m/z: 291.0 (M+H)$^+$; $^1$H NMR (500 MHz, DMSO-d6) δ ppm 8.34 (s, 1H), 7.90 (d, J=9.6 Hz, 1H), 7.57 (d, J=9.6 HzC, 1H), 3.81 (s, 2H), 2.63 (tt, J=8.8, 5.6 Hz, 1H), 1.55-1.49 (m, 2H), 1.25 (s, 6H), 1.11-1.02 (m, 2H).

Intermediate 7. 6-(2,2-difluoioethoxy,)pyrazolo[1.5-apyridine-3-carhoxylic acid.

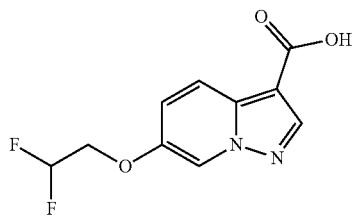 [SMILES: O=C(O)c1cnn2cc(OCC(F)F)ccc12]

Ethyl 6-hydroxypyrazolo[1,5-a]pyridine-3-carboxylate (0.080 g, 0.39 mmol) was suspended in MeCN (3.0 mL), then 2,2-difluoroethyl trifluoromethanesulfonate (0.062 mL, 0.47 mmol) and cesium carbonate (0.379 g, 1.16 mmol) were added. The reaction mixture was stirred under microwave irradiation at 120° C. for 15 min. The reaction mixture was concentrated under reduced pressure, the residue was dissolved in MeOH (1.5 mL)/THF (1.5 mL), and LiOH (1 M aq.) (1.94 mL, 1.94 mmol) was added. The reaction mixture was stirred under microwave irradiation at 120° C. for 15 min. The reaction mixture was purified by preparative HPLC to afford Intermediate 7 (0.064 g, 68% yield) as a white solid. MS (ESI) m/z: 243.0 (M+H)$^+$. $^1$H-NMR: (500 MHz, DMSO-d6) δ ppm 12.41 (s, 1H), 8.72 (d, J=1.7 Hz, 1H), 8.32 (s, 1H), 7.99 (d, J=10.2 Hz, 1H), 7.43 (dd, J=9.6, 2.5 Hz, 1H), 6.45 (tt, J=54.3, 3.5 Hz, 1H), 4.44 (td, J=14.6, 3.4 Hz, 2H). $^{19}$F-NMR: (471 MHz, DMSO-d6) δ ppm −125.92 (s, 2F).

Intermediate 8. Methyl 6-(3,3,3-trifluoropropoxy)pyrazolo[1,5-a]pyridine-3-carboxylate.

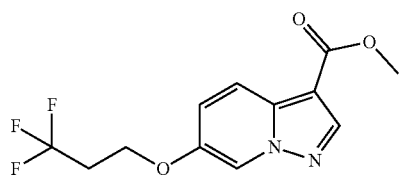 [SMILES: COC(=O)c1cnn2cc(OCCC(F)(F)F)ccc12]

Methyl 6-hydroxypyrazolo[1,5-a]pyridine-3-carboxylate (0.100 g, 0.520 mmol), 3,3,3-trifluoropropan-1-ol (0.096 mL, 1.0 mmol), and 1,1'-(azodicarbonyl)dipiperidine (0.394 g, 1.56 mmol) were placed in a pressure vial. Anhydrous toluene (5 mL) and tri-N-butylphosphine (0.390 mL, 1.56 mmol) were added, and the reaction mixture was stirred at 140° C. under microwave irradiation for 15 min. The reaction mixture was quenched by the addition of MeOH (1 mL), diluted with EtOAc (50 mL), Celite was added, and solvent was removed under reduced pressure. The residue was purified by ISCO (solid loading on Celite, 0-60% EtOAc/DCM gradient) to give Intermediate 8 (0.064 g, 42% yield) as a white solid. MS (ESI) m/z: 289.0 (M+H)$^+$. $^1$H-NMR: (500 MHz, DMSO-d6) δ ppm 8.70 (d, J=1.9 Hz, 1H), 8.38 (s, 1H), 7.98 (d, J=9.6 Hz, 1H), 7.40 (dd, J=9.6, 2.2 Hz, 1H), 4.33 (t, J=5.9 Hz, 2H), 3.82 (s, 3H), 2.85 (qt, J=11.3, 5.8 Hz, 2H). $^{19}$F-NMR: (471 MHz, DMSO-d6) δ ppm −63.03 (s, 3F).

Intermediate 9. Preparation of 6-(3,3,3-trifluoropropoxy)pyrazolo1,5-a]pyridine-3-carhoxylic acid

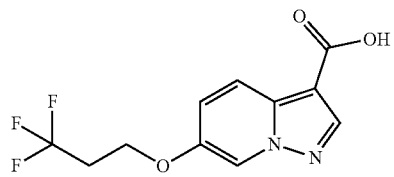 [SMILES: O=C(O)c1cnn2cc(OCCC(F)(F)F)ccc12]

Intermediate 8 (0.675 g, 2.34 mmol) was dissolved in MeOH (24.0 mL)/FHF (24.0 mL), and LiOH (7.03 mL, 7.03 mmol) was added. The reaction mixture was irradiated at 100° C. for 15 min before acidifying with 1.0N HCl solution and then extracted with EtOAc. The combined organic portions were washed with brine, dried over sodium sulfate, filtered, and concentrated under reduced pressure to give Intermediate 9 (0.61 g, 95% yield) as a white solid. $^1$H NMR (500 MHz, CDCl$_3$) δ 8.41 (s, 1H), 8.18 (d, J=1.9 Hz, 1H), 8.14-8.10 (m, 1H), 7.26-7.19 (m, 1H), 4.25 (t, J=6.3 Hz, 2H), 2.76-2.66 (m, 2H).

Intermediate 10. Preparation of methyl 6-(benzyloxy)-1-(difluoromethyl)-1H-indazole-3-carboxylate

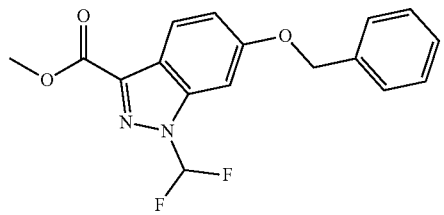 [SMILES: COC(=O)c1nn(C(F)F)c2cc(OCc3ccccc3)ccc12]

Methyl 6-benzyloxy-1H-indazole-3-carboxylate in THF was added dropwise to a suspension of NaH in THF and maintained at rt for 30 min. Chlorodifluoromethane was then bubbled into the reaction mixture, the vial sealed, and the mixture heated to 70° C. overnight. The cooled reaction mixture was diluted with water, extracted with EtOAc and the combined organic portions were washed with brine, dried over sodium sulfate, filtered, and concentrated onto Celite. The residue was purified by flash chromatography to give Intermediate 10 (75%). MS (ESI) m/z: 333.0 (M+H)$^+$. $^1$H NMR (400 MHz, DMSO-d6) δ 8.46-8.15 (m, 1H), 8.05 (d, J=9.0 Hz, 1H), 7.55-7.51 (m, 3H), 7.47-7.41 (m, 2H), 7.41-7.36 (m, 1H), 7.22 (dd, J=9.0, 2.0 Hz, 1H), 5.25 (s, 2H), 3.98 (s, 3H).

Intermediate 11. Preparation of 1-(difluoromethyl)-6-(2-hydroxy-2-methylpropoxy)-1H-indazole-3-carboxylic acid

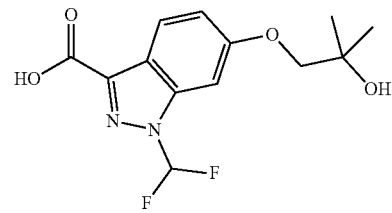 [SMILES: CC(C)(O)COc1ccc2c(C(=O)O)nn(C(F)F)c2c1]

Intermediate 11A. Preparation of methyl 1-(difluoromethyl)-6-hydroxy-1H-indazole-3-carboxylate

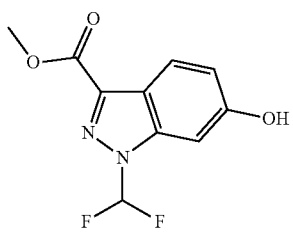 [SMILES: COC(=O)c1nn(C(F)F)c2cc(O)ccc12]

10% Pd—C(0.056 g, 0.053 mmol) was added to Intermediate 10 (0.176 g, 0.530 mmol) in MeOH (15 mL) EtOAc (5 mL) and subjected to a hydrogen atmosphere (50 psi) overnight. The suspension was filtered through a plug of Celite and the filtrate was concentrated to afford Intermediate 11A. This material was carried forward to the next reaction with further purification. MS (ESI) m/z: 242.9 (M+H)⁺.

Intermediate 11

A solution of Intermediate 11A (0.128 g, 0.529 mmol) in CH₃CN (3 mL)/water (0.2 mL) was treated with K₂CO₃ (0.292 g, 2.11 mmol) and 2,2-dimethyloxirane (1.408 mL, 15.86 mmol) and irradiated in the microwave reactor at 120° C. for 35 min. The reaction mixture was partitioned between EtOAc and water. The organic layer was discarded. The remaining aqueous layer was acidified with 0.0N HCl solution and extracted with EtOAc. The organic layer was washed with brine, dried over sodium sulfate, filtered, and concentrated to give Intermediate 11 (0.063 g, 40% yield). MS (ESI) m/z: 300.9 (M+H)⁺.

Intermediate 12. Preparation of methyl 6-(2-oxa-6-azaspiro[3,3]heptan-6-yl) pyrazolo[1,5-a]pyridine-3-carboxylate

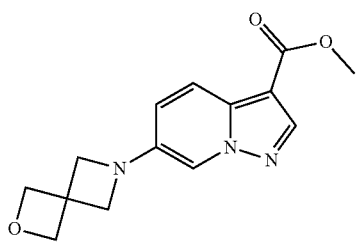 [SMILES: COC(=O)c1cnn2cc(N3CC4(COC4)C3)ccc12]

Methyl 6-bromopyrazolo[1,5-a]pyridine-3-carboxylate (0.250 g, 0.980 mmol), Pd(II) acetate (0.013 g, 0.059 mmol), BINAP (0.055 g, 0.088 mmol) and cesium carbonate (0.798 g, 2.45 mmol) were placed in a pressure vial. The reaction mixture was degassed (3× vacuum/Ar), then Toluene (3.3 ml) and 2-oxa-6-azaspiro[3.3]heptane, 0.5oxalic acid salt (0.155 g, 1.08 mmol) were added. The reaction mixture was degassed again, and stirred at 120° C. for 16 h. The solvent was evaporated under reduced pressure and the residue was purified by flash chromatography (0-85% EtOAc/DCM) to give Intermediate 12 (0.20 g, 73% yield) as an off-white solid. MS (ESI) m/z: 274.0 (M+H)⁺. ¹H-NMR: (500 MHz, DMSO-d6) δ ppm 8.26 (s, 1H), 7.99 (d, J=1.4 Hz, 1H), 7.94-7.88 (m, 1H), 7.09 (dd, J=9.4, 2.2 Hz, 1H), 4.72 (s, 4H), 4.04 (s, 4H), 3.79 (s, 3H).

Intermediate 13. Preparation of 6-bromo-3-(trifluoromethyl)imidazo[1,5-a]pyridine-1-carboxylic acid

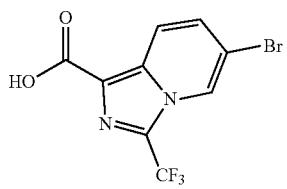 [SMILES: O=C(O)c1nc(C(F)(F)F)n2cc(Br)ccc12]

Intermediate 13A. Preparation of ethyl 2-(5-bromopyridin-2-yl)acetate

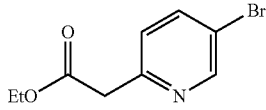 [SMILES: CCOC(=O)Cc1ccc(Br)cn1]

5-bromo-2-iodopyridine (20 g, 70 mmol) was dissolved in dioxane (90 mL). Diethyl malonate (13.54 g, 85.00 mmol), Cs2CO₃ (34.4 g, 106 mmol), and picolinic acid (1.74 g, 14.1 mmol) were added. The suspension was degassed thoroughly by 3 evacuation and nitrogen-back-fill cycles. CuI (1.34 g, 7.04 mmol) was added to the reaction mixture and stirred at 80° C. under nitrogen atmosphere for 5 hours. The reaction mixture cooled to rt and was diluted with 500 mL water then extracted with 100 mL EtOAc×4. The combined organic portions were concentrated under reduced pressure and the residue was dissolved in DMSO (250 mL) and LiCl (2.99 g, 70.4 mmol) in 10 mL water was added. The reaction mixture was heated to 150° C. for 3 hours (observation of gas evolution), adding LiCl (250 mg) in 1 mL water every 30 minutes until double decarboxylation was observed in LCMS. The reaction mixture cooled to rt and was diluted with 500 mL water then extracted with EtOAc 2×200 mL. The combined organic layers were concentrated and the residue was purified by silica gel chromatography, eluting with a linear gradient of 0% to 100% EtOAc. Ethyl 2-(5-bromopyridin-2-yl)acetate (12 g, 70% yield) was isolated as a yellow oil. MS (ESI) m/z: 245.9 (M+H)⁺.

Intermediate 13B. Preparation of (Z)-ethyl 2-(5-bromopyridin-2-yl)-2-(hydroxyimino)acetate

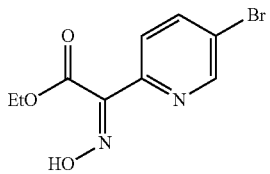 [SMILES: CCOC(=O)/C(=N\O)c1ccc(Br)cn1]

Ethyl 2-(5-bromopyridin-2-yl)acetate (12 g, 49 mmol) was dissolved in HOAc (60 mL). NaNO₂ (3.39 g, 49.2 mmol) in water (15 mL) was added dropwise to the ester. The reaction mixture was stirred at rt for 1 hour and then concentrated to an oil. The residue was diluted with 500 mL water and potassium carbonate was added until a pH of 7-8 was obtained, at which point a white solid precipitated. The solid was filtered and dried to isolate (Z)-ethyl 2-(5-bromopyridin-2-yl)-2-(hydroxyimino)acetate (12 g, 89% yield) as a white solid. MS (ESI) m/z: 275.0 (M+H)⁺.

Intermediate 13C. Preparation of ethyl 6-bromo-3-(trifluoromethyl)imidazo[1,5-a]pyridine-1-carboxlate

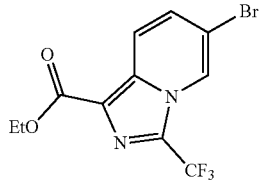

(E)-ethyl 2-(5-bromopyridin-2-yl)-2-(hydroxyimino)acetate (4.5 g, 16 mmol) was dissolved in THF (50 mL) and TFA (6.25 mL) was added. Zinc (2.16 g, 33.0 mmol) was added portion wise followed by TFAA (4.7 mL, 33.0 mmol) and the reaction mixture stirred for 1 hour. The reaction mixture was filtered through Celite® and concentrated under reduced pressure. The residue was dissolved in pyridine (25 mL) and TFAA (4.7 mL, 33.0 mmol) was added. Following about 1 hour at 60° reaction was concentrated and purified by silica gel chromatography eluting with a linear gradient of 0% to 100% EtOAc in hexanes. Ethyl 6-bromo-3-(trifluoromethyl)imidazo[1,5-a]pyridine-1-carboxylate (5.0 g, 90% yield) was isolated as a yellow solid. MS (ESI) m/z: 337.0 (M+H)+.

Intermediate 13

Ethyl 6-bromo-3-(trifluoromethyl)imidazo[1,5-a]pyridine-1-carboxylate (1.4 g, 4.2 mmol) was dissolved in MeOH (50 mL) and NaOH (0.166 g, 4.15 mmol) dissolved in water (10 mL) was carefully added. After 1 hour at t, reaction was complete and a solid had precipitated. The reaction mixture was concentrated to about half of the original volume under reduced pressure and filtered. The solid was dried under vacuum to yield Intermediate 13 (1.1 g, 86% yield) as a white solid. MS (ESI) m/z: 310.8 (M+H)+.

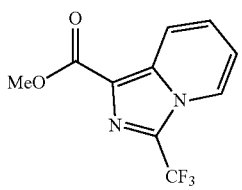 [SMILES: COC(=O)c1nc(C(F)(F)F)n2ccccc12]

Intermediate 14 was synthesized in the same way as Intermediate 13C by substituting 5-bromo-2-iodopyridine with 2-iodopyridine. (ESI) m/z: 244.9 (M+H)+.

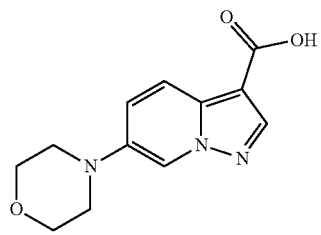 [SMILES: O=C(O)c1cnn2cc(N3CCOCC3)ccc12]

Methyl 6-bromopyrazolo[1,5-a]pyridine-3-carboxylate (0.100 g, 0.392 mmol), Pd(II) acetate (5.3 mg, 0.024 mmol), BINAP (0.022 g, 0.035 mmol) and cesium carbonate (0.192 g, 0.588 mmol) were placed in a pressure vial. The reaction mixture was degassed (3× vacuum/Ar), then toluene (2 mL) and morpholine (0.044 mL, 0.51 mmol) were added. The reaction mixture was degassed again, and stirred at 160° C. under microwave irradiation for 30 min. Additional Pd(II) acetate (5.3 mg, 0.024 mmol), BINAP (0.022 g, 0.035 mmol) and morpholine (0.044 mL, 0.51 mmol) were added, and the reaction mixture was stirred for additional 30 min at 160° C. The solvent was removed under reduced pressure. The residue was dissolved in MeOH (2.0 mL)/THF (2.0 mL), and LiOH (1 M aq.) (1.18 mL, 1.18 mmol) was added. The reaction mixture was stirred under microwave irradiation at 120° C. for 15 min. The reaction mixture was acidified with TFA, then the solvent was evaporated under reduced pressure. The residue was purified by preparative HPLC to afford Intermediate 15 (0.023 g, 24% yield) as an off-white solid. (ESI) m/z: 248.0 (M+H)+. 1H-NMR: (500 MHz, DMSO-d6) δ ppm 12.29 (br s, 1H), 8.27-8.20 (m, 2H), 7.92 (d, J=9.4 Hz, 1H), 7.58 (dd, J=9.6, 2.2 Hz, 1H), 3.81-3.73 (m, 4H), 3.17-3.07 (m, 4H).

Intermediate 16. Preparation of 6-(4-methylpiperazin-1-yl)pyrazolo[1,5-a]pyridine-3-carboxylic acid, TFA

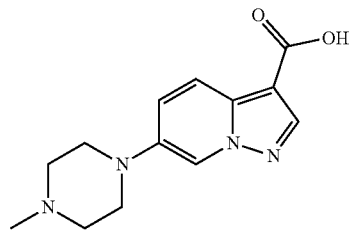 [SMILES: CN1CCN(c2ccc3c(C(=O)O)cnn3c2)CC1]

Methyl 6-bromopyrazolo[1,5-a]pyridine-3-carboxylate (0.050 g, 0.20 mmol), 1-methylpiperazine (0.044 mL, 0.39 mmol), BINAP (11 mg, 0.018 mmol), Pd(II) acetate (2.6 mg, 0.012 mmol) and cesium carbonate (0.16 g, 0.49 mmol) were placed in a pressure vial. The reaction mixture was degassed (3×vacuum/Ar), then toluene (1 mL) was added. The reaction mixture was degassed again, and stirred at 160° C. under microwave irradiation for 30 min. The solvent was evaporated under reduced pressure. The obtained residue was dissolved in MeOH (1.0 mL)/THF (1.0 mL), and LiOH (1 M aq.) (0.59 mL, 0.59 mmol) was added. The reaction mixture was stirred under microwave irradition at 120° C. for 15 min. The mixture was acidified with TFA, the solvent was evaporated under reduced pressure, and the residue was purified by preparative HPLC to afford Intermediate 16 (0.015 g, 20% yield) as a white solid. (ESI) m/z: 261.0 (M+H)+. 1H-NMR: (500 MHz, DMSO-d6) δ ppm 9.81 (br s, 11), 8.41 (d, J=1.4 Hz, 1H), 8.28 (s, 1H), 7.96 (d, J=9.6 Hz, 1), 7.59 (dd, J=9.8, 2.1 Hz, 1H), 3.84 (br d, J=12.9 Hz, 2H), 3.54 (br d, J=11.8 Hz, 2H), 3.21 (br d, J=9.4 Hz, 2H), 3.03 (br t, J=12.2 Hz, 2H), 2.87 (s, 3H).

Intermediate 17. Preparation of 6-(3,3,3-trifluoro-2-hydroxy-2-(trifluoromethyl)propoxy)pyrazolo[1,5-a]pyridine-3-carboxylic acid

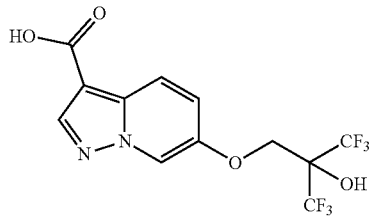

Methyl 6-hydroxypyrazolo[1,5-a]pyridine-3-carboxylate (0.200 g, 1.04 mmol) was suspended in MeCN (10 mL), then 2,2-bis(trifluoromethyl)oxirane (0.138 mL, 1.15 mmol), K$_2$CO$_3$ (0.432 g, 3.12 mmol) and Water (0.667 mL) were added. The reaction mixture was stirred under microwave irradiation at 120° C. for 30 min. The reaction mixture was concentrated under reduced pressure, the residue was dissolved in MeOH (4.0 mL)/THF (4.0 mL), and LiOH (1 M aq.) (3.12 mL, 3.12 mmol) was added. The reaction mixture was stirred under microwave irradiation at 150° C. for 15 min. The reaction mixture was acidified with TFA, filtered, and was purified by preparative HPLC to afford Intermediate 17 (210 mg, 56% yield) as a white solid. (ESI) m/z: 359.0 (M+H)$^+$. $^1$H-NMR (500 MHz, DMSO-d6) δ ppm 12.43 (br s, 1H), 8.81 (d, J=1.7 Hz, 1H), 8.51 (s, 1H), 8.33 (s, 1H), 8.00 (d, J=9.6 Hz, 1H), 7.38 (dd, J=9.6, 2.2 Hz, 1H), 4.54 (s, 2H). $^{19}$F-NMR: (471 MHz, DMSO-d6) δ ppm −74.51 (s, 3F).

Intermediate 18. Preparation of 6-(3,3,3-trifluoro-2-hydroxy-2-(trifluoromethyl)propoxy)pyrazolo[1,5-a]pyridine-3-carboxylic acid

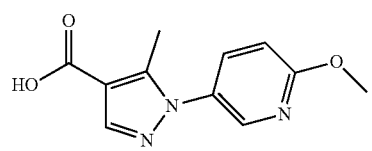 [SMILES: COc1ccc(-n2ncc(C(=O)O)c2C)cn1]

Intermediate 18A. tert-butyl 1-(6-methoxypyridin-3-yl)-5-methyl-1H-pyrazole-4-carboxylate

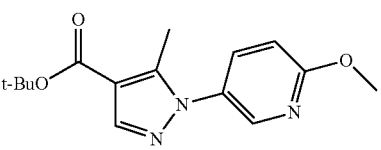 [SMILES: COc1ccc(-n2ncc(C(=O)OC(C)(C)C)c2C)cn1]

To a solution of 5-hydrazinyl-2-methoxypyridine, HCl (82 mg, 0.47 mmol) in acetonitrile (2.3 mL), were added (E)-tert-butyl 2-((dimethylamino)methylene)-3-oxobutanoate (100 mg, 0.469 mmol) and TEA (65.4 μl, 0.469 mmol). The reaction mixture was stirred at rt overnight. The solution was concentrated under reduced pressure and the residue was purified by silica gel flash column chromatography (0-50% ethyl acetate/hexanes gradient) to afford Intermediate 18A (61 mg, 45% yield) as a light yellow oil. (ESI) m/z: 290.1 (M+H)$^+$. $^1$H NMR (400 MHz, chloroform-d) δ 8.24-8.17 (m, 1H), 7.96 (s, 1H), 7.63 (dd, J=8.8, 2.6 Hz, 1H), 6.86 (dd, J=8.8, 0.7 Hz, 1H), 3.99 (s, 3H), 2.51 (s, 3H), 1.58 (s, 9H).

Intermediate 18

To a solution of Intermediate 18A (61 mg, 0.21 mmol) in DCM (2.5 mL), was added TFA (0.487 mL, 6.32 mmol). The reaction mixture was stirred at rt for 4.5 h, then was concentrated under reduced pressure to afford Intermediate 18 (59 mg, 80%). (ESI) m/z: 234.0 (M+H)$^+$.

Example 1. Preparation of 4-(((aR)-6-(1-(4-Chlorophenyl)-5-methyl-1H-pyrazole-4-carboxamido)spiro[3.3]heptan-2-yl)oxy)-2-methylthiazole-5-carboxamide

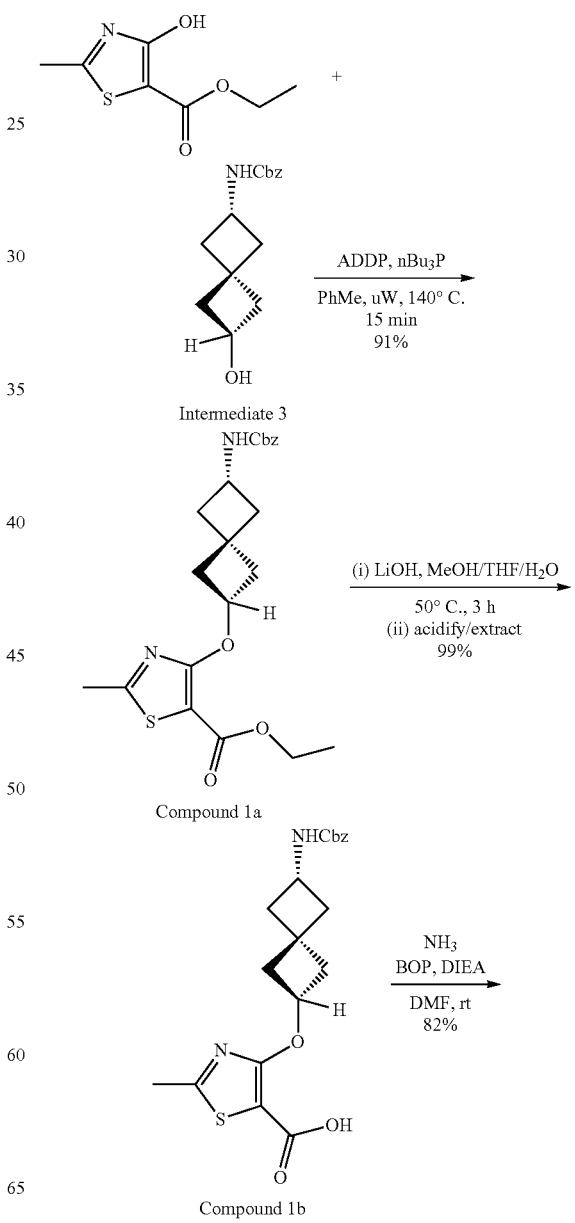

73
-continued

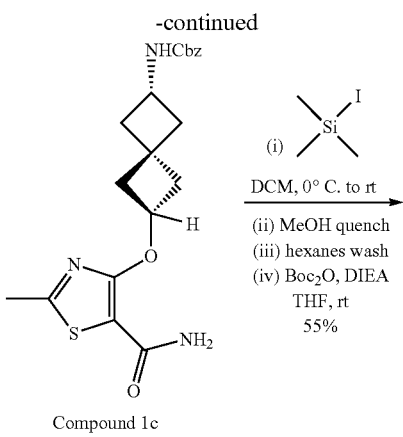

Compound 1c (i) [TMS-I]
DCM, 0° C. to rt
(ii) MeOH quench
(iii) hexanes wash
(iv) Boc₂O, DIEA
THF, rt
55%

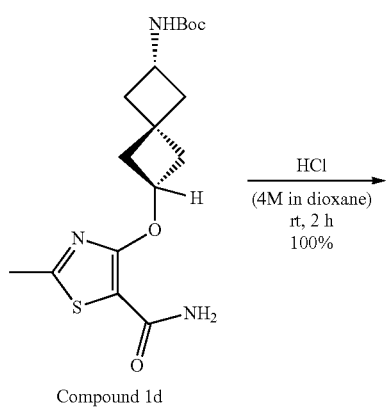

Compound 1d

HCl
(4M in dioxane)
rt, 2 h
100%

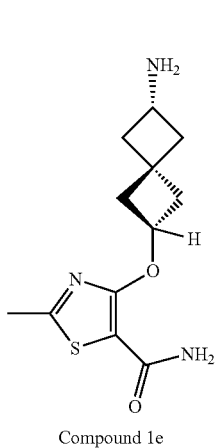

Compound 1e

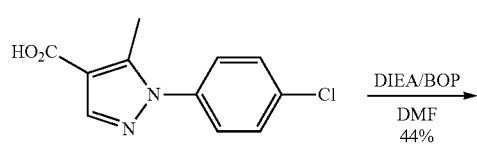

DIEA/BOP
DMF
44%

74
-continued

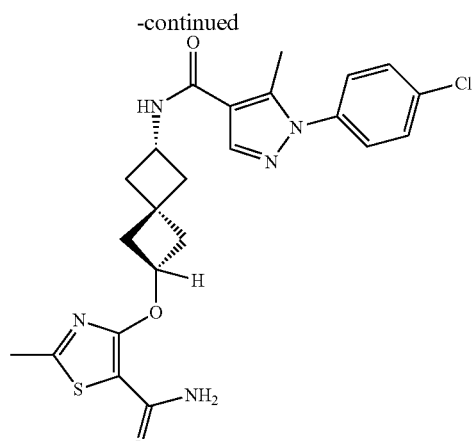

Example 1

Example 1A. Ethyl 4-(((aR)-6-(((benzyloxy)carbonyl)amino)spiro[3.3]heptan-2-yl)oxy)-2-methylthiazole-5-carboxylate Ethyl 4-hydroxy-2-methylthiazole-5-carboxylate (118 mg, 0.631 mmol), benzyl ((aS)-6-hydroxyspiro[3.3]heptan-2-yl)carbamate (150 mg, 0.574 mmol), and 1,1'-(azidodicarbonyl)dipiperidine (434 mg, 1.72 mmol) were placed in a pressure vial. Anhydrous toluene (12 mL) and tri-N-butylphosphine (0.430 mL, 1.72 mmol) were added and the reaction mixture was stirred at 140° C. under microwave irradiation for 15 min. The reaction mixture was quenched by the addition of MeOH (5 mL), and the solvent was removed under reduced pressure. The residue was purified by flash chromatography (0-40% EtOAc/DCM gradient) to give Example 1A (230 mg, 91% yield) as a colorless film. MS (ESI) m/z: 431.1 (M+H)⁺. ¹H-NMR (500 MHz, CDCl₃) δ ppm 7.41-7.29 (m, 5H), 5.16-5.10 (m, 1H), 5.08 (br s, 2H), 4.82 (br d, J=6.1 Hz, 1H), 4.27 (q, J=7.2 Hz, 2H), 2.68-2.61 (m, 1H), 2.60 (s, 3H), 2.55-2.49 (m, 1H), 2.48-2.39 (m, 2H), 2.29 (td, J=11.3, 7.4 Hz, 2H), 1.99-1.86 (m, 2H), 1.33 (t, J=7.2 Hz, 3H)

Example 1B. 4-(((aR)-6-(((benzyloxy)carbonyl)amino)spiro[3.3]heptan-2-yl)oxy)-2-methylthiazole-5-carboxylic acid

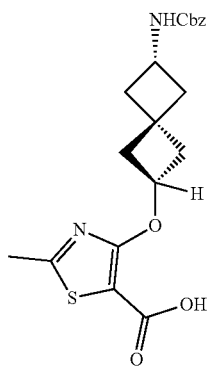

Example 1A (225 mg, 0.523 mol) was dissolved in MeOH (3.0 mL)/THF (3.0 mL), and LiOH (1 M aq.) (1.57 mL, 1.57 mmol) was added. The reaction mixture was stirred at 50° C. for 3 h. The solvent was removed under reduced pressure. The residue was suspended in water (~10 mL), EtOAc (10 mL) was added, and the mixture was slowly acidified with HCl (1 M aq.) (1.57 mL, 1.57 mmol). The organic phase was separated and the aq. phase was extracted with EtOAc (2×15 mL). The combined organic fractions were washed with brine, dried ($Na_2SO_4$) and filtered. The solvent was removed in vacuo to afford Example 1B (210 mg, 99% yield) as an off-white solid. MS (ESI) m/z: 403.1. $^1$H-NMR (500 MHz, DMSO-d6) δ ppm 7.50 (br d, J=7.7 Hz, 1H), 7.41-7.25 (m, 5H), 5.07-5.00 (m, 1H), 5.00-4.93 (m, 2H), 3.89 (sxt, J=7.9 Hz, 1H), 2.58 (s, 3H), 2.56-2.53 (m, 1H), 2.41-2.29 (m, 2H), 2.27-2.20 (m, 1H), 2.15-2.10 (m, 1H), 2.09-2.04 (m, 1H), 2.01-1.94 (m, 2H)

Example 1C. Benzyl ((aR)-6-((5-carbamoyl-2-methylthiazol-4-yl)oxy)spiro[3.3]heptan-2-yl)carbamate

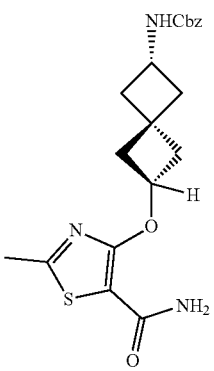

Example 1B (208 mg, 0.517 mmol) was dissolved in anhydrous DMF (2 mL), then treated with ammonia (0.5 M in dioxane)(3.10 mL, 1.55 mmol) and DIEA (0.451 mL, 2.58 mmol), followed by BOP (297 mg, 0.672 mmol) The reaction mixture was stirred at rt for 1 h. The reaction mixture was quenched by the addition of MeOH (1.0 mL), and the solvent was removed under reduced pressure. To the semi-solid residue was added EtOAc (100 mL) and water (50 mL), and the reaction mixture was vigorously stirred for 15 min. The organic phase was separated, washed with water (2×), brine (1), dried ($Na_2SO_4$), filtered and concentrated. The crude material was redissolved in EtOAc (100 mL), washed with $NaHCO_3$ (aq. sat.), water and brine, dried ($Na_2SO_4$) and concentrated to afford Example 1C (171 mg, 82% yield) as an off-white solid. MS (ESI) m/z: 402.1. $^1$H-NMR (500 MHz, DMSO-d6) δ ppm 7.53 (br s, 1H), 7.50 (br d, J=8.0 Hz, 1H), 7.41-7.28 (m, 5H), 6.80 (br s, 1H), J=5.08 (quin, J=7.0 Hz, 1H), 4.99 (s, 2H), 3.95-3.84 (m, 1H), 2.57 (s, 3H), 2.40-2.30 (m, 3H), 2.28-2.16 (m, 3H), 2.03-1.93 (m, 2H)

Example 1D. tert-butyl ((aR)-6-((5-Carbamoyl-2-methylthiazol-4-yl)oxy)spiro[3.3]heptan-2-yl)carbamate

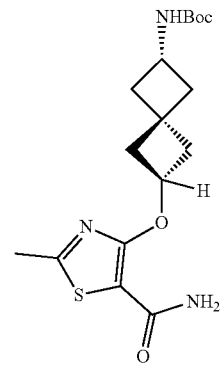

Example 1C (171 mg, 0.426 mmol) was dissolved in DCM (5 mL). The reaction mixture was cooled to 0° C., and iodotrimethylsilane (0.174 mL, 1.28 mmol) was added dropwise. The reaction mixture was stirred at 0° C. for 30 min, then the cooling bath was removed, and the reaction was stirred at rt for 30 min. The reaction mixture was cooled to 0° C. and carefully quenched by the addition of MeOH (3 mL). The volatile solvents were removed under reduced pressure, and the residue was suspended with sonication in EtOAc/hexanes (1:1, ~30 mL). The solvent was decanted and the residual solids/gum sonicated again with EtOAc/hexanes (1:1, ~30 mL). The solvent was decanted and the residue was dissolved in MeOH, and then concentrated under reduced pressure to afford a brown solid which was dissolved in anhydrous THF (5 mL), then di-tert-butyl carbonate (0.347 mL, 1.50 mmol) was added, followed by DIEA (0.327 mL, 1.87 mmol). The reaction mixture was stirred at rt for 1 h. The reaction mixture was quenched by the addition of MeOH (1 mL), concentrated under reduced pressure and purified by flash chromatography (20-100/EtOAc/hex gradient) to give Example 1D (76 mg, 55% yield) as a white foam. MS (ESI) m/z: 368.1. $^1$H-NMR (500 MHz, DMSO-d6) δ ppm 7.52 (br s, 1H), 7.05 (br d, J=8.0 Hz, 1H), 6.80 (br s, 1H), 5.07 (quin, J=7.1 Hz, 1H), 3.90-3.77 (m, 1H), 2.57 (s, 3H), 2.38-2.31 (m, 1H), 2.31-2.25 (m, 1H), 2.25-2.14 (m, 3H), 1.95 (q, J=9.7 Hz, 2H), 1.36 (s, 8H)

Example 1E. 4-(((aR)-6-Aminospiro[3.3]heptan-2-yl)oxy)-2-methylthiazole-5-carboxamide

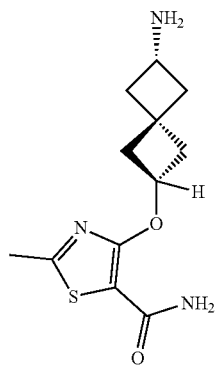

Example 1D (76 mg, 0.21 mmol) was dissolved in HCl (4 M in dioxane) (3 ml, 12.0 mmol), and the reaction mixture was stirred at rt for 2 h. The solvent was removed under reduced pressure, and the residue was co-evaporated with Et$_2$O (2×10 mL) to afford Example 1E (63 mg, 100% yield) as a HCl salt. MS (ESI) m/z: 368.1. $^1$H-NMR (500 MHz, DMSO-d) δ ppm 8.10 (br s, 2H), 7.56 (br s, 1H), 6.80 (br s, 1H), 5.08 (quin, J=7.0 Hz, 1H), 3.74-3.66 (m, 1H), 3.64-3.52 (m, 3H), 3.52-3.43 (m, 1H), 2.46-2.40 (m, 1H), 2.39-2.33 (m, 1H), 2.31-2.24 (m, 3H), 2.24-2.16 (m, 2H).

Example 1

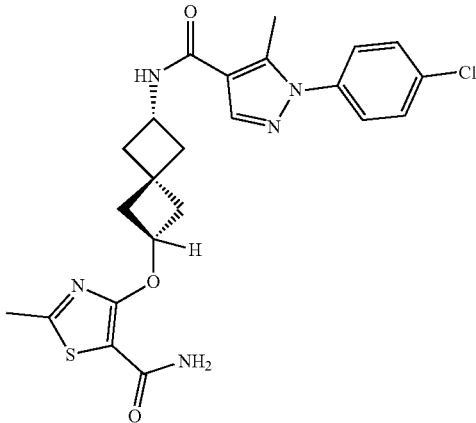

To Example 1E (10 mg, 0.037 mmol) and 1-(4-chlorophenyl)-5-methyl-1H-pyrazole-4-carboxylic acid (13.7 mg, 0.0580 mmol) in DMF (880 μl), was added DIEA (46.0 μl, 0.264 mmol), followed by addition of BOP (25.7 mg, 0.0580 mmol). The reaction mixture was stirred at rt for 4 h then quenched by the addition of a few a drops of water, diluted with methanol, filtered and purified on preparative HPLC to yield Example 1 (11 mg, 44%) as a white powder. MS (ESI) m/z: 486.0. $^1$H NMR (500 MHz, DMSO-d$_6$) δ 8.20 (s, 1H), 7.92 (br s, 1H), 7.75-7.43 (m, 3H), 7.33-7.15 (m, 1H), 6.60-6.25 (m, 3H), 3.59 (br d, J=6.1 Hz, 2H), 3.19 (br s, 1H), 2.70 (s, 3H), 2.55 (s, 3H), 1.65 (d, J=6.8 Hz, 2H), 1.02 (d, J=6.3 Hz, 3H).

Example 2. Preparation of N-((aR)-6-((2-Carbamoylbenzo[b]thiophen-3-yl)oxy)spiro[3.3]heptan-2-yl)-7-cyclopropyl-6-(2-hydroxy-2-methyl)propoxy)pyrazolo[1,5-a]pyridine-3-carboxamide

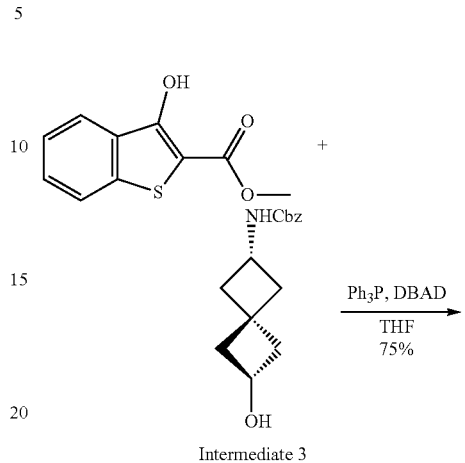

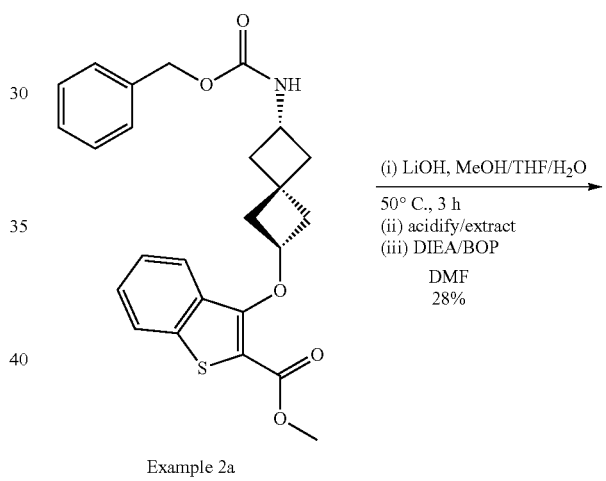

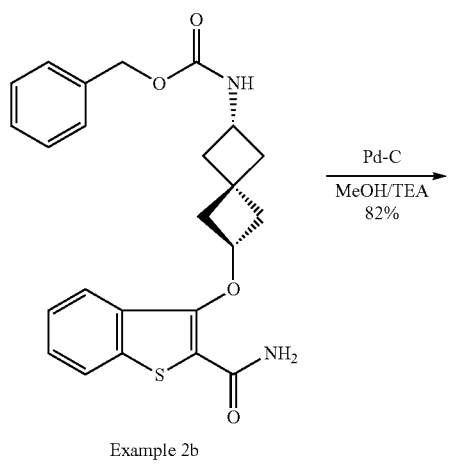

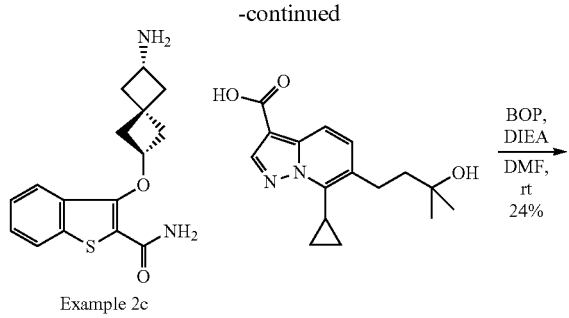

Example 2c

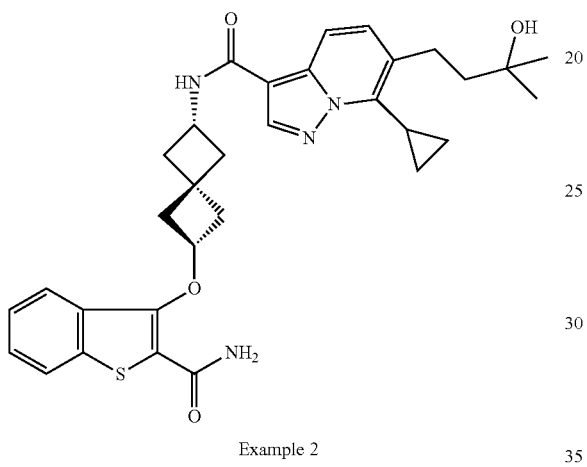

Example 2

Example 2A. Methyl 3-(((aR)-6-(((benzyloxy)carbonyl)amino)spiro[3.3]heptan-2-yl)oxy)benzo[b]thiophene-2-carboxylate

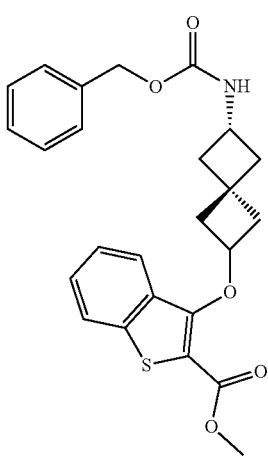

To a stirred solution of methyl 3-hydroxybenzo[b]thiophene-2-carboxylate (100 mg, 0.480 mmol), benzyl ((aS)-6-hydroxyspiro[3.3]heptan-2-yl)carbamate (125 mg, 0.480 mmol) and triphenylphosphine (3 mmol/g resin, 478 mg, 1.44 mmol) in THF (2 mL) at it, was added di-tert-butylazodicarboxylate (339 mg, 1.44 mmol). The resulting solution was stirred at 50° C. for 4 h. After cooling to room temperature, the reaction was filtered, washed with ethyl acetate and concentrated. The crude product was purified by flash chromatography (0-100% EtOAc/hexanes gradient) to give Example 2A (162 mg, 75% yield) as a clear glass. $^1$H NMR (400 MHz, CHLOROFORM-d) δ 7.90-7.84 (m, 1H), 7.77 (dt, J=8.1, 0.9 Hz, 1H), 7.50 (ddd, J=8.2, 7.0, 1.3 Hz, 1H), 7.43 (ddd, J=8.0, 7.0, 1.0 Hz, 1H), 7.39-7.33 (m, 5H), 5.10 (s, 2H), 4.96 (quin, J=7.2 Hz, 1H), 4.88-4.78 (m, 1H), 3.94 (s, 3H), 2.63-2.31 (m, 7H), 2.04-1.84 (m, 2H).

Example 2B. Benzyl ((aR)-6-((2-carbamoylbenzo[b]thiophen-3-yl)oxy)spiro[3.3]heptan-2-yl)carbamate To a solution of Example 2A (162 mg, 0.359 mmol) in THF (1 mL) and MeOH (0.3 mL), was added LiOH (1 M aq.) (1.8 mL, 1.8 mmol). The reaction mixture was stirred at 50° C. for 3 h. After cooling to rt, the solvent was removed under reduced pressure. The residue was suspended in water (~10 mL), EtOAc (10 mL) was added, and the mixture was slowly acidified with HCl (1 M aq.) (1.57 mL, 1.57 mmol) (pH ~3.0). The organic phase was separated and the aq. phase was extracted with EtOAc (2×15 mL). The combined organic fractions were washed with brine, dried (Na$_2$SO$_4$) and filtered. The solvent was removed to afford a white solid which was dissolved in DMF (2 mL) and sequentially treated with HATU (164 mg, 0.431 mmol), ammonia (0.5M in dioxane, 2.87 mL, 1.44 mmol) and Et$_3$N (0.250 mL, 1.8 mmol). The reaction mixture was stirred at rt for 1 h, then was quenched with MeOH (1.0 mL), and most of the solvent was removed under reduced pressure. To the obtained semi-solid residue, was added EtOAc (100 mL) and water (50 mL), and the mixture was vigorously stirred for 15 min. The organic phase was separated, washed with water (2×), brine, dried (Na$_2$SO$_4$), filtered and concentrated. The residue was purified by flash chromatography (0-100% Hexanes/EtOAc gradient) to afford Example 2B (44 mg, 28%) as a white foam. MS (ESI) m/z: 437.0.

Example 2C. 3-(((aR)-6-Aminospiro[3.3]heptan-2-yl)oxy)benzo[b]thiophene-2-carboxamide

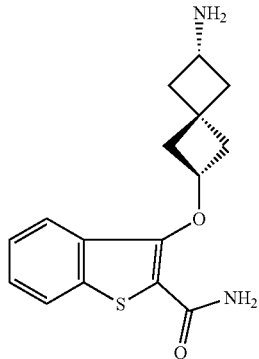

Example 2B (44 mg, 0.101 mmol) was dissolved in THF (2 mL) and MeOH (2 mL) and treated with TEA (0.070 mL, 0.504 mmol). 10% Pd—C (22 mg, 0.021 mmol) was added and the reaction stirred under a hydrogen atmosphere (balloon) for 16 h. The reaction mixture was filtered over celite and washed with MeOH. The filtrate was concentrated to afford Example 2C (25 mg, 82%) as an off white solid, which was used in the next step without further purification. MS (ESI) m/z: 303.0.

Example 2. N-((aR)-6-((2-Carbamoylbenzo[b]thiophen-3-yl)oxy)spiro[3.3]heptan-2-yl)-7-cyclopropyl-6-(2-hydroxy-2-methylpropoxy)pyrazolo[1,5-a]pyridine-3-carboxamide

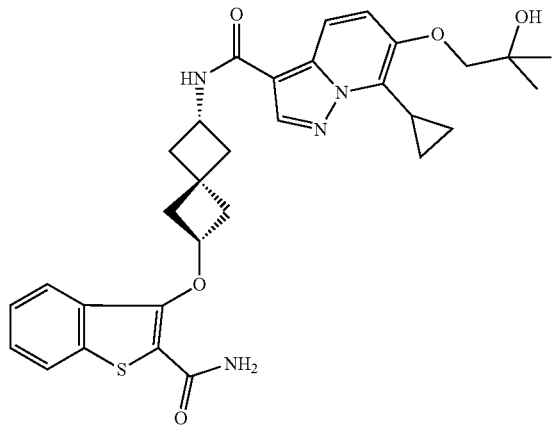

Following a similar procedure as described for Example 1, Example 2C afforded Example 2 (6.0 mg, 24%) as a colorless film. MS (ESI) m/z: 575.2. $^1$H NMR (500 MHz, DMSO-d6) δ 8.48 (s, 1H), 8.24 (br d, J=7.6 Hz, 1H), 8.02 (d, J=9.8 Hz, 1H), 7.96 (br d, J=7.9 Hz, 1H), 7.86 (br d, J=7.9 Hz, 2H), 7.55-7.42 (m, 3H), 7.39 (br s, 1H), 4.97-4.86 (m, 1H), 4.40-4.29 (m, 1H), 3.79 (s, 2H), 2.59 (br t, J=5.5 Hz, 2H), 2.44-2.27 (m, 5H), 2.20-2.00 (m, 2H), 1.55-1.38 (m, 2H), 1.24 (s, 6H), 1.08-1.02 (m, 2H)

Example 3. Preparation of 2-cyclopropyl-4-(((aR)-6-(6-(2-oxopyridin-(2H)-yl-3-(trifluoromethyl)imidazo[1,5-a]pyridin-1-carboxamido)spiro[3.3]heptan-2-yl)oxy)thiazole-5-carboxamide

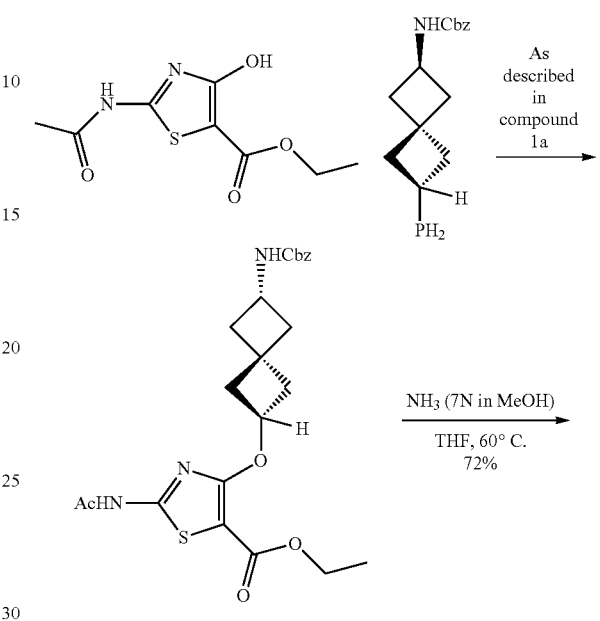

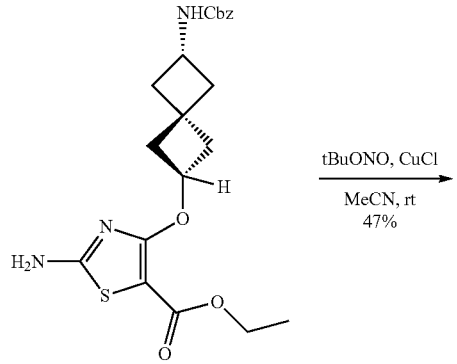

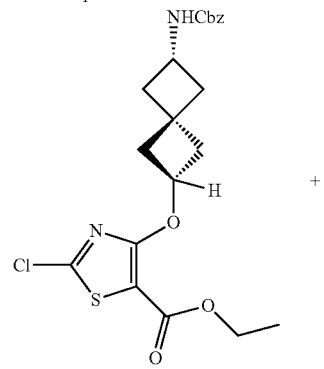

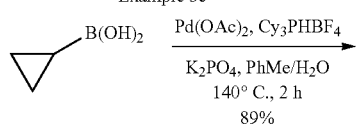

-continued

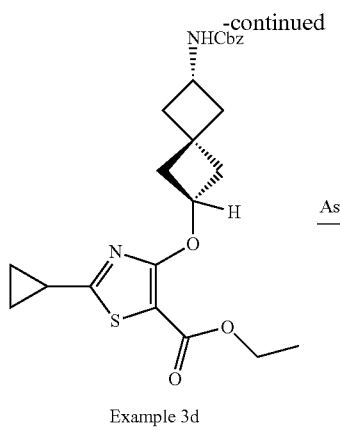

Example 3d

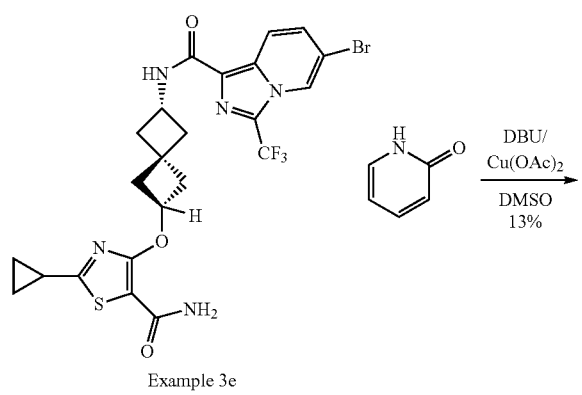

Example 3e

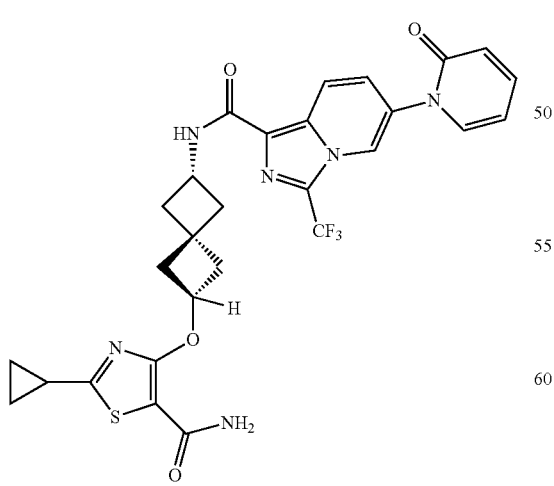

Example 3

Example 3A. Ethyl 2-acetamido-4-(((aR)-6-(((benzyloxy)carbonyl)amino)spiro[3.3]heptan-2-yl)oxy)thiazole-5-carboxylate

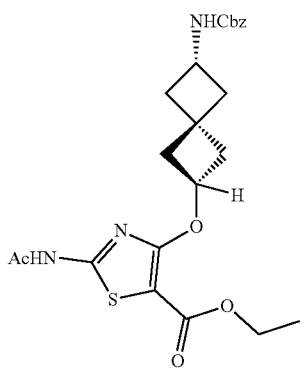

Example 3A was prepared from ethyl 2-acetamido-4-hydroxythiazole-5-carboxylate (*PCT Int. Appl.*, 2005075470) following a similar procedure as described for Example 1A (197 mg, 73% yield) as a yellow solid. MS (ESI) m/z: 574.1. $^1$H-NMR (500 MHz, DMSO-d6) δ ppm 8.80 (s, 1H), 7.41-7.29 (m, 5H), 5.09 (br s, 2H), 4.96 (quin, J=7.2 Hz, 1H), 4.84 (br d, J=5.5 Hz, 1H), 4.27 (q, J=7.2 Hz, 2H), 4.14-4.07 (m, 1H), 2.58 (dt, J=11.3, 5.6 Hz, 1H), 2.52-2.44 (m, 1H), 2.41 (td, J=12.0, 6.6 Hz, 2H), 2.31-2.25 (m, 4H), 1.98-1.87 (m, 2H), 1.35-1.30 (m, 3H).

Example 3B. Ethyl 2-amino-4-(((aR)-6-(((benzyloxy)carbonyl)amino)spiro[3.3]heptan-2-yl)oxy)thiazole-5-carboxylate

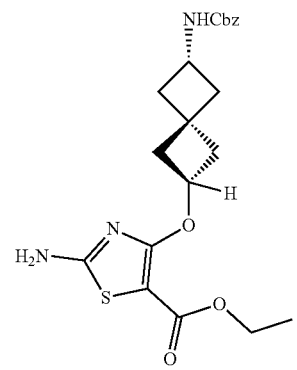

Example 3A (165 mg, 0.35 mmol) was dissolved in THF (1 mL), and ammonia (7 M in MeOH, 0.996 mL, 6.97 mmol) was added. The reaction mixture was capped, and stirred at 60° C. After 16 h, more ammonia (7 M in MeOH) (0.996 mL, 6.97 mmol) was added and the reaction stirred at 60° C. for 2 days. The reaction was cooled to rt and concentrated. The residue was dissolved in EtOAc (50 mL), washed with water (2×), brine, dried (Na$_2$SO$_4$), filtered and concentrated to afford Example 3B (108 mg, 72%) as an amber oil. MS (ESI) m/z: 432.1. $^1$H-NMR (500 MHz, DMSO-d6) δ ppm 7.96 (s, 2H), 7.49 (br d, J=7.7 Hz, 1H), 7.39-7.27 (m, 5H), 4.98 (s, 2H), 4.05 (q, J=7.2 Hz, 2H), 3.94-3.85 (m, 1H), 2.34-2.29 (m, 1H), 2.28 (br dd, J=10.2, 2.8 Hz, 1H), 2.252.19 (m, 1H), 2.10-2.05 (m, 1H), 2.03 (br dd, J=11.8, 7.4 Hz, 1H), 1.99-1.90 (m, 3H), 1.17 (t, J=7.2 Hz, 3H) -

Example 3C. ethyl 4-(((aR)-6-(((benzyloxy)carbonyl)amino)spiro[3.3]heptan-2-yl)oxy)-2-chlorothiazole-5-carboxylate

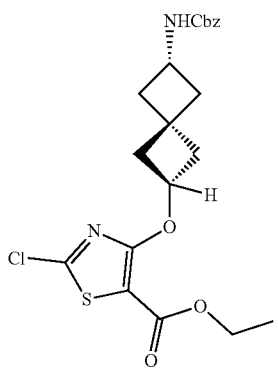

Example 3B (0.107 g, 0.248 mmol) was dissolved in anhydrous MeCN (5.0 mL), and copper(I)chloride (0.029 g, 0.298 mmol) was added, followed by tert-butyl nitrite (0.044 mL, 0.372 mmol). The reaction mixture was stirred at rt for 16 h. The reaction mixture was concentrated and the residue was suspended in EtOAc (50 mL)/HCl (25 mL, 1 N aq.) and stirred at rt for 15 min. The organic layer was separated, washed with brine, dried (Na$_2$SO$_4$) and filtered. EtOAc was removed under reduced pressure and the residue was purified by flash chromatography (0-50% EtOAc/hexanes gradient) to give Example 3C (0.053 g, 47% yield) as a colorless film. MS (ESI) m/z: 451.1. $^1$H-NMR (500 MHz, DMSO-d6) δ ppm 7.51 (br d, J=7.7 Hz, 1H), 7.41-7.27 (m, 5H), 5.05-5.00 (m, 1H), 4.99 (s, 2H), 4.21 (q, J=7.2 Hz, 2H), 3.96-3.85 (m, 1H), 2.61-2.54 (m, 1H), 2.44-2.37 (m, 1H), 2.36-2.29 (m, 1H), 2.29-2.21 (m, 1H), 2.18-2.13 (m, 1H), 2.10 (dd, J=12.0, 7.3 Hz, 1H), 2.03-1.93 (m, 2H), 1.25 (t, J=7.2 Hz, 3H).

Example 3d. ethyl 4-(((aR)-6-(((Benzyloxy)carbonyl)amino)spiro[3.3]heptan-2-yl)oxy)-2-cyclopropylthiazole-5-carboxylate

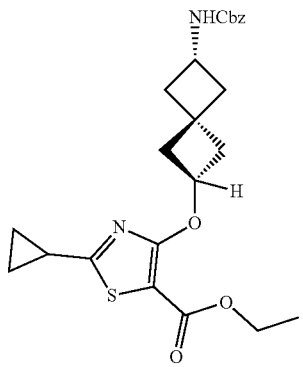

Example 3C (100 mg, 0.222 mmol), cyclopropylboronic acid (114 mg, 1.33 mmol), palladium (II) acetate (9.96 mg, 0.044 mmol), tricyclohexylphosphonium tetrafluoroborate (32.7 mg, 0.089 mmol) and Phosphoric acid, potassium salt (188 mg, 0.887 mmol) were placed in a pressure vial, and the mixture was degassed (3× Ar/vacuum). The reaction mixture was combined with toluene (1.0 mL) and water (0.2 mL) and capped. The reaction mixture was heated to 150° C. for 2 h. The reaction mixture was filtered through celite and the filtrate concentrated. The residue was purified by flash chromatography (0-100% EtOAc/hexanes gradient) to afford Example 3D (70 mg, 69%) as a light brown solid. MS (ESI) m/z: 457.1. $^1$H NMR (500 MHz, CHLOROFORM-d) δ 7.43-7.30 (m, 5H), 5.13-5.08 (m, 2H), 5.09-5.03 (m, 1H), 4.86 (br d, J=6.6 Hz, 1H), 4.28 (q, J=7.2 Hz, 2H), 2.61 (br d, J=5.5 Hz, 1H), 2.56-2.47 (m, 1H), 2.47-2.39 (m, 2H), 2.35-2.24 (m, 2H), 2.22-2.12 (m, 1H), 2.00-1.88 (m, 2H), 1.28 (t, J=7.2 Hz, 3H), 1.17 (dt, J=8.1, 3.0 Hz, 2H), 1.13-1.07 (m, 2H).

Example 3E. 4-(((aR)-6-(6-bromo-3-(trifluoromethyl)imidazo[1,5-a]pyridine-1-carboxamido)spiro[3.3]heptan-2-yl)oxy)-2-cyclopropylthiazole-5-carboxamide

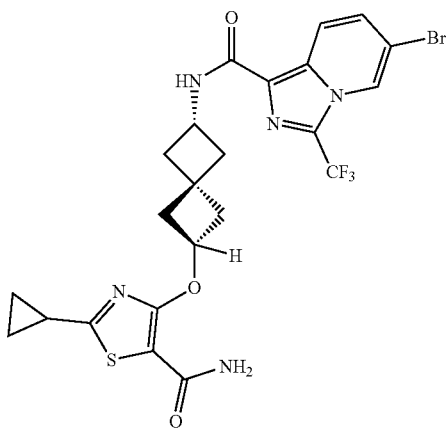

Example 3E (90 mg, 25%) was prepared from Example 3D following a similar procedure described for Example 2. MS (ESI) m/z: 584.7.

Example 3. 2-Cyclopropyl-4-(((aR)-6-(6-(2-oxopyridin-1(2H)-yl)-3-(trifluoromethyl)imidazo[1,5-a]pyridine-1-carboxamido)spiro[3.3]heptan-2-yl)oxy)thiazole-5-carboxamide

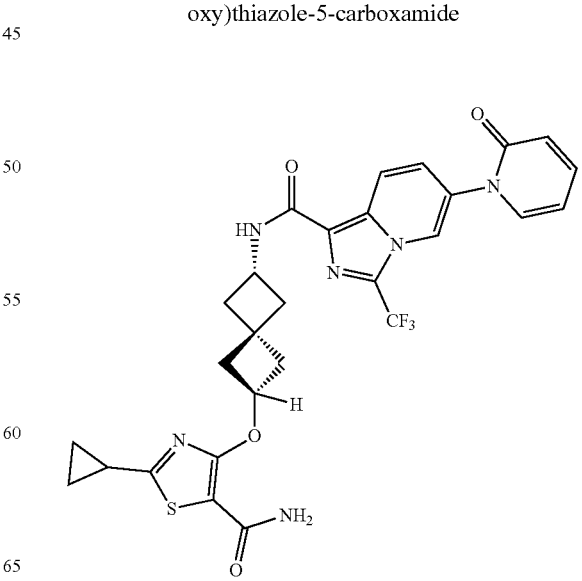

A mixture of pyridin-2(1H)-one (4.9 mg, 0.051 mmol) and anhydrous copper(II) acetate (4.7 mg, 0.026 mmol) was dissolved in dry DMSO (1.0 mL). The reaction mixture was sequentially treated with example 3e (15 mg, 0.026 mmol) and DBU (7.68 μl, 0.051 mmol). The vial was sealed and the mixture was heated for 1 h at 140° C. in an oil bath. The reaction mixture was allowed to cool to ambient temperature, diluted with methanol and filtered through celite. The mixture was further diluted with MeOH and purified by preparative HPLC (Method C) to afford Example 3 (2.0 mg, 13%) as a clear glass. MS (ESI) m/z: 599.1. $^1$H NMR (500 MHz, DMSO-d6) δ 8.85 (s, 1H), 8.56 (br d, J=8.2 Hz, 1H), 8.36 (br d, J=9.8 Hz, 1H), 7.77 (br d, J=6.4 Hz, 1H), 7.59 (br t, J=7.5 Hz, 1H), 7.53-7.42 (m, 2H), 6.80 (br s, 1H), 6.55 (br d, J=9.2 Hz, 1H), 6.40 (br t, J=6.7 Hz, 1H), 5.07 (br t, J=7.0 Hz, 1H), 4.56-4.35 (m, 1H), 2.69-2.59 (m, 1H), 2.47-2.16 (m, 7H), 1.23-1.10 (m, 2H), 0.99 (br s, 2H)

Example 4. Preparation of N-((aR)-6-((4-Carbamoyl-1-methyl-1H-pyrazol-3-yl)oxy)spiro[3.3]heptan-2-yl)-6-(3,3,3-trifluoropropoxy)pyrazolo[1,5-a]pyridine-3-carboxamide

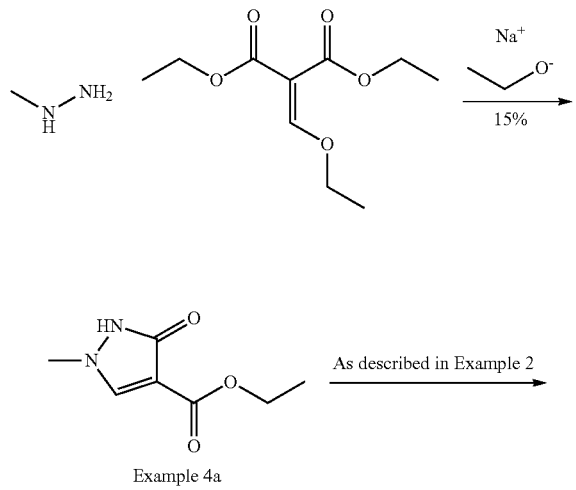

Example 4a

Example 4A. Ethyl 1-methyl-3-oxo-2,3-dihydro-1H-pyrazole-4-carboxylate

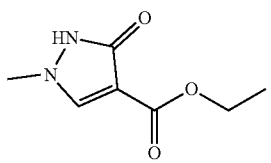

Sodium ethoxide (21% in EtOH, 4.66 mL, 12.5 mmol), diethylethoxymethylenemalonate (1.26 mL, 6.24 mmol) and methylhydrazine (0.33 mL, 6.24 mmol) were combined in a microwave tube and capped. The solution was heated by microwave irradiation at 60° C. for 2 h. After cooling to rt, the reaction mixture was combined with 2N HCl solution (25 mL). The resulting solids were filtered and washed cold water to afford Example 4A (0.16 g, 15% yield). MS (ESI) m/z: 171.0. $^1$H NMR (500 MHz, CHLOROFORM-d) δ 7.54 (s, 1H), 4.32 (q, J=7.2 Hz, 2H), 3.76 (s, 3H), 1.35 (t, J=7.2 Hz, 3H).

Example 4

Example 4 was prepared from Example 4A following a similar procedure as described for Example 2. MS (ESI) m/z: 507.2. $^1$H NMR (500 MHz, DMSO-d6) δ 8.52 (s, 1H), 8.44 (s, 1H), 8.30 (d, J=7.3 Hz, 1H), 8.08 (d, J=9.5 Hz, 1H), 7.88 (s, 1H), 7.31-7.19 (m, 1H), 7.06 (br. s., 1H), 6.55 (br. s., 1H), 4.87 (t, J=7.0 Hz, 1H), 4.42-4.32 (m, 1H), 4.28 (t, J=5.6 Hz, 2H), 3.67 (s, 3H), 2.86-2.76 (m, 2H), 2.65-2.58 (m, 1H), 2.47-2.37 (m, 2H), 2.36-2.28 (m, 1H), 2.26-2.09 (m, 4H)

Example 5. Preparation of N-(aR)-6-((4-Carbamoyl-1-(cyclopropylmethyl)-1H-pyrazol-3-yl)oxy)spiro[3.3]heptan-2-yl)-7-cyclopropyl-6-(2-hydroxy-2-methylpropoxy)pyrazolo[1,5-a]pyridine-3-carboxamide

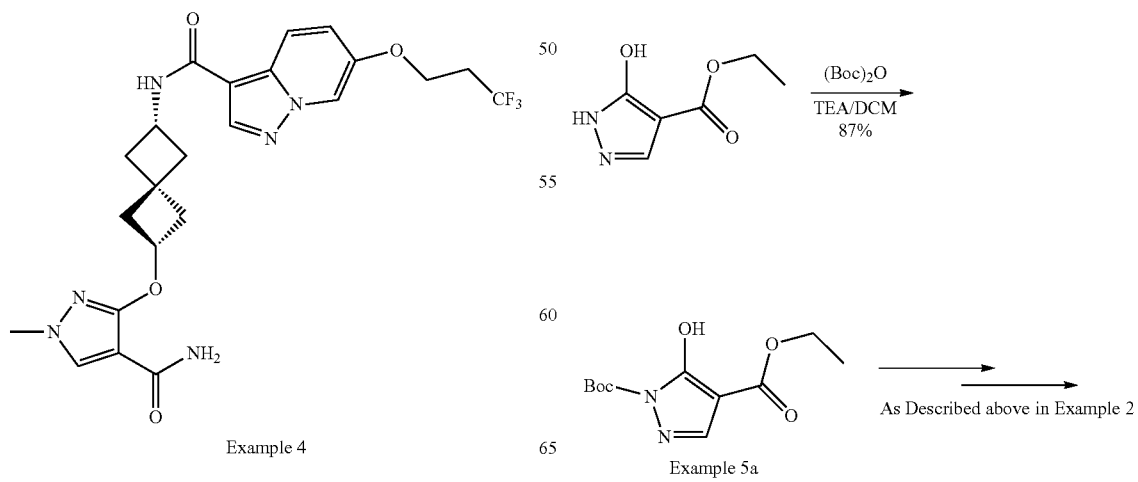

Example 5a

-continued

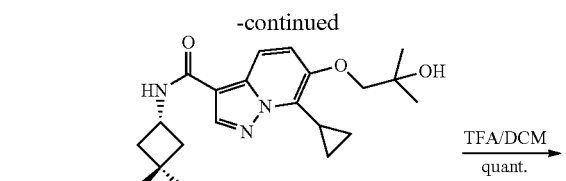

Example 5b

TFA/DCM
quant.

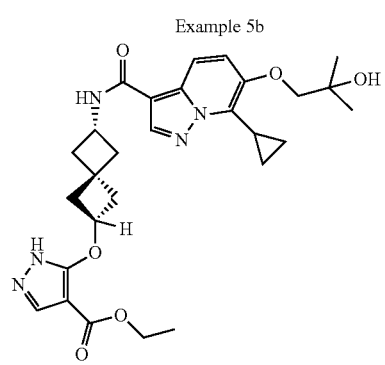

Example 5c

1. Br-△
2. LiOH
3. NH₃, BOP
31%

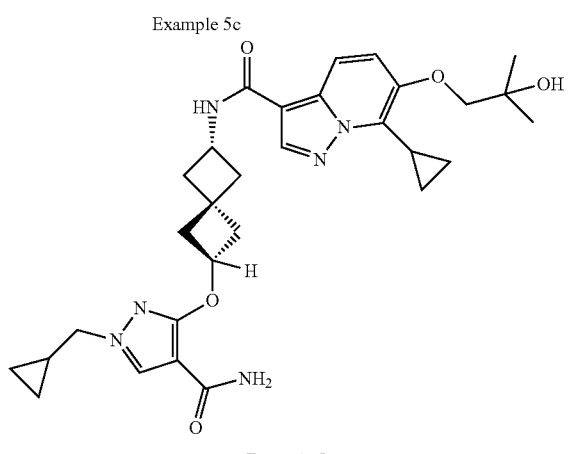

Example 5

Example 5A. 1-(tert-Butyl) 4-ethyl 5-hydroxy-1H-pyrazole-1,4-dicarboxylate

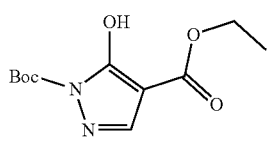

To a suspension of ethyl 5-hydroxy-1H-pyrazole-4-carboxylate (0.5 g, 3.20 mmol) in dichloromethane (10 mL), was added a solution of Boc-anhydride (0.743 mL, 3.20 mmol) and Et₃N (0.491 mL, 3.52 mmol) at rt. After 3 h, the reaction was concentrated in vacuo and the resulting solid was triturated in ether to give Example 5A (717 mg, 87% yield) as a white solid. MS (ESI) m/z: 257.1. ¹H NMR (500 MHz, Chloroform-d) δ 8.33 (s, 1H), 4.36 (q, J=7.2 Hz, 2H), 1.65 (s, 9H), 1.37 (t, J=7.2 Hz, 3H).

Example 5B. 1-(tert-Butyl) 4-ethyl 5-(((aR)-6-(7-cyclopropyl-6-(2-hydroxy-2-methylpropoxy)pyrazolo[1,5-a]pyridine-3-carboxamido)spiro[3.3]heptan-2-yl)oxy)-1H-pyrazole-1,4-dicarboxylate

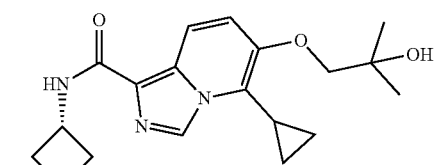

Example 5B was prepared from Example 5A following a similar procedure as described for Example 2 (120 mg, 53%). MS (ESI) m/z: 638.3.

Example 5C. Ethyl 5-(((aR)-6-(7-cyclopropyl-6-(2-hydroxy-2-methylpropoxy)pyrazolo[1,5-a]pyridine-3-carboxamido)spiro[3.3]heptan-2-yl)oxy)-1H-pyrazole-4-carboxylate A solution of Example 5B (100 mg, 0.157 mmol) in TFA (1 ml, 13.0 mmol) and dichloromethane (1 mL) was stirred at rt for 1 h. The reaction was concentrated and coevaporated with toluene (2×) to afford Example 5C (110 mg, 100%) that was used in the next step without further purification. MS (ESI) m/z: 538.3.

Example 5

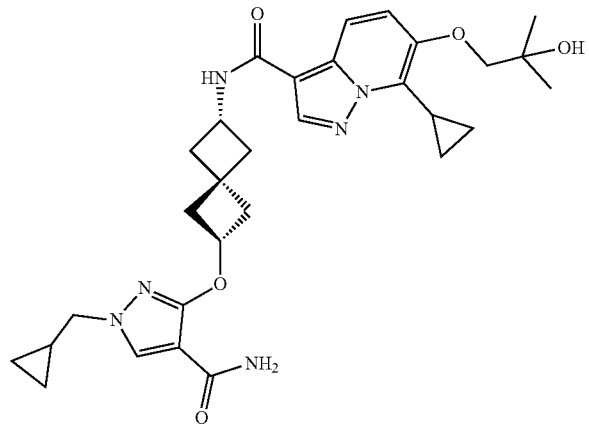

Example 5C (25 mg, 0.047 mmol), cesium carbonate (31.8 mg, 0.098 mmol) and (bromomethyl)cyclopropane (9.02 µL, 0.093 mmol) were combined in DMF (1 mL) and stirred at rt for 16 h. The reaction was poured into water ice and extracted with EtOAc (2×). The organics were pooled together, dried over $Na_2SO_4$, filtered and concentrated. The resultant gummy solid was dissolved in THF (1.0 mL) and MeOH (1.0 mL) and treated with LiOH (1 N, aq.) (0.47 mL, 0.47 mL). The reaction was heated at 50° C. for 16 h. After cooling to rt, the solvent was removed. The residue was suspended in water (~10 mL), EtOAc (10 mL) was added, and the mixture was slowly acidified with HCl (1 M aq.) (1.568 mL, 1.568 mmol) (pH ~3.0). The organic phase was separated and the aq. phase was extracted with EtOAc (2×). The combined organic fractions were washed with brine, dried ($Na_2SO_4$) and filtered. The solvent was removed in vacuo to afford a white solid that was dissolved in DMF (1.0 mL) and treated sequentially with BOP (24.7 mg, 0.056 mmol), DIEA (24 µL, 0.14 mmol) and ammonia (0.5M in dioxane, 0.5 mL, 0.250 mmol). After 1 h, the reaction was quenched with MeOH, filtered and purified on prep HPLC to afford Example 5 (8.4 mg, 31%) as a white solid. MS (ESI) m/z: 563.5. $^1$H NMR (500 MHz, DMSO-$d_6$) δ 8.48 (s, 1H), 8.27 (br d, J=7.6 Hz, 1H), 8.02 (d, J=−9.8 Hz, 1H), 7.95 (s, 1H), 7.45 (d, J=9.8 Hz, 1H), 7.06 (br s, 1H), 6.57 (br s, 1H), 4.89 (quin, J=7.0 Hz, 1H), 4.41-4.30 (m, 1H), 3.82-3.75 (m, 3H), 3.17 (d, J=4.9 Hz, 1H), 2.99 (s, 1H), 2.66-2.57 (m, 2H), 2.47-2.37 (m, 2H), 2.36-2.28 (m, 1H), 2.26-2.09 (m, 4H), 1.52-1.41 (m, 2H), 1.24 (s, 6H), 1.20-1.13 (m, 1H), 1.06 (br dd, J=8.9, 2.1 Hz, 2H), 0.56-0.47 (m, 2H), 0.37-0.29 (m, 2H).

Example 6. Preparation of N-((aR-6-((3-Carbamoylpyrazolo[1,5-a]pyridin-2-yl)oxy)spiro[3.3]heptan-2-yl)-7-cyclopropyl-6-(7-hydroxy-2-methylpropoxy)pyrazolo[1,5-a]pyridine-3-carboxamide

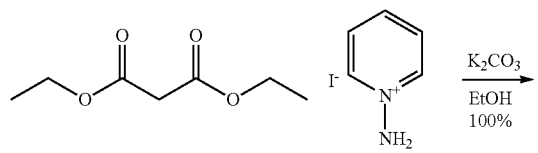

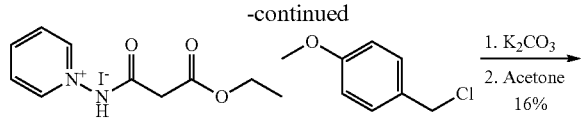

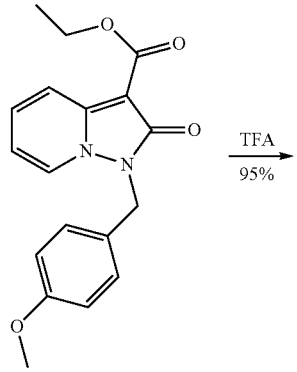

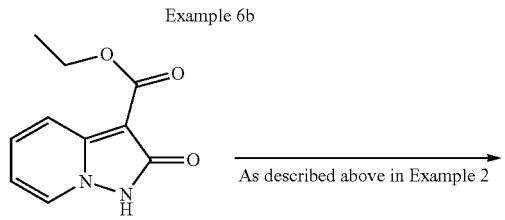

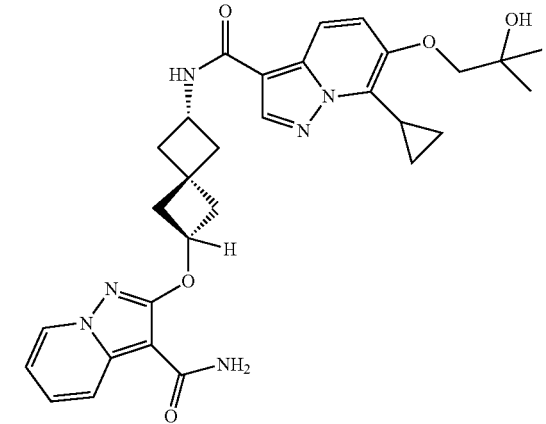

Example 6

Example 6A.
1-(3-Ethoxy-3-oxopropanamido)pyridin-1-ium iodide

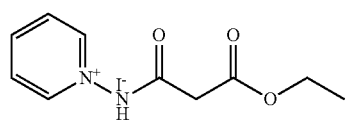

A mixture of 1-aminopyridin-1-ium iodide (0.75 g, 3.38 mmol), diethyl malonate (4.5 ml, 29.6 mmol) and $K_2CO_3$ (5.6 g, 40.5 mmol) in Ethanol (20 mL) were stirred at rt for 16 h. The reaction was filtered and the filtrate evaporated. The resultant solid was washed with hexane several times to remove residual ethyl malonate. The pink solid was dried under high vacuum to afford Example 6A (0.70 g, 100% yield). MS (ESI) m/z: 209.1. $^1$H NMR (400 MHz, CHLOROFORM-d) δ 8.84-8.65 (m, 2H), 8.08-7.86 (m, 1H), 7.69 (t, J=7.2 Hz, 2H), 4.26 (q, J=7.0 Hz, 2H), 3.42 (s, 2H), 1.34 (t, J=7.2 Hz, 3H).

Example 6B. Ethyl 1-(4-methoxybenzyl)-2-oxo-1,2-dihydropyrazolo[1,5-a]pyridine-3-carboxylate

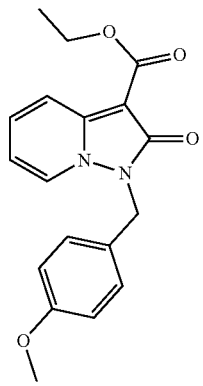 [SMILES: CCOC(=O)c1c(=O)n(Cc2ccc(OC)cc2)n2ccccc12]

A mixture of Example 6A (0.30 g, 1.44 mmol) and 1-(chloromethyl)-4-methoxybenzene (0.196 mL, 1.44 mmol) in acetone (5 mL) was treated with K$_2$CO$_3$ (0.458 g, 3.31 mmol) and stirred at 56° C. for 2 days. After cooling to rt, the reaction was filtered, concentrated and purified on silica geby flash chromatographyl (0-20% MeOH/DCM gradient) to afford Example 6B (0.077 g, 16% yield) as a brown foam. MS (ESI) m/z: 327.1. $^1$H NMR (500 MHz, CHLOROFORM-d) δ 8.09 (d, J=8.8 Hz, 1H), 7.76 (d, J=6.9 Hz, 1H), 7.38 (ddd, J=8.9, 7.4, 1.1 Hz, 1H), 7.23-7.15 (m, 2H), 6.87-6.78 (m, 2H), 6.70 (td, J=7.0, 1.4 Hz, 1H), 5.33 (s, 2H), 4.39 (q, J=7.2 Hz, 2H), 3.75 (s, 3H), 1.42 (t, J=7.0 Hz, 3H).

Example 6C. Ethyl 2-oxo-1,2-dihydropyrazolo[1,5-a]pyridine-3-carboxylate

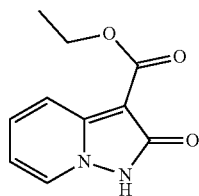

Example 6B (95 mg, 0.291 mmol) was combined with TFA (0.5 mL, 6.49 mmol) and stirred at rt for 16 h. The TFA was evaporated. The resulting solid was dissolved in EtOAc and washed with NaHCO$_3$. The organic layer was dried over sodium sulfate, filtered, concentrated and purified via flash chromatography (0-10% MeOH/DCM gradient) to afford Example 6C (57 mg, 95%) as a brown oil. MS (ESI) m/z: 207.8. $^1$H NMR (500 MHz, CHLOROFORM-d) δ 9.08 (br s, 1H), 8.36 (dt, J=6.7, 1.0 Hz, 1H), 7.77 (d, J=8.8 Hz, 1H), 7.42 (ddd, J=8.6, 7.1, 1.1 Hz, 1H), 6.94-6.89 (m, 1H), 4.46 (q, J=7.2 Hz, 2H), 1.46 (t, J=7.2 Hz, 3H).

Example 6

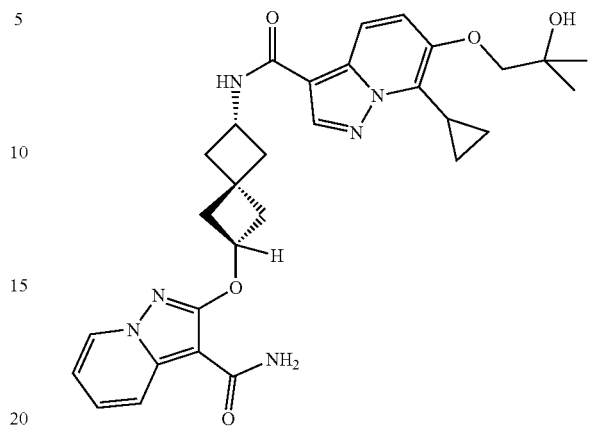

Example 6 was prepared from Example 6C following a similar procedure as described for Example 2 (120 mg, 53%). MS (ESI) m/z: 559.4. $^1$H NMR (500 MHz, DMSO-d6) δ 8.58 (d, J=7.0 Hz, 1H), 8.50 (s, 1H), 8.28 (br d, J=7.6 Hz, 1H), 8.08-7.98 (m, 2H), 7.50-7.39 (m, 2H), 7.12 (br s, 1H), 6.97 (br t, J=6.9 Hz, 1H), 6.60 (br s, 1H), 5.12 (quin, J=6.9 Hz, 11), 4.44-4.31 (m, 1H), 3.79 (s, 2H), 2.71 (dt, J=11.4, 5.9 Hz, 1H), 2.64-2.57 (m, 1H), 2.48-2.42 (m, 1H), 2.41-2.25 (m, 3H), 2.22-2.12 (m, 2H), 1.51-1.43 (m, 2H), 1.24 (s, 6H), 1.09-1.02 (m, 2H).

Example 7. Preparation of 2-(((aR)-6-(7-Cyclopropyl-6-(2-hydroxy-2-methylpropoxy)pyrazolo[1,5-a]pyridine-3-carboxamido)spiro[3.3]heptan-2-yl)oxy)-1,8-naphthyridine-3-carboxamide

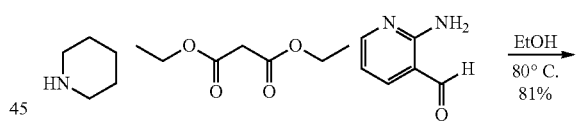

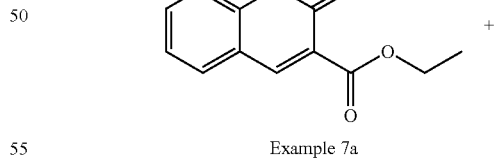

Example 7a

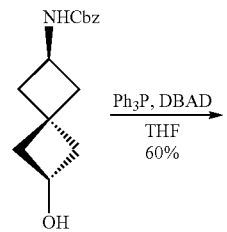

-continued

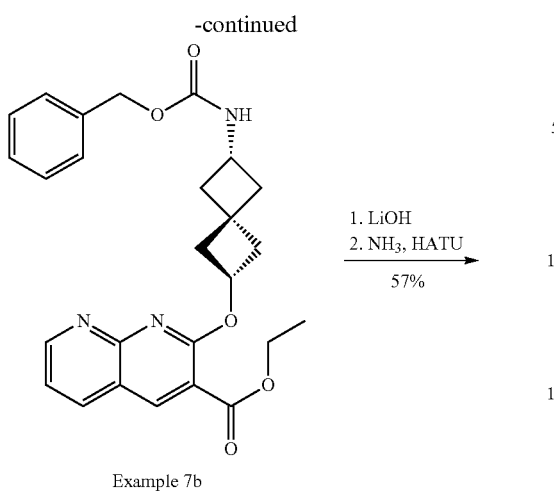
Example 7b

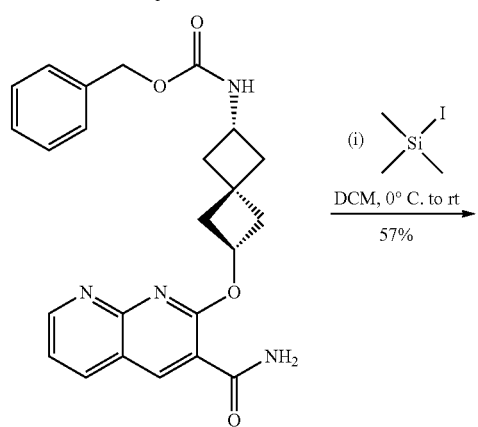
Example 7c

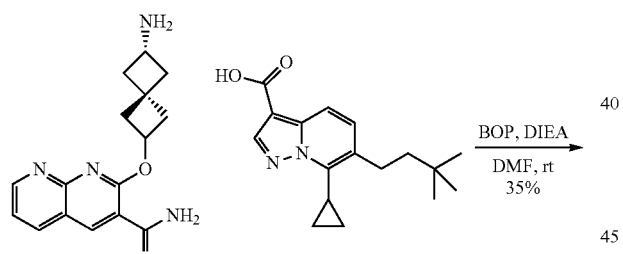
Example 7d

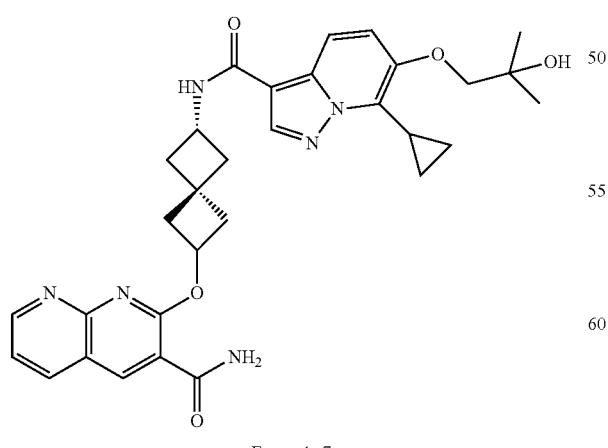
Example 7

Example 7A. Ethyl 2-oxo-1,2-dihydro-1,8-naphthyridine-3-carboxylate

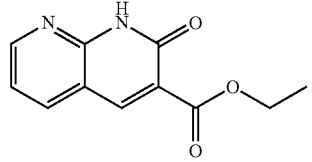 [SMILES: CCOC(=O)c1cc2cccnc2[nH]c1=O]

2-Aminonicotinaldeyde (500 mg, 4.09 mmol), diethyl malonate (0.932 mL, 6.14 mmol) and piperidine (0.121 mL, 1.228 mmol) were combined with EtOH (7 mL) in a microwave tube and sealed. The reaction mixture was heated via microwave irradiation at 80° C. for 6 h. The reaction precipitate was collected, washed with ethanol and dried to afford Example 7A (721 mg, 81% yield). MS (ESI) m/z: 219.0. $^1$H NMR (400 MHz, DMSO-$d_6$) δ 12.43 (s, 1H), 8.61 (dd, J=4:6, 1.8 Hz, 1H), 8.50 (s, 1H), 8.27 (dd, J=7.8, 1.9 Hz, 1H), 7.30 (dd, J=7.7, 4.6 Hz, 1H), 4.29 (q, J=7.0 Hz, 2H), 1.31 (t, J=7.0 Hz, 3).

Example 7B. Preparation of ethyl 2-(((aR)-6-(((benzyloxy)carbonyl)amino)spiro[3.3]heptan-2-yl)oxy)-1,8-naphthyridine-3-carboxylate

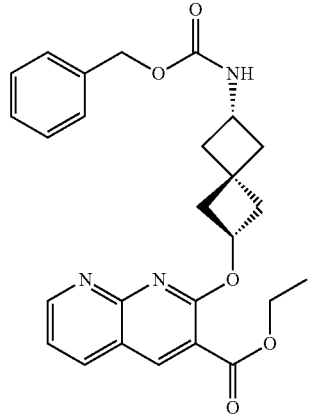

To a stirred solution of ethyl 2-oxo-1,2-dihydro-1,8-naphthyridine-3-carboxylate (84 mg, 0.383 mmol), benzyl((aS)-6-hydroxyspiro[3.3]heptan-2-yl)carbamate (100 mg, 0.383 mmol) and triphenylphosphine (3 mmol/g resin, 381 mg, 1.15 mmol) in THF (2 mL) at rt was added di-tert-butylazodicarboxylate (270 mg, 1.15 mmol). The resulting solution was stirred at 50° C. for 4 h. After cooling to t, the reaction was filtered, washed with ethyl acetate and concentrated. The crude product was purified via flash chromatography (0-100% EtOAc/hexanes gradient) to afford Example 7B (97 mg, 55%). MS (ESI) m/z: 462.1.

Example 7C. Benzyl ((aR)-6-((3-carbamoyl-1,8-naphthyridin-2-yl)oxy)spiro[3.3]heptan-2-yl)carbamate

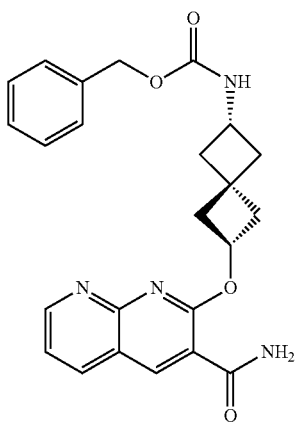

Example 7C was prepared from Example 7B following a similar procedure as described for Example 2B (120 mg, 53%). MS (ESI) m/z: 433.1.

Example 7D. 2-(((aR)-6-Aminospiro[3.3]heptan-2-yl)oxy)-1,8-naphthyridine-3-carboxamide

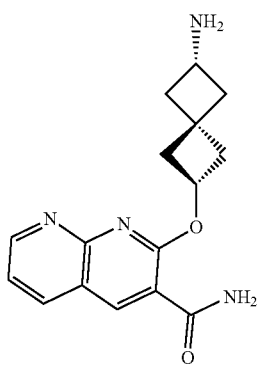

Example 7C (22 mg, 0.051 mmol) was dissolved in DCM (1 mL). The reaction mixture was cooled to 0° C. and treated with iodotrimethylsilane (0.021 mL, 0.153 mmol). After 5 min the cooling bath was removed and the reaction was further stirred at rt for 30 min. The reaction mixture was cooled to 0° C., and carefully quenched with MeOH (5 mL), volatiles were removed under reduced pressure to give Example 7D (26 mg, 92%) as an orange film which was used as is in the the next step. MS (ESI) m/z: 299.1.

Example 7

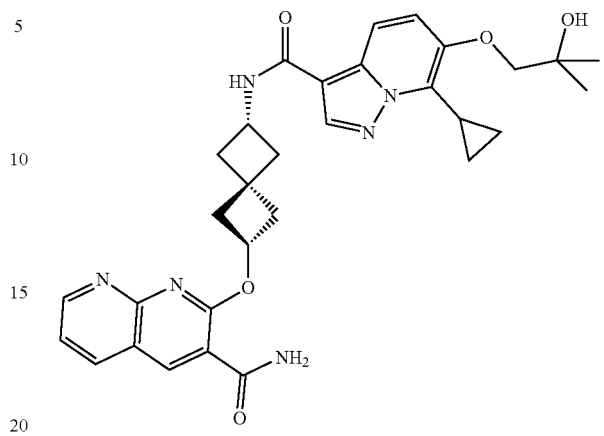

Example 7 was prepared from Example 7D following a similar procedure as described for Example 2. MS (ESI) m/z: 571.4. $^1$H NMR (500 MHz, DMSO-d6) δ 8.96 (br d, J=2.4 Hz, 1H), 8.71 (s, 1H), 8.51 (s, 1H), 8.47 (dd, J=7.9, 1.5 Hz, 1H), 8.29 (br d, J=7.6 Hz, 1H), 8.04 (d, J=9.8 Hz, 1H), 7.81 (br d, J=3.1 Hz, 2H), 7.52 (dd, J=7.9, 4.3 Hz, 1H), 7.46 (d, J=9.5 Hz, 1H), 5.40 (quin, J=7.2 Hz, 1H), 4.46-4.35 (m, 1H), 3.79 (s, 2H), 2.81-2.71 (m, 1H), 2.64-2.57 (m, 2H), 2.43-2.13 (m, 5H), 1.47 (dd, J=5.5, 2.1 Hz, 2H), 1.24 (s, 6H), 1.10-1.02 (m, 2H).

Example 8. Preparation of 2-(((aR)-6-(7-Cyclopropyl-6-(2-hydroxy-2-methylpropoxy)pyrazolo[1,5-a]pyridine-3-carboxamido)spiro[3.3]heptan-2-yl)oxy)-5,6,7,8-tetrahydro-1,8-naphthyridine-3-carboxamide

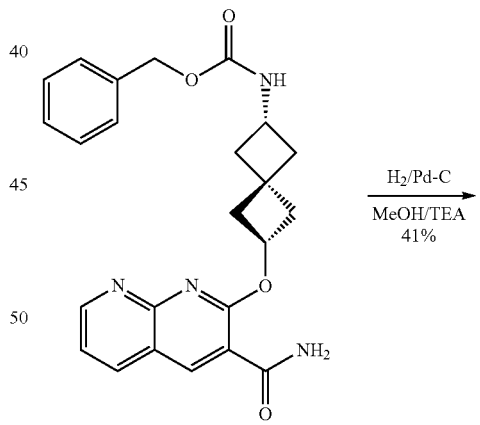

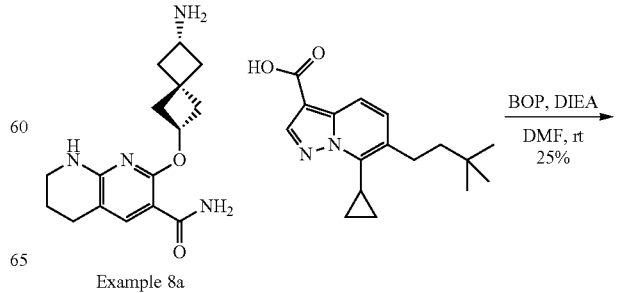

Example 8a

99
-continued

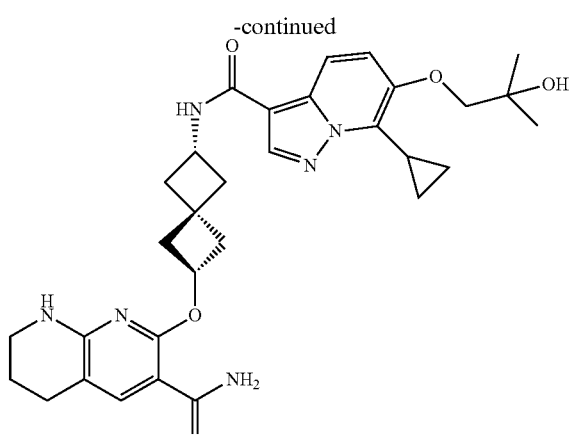

Example 8

100
Example 8

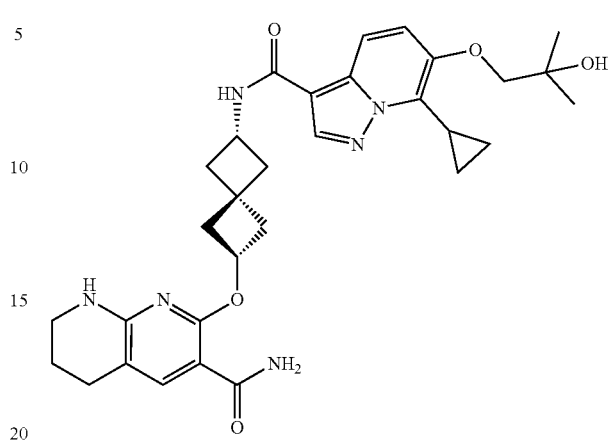

Example 8A. 2-(((aR)-6-Aminospiro[3.3]heptan-2-yl)oxy)-5,6,7,8-tetrahydro-1,8-naphthyridine-3-carboxamide Example 8 was prepared from Example 8A following a similar procedure as described for Example 2. MS (ESI) m/z: 575.3. ¹H NMR (500 MHz, DMSO-d6) δ 8.50 (s, 1H), 8.26 (br d, J=7.6 Hz, 1H), 8.03 (d, J=9.8 Hz, 1H), 7.68 (s, 1H), 7.46 (d, J=9.5 Hz, 1H), 7.23 (br s, 1H), 7.10-6.98 (m, 2H), 5.12 (quin, J=7.2 Hz, 1H), 4.44-4.31 (m, 1H), 3.79 (s, 1H), 3.26 (br s, 1H), 2.70-2.62 (m, 1H), 2.62-2.57 (m, 2H), 2.49-2.38 (m, 2H), 2.37-2.29 (m, 1H), 2.25-2.09 (m, 3H), 1.75 (br s, 2H), 1.48 (br d, J=3.4 Hz, 2H), 1.28-1.17 (m, 6H), 1.06 (br dd, J=8.7, 2.3 Hz, 2H)

Example 9. Preparation of 5-((6-(4-(Trifluoromethyl)cyclohexane-1-carboxamido)spiro[3.3]heptan-2-yl)oxy)thieno[3,2-b]pyridine-6-carboxamide

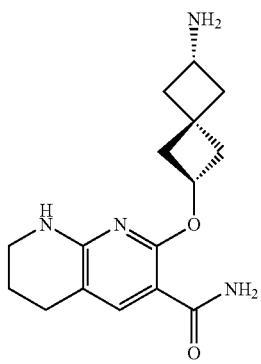

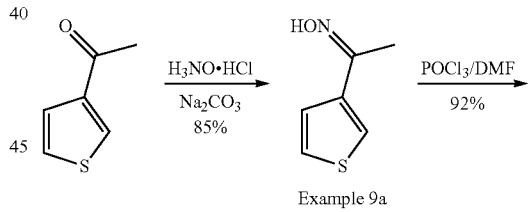

Example 9a

Example 7C (104 mg, 0.240 mmol) was dissolved in THF (2 mL), MeOH (2 mL), and TEA (0.168 mL, 1.20 mmol) under nitrogen. 10% Pd—C(25.6 mg, 0.024 mmol) was added and the reaction stirred under a balloon of hydrogen for 3 h. The reaction was filtered and concentrated to afford Example 8A (100 mg, 41%) as an off white foam. MS (ESI) m/z: 303.1. ¹H NMR (500 MHz, METHANOL-d₄) δ 7.76 (s, 1H), 5.21 (t, J=7.0 Hz, 1H), 3.72 (t, J=8.1 Hz, 1H), 2.78-2.70 (m, 1H), 2.68 (t, J=6.2 Hz, 2H), 2.63-2.49 (m, 2H), 2.44 (ddd, J=12.2, 7.4, 5.0 Hz, 1H), 2.32-2.19 (m, 4H), 1.91-1.81 (m, 2H).

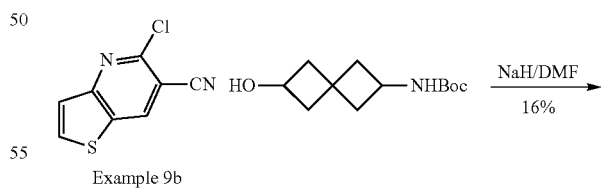

Example 9b

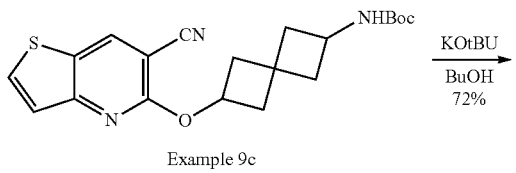

Example 9c

-continued

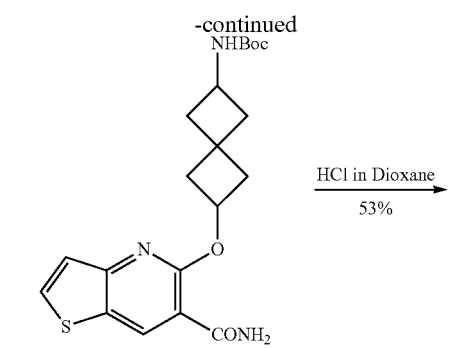
Example 9d

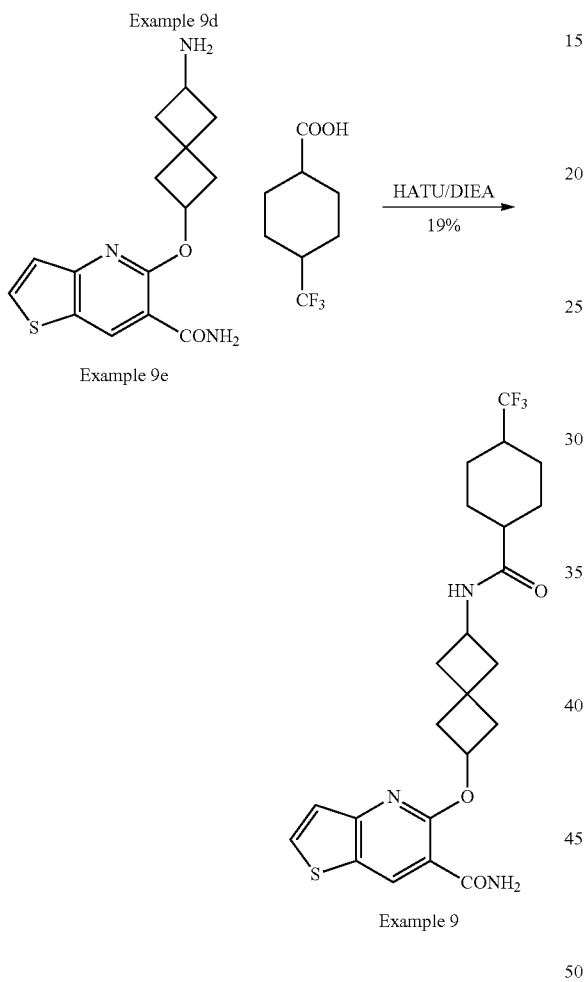
Example 9e

Example 9

Example 9A. (Z)-1-(Thiophen-3-yl)ethan-1-one oxime

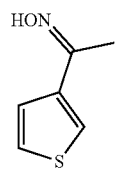

To a stirred solution of hydroxylamine hydrochloride (5.51 g, 79 mmol) in ethanol (100 mL), 1-(thiophen-3-yl)ethan-1-one (5 g, 39.6 mmol) in ethanol (30 mL) was added dropwise over 5 min, followed by Na$_2$CO$_3$ (4.20 g, 39.6 mmol) in water (20 mL) over 5 min. The reaction was heated to 65° C. for 12 h. After cooling to rt, the reaction mixture was evaporated to afford a dark brown residue. The residue was partitioned between water (100 mL) and ether (150 mL). The organic layer was separated, dried over sodium sulphate and concentrated pressure to afford Example 9A (5.0 g, 85%) as yellow solid.

Example 9B. 5-Chlorothieno[3,2-b]pyridine-6-carbonitrile

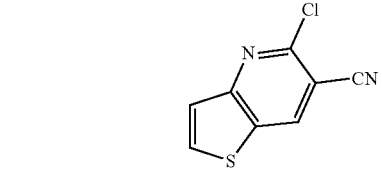 [SMILES: N#Cc1cc2sccc2nc1Cl]

To POCl$_3$ (19.80 mL, 212 mmol) at 10° C., DMF (4.11 mL, 53.1 mmol) was added dropwise for 10 min and stirred at rt for 10 min. Example 9A (3.0 g, 21.3 mmol) in DMF (3 mL) was added dropwise and the reaction was heated to 110° C. for 2 h. The reaction was cooled to rt and treated with hydroxylamine hydrochloride (2.95 g, 42.5 mmol) portionwise over 10 min. The reaction was stirred at 110° C. for 30 min. After cooling to rt, the reaction was poured onto ice cubes (200 g) and stirred for 10 min. The resultant yellow precipitate was collected by filtration and dried to afford Example 9B (1.0 g, 22%). MS (ES): m/z=195.0 [M+H]$^+$ Example 9C. tert-Butyl (6-((6-cyanothieno[3,2-b]pyridin-5-yl)oxy)spiro[3.3]heptan-2-yl)carbamate

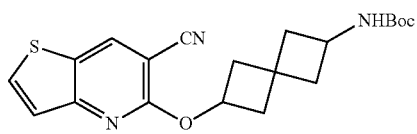 [SMILES: CC(C)(C)OC(=O)NC1CC2(C1)CC(Oc1nc3ccsc3cc1C#N)C2]

To a stirred solution of tert-butyl (6-hydroxyspiro[3.3]heptan-2-yl)carbamate (17.5 mg, 0.077 mmol) in DMF (1 mL) at 0° C., was added NaH (9.3 mg, 0.231 mmol). The reaction was stirred at 0° C. for 10 min and treated with Example 9B (15 mg, 0.077 mmol) in DMF (0.5 mL) over 10 min. After 5 h, the reaction mixture was partitioned between water (10 mL) and ethyl acetate (10 mL). The organic layer was separated, dried over sodium sulphate and concentrated. The crude product was purified by flash chromatography (MeOH/DCM) to afford Example 9C (5.0 mg, 17%) as a yellow solid. MS (ES): m/z=403.2 [M+18]$^+$

Example 9D. tert-Butyl (6-((6-carbamoylthieno[3,2-b]pyridin-5-yl)oxy)spiro[3.3]heptan-2-yl)carbamate

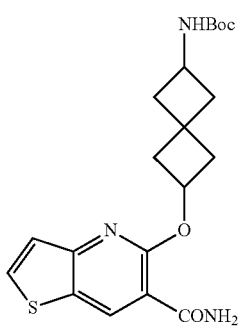 [SMILES: CC(C)(C)OC(=O)NC1CC2(C1)CC(Oc1nc3ccsc3cc1C(N)=O)C2]

To a stirred solution of Example 9C (400 mg, 1.04 mmol) in BuOH (8 mL), was added Kot-Bu (582 mg, 5.19 mmol). The mixture was stirred at rt for 16 h. The reaction mixture was evaporated. The residue was partitioned between water (100 mL) and ethyl acetate (150 mL). The organic layer was separated, dried over sodium sulphate and concentrated to afford the Example 9D (300 mg, 72%) as an orange semi-solid. MS (ES): m/z=404.5 [M+H]$^+$

Example 9E. 5-((6-aminospiro[3.3]heptan-2-yl)oxy)thieno[3,2-b]pyridine-6-carboxamide

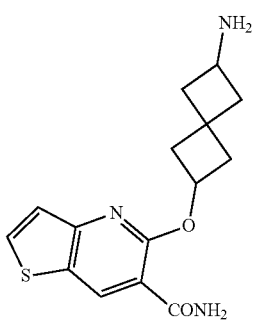 [SMILES: NC(=O)c1cc2sccc2nc1OC1CC2(CC(N)C2)C1]

To the stirred Example 9D (300 mg, 0.743 mmol) in DCM (5 mL) at rt, was added HCl (4M in 1,4-dioxane, 1.86 mL, 7.43 mmol). The reaction was stirred at rt for 5 h. The reaction mixture was evaporated to dryness under reduced pressure to afford the Example 9E (120 mg, 53%) as a brown semisolid.

Example 9

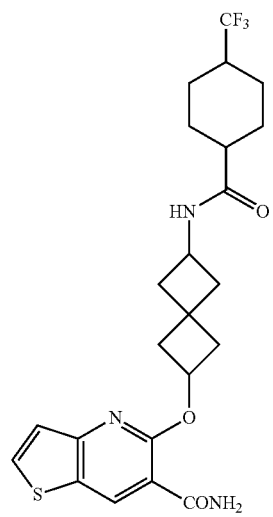 [SMILES: NC(=O)c1cc2sccc2nc1OC1CC2(CC(NC(=O)C3CCC(C(F)(F)F)CC3)C2)C1]

Example 9E (20 mg, 0.066 mmol) and 4-(trifluoromethyl)cyclohexane-1-carboxylic acid (12.9 mg, 0.066 mmol) in DMF (1 mL) was treated with HATU (25.1 mg, 0.066 mmol) and DIPEA (0.035 mL, 0.198 mmol) at rt. After 2 h, the reaction was purified by prep HPLC to afford Example 9 (6.2 mg, 19%). MS (ES): m/z=428.2 [M+H]$^+$. $^1$H NMR (400 MHz, DMSO-d6) δ 8.79 (s, 1H), 8.19 (d, J=5.4 Hz, 1H), 7.92 (d, J=7.6 Hz, 1H), 7.68 (br. s., 2H), 7.42 (d, J=5.6 Hz, 1H), 5.25 (t, J=7.1 Hz, 1H), 4.15-4.08 (m, 1H), 2.68-2.62 (m, 1H), 2.37 (d, J=11.7 Hz, 1H), 2.30-2.15 (m, 5H), 2.02-1.92 (m, 2H), 1.91-1.79 (m, 3H), 1.60 (br. s., 4H), 1.52-1.41 (m, 2H).

Example 10. Preparation of 1-Cyclopropyl-3-(((aR)-6-(4-isobutyl-2,5-dioxoimidazolidin-1-yl)spiro[3.3]heptan-2-yloxy)-1H-pyrazole-4-carboxamide

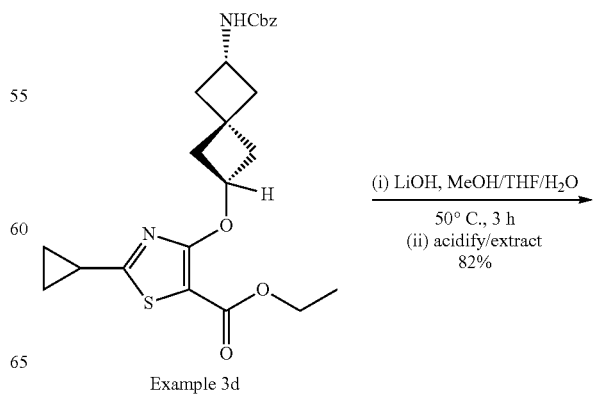

Example 3d

-continued

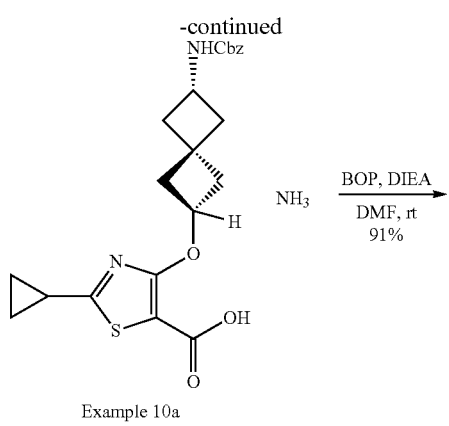
Example 10a

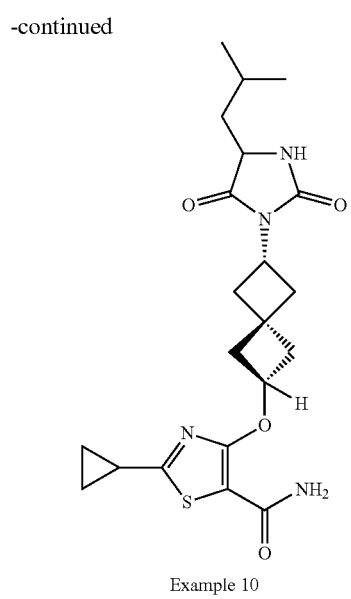
Example 10

Example 10A. 4-(((aR)-6-(((benzyloxy)carbonyl)amino)spiro[3.3]heptan-2-yl)oxy)-2-cyclopropylthiazole-5-carboxylic acid

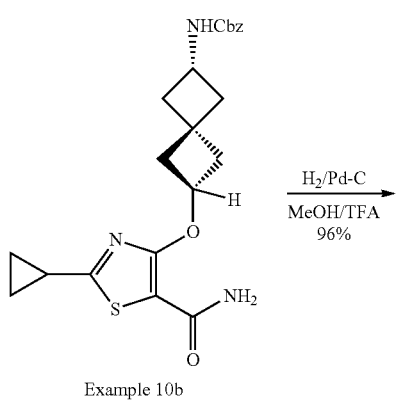
Example 10b

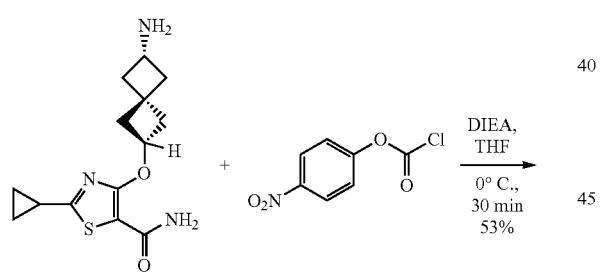
Example 10c

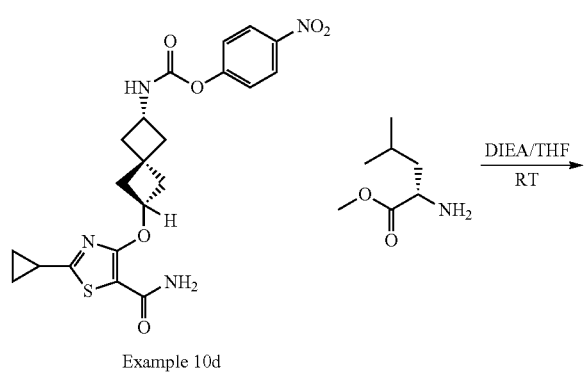
Example 10d

Example 3D (547 mg, 1.198 mmol) was dissolved in MeOH (5 mL)/THF (5 mL), and LiOH (1 M aq.) (3.59 mL, 3.59 mmol) was added. The reaction mixture was stirred at 50° C. for 3 h. After cooling to rt, the solvent was removed under reduced pressure and the residue was suspended in water (~10 mL) and EtOAc (10 mL). The mixture was acidified with HCl (1 M aq.) (3.59 mL, 3.59 mmol) (pH ~3.0). The organic phase was separated. The aq. phase was extracted with EtOAc (2×). The combined organic fractions were washed with brine, dried ($Na_2SO_4$) and filtered. EtOAc was removed under reduced pressure to afford Example 10A (420 mg, 82% yield) as an off-white solid. MS (ES): m/z=429.1 [M+H]$^+$

Example 10B. Benzyl ((aR)-6-((-carbamoyl-2-cyclopropylthiazol-4-yl)oxy)spiro[3.3]heptan-2-yl)carbamate

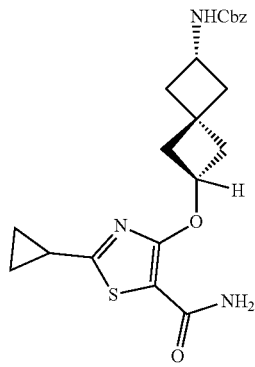

Example 10A (420 mg, 0.980 mmol) was dissolved in anhydrous DMF (6.0 mL), then ammonia (7.0 M in MeOH) (0.420 mL, 2.94 mmol) and DIEA (0.856 mL, 4.90 mmol) were added, followed by BOP (564 mg, 1.27 mmol). The reaction mixture was stirred at rt for 1 h. The reaction mixture was was poured in brine solution and extracted with EtOAc (2×). The combined organic extracts were dried over sodium sulfate, filtered and concentrated. The crude product was purified via flash chromatography (0-100% EtOAc gradient) to afford Example 10B (380 mg, 91% yield) as a white solid. MS (ES): m/z=428.1 [M+H]+

Example 10C. 4-(((aR)-6-Aminospiro[3.3]heptan-2-yl)oxy)-2-cyclopropylthiazole-5-carboxamide

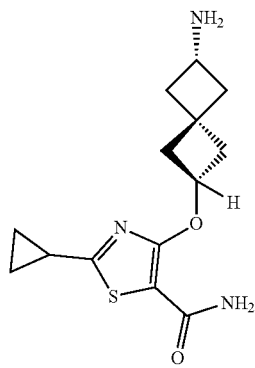

Example 10B (380 mg, 0.889 mmol) was dissolved in THF (2 mL) and MeOH (2 mL), then TFA (0.619 mL, 4.44 mmol) was added. 10% Pd—C(95 mg, 0.089 mmol) was added and the reaction stirred under hydrogen (balloon) for 2 h. The reaction was filtered and the filtrate was concentrated to afford Example 10C (250 mg, 96%) as a clear glass. MS (ES): m/z=428.1 [M+H]+

Example 10D. 4-nitrophenyl ((aR)-6-((5-carbamoyl-2-cyclopropylthiazol-4-yl)oxy)spiro[3.3]heptan-2-yl)carbamate

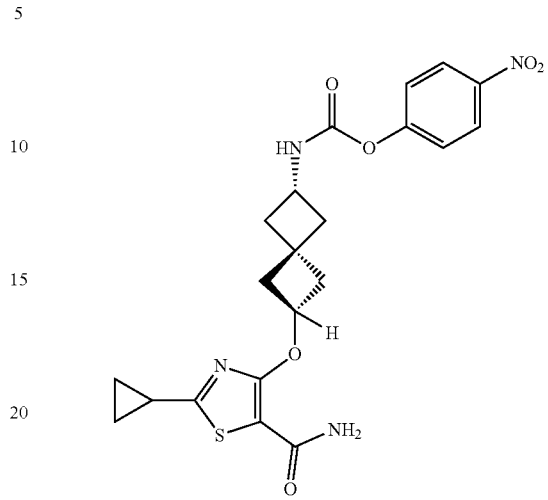

Example 10C (95 mg, 0.344 mmol) was suspended in anhydrous THF (5.0 mL), then DIEA (0.090 mL, 0.516 mmol) was added. The reaction mixture was cooled to 0° C., and treated with 4-nitrophenyl carbonochloridate (83 mg, 0.413 mmol). The reaction mixture was stirred at 0° C. for 30 min, filtered, and concentrated. The product was used as is in the subsequent step without further purification. MS (ES): m/z=459.1 [M+H]+

Example 10

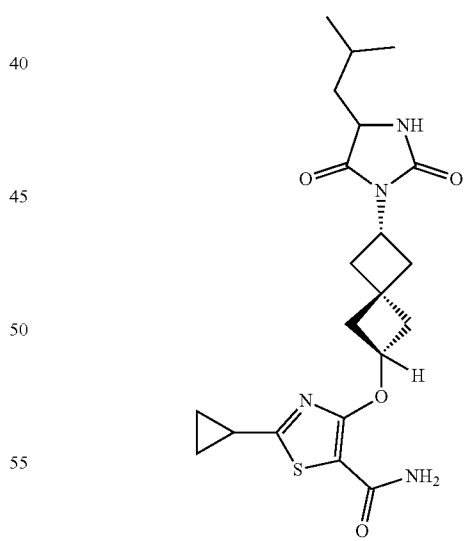

Methyl L-leucinate (14.9 mg, 0.103 mmol) and DIEA (0.072 mL, 0.41 mmol) was dissolved in anhydrous THF (0.5 mL), and Example 10D (47 mg, 0.1 mmol) was added. The reaction mixture was stirred at rt for 30 min. The reaction was partitioned between EtOAc and 1M K₂HPO₄. The organic layer was concentrated. The resultant yellow glass was dissolved in MeOH and treated with 4M sodium methoxide (0.034 mL, 0.147 mmol). The reaction was stirred at 50° C. for 16 h. After cooling to rt, the reaction was diluted with DMF, filtered and purified by preparative HPLC to afford Example 10 (11 mg, 26%) as a clear oil. MS (ES): m/z=433.1 [M+H]+. ¹H NMR (500 MHz, METHANOL-d₄) δ 5.16 (t, J=7.0 Hz, 1H), 4.47 (t, J=8.8 Hz, 1H), 4.02 (dd, J=9.1, 4.4 Hz, 1H), 3.03-2.88. (m, 2H), 2.78-2.52 (m, 2H), 2.43-2.20 (m, 5H), 1.91-1.75 (m, 1H), 1.66 (ddd, J=13.6, 8.9, 4.4 Hz, 1H), 1.49 (ddd, J=14.0, 8.9, 5.5 Hz, 1H), 1.20 (dd, J=8.0, 3.0 Hz, 2H), 1.14-1.05 (m, 2H), 0.97 (d, J=6.6 Hz, 7H).

Example 11. Preparation of 2-cyclopropyl-4-(((aR)-6-(6-(2,2-difluoroethoxy)pyrazolo[1,5-a]pyridine-3-carboxamido)spiro[3.3]heptan-2-yl)oxy)thiazole-5-carboxamide

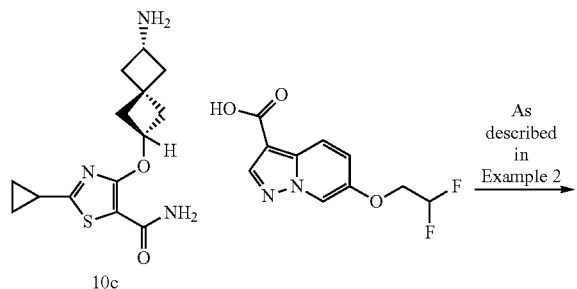

10c

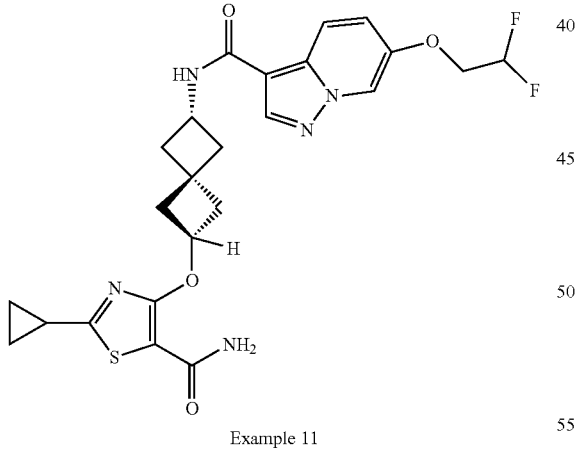

Example 11

Example 11 was prepared from Example 10C following a similar procedure as described for Example 2 (6 mg, 75%). MS (ESI) m/z: 518.2. ¹H NMR (500 MHz, METHANOL-d₄) δ 8.47-8.31 (m, 2H), 8.17 (d, J=9.6 Hz, 1H), 7.34 (dd, J=9.8, 2.1 Hz, 1H), 6.44-5.95 (m, 1H), 5.18 (t, J=7.0 Hz, 1H), 4.47 (t, =8.1 Hz, 1H), 4.35 (td, J=13.7, 3.7 Hz, 2H), 2.79-2.66 (m, 1H), 2.61-2.42 (m, 3H), 2.39-2.14 (m, 5H), 1.26-1.14 (m, 2H), 1.18-1.01 (m, 2H).

Example 12. Preparation of 6-(2-hydroxy-2-methyl-propoxy)-N-[(aR)-6-({3-carbamoyl-5H,7H,8H-pyrano[4,3-b]pyridin-2-yl}oxy)spiro[3.3]heptan-2-yl]pyrazolo[1,5-a]pyridine-3-carboxamide

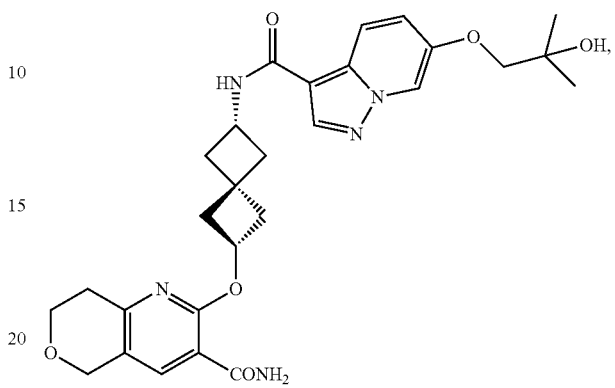

Example 12A. Benzyl ((aR)-6-((3-cyano-7,8-di-hydro-5H-pyrano[4,3-b]pyridin-2-yl)oxy)spiro[3.3]heptan-2-yl)carbamate

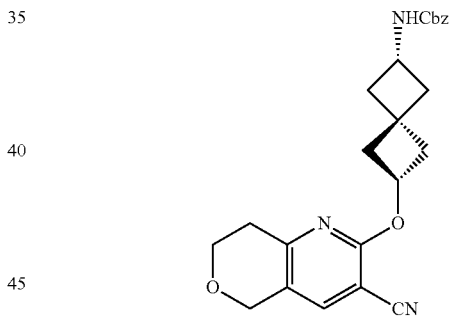

To a stirred solution of benzyl ((aR)-6-hydroxyspiro[3.3]heptan-2-yl)carbamate (2.01 g, 7.71 mmol) in THF (40 mL) at 0° C., 60% NaH (0.771 g, 19.3 mmol) was added portionwise over 10 min. The mixture was stirred for 10 min, then 2-chloro-7,8-dihydro-5H-pyrano[4,3-b]pyridine-3-carbonitrile (1.5 g, 7.71 mmol) was added and the mixture was stirred at rt for 12 h. The reaction mixture was cooled to 0° C., and MeOH (10 mL) was added dropwise over 10 min. The mixture was stirred for 5 min. The reaction mixture was evaporated to dryness and the residue was partitioned between water (200 mL) and ethyl acetate (250 mL). The organic layer was separated, dried over sodium sulphate and concentrated under reduced pressure to afford Example 12A (2.5 g, 44% yield) as a brown semisolid. MS (ESI) m/z: 518.2.

Example 12B. Benzyl ((2S,4s,6S)-6-((3-carbamoyl-7,8-dihydro-5H-pyrano[4,3-b]pyridin-2-yl)oxy)spiro[3.3]heptan-2-yl)carbamate

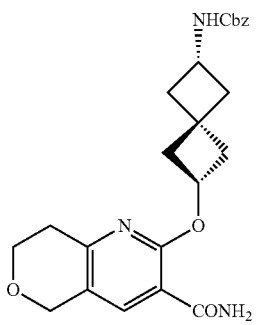

To the stirred solution of Example 12A (2 g, 4.77 mmol) in DMSO (1 mL) at 10° C., 50% $H_2O_2$ (2.92 mL, 47.7 mmol) was added, followed by 2.5M NaOH (9.54 mL, 23.8 mmol). The mixture was stirred at rt for 2 h. The reaction mixture was quenched with 1.5N HCl (10 mL) and the solid precipitated was collected by filteration and dried to afford Example 12B (1.35 g, 65% yield) as a yellow solid.

Example 12C. 2-(((aR)-6-aminospiro[3.3]heptan-2-yl)oxy)-7,8-dihydro-5H-pyrano[4,3-b]pyridine-3-carboxamide

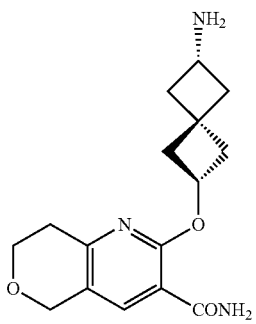

To the stirred solution of Example 12B (1.3 g, 2.97 mmol) in a THF (10 mL): MeOH (20 mL), Pd/C (0.632 g, 0.594 mmol) was added. The mixture was stirred under H2 (balloon) for 6 h. The mixture was filtered and concentrated to afford Example 12C (0.8 g, 49% yield) as a yellow solid. MS (ESI) m/z: 304.2.

Example 12

To the stirred solution of Example 12C (60 mg, 0.198 mmol) and 6-(2-hydroxy-2-methylpropoxy)pyrazolo[1,5-a]pyridine-3-carboxylic acid (49.5 mg, 0.198 mmol) in DMF (2 mL), was added HATU (75 mg, 0.198 mmol), followed by DIPEA (0.104 mL, 0.593 mmol). The mixture was stirred at rt for 2 h. The reaction mixture was purified by preparative HPLC to afford Example 12 (11.2 mg, 11% yield). $^1$H NMR (400 MHz, DMSO-d6) δ 8.43 (s, 2H), 8.24 (d, J=7.6 Hz, 1H), 8.07 (d, J=9.8 Hz, 1H), 7.91 (s, 1H), 7.66 (br. s., 1), 7.54 (br. s., 1H), 7.27 (d, J=9.5 Hz, 1H), 5.24-5.18 (m, 1H), 4.69 (s, 1H), 4.66 (br. s., 2H), 4.42-4.33 (m, 1H), 3.94 (br. s., 2H), 3.79 (s, 2H), 2.80 (br. s., 2H), 2.29-2.10 (m, 4H), 1.21 (s, 6H)MS (ESI) m/z: 536.3 (M+H). Analytical HPLC RT=1.37 min and (Method A) 1.37 min (Method B).

Example 13. Preparation of 2-(((aR-6-(4-benzyl-2,6-dioxopiperazin-1-yl)spiro[3.3]heptan-2-yl)oxy)-7,8-dihydro-5H-pyrano[4,3-b]pyridine-3-carboxamide

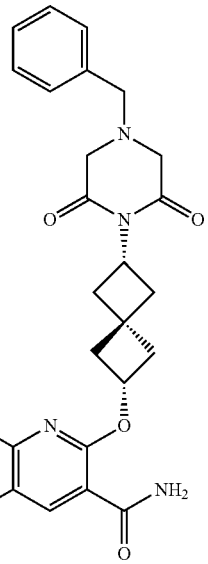

To a stirred solution of 4-benzylmorpholine-2,6-dione (27.1 mg, 0.132 mmol) in ethyl acetate (3 mL), 2-(((aR)-6-aminospiro[3.3]heptan-2-yl)oxy)-7,8-dihydro-5H-pyrano[4,3-b]pyridine-3-carboxamide (40 mg, 0.132 mmol) was added. The mixture was stirred at rt for 1 h, then $Ac_2O$ (0.062 mL, 0.66 mmol) was added, followed by TEA (0.055 mL, 0.40 mmol). The mixture was heated to 60° C. for 12 h. The reaction mixture was evaporated and the residue was purified by preparative HPLC to afford Example 13 (5.5 mg, 8% yield). MS (ESI) m/z: 491.3 (M+H)⁺. $^1$H NMR (400 MHz, DMSO-d6) δ 7.91 (s, 1H), 7.63 (br. s., 1H), 7.53 (br. s., 1H), 7.41-7.22 (m, 5H), 5.17 (t, J=7.1 Hz, 1H), 4.73-4.60 (m, 3H), 3.94 (t, J=5.7 Hz, 2H), 3.62 (s, 2H), 3.18 (d, J=5.4 Hz, 1H), 2.79 (t, J=5.9 Hz, 2H), 2.69-2.62 (m, 3H), 2.43-2.35 (m, 1H), 2.30-2.15 (m, 3H). Analytical HPLC RT=1.81 min and (Method A) 1.76 min (Method B), purity=96%.

The following examples in Table 1 were prepared using procedures similar to those which were used in the preparation of the examples above.

TABLE 1

| Example | Structure | Name | LCMS (M + H)+ | HPLC Method, RT (min.) | 1H NMR |
|---|---|---|---|---|---|
| 14 | 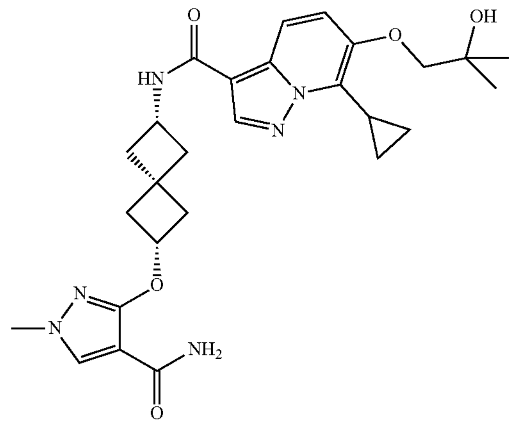 | 3-{[(aR)-6-[7-cyclopropyl-6-(2-hydroxy-2-methyl)propoxy)pyrazolo[1,5-a]pyridine-3-amido]spiro[3.3]heptan-2-yl}oxy)-1-methyl-1H-pyrazole-4-carboxamide | 523.0 | A: 1.41 B: 1.41 | (500 MHz, DMSO-d6) δ ppm 8.48 (s, 1H), 8.32 (br. s, 1H), 8.01 (d, J = 9.6 Hz, 1H), 7.87 (s, 1H), 7.45 (d, J = 9.8 Hz, 1H), 7.08 (br. s., 1H), 6.59 (br. s, 1H), 4.98-4.78 (m, 2H), 4.34 (d, J = 8.0 Hz, 1H), 2.66-2.57 (m, 1H), 2.47-2.36 (m, 2H), 2.34-2.26 (m, 1H), 2.25-2.07 (m, 4H), 1.44 (br. s., 2H), 1.23 (s, 6H), 1.09-1.01 (m, 2H) |
| 15 | 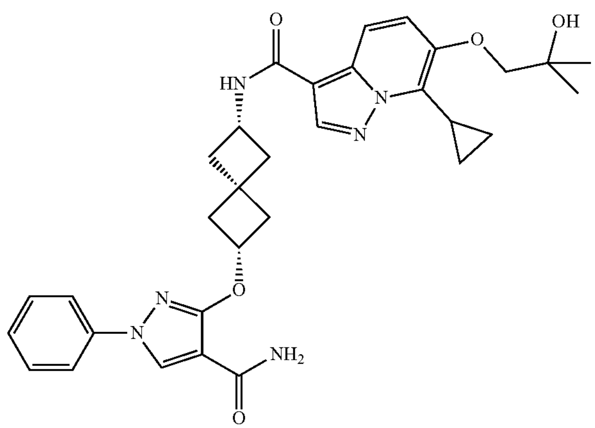 | 3-{[(aR)-6-[7-cyclopropyl-6-(2-hydroxy-2-methyl)propoxy)pyrazolo[1,5-a]pyridine-3-amido]spiro[3.3]heptan-2-yl}oxy)-1-phenyl-1H-pyrazole-4-carboxamide | 585.5 | A: 1.73 B: 1.71 | (500 MHz, DMSO-d6) δ 8.66 (br. s., 1H), 8.48 (s, 1H), 8.34 (d, J = 5.8 Hz, 1H), 8.01 (d, J = 9.8 Hz, 1H), 7.76 (d, J = 7.7 Hz, 2H), 7.56-7.40 (m, 3H), 7.34-7.23 (m, 2H), 6.81 (br. s., 1H), 5.01 (t, J = 6.9 Hz, 1H), 4.45-4.27 (m, 1H), 2.77-2.62 (m, 1H), 2.44 (br. s., 1H), 2.37-2.21 (m, 3H), 2.15 (t, J = 9.7 Hz, 2H), 1.43 (br. s., 2H), 1.23 (s, 6H), 1.10-1.02 (m, 2H). |

TABLE 1-continued

| Example | Structure | Name | LCMS (M + H)+ | HPLC Method, RT (min.) | 1H NMR |
|---|---|---|---|---|---|
| 16 | 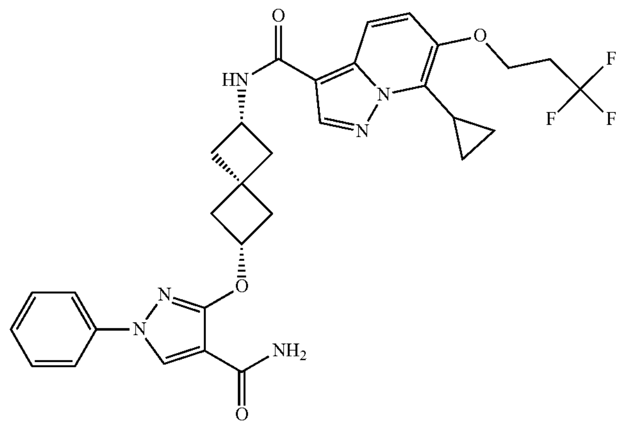 | 1-phenyl-3-({(aR)-6-[6-(3,3,3-trifluoropropoxy)pyrazolo[1,5-a]pyridine-3-amido]spiro[3.3]heptan-2-yl}oxy)-1H-pyrazole-4-carboxamide | 569.4 | A: 1.86 B: 1.85 | (500 MHz, DMSO-d6) δ 8.66 (s, 1H), 8.50 (s, 1H), 8.44 (s, 1H), 8.34 (d, J = 7.3 Hz, 1H), 8.08 (d, J = 9.8 Hz, 1H), 7.77 (d, J = 7.9 Hz, 2H), 7.49 (t, J = 7.8 Hz, 2H), 7.35-7.22 (m, 3H), 6.79 (br. s., 1H), 5.02 (t, J = 7.0 Hz, 1H), 4.42-4.31 (m, 1H), 4.27 (t, J = 5.8 Hz, 2H), 2.89-2.76 (m, 2H), 2.74-2.68 (m, 1H), 2.47-2.41 (m, 1H), 2.39-2.21 (m, 3H), 2.16 (t, J = 9.8 Hz, 2H). |
| 17 | 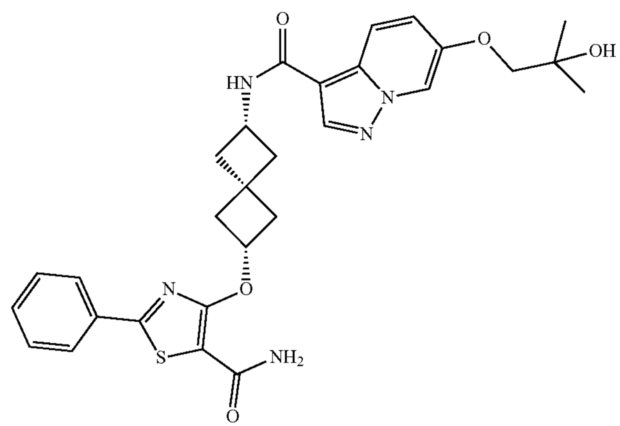 | 4-{[(aR)-6-[6-(2-hydroxy-2-methylpropoxy)pyrazolo[1,5-a]pyridine-3-amido]spiro[3.3]heptan-2-yl]oxy}-2-phenyl-1,3-thiazole-5-carboxamide | 562.2 | A: 1.78 B: 1.78 | (500 MHz, DMSO-d6) δ ppm 8.42 (br d, J = 9.2 Hz, 2H), 8.28 (br d, J = 7.6 Hz, 1H), 8.07 (d, J = 9.5 Hz, 1H), 7.94 (br d, J = 5.8 Hz, 2H), 7.65 (br s, 1H), 7.58-7.48 (m, 3H), 7.27 (br d, J = 9.8 Hz, 1H), 6.95 (br s, 1H), 5.24 (quin, J = 6.9 Hz, 1H), 4.42-4.33 (m, 1H), 3.78 (s, 2H), 2.77-2.67 (m, 1H), 2.48-2.42 (m, 1H), 2.41-2.28 (m, 3H), 2.21-2.12 (m, 2H), 1.21 (s, 6H) |

TABLE 1-continued

| Example | Structure | Name | LCMS (M + H)+ | HPLC Method, RT (min.) | 1H NMR |
|---|---|---|---|---|---|
| 18 | 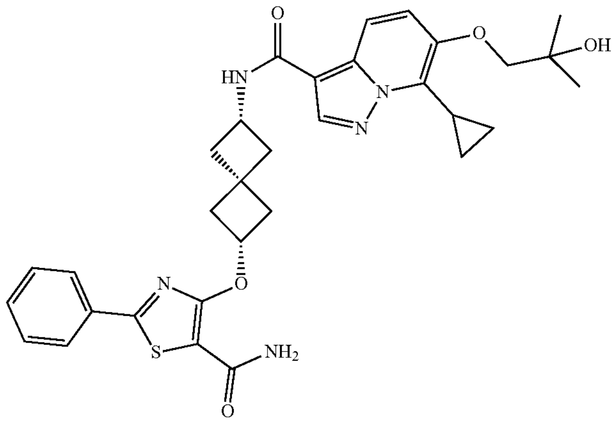 | 4-({[(aR)-6-[7-cyclopropyl-6-(2-hydroxy-2-methylpropoxy)pyrazolo[1,5-a]pyridine-3-amido]spiro[3.3]heptan-2-yl}oxy)-2-phenyl-1,3-thiazole-5-carboxamide | 602.4 | A: 1.92 B: 1.88 | (500 MHz, DMSO-d6) δ ppm 8.49 (s, 1H), 8.27 (br d, J = 7.3 Hz, 1H), 8.02 (d, J = 9.5 Hz, 1H), 7.94 (br d, J = 5.5 Hz, 2H), 7.65 (br s, 1H), 7.57-7.48 (m, 3H), 7.45 (d, J = 9.5 Hz, 1H), 6.95 (br s, 1H), 5.24 (quin, J = 7.1 Hz, 1H), 4.38 (dq, J = 16.1, 8.0 Hz, 1H), 2.76-2.67 (m, 1H), 2.63-2.56 (m, 1H), 2.48-2.42 (m, 2H), 2.41-2.27 (m, 3H), 2.22-2.10 (m, 2H), 1.46 (br d, J = 3.7 Hz, 2H), 1.23 (s, 6H), 1.05 (br dd, J = 8.7, 2.3 Hz, 2H). |
| 19 | 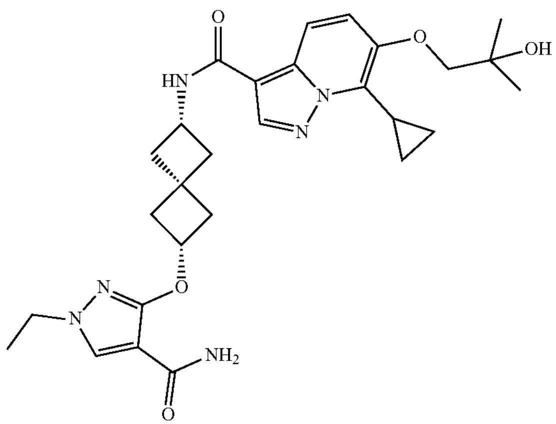 | 3-({[(aR)-6-[7-cyclopropyl-6-(2-hydroxy-2-methylpropoxy)pyrazolo[1,5-a]pyridine-3-amido]spiro[3.3]heptan-2-yl}oxy)-1-ethyl-1H-pyrazole-4-carboxamide | 537.0 | A: 1.50 B: 1.50 | (500 MHz, DMSO-d6) δ 8.49 (s, 1H), 8.26 (br d, J = 6.7 Hz, 1H), 8.02 (br d, J = 9.7 Hz, 1H), 7.76 (s, 1H), 7.46 (br d, J = 9.7 Hz, 1H), 7.33 (br s, 1H), 6.92 (br s, 1H), 5.30-5.08 (m, 1H), 4.45-4.27 (m, 1H), 3.96 (q, J = 7.1 Hz, 2H), 3.79 (s, 2H), 2.68-2.58 (m, 1H), 2.37-2.24 (m, 3H), 2.20-2.02 (m, 4H), 1.48 (br d, J = 3.5 Hz, 2H), 1.38-1.14 (m, 9H), 1.05 (br d, J = 6.6 Hz, 2H). |

TABLE 1-continued

| Example | Structure | Name | LCMS (M + H)+ | HPLC Method, RT (min.) | 1H NMR |
|---|---|---|---|---|---|
| 20 | 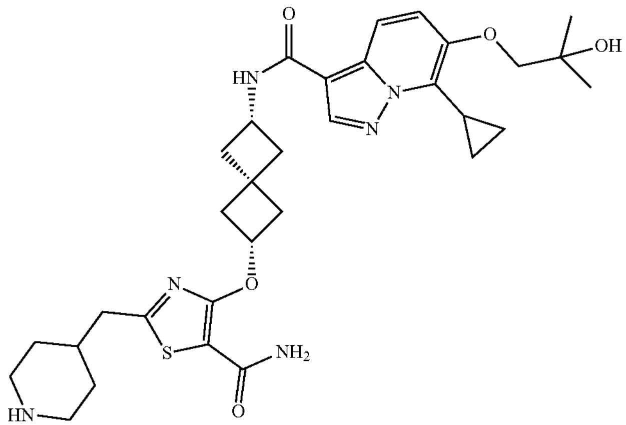 | 3-({[(aR)-6-[7-cyclopropyl-6-(2-hydroxy-2-methylpropoxy)pyrazolo[1,5-a]pyridine-3-amido]spiro[3.3]heptan-2-yl]oxy}-1-[(piperidin-4-yl)methyl]-1H-pyrazole-4-carboxamide | 606.6 | A: 1.12 B: 1.14 | (500 MHz, DMSO-d6) δ 8.49 (s, 1H), 8.27 (br d, J = 6.9 Hz, 1H), 8.02 (d, J = 9.7 Hz, 1H), 7.84-7.66 (m, 1H), 7.46 (br d, J = 9.7 Hz, 1H), 7.36 (br s, 1H), 6.92 (br s, 1H), 5.26-5.13 (m, 1H), 4.42-4.25 (m, 1H), 3.86-3.73 (m, 3H), 2.99 (br d, J = 11.4 Hz, 1H), 2.65-2.57 (m, 2H), 2.35-2.25 (m, 3H), 2.21-2.04 (m, 4H), 1.96-1.87 (m, 1H), 1.83 (br s, 2H), 1.53-1.40 (m, 4H), 1.24 (s, 6H), 1.20-1.10 (m, 2H), 1.08-1.02 (m, 2H). |
| 21 | 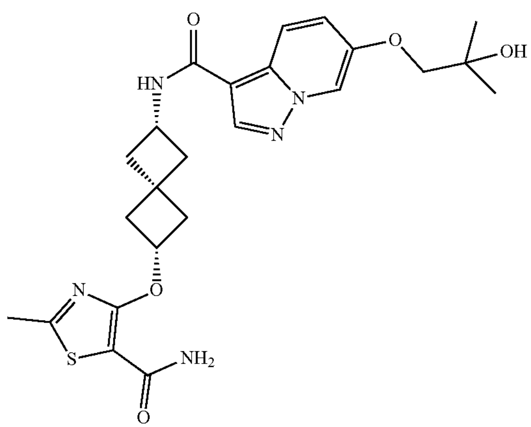 | 4-({[(aR)-6-[6-(2-hydroxy-2-methylpropoxy)pyrazolo[1,5-a]pyridine-3-amido]spiro[3.3]heptan-2-yl]oxy}-2-methyl-1,3-thiazole-5-carboxamide | 500.3 | A: 1.36 B: 1.14 | (500 MHz, DMSO-d6) δ ppm 8.41 (s, 1H), 8.39 (s, 1H), 8.29 (br d, J = 7.6 Hz, 1H), 8.06 (d, J = 9.8 Hz, 1H), 7.48 (br s, 1H), 7.31-7.23 (m, 1H), 6.85 (br s, 1H), 5.10 (quin, J = 7.0 Hz, 1H), 4.34 (sxt, J = 8.1 Hz, 1H), 3.77 (s, 1H), 2.64-2.59 (m, 1H), 2.56 (s, 3H), 2.47-2.37 (m, 2H), 2.36-2.25 (m, 2H), 2.23-2.17 (m, 1H), 2.13 (q, J = 9.5 Hz, 2H), 1.20 (s, 6H). |

TABLE 1-continued

| Example | Structure | Name | LCMS (M + H)+ | HPLC Method, RT (min.) | 1H NMR |
|---|---|---|---|---|---|
| 22 | 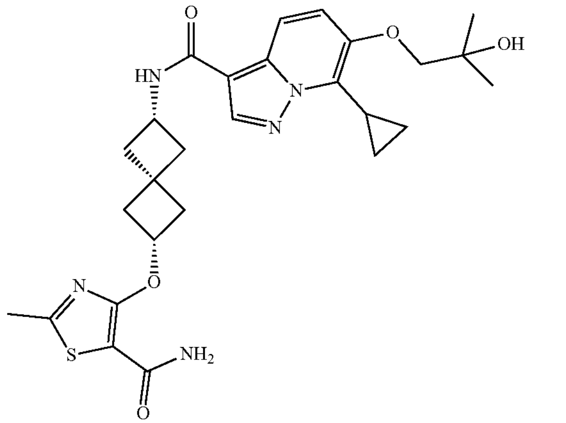 | 4-({[(aR)-6-[7-cyclopropyl-6-(2-hydroxy-2-methyl)propoxy)pyrazolo[1,5-a]pyridine-3-amido]spiro[3.3]heptan-2-yl]oxy})-2-methyl-1,3-thiazole-5-carboxamide | 540.0 | A: 1.56 B: 1.57 | (500 MHz, DMSO-d6) δ ppm 8.47 (s, 1H), 8.28 (br d, J = 7.6 Hz, 1H), 8.00 (d, J = 9.5 Hz, 1H), 7.47 (br s, 1H), 7.44 (d, J = 9.5 Hz, 1H), 6.86 (br s, 1H), 5.10 (quin, J = 7.1 Hz, 1H), 4.40-4.27 (m, 1H), 3.77 (s, 1H), 3.16 (d, J = 5.2 Hz, 1H), 2.64-2.58 (m, 1H), 2.56 (s, 3H), 2.54 (br s, 1H), 2.47-2.37 (m, 2H), 2.36-2.25 (m, 2H), 2.22 (br dd, J = 11.7, 7.2 Hz, 1H), 2.13 (q, J = 9.5 Hz, 2H), 1.46-1.41 (m, 2H), 1.22 (s, 6H), 1.08-1.01 (m, 2H) |
| 23 | 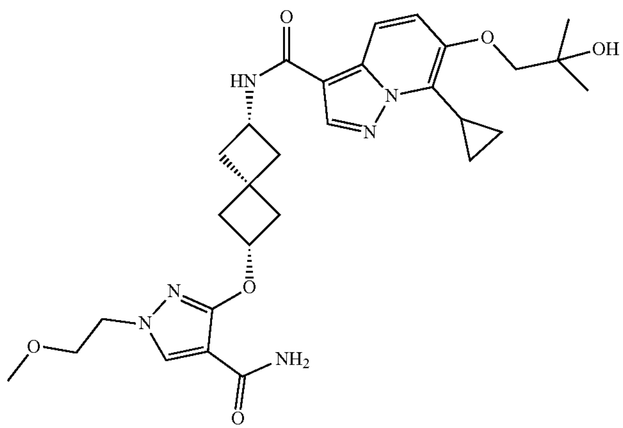 | 3-({[(aR)-6-[7-cyclopropyl-6-(2-hydroxy-2-methyl)propoxy)pyrazolo[1,5-a]pyridine-3-amido]spiro[3.3]heptan-2-yl]oxy})-1-(2-methoxyethyl)-1H-pyrazole-4-carboxamide | 567.1 | A: 1.41 B: 1.39 | (500 MHz, DMSO-d6) δ 9.06-9.05 (m, 1H), 8.49 (s, 1H), 8.26 (br d, J = 7.8 Hz, 1H), 8.02 (br d, J = 9.7 Hz, 1H), 7.77 (s, 1H), 7.46 (br dd, J = 9.7 Hz, 1H), 5.27-5.11 (m, 1H), 4.34 (br dd, J = 16.1, 7.7 Hz, 1H), 4.07 (br t, J = 5.2 Hz, 2H), 3.79 (s, 2H), 3.70-3.63 (m, 2H), 3.21 (s, 2H), 2.93 (q, J = 7.2 Hz, 2H), 2.37-2.00 (m, 7H), 1.48 (br d, J = 3.5 Hz, 2H), 1.24 (s, 5H), 1.16 (t, J = 7.3 Hz, 3H), 1.09-1.02 (m, 2H). |

TABLE 1-continued

| Example | Structure | Name | LCMS (M + H)+ | HPLC Method, RT (min.) | 1H NMR |
|---|---|---|---|---|---|
| 24 | 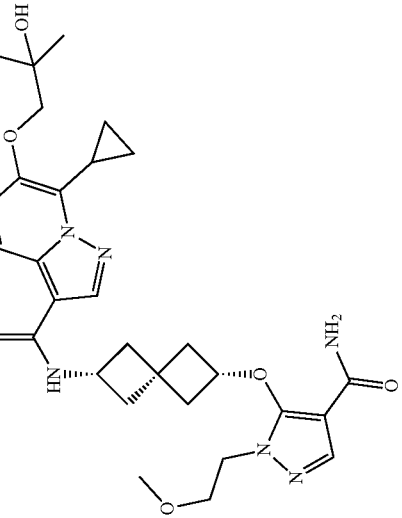 | 5-({[(aR)-6-[7-cyclopropyl-6-(2-hydroxy-2-methylpropoxy)pyrazolo[1,5-a]pyridine-3-amido]spiro[3.3]heptan-2-yl]oxy)-1-(2-methoxyethyl)-1H-pyrazole-4-carboxamide | 567.2 | A: 1.41 B: 1.39 | (500 MHz, DMSO-d6) δ 9.06-9.05 (m, 1H), 8.49 (s, 1H), 8.26 (br d, J = 7.8 Hz, 1H), 8.02 (br d, J = 9.7 Hz, 1H), 7.77 (s, 1H), 7.46 (br d, J = 9.7 Hz, 1H), 5.27-5.11 (m, 1H), 4.34 (br dd, J = 16.1, 7.7 Hz, 1H), 4.07 (br t, J = 5.2 Hz, 2H), 3.79 (s, 2H), 3.70-3.63 (m, 2H), 3.21 (s, 2H), 2.93 (q, J = 7.2 Hz, 2H), 2.37-2.00 (m, 7H), 1.48 (br d, J = 3.5 Hz, 2H), 1.24 (s, 5H), 1.16 (t, J = 7.3 Hz, 3H), 1.09-1.02 (m, 2H). |
| 25 | 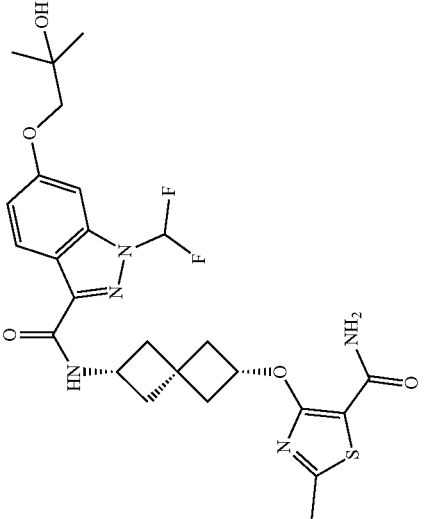 | N-{(aR)-6-[(5-carbamoyl-2-methyl-1,3-thiazol-4-yl)oxy]spiro[3.3]heptan-2-yl}-1-(difluoromethyl)-6-(2-hydroxy-2-methylpropoxy)-1H-indazole-3-carboxamide | 550.4 | A: 1.62 B: 1.62 | (500 MHz, DMSO-d6) δ ppm 8.85 (br d, J = 7.2 Hz, 1H), 8.31-8.11 (m, 1H), 8.04 (br d, J = 8.9 Hz, 1H), 7.50 (br s, 1H), 7.31 (br s, 1H), 7.07 (br d, J = 9.0 Hz, 1H), 6.87 (br s, 1H), 5.13-5.04 (m, 1H), 4.42-4.34 (m, 1H), 3.81 (br s, 3H), 3.15 (d, J = 5.1 Hz, 3H), 2.66-2.58 (m, 1H), 2.45-2.36 (m, 2H), 2.33-2.16 (m, 5H), 1.22 (s, 6H) |

TABLE 1-continued

| Example | Structure | Name | LCMS (M + H)+ | HPLC Method, RT (min.) | 1H NMR |
|---|---|---|---|---|---|
| 26 | 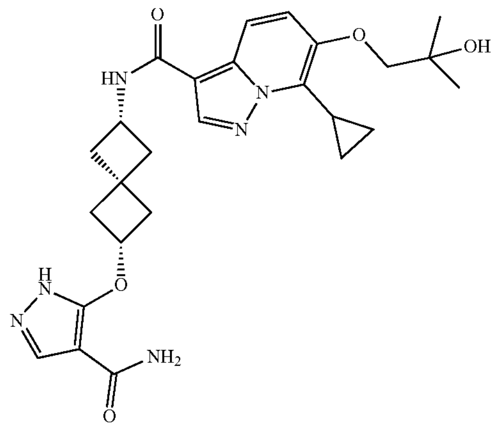 | 5-({[(aR)-6-[7-cyclopropyl-6-(2-hydroxy-2-methylpropoxy)pyrazolo[1,5-a]pyridine-3-amido]spiro[3.3]heptan-2-yl]oxy)-1H-pyrazole-4-carboxamide | 509.5 | A: 1.23 B: 1.19 | (500 MHz, DMSO-d6) δ 8.49 (s, 1H), 8.30 (br s, 1H), 8.02 (br d, J = 9.6 Hz, 1H), 7.92 (s, 1H), 7.46 (br d, J = 9.8 Hz, 1H), 7.10 (br s, 1H), 6.62 (br s, 1H), 4.89 (br t, J = 7.0 Hz, 1H), 4.40-4.29 (m, 1H), 3.78 (s, 2H), 3.16 (br s, 1H), 2.67-2.57 (m, 2H), 2.42 (br dd, J = 11.4, 5.7 Hz, 2H), 2.35-2.25 (m, 1H), 2.24-2.06 (m, 4H), 1.46 (br s, 2H), 1.32-1.16 (m, 6H), 1.09-1.02 (m, 2H). |
| 27 | 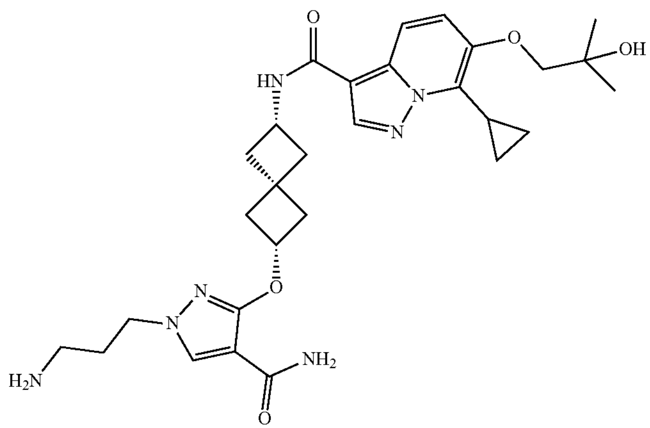 | 1-(3-aminopropyl)-3-({[(aR)-6-[7-cyclopropyl-6-(2-hydroxy-2-methylpropoxy)pyrazolo[1,5-a]pyridine-3-amido]spiro[3.3]heptan-2-yl]oxy)-1H-pyrazole-4-carboxamide | 566.0 | A: 1.12 B: 1.10 | (500 MHz, DMSO-d6) δ 8.55-8.42 (m, 1H), 8.26 (br d, J = 7.3 Hz, 1H), 8.02 (br d, J = 9.8 Hz, 1H), 7.94 (s, 1H), 7.45 (br d, J = 9.8 Hz, 1H), 7.07 (br s, 1H), 6.55 (br s, 1H), 4.96-4.80 (m, 1H), 4.49-4.25 (m, 1H), 3.99 (br t, J = 6.7 Hz, 2H), 3.79 (s, 2H), 2.67-2.57 (m, 2H), 2.46-2.26 (m, 4H), 2.24-2.08 (m, 4H), 1.87-1.71 (m, 4H), 1.47 (br d, J = 3.7 Hz, 2H), 1.24 (s, 6H), 1.10-1.04 (m, 2H), 1.00 (d, J = 6.1 Hz, 1H) |

TABLE 1-continued

| Example | Structure | Name | LCMS (M + H)+ | HPLC Method, RT (min.) | 1H NMR |
|---|---|---|---|---|---|
| 28 | 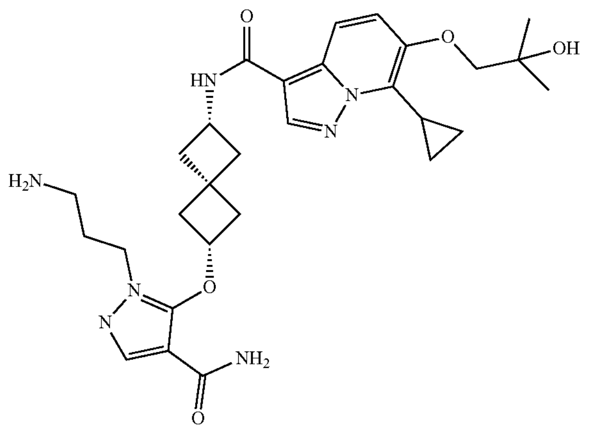 | 1-(3-aminopropyl)-5-({(aR)-6-[7-cyclopropyl-6-(2-hydroxy-2-methylpropoxy)pyrazolo[1,5-a]pyridine-3-amido]spiro[3.3]heptan-2-yl}oxy)-1H-pyrazole-4-carboxamide | 566.0 | A: 1.12 B: 1.10 | (500 MHz, DMSO-d6) δ 8.49 (s, 1H), 8.26 (br d, J = 7.2 Hz, 1H), 8.02 (br d, J = 9.7 Hz, 1H), 7.77 (s, 1H), 7.46 (br d, J = 9.7 Hz, 1H), 7.35 (br s, 1H), 6.93 (br s, 1H), 5.20 (br t, J = 7.2 Hz, 1H), 4.42-4.25 (m, 1H), 4.00 (br t, J = 6.7 Hz, 2H), 3.79 (s, 2H), 2.67-2.57 (m, 3H), 2.40-2.23 (m, 3H), 2.20-2.00 (m, 4H), 1.93-1.75 (m, 6H), 1.49 (br d, J = 3.5 Hz, 2H), 1.24 (s, 6H), 1.13-1.03 (m, 2H) |
| 29 | 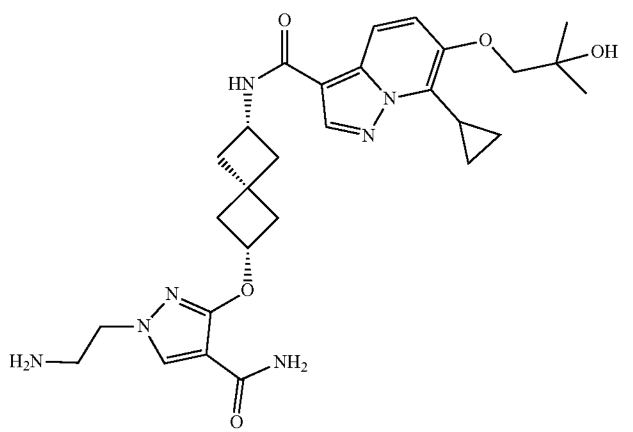 | 1-(2-aminoethyl)-3-({(aR)-6-[7-cyclopropyl-6-(2-hydroxy-2-methylpropoxy)pyrazolo[1,5-a]pyridine-3-amido]spiro[3.3]heptan-2-yl}oxy)-1H-pyrazole-4-carboxamide | 552.2 | A: 1.11 B: 1.08 | (500 MHz, DMSO-d6) δ 8.49 (s, 1H), 8.27 (br d, J = 7.1 Hz, 1H), 8.02 (br d, J = 9.6 Hz, 1H), 7.86 (s, 1H), 7.58-7.36 (m, 2H), 7.00 (br s, 1H), 5.26 (br t, J = 7.2 Hz, 1H), 4.46-4.28 (m, 1H), 4.19 (br t, J = 6.1 Hz, 2H), 3.79 (s, 2H), 3.19 (br t, J = 6.2 Hz, 2H), 3.02-2.84 (m, 2H), 2.61 (ddd, J = 14.2, 8.7, 5.9 Hz, 1H), 2.39-2.23 (m, 3H), 2.21-1.99 (m, 4H), 1.48 (br d, J = 3.5 Hz, 2H), 1.24 (s, 6H), 1.16 (t, J = 7.2 Hz, 3H), 1.09-1.01 (m, 2H). |

TABLE 1-continued

| Example | Structure | Name | LCMS (M + H)+ | HPLC Method, RT (min.) | 1H NMR |
|---------|-----------|------|---------------|------------------------|--------|
| 30 | 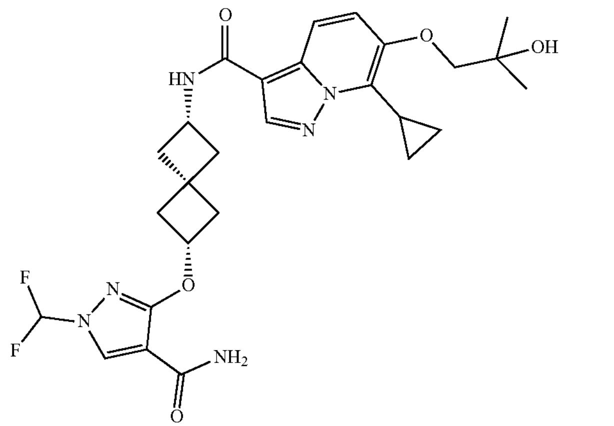 | 3-({(aR)-6-[7-cyclopropyl-6-(2-hydroxy-2-methylpropoxy)pyrazolo[1,5-a]pyridine-3-amido]spiro[3.3]heptan-2-yl}oxy)-1-(difluoromethyl)-1H-pyrazole-4-carboxamide | 559.0 | A: 1.49 B: 1.45 | (500 MHz, DMSO-d6) δ 8.47 (s, 1H), 8.40 (s, 1H), 8.31 (br d, J = 7.9 Hz, 1H), 8.01 (d, J = 9.8 Hz, 1H), 7.70-7.53 (m, 1H), 7.48-7.41 (m, 1H), 7.37 (br s, 1H), 6.88 (br s, 1H), 4.98-4.88 (m, 1H), 4.39-4.27 (m, 1H), 3.78 (s, 1H), 3.70 (br s, 1H), 3.17 (br d, J = 4.9 Hz, 1H), 2.70-2.59 (m, 1H), 2.47-2.07 (m, 7H), 1.49-1.34 (m, 2H), 1.23 (s, 6H), 1.11-1.02 (m, 2H). |
| 31 | 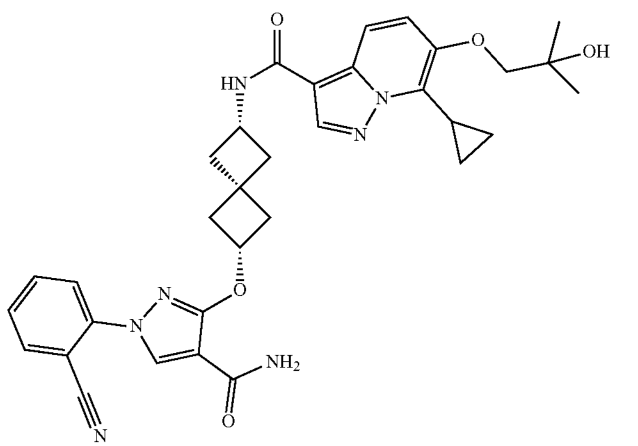 | 1-(2-cyanophenyl)-3-({(aR)-6-[7-cyclopropyl-6-(2-hydroxy-2-methylpropoxy)pyrazolo[1,5-a]pyridine-3-amido]spiro[3.3]heptan-2-yl}oxy)-1H-pyrazole-4-carboxamide | 610.5 | A: 1.57 B: 1.58 | (500 MHz, DMSO-d6) δ 8.65 (s, 1H), 8.49 (s, 1H), 8.26 (br d, J = 7.6 Hz, 1H), 8.06-7.94 (m, 2H), 7.87-7.78 (m, 2H), 7.59-7.51 (m, 1H), 7.45 (d, J = 9.8 Hz, 1H), 7.39 (br s, 1H), 6.82 (br s, 1H), 5.00 (quin, J = 7.0 Hz, 1H), 4.72 (s, 1H), 4.42-4.30 (m, 1H), 3.79 (s, 2H), 2.78-2.69 (m, 1H), 2.64-2.54 (m, 2H), 2.45-2.22 (m, 4H), 2.16 (q, J = 9.5 Hz, 2H), 1.47 (br d, J = 3.4 Hz, 2H), 1.24 (s, 6H), 1.09-1.02 (m, 2H). |

TABLE 1-continued

| Example | Structure | Name | LCMS (M + H)+ | HPLC Method, RT (min.) | 1H NMR |
|---|---|---|---|---|---|
| 32 | 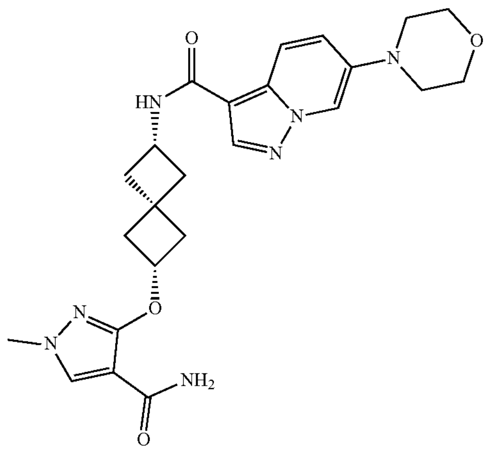 | 1-methyl-3-{[(aR)-6-[6-(morpholin-4-yl)pyrazolo[1,5-a]pyridine-3-amido]spiro[3.3]heptan-2-yl]oxy}-1H-pyrazole-4-carboxamide | 480.5 | A: 1.03 B: 1.04 | (500 MHz, DMSO-d6) δ 8.39 (s, 1H), 8.25 (d, J = 7.3 Hz, 1H), 8.11 (s, 1H), 8.03 (d, J = 9.8 Hz, 1H), 7.88 (s, 1H), 7.46 (dd, J = 9.8, 1.8 Hz, 1H), 7.05 (br s, 1H), 6.55 (br s, 1H), 4.87 (t, J = 7.0 Hz, 1H), 4.41-4.22 (m, 1H), 3.79-3.73 (m, 3H), 3.67 (s, 1H), 3.11-3.03 (m, 3H), 2.61 (dt, J = 11.2, 5.8 Hz, 1H), 2.55 (s, 3H), 2.47-2.36 (m, 2H), 2.35-2.28 (m, 1H), 2.25-2.08 (m, 4H). |
| 33 | 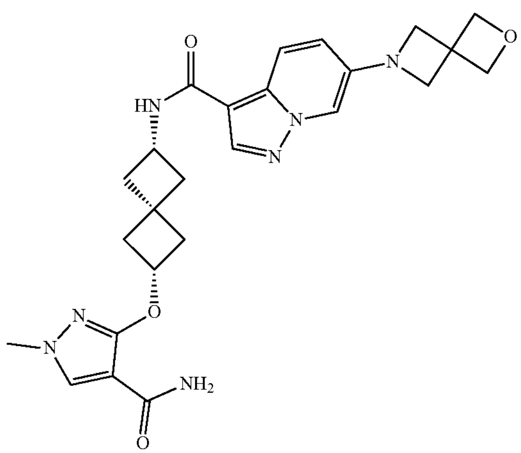 | 1-methyl-3-{[(aR)-6-(6-{2-oxa-6-azaspiro[3.3]heptan-6-yl}pyrazolo[1,5-a]pyridine-3-amido)spiro[3.3]heptan-2-yl]oxy}-1H-pyrazole-4-carboxamide | 492.2 | A: 0.98 B: 1.01 | (500 MHz, DMSO-d6) δ 8.37-8.32 (m, 1H), 8.19 (d, J = 7.3 Hz, 1H), 8.02 (d, J = 9.5 Hz, 1H), 7.89 (s, 1H), 7.85 (s, 1H), 7.07 (br s, 1H), 6.99-6.93 (m, 1H), 6.52 (br s, 1H), 4.93-4.83 (m, 1H), 4.72 (s, 3H), 4.41-4.28 (m, 1H), 4.01 (s, 3H), 3.68 (s, 2H), 2.66-2.57 (m, 1H), 2.47-2.35 (m, 2H), 2.34-2.27 (m, 1H), 2.25-2.09 (m, 4H), 1.79-1.70 (m, 3H). |

TABLE 1-continued

| Example | Structure | Name | LCMS (M + H)+ | HPLC Method, RT (min.) | 1H NMR |
|---|---|---|---|---|---|
| 34 | 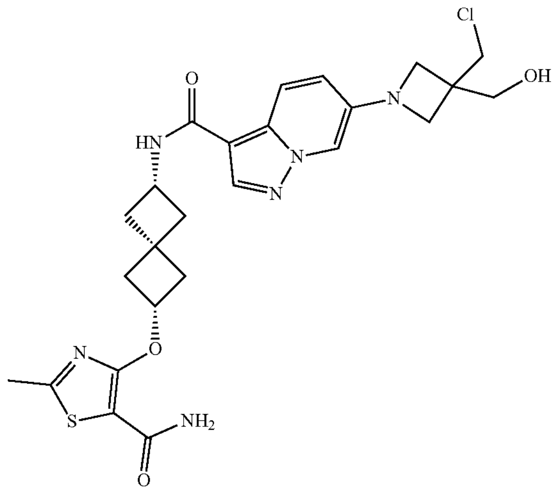 | 4-[((aR)-6-[6-[3-(chloromethyl)-3-(hydroxymethyl)azetidin-1-yl]pyrazolo[1,5-a]pyridine-3-amido}spiro[3.3]heptan-2-yl]oxy]-2-methyl-1,3-thiazole-5-carboxamide | 545.2 | A: 1.34 B: 1.31 | (500 MHz, DMSO-d6) δ ppm 8.34 (s, 1H), 8.18 (br d, J = 7.6 Hz, 1H), 8.01 (d, J = 9.5 Hz, 1H), 7.87 (s, 1H), 7.53 (br s, 1H), 6.98 (dd, J = 9.5, 1.8 Hz, 1H), 6.83 (br s, 1H), 5.12 (quin, J = 7.1 Hz, 1H), 4.40-4.29 (m, 1H), 3.93 (s, 2H), 3.67 (d, J = 7.6 Hz, 2H), 3.65-3.57 (m, 3H), 2.66-2.59 (m, 1H), 2.57 (s, 3H), 2.47-2.37 (m, 3H), 2.35-2.28 (m, 2H), 2.24 (br dd, J = 11.6, 7.3 Hz, 1H), 2.18-2.09 (m, 3H) |
| 35 | 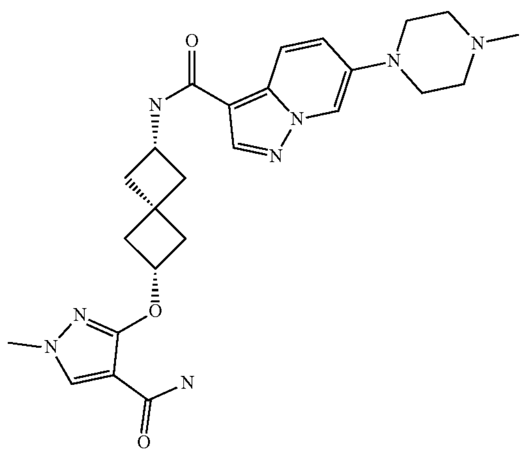 | 1-methyl-3-({(aR)-6-[6-(4-methylpiperazin-1-yl)pyrazolo[1,5-a]pyridine-3-amido]spiro[3.3]heptan-2-yl]oxy)-1H-pyrazole-4-carboxamide | 493.3 | A: 0.82 B: 0.78 | (500 MHz, DMSO-d6) δ 8.43 (s, 1H), 8.30-8.24 (m, 2H), 8.07 (d, J = 9.8 Hz, 1H), 7.88 (s, 1H), 7.51-7.44 (m, 1H), 7.06 (br s, 1H), 6.54 (br s, 1H), 4.87 (quin, J = 6.9 Hz, 1H), 4.41-4.29 (m, 1H), 3.67 (s, 2H), 2.89 (s, 1H), 2.85 (s, 3H), 2.73 (s, 1H), 2.67-2.58 (m, 1H), 2.55 (s, 3H), 2.47-2.35 (m, 2H), 2.35-2.28 (m, 1H), 2.25-2.09 (m, 4H) |

TABLE 1-continued

| Example | Structure | Name | LCMS (M + H)+ | HPLC Method, RT (min.) | 1H NMR |
|---|---|---|---|---|---|
| 36 | 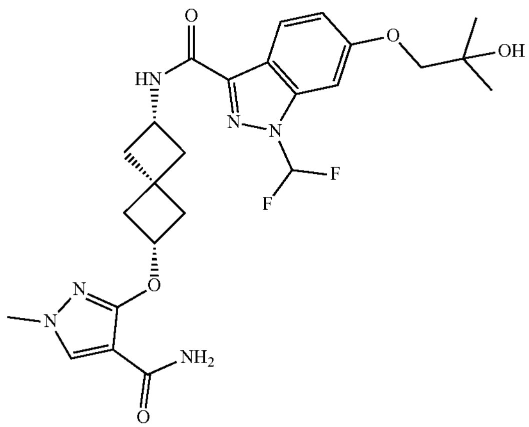 | N-{(aR)-6-[(4-carbamoyl-1-methyl-1H-pyrazol-3-yl)oxy]spiro[3.3]heptan-2-yl]-1-(difluoromethyl)-6-(2-hydroxy-2-methylpropoxy)-1H-indazole-3-carboxamide | 533.3 | A: 1.41 B: 1.40 | (500 MHz, DMSO-d6) δ 8.80 (br d, J = 7.6 Hz, 1H), 8.04 (br d, J = 8.9 Hz, 1H), 7.86 (s, 1H), 7.31 (s, 1H), 7.16-6.89 (m, 2H), 6.55 (br s, 1H), 4.96-4.73 (m, 1H), 4.50-4.22 (m, 1H), 3.82 (s, 1H), 3.70-3.52 (m, 3H), 2.67-2.56 (m, 1H), 2.46-2.33 (m, 2H), 2.32-2.08 (m, 4H), 1.28-1.11 (m, 6H). |
| 37 | 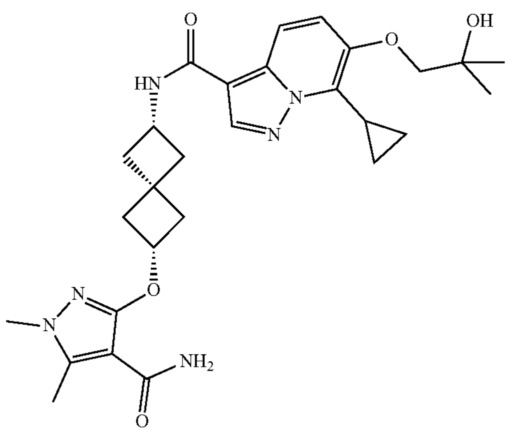 | 3-{[(aR)-6-[7-cyclopropyl-6-(2-hydroxy-2-methylpropoxy)pyrazolo[1,5-a]pyridine-3-amido]spiro[3.3]heptan-2-yl]oxy}-1,5-dimethyl-1H-pyrazole-4-carboxamide | 537.2 | A: 1.48 B: 1.43 | (500 MHz, DMSO-d6) δ 8.50 (s, 1H), 8.24 (br d, J = 7.6 Hz, 1H), 8.03 (d, J = 9.8 Hz, 1H), 7.46 (d, J = 9.8 Hz, 1H), 6.99 (br s, 1H), 6.51 (br s, 1H), 4.89 (quin, J = 7.0 Hz, 1H), 4.40-4.30 (m, 1H), 3.79 (s, 2H), 3.58 (s, 2H), 2.67-2.57 (m, 2H), 2.47-2.37 (m, 5H), 2.36-2.29 (m, 1H), 2.28-2.03 (m, 4H), 1.56-1.42 (m, 2H), 1.25 (s, 6H), 1.10-1.03 (m, 2H). |

TABLE 1-continued

| Example | Structure | Name | LCMS (M + H)+ | HPLC Method, RT (min.) | 1H NMR |
|---|---|---|---|---|---|
| 38 | 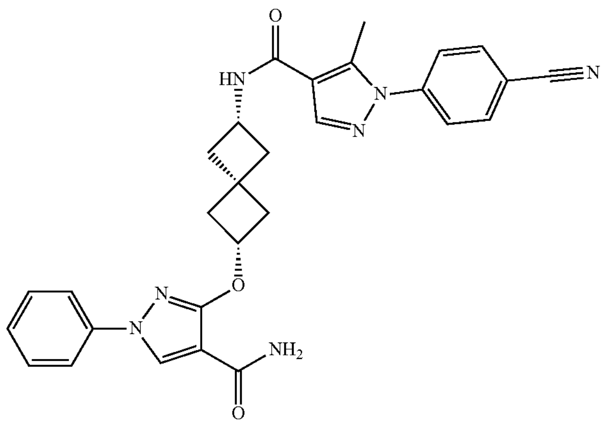 | 3-{[(aR)-6-[1-(4-cyanophenyl)-5-methyl-1H-pyrazole-4-amido]spiro[3.3]heptan-2-yl]oxy}-1-phenyl-1H-pyrazole-4-carboxamide | 522.3 | A: 1.71 B: 1.68 | (500 MHz, DMSO-d6) δ 8.72 (s, 1H), 8.29 (br d, J = 7.6 Hz, 1H), 8.19 (s, 1H), 8.03 (br d, J = 8.5 Hz, 2H), 7.78 (br dd, J = 11.4, 8.4 Hz, 4H), 7.49 (br t, J = 7.8 Hz, 2H), 7.35-7.24 (m, 2H), 6.75 (br s, 1H), 5.03 (quin, J = 7.1 Hz, 1H), 4.41-4.25 (m, 1H), 3.17 (d, J = 4.9 Hz, 1H), 2.77-2.66 (m, 1H), 2.57 (s, 3H), 2.48-2.40 (m, 1H), 2.39-2.21 (m, 3H), 2.16 (br t, J = 9.9 Hz, 2H). |
| 39 | 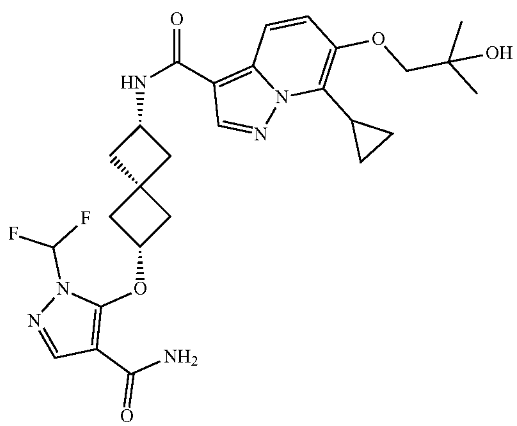 | 5-{[(aR)-6-[7-cyclopropyl-6-(2-hydroxy-2-methylpropoxy)pyrazolo[1,5-a]pyridine-3-amido]spiro[3.3]heptan-2-yl]oxy}-1-(difluoromethyl)-1H-pyrazole-4-carboxamide | 559.1 | A: 1.40 B: 1.42 | (500 MHz, DMSO-d6) δ 8.47 (s, 1H), 8.12 (br d, J = 7.4 Hz, 1H), 8.05-7.96 (m, 2H), 7.44 (d, J = 9.7 Hz, 1H), 5.34 (quin, J = 7.1 Hz, 1H), 4.34 (sxt, J = 7.9 Hz, 1H), 3.80 (s, 2H), 2.64-2.57 (m, 1H), 2.42-2.28 (m, 3H), 2.27-2.07 (m, 4H), 1.52-1.44 (m, 2H), 1.26 (s, 6H), 1.11-1.03 (m, 2H) |

TABLE 1-continued

| Example | Structure | Name | LCMS (M + H)+ | HPLC Method, RT (min.) | 1H NMR |
|---|---|---|---|---|---|
| 40 | 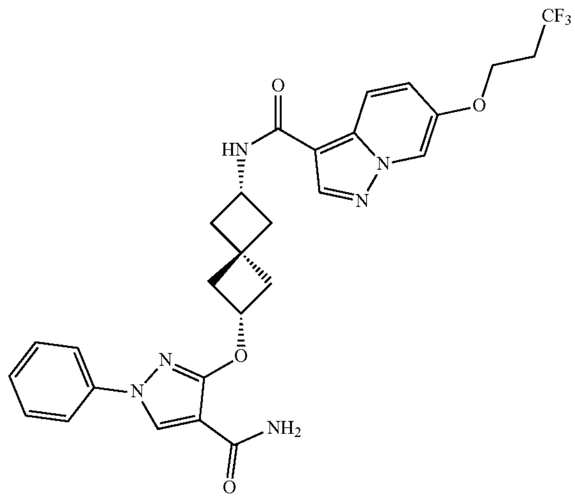 | 1-phenyl-3-{[(aR)-6-[6-(3,3,3-trifluoropropoxy)pyrazolo[1,5-a]pyridine-3-amido]spiro[3.3]heptan-2-yl]oxy}-1H-pyrazole-4-carboxamide | 569.3 | A: 1.85 B: 1.82 | (500 MHz, DMSO-d6) δ 8.72 (s, 1H), 8.54 (d, J = 1.2 Hz, 1H), 8.46 (s, 1H), 8.30 (br d, J = 7.3 Hz, 1H), 8.10 (d, J = 9.5 Hz, 1H), 7.80 (br d, J = 7.9 Hz, 2H), 7.49 (br t, J = 7.9 Hz, 2H), 7.35-7.21 (m, 3H), 6.75 (br s, 1H), 5.03 (quin, J = 7.1 Hz, 1H), 4.45-4.32 (m, 1H), 4.29 (t, J = 5.8 Hz, 2H), 3.58-3.40 (m, 1H), 2.83 (qt, J = 11.3, 5.6 Hz, 2H), 2.72 (dt, J = 11.0, 5.8 Hz, 1H), 2.48-2.41 (m, 1H), 2.40-2.23 (m, 3H), 2.17 (br t, J = 9.8 Hz, 2H). |
| 41 | 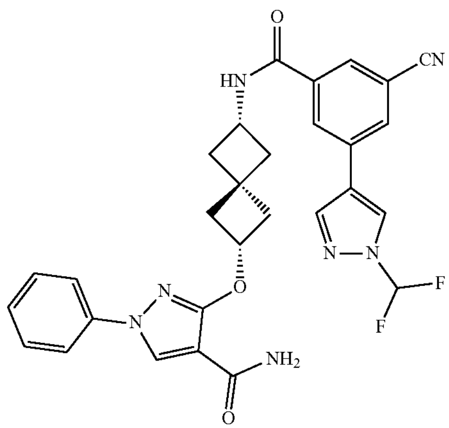 | 1-phenyl-3-{[(aR)-6-{3-cyano-5-[1-(difluoromethyl)-1H-pyrazol-4-yl]benzamido}spiro[3.3]heptan-2-yl]oxy}-1H-pyrazole-4-carboxamide | 558.4 | A: 1.84 B: 1.81 | (500 MHz, DMSO-d6) δ 8.91 (s, 1H), 8.82 (br d, J = 7.3 Hz, 1H), 8.72 (s, 1H), 8.48-8.35 (m, 3H), 8.12 (s, 1H), 8.00-7.71 (m, 3H), 7.49 (t, J = 7.9 Hz, 2H), 7.34-7.25 (m, 2H), 6.75 (br s, 1H), 5.10-4.95 (m, 1H), 4.42-4.34 (m, 1H), 2.80-2.69 (m, 1H), 2.44-2.25 (m, 3H), 2.22 (br t, J = 10.1 Hz, 2H). |

| Example | Structure | Name | LCMS (M + H)+ | HPLC Method, RT (min.) | 1H NMR |
|---|---|---|---|---|---|
| 42 | 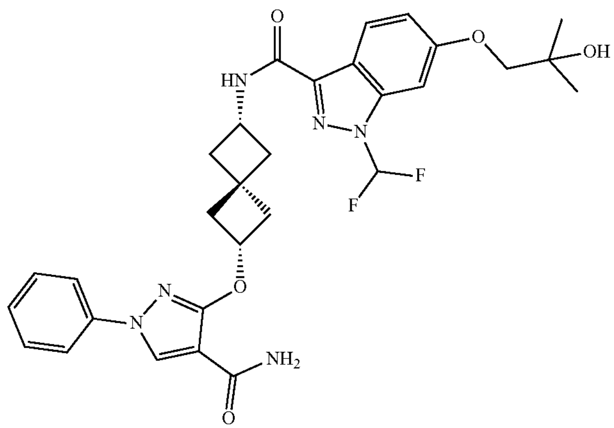 | 1-(difluoromethyl)-6-(2-hydroxy-2-methylpropoxy)-N-[(aR)-6-[(4-carbamoyl-1-phenyl-1H-pyrazol-3-yl)oxy]spiro[3.3]heptan-2-yl]-1H-indazole-3-carboxamide | 595.4 | A: 1.87 B: 1.83 | (500 MHz, DMSO-d6) δ 8.84 (br d, J = 7.6 Hz, 1H), 8.70 (s, 1H), 8.35-8.03 (m, 2H), 7.79 (br d, J = 7.9 Hz, 2H), 7.50 (t, J = 7.9 Hz, 2H), 7.38-7.23 (m, 3H), 7.09 (dd, J = 9.0, 1.4 Hz, 1H), 6.77 (br s, 1H), 5.03 (quin, J = 7.0 Hz, 1H), 4.48-4.38 (m, 1H), 3.84 (s, 2H), 3.54 (br s, 1H), 2.73 (dt, J = 11.2, 5.8 Hz, 1H), 2.47-2.40 (m, 1H), 2.39-2.19 (m, 5H), 1.25 (s, 6H). |
| 43 | 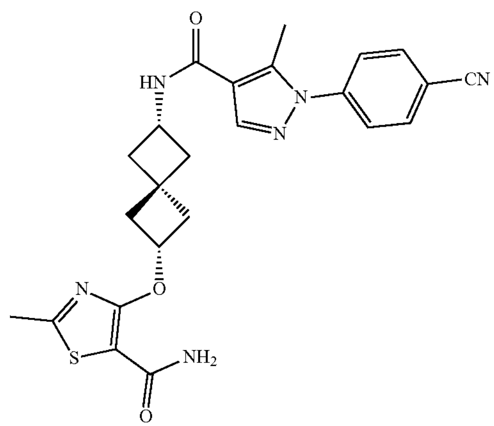 | 2-methyl-4-[[(aR)-6-[1-(4-cyanophenyl)-5-methyl-1H-pyrazole-4-amido]spiro[3.3]heptan-2-yl]oxy]-1,3-thiazole-5-carboxamide | 477.2 | A: 1.50 B: 1.37 | (500 MHz, DMSO-d6) δ 8.29 (br d, J = 7.6 Hz, 1H), 8.18 (s, 1H), 8.03 (d, J = 8.5 Hz, 2H), 7.77 (d, J = 8.5 Hz, 2H), 7.52 (br s, 1H), 6.86 (br s, 1H), 5.13 (t, J = 7.0 Hz, 1H), 4.41-4.22 (m, 1H), 2.59 (s, 3H), 2.52 (m, 5H), 2.49-2.22 (m, 5H), 2.19-2.08 (m, 2H) |

TABLE 1-continued

| Example | Structure | Name | LCMS (M + H)+ | HPLC Method, RT (min.) | 1H NMR |
|---|---|---|---|---|---|
| 44 | 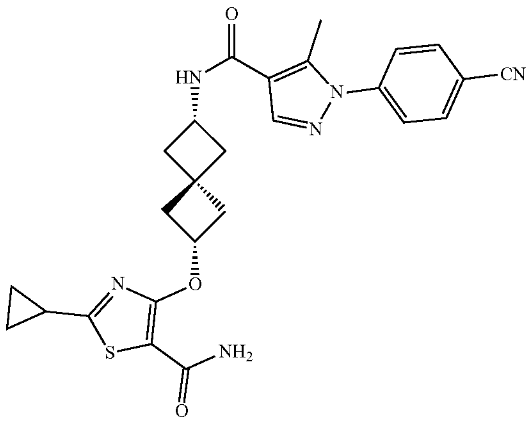 | 2-cyclopropyl-4-{[(aR)-6-[1-(4-cyanophenyl)-5-methyl-1H-pyrazole-4-amido]spiro[3.3]heptan-2-yl]oxy}-1,3-thiazole-5-carboxamide | 502.9 | A: 1.64 B: 1.62 | (500 MHz, DMSO-d6) δ 8.28 (br d, J = 7.6 Hz, 1H), 8.19 (s, 1H), 8.04 (d, J = 8.5 Hz, 2H), 7.78 (d, J = 8.5 Hz, 2H), 7.54 (br s, 1H), 6.80 (br s, 1H), 5.14-5.00 (m, 1H), 4.39-4.26 (m, 1H), 3.18 (d, J = 5.2 Hz, 1H), 2.58 (s, 2H), 2.46-2.21 (m, 5H), 2.18-2.06 (m, 2H), 1.23-1.10 (m, 2H), 1.06-0.91 (m, 2H) |
| 45 | 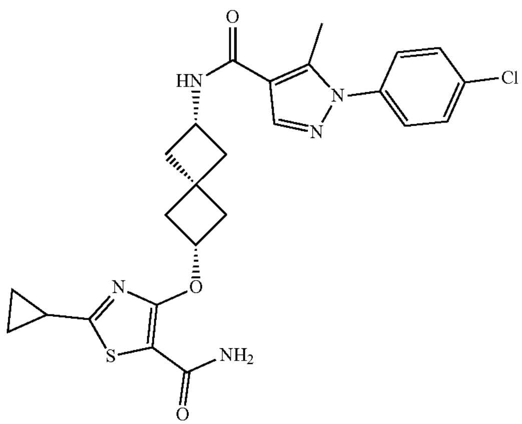 | 2-cyclopropyl-4-{[(aR)-6-[1-(4-chlorophenyl)-5-methyl-1H-pyrazole-4-amido]spiro[3.3]heptan-2-yl]oxy}-1,3-thiazole-5-carboxamide | 512.1 | A: 1.87 B: 1.83 | (500 MHz, DMSO-d6) δ 8.23 (br d, J = 7.6 Hz, 1H), 8.13 (s, 1H), 7.66-7.58 (m, 2H), 7.59-7.50 (m, 2H), 6.80 (br s, 1H), 5.07 (br t, J = 7.1 Hz, 1H), 4.39-4.26 (m, 1H), 2.70-2.57 (m, 2H), 2.55 (s, 3H), 2.45-2.19 (m, 5H), 2.18-2.09 (m, 2H), 1.17 (br dd, J = 8.0, 2.9 Hz, 2H), 1.03-0.94 (m, 2H) |

TABLE 1-continued

| Example | Structure | Name | LCMS (M + H)+ | HPLC Method, RT (min.) | 1H NMR |
|---|---|---|---|---|---|
| 46 | 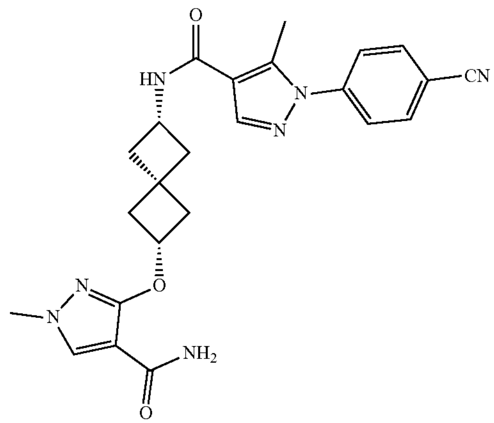 | 1-(4-cyanophenyl)-5-methyl-N-[(aR)-6-[(4-carbamoyl-1-methyl-1H-pyrazol-3-yl)oxy]spiro[3.3]heptan-2-yl]-1H-pyrazole-4-carboxamide | 460.2 | A: 1.15 B: 1.20 | (500 MHz, DMSO-$d_6$) δ 8.26 (br d, J = 7.3 Hz, 1H), 8.20 (s, 1H), 8.04 (d, J = 8.5 Hz, 2H), 7.90 (s, 1H), 7.78 (d, J = 8.5 Hz, 2H), 7.08 (br s, 1H), 6.52 (br s, 1H), 4.89 (t, J = 7.0 Hz, 1H), 4.41-4.25 (m, 1H), 3.69 (s, 2H), 2.66-2.59 (m, 1H), 2.58 (s, 3H), 2.43 (br dd, J = 11.6, 6.4 Hz, 3H), 2.27-2.06 (m, 4H) |
| 47 | 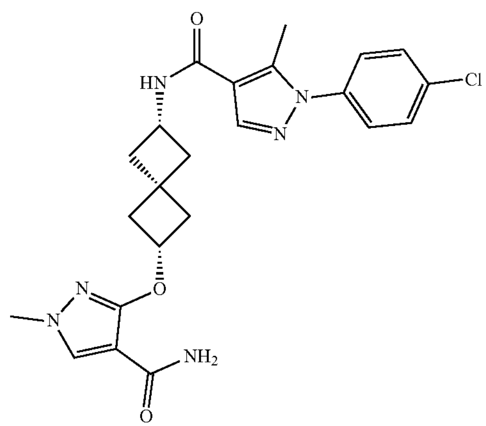 | 1-(4-chlorophenyl)-5-methyl-N-[(aR)-6-[(4-carbamoyl-1-methyl-1H-pyrazol-3-yl)oxy]spiro[3.3]heptan-2-yl]-1H-pyrazole-4-carboxamide | 469.4 | A: 1.45 B: 1.46 | (500 MHz, DMSO-$d_6$) δ 8.24 (br d, J = 7.4 Hz, 1H), 8.13 (s, 1H), 7.90 (s, 1H), 7.66-7.59 (m, 2H), 7.58-7.53 (m, 2H), 7.11 (br s, 1H), 6.53 (br s, 1H), 4.87 (t, J = 7.0 Hz, 1H), 4.38-4.25 (m, 1H), 3.68 (s, 3H), 2.60 (br dd, J = 11.4, 6.1 Hz, 1H), 2.55 (s, 3H), 2.42 (br dd, J = 12.5, 7.1 Hz, 2H), 2.36-2.26 (m, 1H), 2.26-2.09 (m, 4H) |

TABLE 1-continued

| Example | Structure | Name | LCMS (M + H)+ | HPLC Method, RT (min.) | 1H NMR |
|---|---|---|---|---|---|
| 48 | 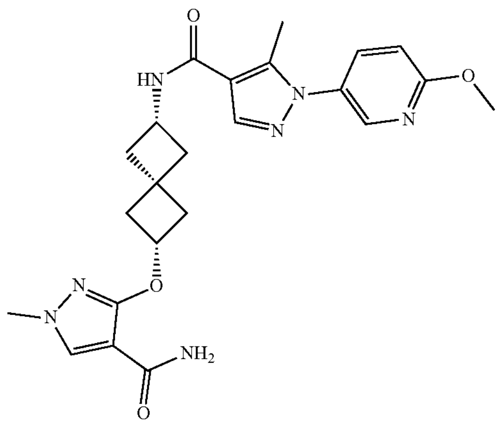 | 1-(6-methoxypyridin-3-yl)-5-methyl-N-[(aR)-6-[(4-carbamoyl-1-methyl-1H-pyrazol-3-yl)oxy]spiro[3.3]heptan-2-yl]-1H-pyrazole-4-carboxamide | 466.2 | A: 1.17 B: 1.15 | (500 MHz, DMSO-$d_6$) δ 8.33 (d, J = 2.5 Hz, 1H), 8.23 (br d, J = 7.4 Hz, 1H), 8.16-8.04 (m, 1H), 7.95-7.79 (m, 2H), 7.11 (br s, 1H), 7.00 (d, J = 8.8 Hz, 1H), 6.54 (br s, 1H), 4.94-4.78 (m, 1H), 4.41-4.23 (m, 1H), 3.93 (s, 3H), 3.62-3.46 (m, 1H), 2.61 (br dd, J = 11.1, 5.7 Hz, 1H), 2.46 (s, 3H), 2.44-2.35 (m, 2H), 2.35-2.28 (m, 1H), 2.26-2.09 (m, 4H) |
| 49 | 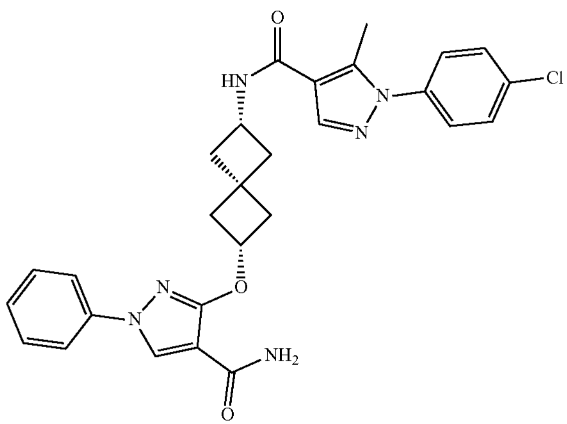 | 1-phenyl-3-{[(aR)-6-[1-(4-chlorophenyl)-5-methyl-1H-pyrazole-4-amido]spiro[3.3]heptan-2-yl]oxy}-1H-pyrazole-4-carboxamide | 531.2 | A: 1.90 B: 1.87 | (500 MHz, DMSO-$d_6$) δ 8.75 (s, 1H), 8.23 (br d, J = 7.3 Hz, 1H), 8.14 (s, 1H), 7.82 (br d, J = 7.9 Hz, 2H), 7.65-7.60 (m, 2H), 7.59-7.54 (m, 2H), 7.50 (t, J = 7.9 Hz, 2H), 7.34-7.27 (m, 2H), 6.74 (br s, 1H), 5.04 (t, J = 7.0 Hz, 1H), 4.42-4.30 (m, 1H), 2.72 (dt, J = 11.2, 5.5 Hz, 1H), 2.55 (s, 3H), 2.50-2.42 (m, 1H), 2.40-2.23 (m, 3H), 2.17 (br t, J = 9.9 Hz, 2H) |

| Example | Structure | Name | LCMS (M + H)+ | HPLC Method, RT (min.) | 1H NMR |
|---|---|---|---|---|---|
| 50 | 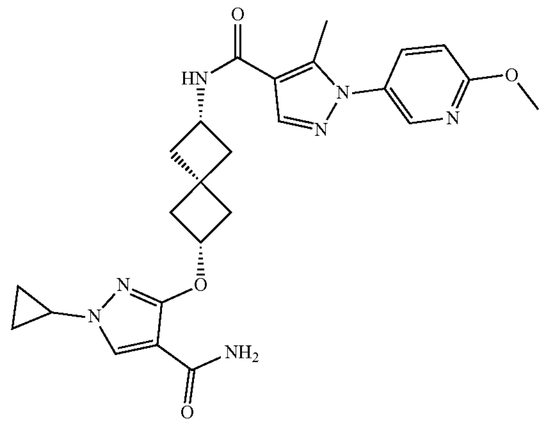 | 1-cyclopropyl-3-{[(aR)-6-[1-(6-methoxypyridin-3-yl)-5-methyl-1H-pyrazole-4-amido]spiro[3.3]heptan-2-yl]oxy}-1H-pyrazole-4-carboxamide | 492.2 | A: 1.29 B: 1.25 | (500 MHz, DMSO-d6) δ 8.33 (d, J = 2.4 Hz, 1H), 8.20 (br d, J = 7.6 Hz, 1H), 8.13 (s, 1H), 7.96 (s, 1H), 7.88 (dd, J = 8.9, 2.4 Hz, 1H), 7.09 (br s, 1H), 7.00 (d, J = 8.9 Hz, 1H), 6.55 (br s, 1H), 4.89 (quin, J = 7.0 Hz, 1H), 4.41-4.22 (m, 1H), 3.57 (dt, J = 7.0, 3.5 Hz, 1H), 2.61 (br dd, J = 11.0, 6.1 Hz, 1H), 2.46 (s, 3H), 2.45-2.36 (m, 2H), 2.35-2.27 (m, 1H), 2.26-2.09 (m, 4H), 1.04-0.97 (m, 2H), 0.96-0.88 (m, 2H) |
| 51 | 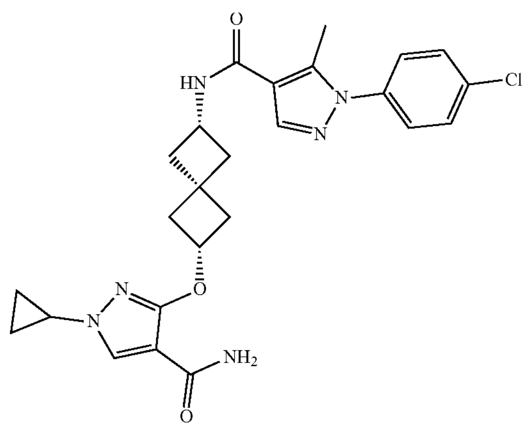 | 1-cyclopropyl-3-{[(aR)-6-[1-(4-chlorophenyl)-5-methyl-1H-pyrazole-4-amido]spiro[3.3]heptan-2-yl]oxy}-1H-pyrazole-4-carboxamide | 495.2 | A: 1.62 B: 1.60 | (500 MHz, DMSO-d6) δ 8.22 (br d, J = 7.3 Hz, 1H), 8.13 (s, 1H), 7.96 (s, 2H), 7.65-7.59 (m, 2H), 7.58-7.53 (m, 2H), 7.41-7.29 (m, 1H), 7.09 (br s, 1H), 6.55 (br s, 1H), 4.89 (br t, J = 7.0 Hz, 1H), 4.38-4.28 (m, 1H), 2.61 (br dd, J = 11.1, 6.0 Hz, 1H), 2.56 (s, 2H), 2.48-2.27 (m, 4H), 2.27-2.08 (m, 3H), 0.99 (br d, J = 2.7 Hz, 2H), 0.92 (br d, J = 5.8 Hz, 2H) |

TABLE 1-continued

| Example | Structure | Name | LCMS (M + H)+ | HPLC Method, RT (min.) | 1H NMR |
|---|---|---|---|---|---|
| 52 | 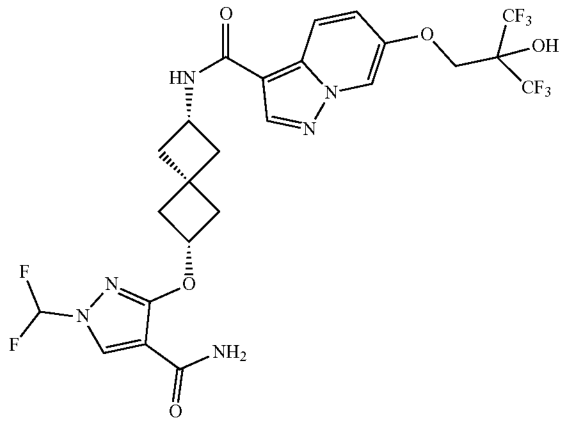 | 1-(difluoromethyl)-3-{[(aR)-6-{6-[3,3,3-trifluoro-2-hydxoxy-2-(trifluoromethyl)propoxy]pyrazolo[1,5-a]pyridine-3-amido}spiro[3.3]heptan-2-yl]oxy}-1H-pyrazole-4-carboxamide | 627.2 | A: 1.66 B: 1.66 | (500 MHz, DMSO-d6) δ 8.67 (s, 1H), 8.48 (s, 1H), 8.42 (s, 1H), 8.33 (br d, J = 7.3 Hz, 1H), 8.12 (d, J = 9.8 Hz, 1H), 7.75-7.46 (m, 1H), 7.40 (br s, 1H), 7.31-7.24 (m, 1H), 6.86 (br s, 1H), 4.95 (br t, J = 7.0 Hz, 1H), 4.51 (s, 2H), 4.43-4.29 (m, 1H), 2.73-2.59 (m, 2H), 2.49-2.39 (m, 2H), 2.39-2.10 (m, 5H) |
| 53 | 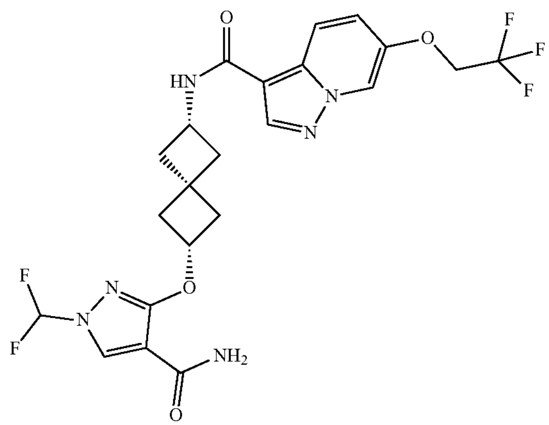 | 1-(difluoromethyl)-3-{[(aR)-6-{6-(2,2,2-trifluoroethoxy)pyrazolo[1,5-a]pyridine-3-amido}spiro[3.3]heptan-2-yl]oxy}-1H-pyrazole-4-carboxamide | 529.3 | A: 1.57 B: 1.57 | (500 MHz, DMSO-d6) δ 8.68 (s, 1H), 8.50 (s, 1H), 8.43 (s, 1H), 8.33 (br d, J = 7.6 Hz, 1H), 8.13 (d, J = 9.8 Hz, 1H), 7.79-7.47 (m, 1H), 7.45-7.31 (m, 2H), 6.85 (br s, 1H), 4.96 (br t, J = 7.0 Hz, 1H), 4.87 (q, J = 8.9 Hz, 2H), 4.47-4.29 (m, 1H), 2.74-2.60 (m, 1H), 2.50-2.21 (m, 5H), 2.16 (br t, J = 9.2 Hz, 2H) |

TABLE 1-continued

| Example | Structure | Name | LCMS (M + H)+ | HPLC Method, RT (min.) | 1H NMR |
|---|---|---|---|---|---|
| 54 | 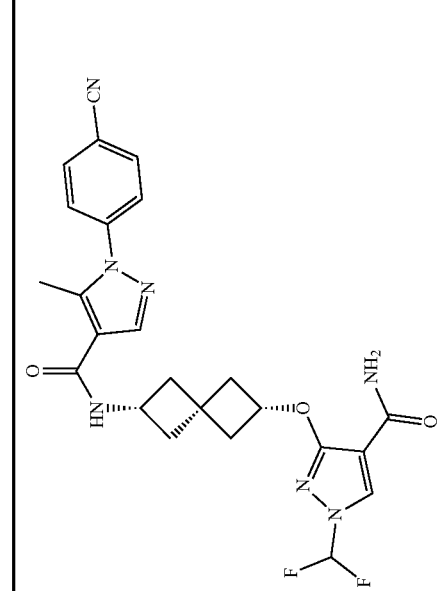 | 1-(4-cyanophenyl)-5-methyl-N-[(aR)-6-{[4-carbamoyl-1-(difluoromethyl)-1H-pyrazol-3-yl]oxy}spiro[3.3]heptan-2-yl]-1H-pyrazole-4-carboxamide | 495.9 | A: 1.44 B: 1.45 | (500 MHz, DMSO-d6) δ 8.39 (s, 1H), 8.15 (s, 2H), 8.00 (br d, J = 8.6 Hz, 2H), 7.75 (br d, J = 8.5 Hz, 2H), 7.56 (s, 1H), 5.03-4.90 (m, 2H), 4.31 (br d, J = 8.8 Hz, 1H), 2.64 (br d, J = 2.1 Hz, 2H), 2.45-2.31 (m, 3H), 2.30-2.11 (m, 4H) |
| 55 | 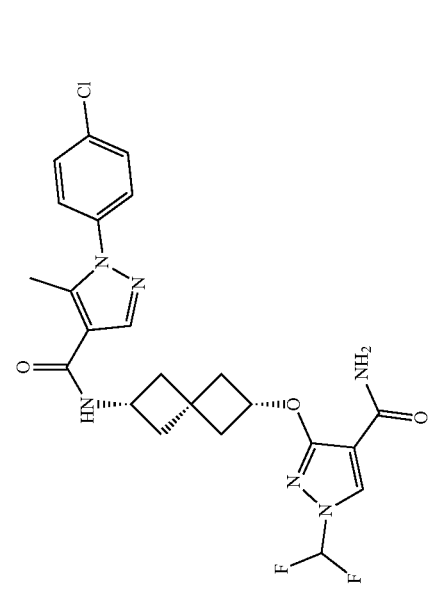 | 1-(4-chlorophenyl)-5-methyl-N-[(aR)-6-{[4-carbamoyl-1-(difluoromethyl)-1H-pyrazol-3-yl]oxy}spiro[3.3]heptan-2-yl]-1H-pyrazole-4-carboxamide | 505.3 | A: 1.66 B: 1.67 | (500 MHz, DMSO-d6) δ 8.42 (s, 1H), 8.25 (br d, J = 7.3 Hz, 1H), 8.12 (s, 1H), 7.76-7.45 (m, 5H), 7.40 (br s, 1H), 6.86 (br s, 1H), 4.95 (t, J = 7.0 Hz, 1H), 4.39-4.27 (m, 1H), 2.69-2.57 (m, 1H), 2.49 (s, 3H), 2.47-2.37 (m, 2H), 2.36-2.18 (m, 3H), 2.14 (br t, J = 9.2 Hz, 2H) |

| Example | Structure | Name | LCMS (M + H)+ | HPLC Method, RT (min.) | 1H NMR |
|---|---|---|---|---|---|
| 56 | 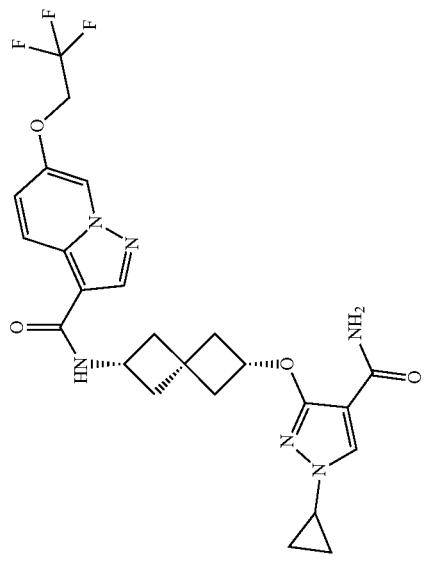 | 1-cyclopropyl-3-{[(aR)-6-[6-(2,2,2-trifluoroethoxy)pyrazolo[1,5-a]pyridine-3-amido]spiro[3.3]heptan-2-yl]oxy}-1H-pyrazole-4-carboxamide | 519.0 | A: 1.51 B: 1.51 | (500 MHz, DMSO-$d_6$) δ 8.69 (s, 1H), 8.50 (s, 1H), 8.30 (br d, J = 7.6 Hz, 1H), 8.13 (d, J = 9.8 Hz, 1H), 7.96 (s, 1H), 7.37 (dd, J = 9.8, 1.8 Hz, 1H), 7.10 (br d, J = 8.2 Hz, 1H), 6.54 (br s, 1H), 4.99-4.77 (m, 3H), 4.45-4.27 (m, 1H), 3.57 (dt, J = 7.1, 3.6 Hz, 1H), 2.63 (dt, J = 11.3, 5.6 Hz, 1H), 2.44 (br dd, J = 11.4, 4.7 Hz, 2H), 2.34 (br s, 1H), 2.27-2.10 (m, 4H), 0.99 (br d, J = 3.1 Hz, 2H), 0.94-0.87 (m, 2H) |
| 57 | 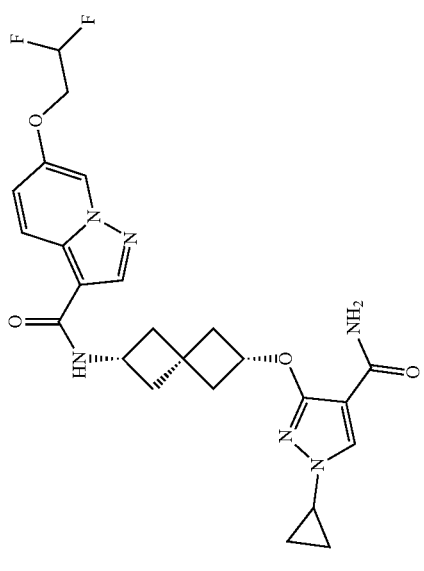 | 1-cyclopropyl-3-{[(aR)-6-[6-(2,2-difluoroethoxy)pyrazolo[1,5-a]pyridine-3-amido]spiro[3.3]heptan-2-yl]oxy}-1H-pyrazole-4-carboxamide | 501.3 | A: 1.31 B: 1.32 | (500 MHz, CHLOROFORM-d) δ 8.25-8.04 (m, 3H), 7.90-7.70 (m, 1H), 7.19 (br d, J = 9.6 Hz, 1H), 6.31-5.92 (m, 1H), 5.10-4.86 (m, 1H), 4.63-4.36 (m, 1H), 4.30-4.09 (m, 2H), 3.55-3.29 (m, 2H), 2.81-2.38 (m, 5H), 2.31-2.04 (m, 4H), 1.11-0.80 (m, 4H) |

TABLE 1-continued

| Example | Structure | Name | LCMS (M + H)+ | HPLC Method, RT (min.) | 1H NMR |
|---|---|---|---|---|---|
| 58 | 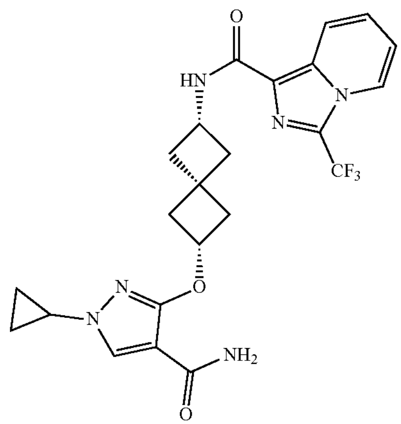 | 1-cyclopropyl-3-{[(1aR)-6-[3-(trifluoromethyl)imidazo[1,5-a]pyridine-1-amido]spiro[3.3]heptan-2-yl]oxy}-1H-pyrazole-4-carboxamide | 489.0 | A: 1.63 B: 1.61 | (500 MHz, DMSO-d$_6$) δ 8.52 (br d, J = 7.2 Hz, 1H), 8.38-8.18 (m, 2H), 7.93 (s, 1H), 7.45-7.32 (m, 1H), 7.26-7.09 (m, 1H), 4.97-4.83 (m, 1H), 4.50-4.32 (m, 1H), 3.58 (dt, J = 7.3, 3.6 Hz, 1H), 2.62 (br dd, J = 11.4, 6.5 Hz, 2H), 2.48-2.09 (m, 6H), 1.07-0.95 (m, 2H), 0.96-0.84 (m, 2H) |
| 59 | 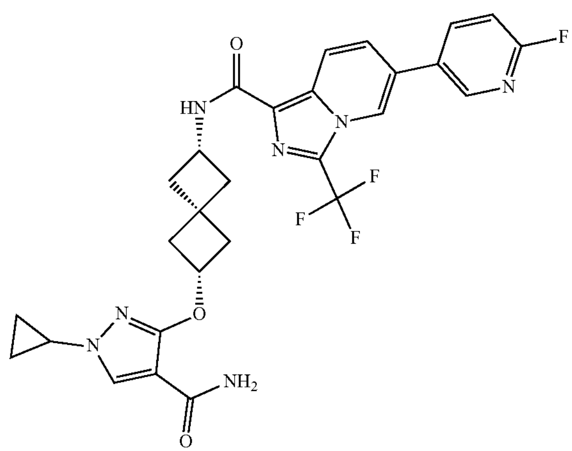 | 1-cyclopropyl-3-{[(1aR)-6-[6-(6-fluoropyridin-3-yl)-3-(trifluoromethyl)imidazo[1,5-a]pyridine-1-amido]spiro[3.3]heptan-2-yl]oxy}-1H-pyrazole-4-carboxamide | 584.2 | A: 1.76 B: 1.76 | (500 MHz, DMSO-d$_6$) δ 8.66 (br d, J = 14.4 Hz, 2H), 8.47-8.27 (m, 3H), 7.92 (s, 1H), 7.74 (br d, J = 9.4 Hz, 1H), 7.34 (dd, J = 8.5, 2.7 Hz, 1H), 4.90 (br t, J = 6.9 Hz, 1H), 4.52-4.34 (m, 1H), 3.57 (dt, J = 7.3, 3.4 Hz, 1H), 3.19 (br d, J = 4.8 Hz, 1H), 2.63 (br dd, J = 10.9, 5.8 Hz, 1H), 2.47-2.27 (m, 5H), 2.26-2.12 (m, 2H), 0.99 (br d, J = 3.3 Hz, 2H), 0.96-0.87 (m, 2H) |

TABLE 1-continued

| Example | Structure | Name | LCMS (M + H)+ | HPLC Method, RT (min.) | 1H NMR |
|---|---|---|---|---|---|
| 60 | 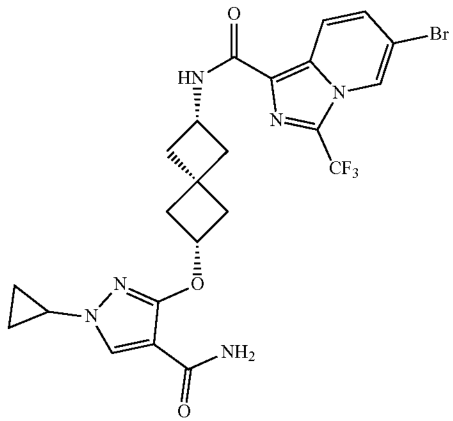 | 1-cyclopropyl-3-{[(aR)-6-[6-bromo-3-(trifluoromethyl)imidazo[1,5-a]pyridine-1-amido]spiro[3.3]heptan-2-yl]oxy}-1H-pyrazole-4-carboxamide | 569.1 | C: 9.19 D: 10.18 | (500 MHz, CHLOROFORM-d) δ 8.37 (d, J = 9.6 Hz, 1H), 8.33 (s, 1H), 7.31-7.22 (m, 3H), 6.64 (br s, 1H), 5.48 (br s, 1H), 5.11-4.95 (m, 1H), 4.65-4.47 (m, 1H), 2.66-2.49 (m, 4H), 2.31-2.19 (m, 4H), 1.07-1.01 (m, 4H) |
| 61 | 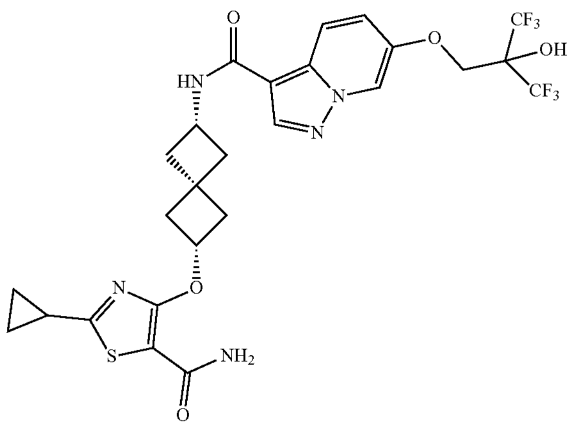 | 2-cyclopropyl-4-{[(aR)-6-[3,3,3-trifluoro-2-hydroxy-2-(trifluoromethyl)propoxy]pyrazolo[1,5-a]pyridine-3-amido]spiro[3.3]heptan-2-yl]oxy}-1,3-thiazole-5-carboxamide | 634.1 | A: 1.82 B: 1.80 | (500 MHz, DMSO-d6) δ 8.68 (d, J = 1.5 Hz, 1H), 8.48 (s, 1H), 8.30 (br d, J = 7.3 Hz, 1H), 8.12 (d, J = 9.8 Hz, 1H), 7.50 (br s, 1H), 7.28 (dd, J = 9.8, 1.8 Hz, 1H), 6.79 (br s, 1H), 5.08 (t, J = 7.0 Hz, 1H), 4.53 (s, 2H), 4.45-4.26 (m, 1H), 2.67-2.57 (m, 1H), 2.42 (br dd, J = 11.3, 5.5 Hz, 2H), 2.39-2.20 (m, 4H), 1.21-1.13 (m, 2H), 1.02-0.94 (m, 2H) |

TABLE 1-continued

| Example | Structure | Name | LCMS (M + H)+ | HPLC Method, RT (min.) | 1H NMR |
|---|---|---|---|---|---|
| 62 | 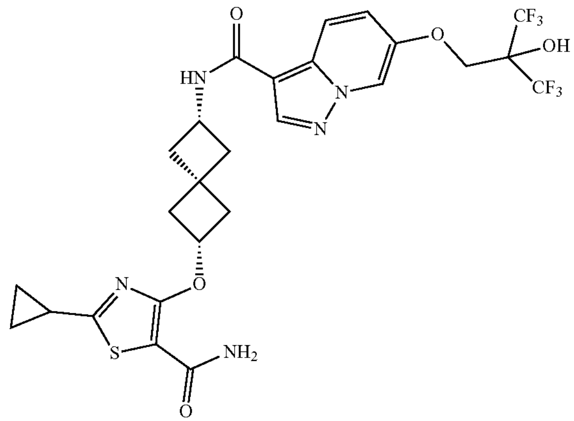 | 2-cyclopropyl-4-{[(aR)-6-[6-(2,2,2-trifluoroethoxy)pyrazolo[1,5-a]pyridine-3-amido]spiro[3.3]heptan-2-yl]oxy}-1,3-thiazole-5-carboxamide | 535.9 | A: 1.75 B: 1.73 | (500 MHz, DMSO-d$_6$) δ 8.66 (s, 1H), 8.49 (s, 1H), 8.34 (br d, J = 7.3 Hz, 1H), 8.12 (d, J = 9.8 Hz, 1H), 7.47 (br s, 1H), 7.37 (br d, J = 11.0 Hz, 1H), 6.80 (br s, 1H), 5.07 (br t, J = 7.0 Hz, 1H), 4.85 (q, J = 8.5 Hz, 2H), 4.44-4.19 (m, 1H), 2.60 (br dd, J = 11.1, 6.3 Hz, 1H), 2.42 (br d, J = 6.1 Hz, 2H), 2.36-2.20 (m, 4H), 2.19-2.09 (m, 2H), 1.21-1.12 (m, 2H), 0.97 (br d, J = 3.4 Hz, 2H) |
| 63 | 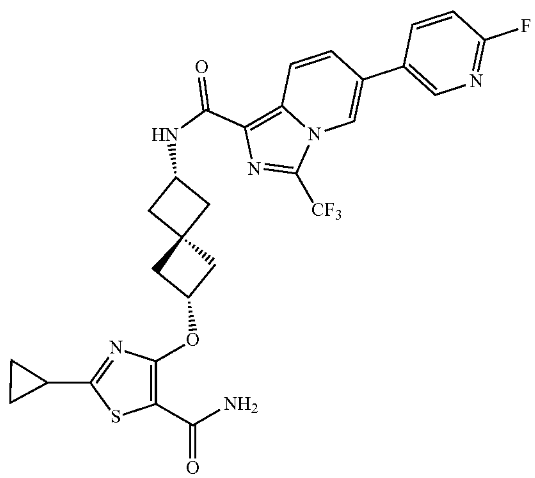 | 2-cyclopropyl-4-{[(aR)-6-[6-(6-fluoropyridin-3-yl)-3-(trifluoromethyl)imidazo[1,5-a]pyridine-1-amido]spiro[3.3]heptan-2-yl]oxy}-1,3-thiazole-5-carboxamide | 601.0 | A: 2.05 B: 2.02 | (500 MHz, DMSO-d$_6$) δ 8.72 (s, 1H), 8.67 (d, J = 1.8 Hz, 1H), 8.52 (d, J = 8.2 Hz, 1H), 8.45-8.37 (m, 2H), 7.76 (d, J = 9.8 Hz, 1H), 7.50 (br s, 1H), 7.37 (dd, J = 8.5, 2.4 Hz, 1H), 6.79 (br s, 1H), 5.07 (quin, J = 7.0 Hz, 1H), 4.49-4.38 (m, 1H), 2.61 (dt, J = 11.2, 5.8 Hz, 1H), 2.46-2.26 (m, 7H), 2.23 (dd, J = 11.7, 7.2 Hz, 1H), 1.17 (dd, J = 7.9, 3.1 Hz, 2H), 0.99 (quin, J = 3.6 Hz, 2H) |

TABLE 1-continued

| Example | Structure | Name | LCMS (M + H)+ | HPLC Method, RT (min.) | 1H NMR |
|---|---|---|---|---|---|
| 64 | 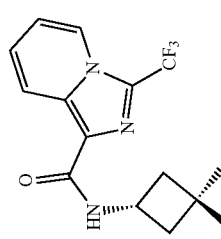 | 2-cyclopropyl-4-{[(aR)-6-[3-(trifluoromethyl)imidazo[1,5-a]pyridine-1-amido]spiro[3.3]heptan-2-yl]oxy}-1,3-thiazole-5-carboxamide | 506.3 | A: 1.93 B: 1.88 | 1H NMR (500 MHz, DMSO-$d_6$) δ 8.49 (br d, J = 7.0 Hz, 1H), 8.30 (br d, J = 9.1 Hz, 1H), 8.25 (br d, J = 7.8 Hz, 1H), 7.38 (dd, J = 8.8, 7.0 Hz, 1H), 7.16 (br t, J = 6.9 Hz, 1H), 5.06 (quin, J = 6.9 Hz, 1H), 4.40 (dq, J = 16.0, 7.8 Hz, 1H), 2.65-2.57 (m, 1H), 2.46-2.36 (m, 2H), 2.35-2.24 (m, 5H), 2.21 (br dd, J = 11.7, 7.1 Hz, 1H), 1.15 (br dd, J = 8.0, 2.8 Hz, 2H), 0.96 (br d, J = 2.9 Hz, 2H) |
| 65 | 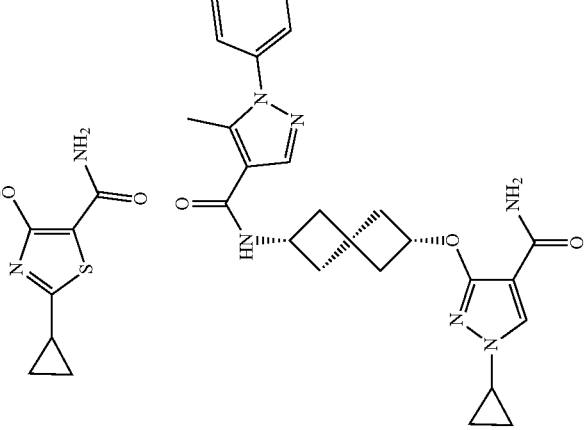 | 1-cyclopropyl-3-{[(aR)-6-(5-methyl-1-phenyl-1H-pyrazole-4-amido)spiro[3.3]heptan-2-yl]oxy}-1H-pyrazole-4-carboxamide | 461.0 | A: 1.41 B: 1.41 | (500 MHz, DMSO-$d_6$) δ 8.21 (br d, J = 7.3 Hz, 1H), 8.10 (s, 1H), 7.60-7.52 (m, 2H), 7.49 (br d, J = 7.6 Hz, 3H), 7.07 (br s, 1H), 6.56 (br s, 1H), 4.93-4.82 (m, 1H), 4.38-4.24 (m, 1H), 2.65-2.58 (m, 1H), 2.48 (s, 3H), 2.46-2.26 (m, 3H), 2.26-2.09 (m, 4H), 0.98 (br d, J = 3.4 Hz, 2H), 0.91 (br d, J = 5.5 Hz, 2H) |

| Example | Structure | Name | LCMS (M + H)+ | HPLC Method, RT (min.) | 1H NMR |
|---|---|---|---|---|---|
| 66 | 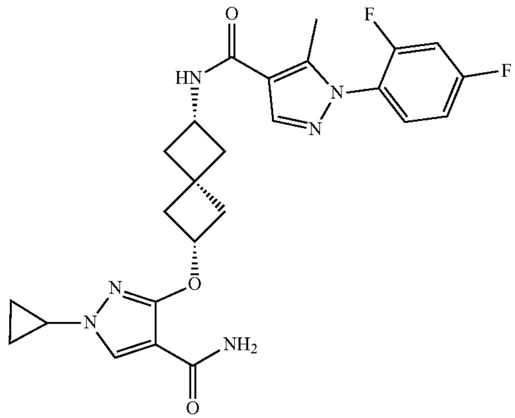 | 1-cyclopropyl-3-{[(aR)-6-[1-(2,4-difluorophenyl)-5-methyl-1H-pyrazole-4-amido]spiro[3.3]heptan-2-yl]oxy}-1H-pyrazole-4-carboxamide | 497.2 | A: 1.46 B: 1.47 | (500 MHz, DMSO-d6) δ 8.27 (br d, J = 7.3 Hz, 1H), 8.12 (s, 1H), 7.92 (s, 1H), 7.67-7.50 (m, 2H), 7.28 (br t, J = 8.0 Hz, 1H), 7.07 (br s, 1H), 6.58 (br s, 1H), 4.86 (quin, J = 6.9 Hz, 1H), 4.36-4.22 (m, 1H), 2.58 (td, J = 11.3, 5.6 Hz, 1H), 2.45-2.34 (m, 2H), 2.30 (s, 3H), 2.23-2.06 (m, 4H), 1.00-0.92 (m, 2H), 0.92-0.84 (m, 2H) |
| 67 | 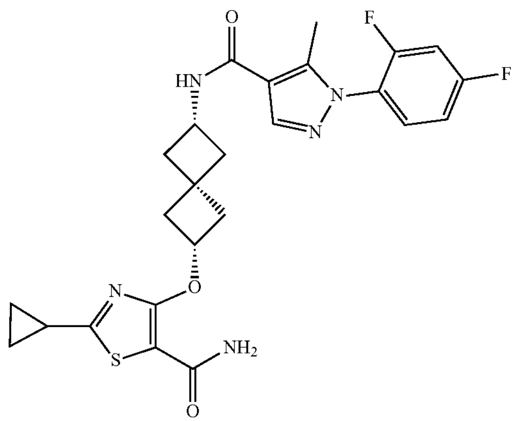 | 2-cyclopropyl-4-{[(aR)-6-[1-(2,4-difluorophenyl)-5-methyl-1H-pyrazole-4-amido]spiro[3.3]heptan-2-yl]oxy}-1,3-thiazole-5-carboxamide | 514.3 | A: 1.74 B: 1.72 | (500 MHz, DMSO-d6) δ 8.29 (br d, J = 7.2 Hz, 1H), 8.11 (s, 1H), 7.67-7.49 (m, 2H), 7.45 (br s, 1H), 7.28 (br t, J = 8.0 Hz, 1H), 6.81 (br s, 1H), 5.04 (quin, J = 6.9 Hz, 1H), 4.34-4.22 (m, 1H), 2.44-2.34 (m, 2H), 2.29 (s, 3H), 2.28-2.05 (m, 4H), 1.28-1.20 (m, 2H), 1.18-1.10 (m, 2H), 0.94 (br d, J = 2.9 Hz, 2H) |

TABLE 1-continued

| Example | Structure | Name | LCMS (M + H)+ | HPLC Method, RT (min.) | 1H NMR |
|---|---|---|---|---|---|
| 68 | 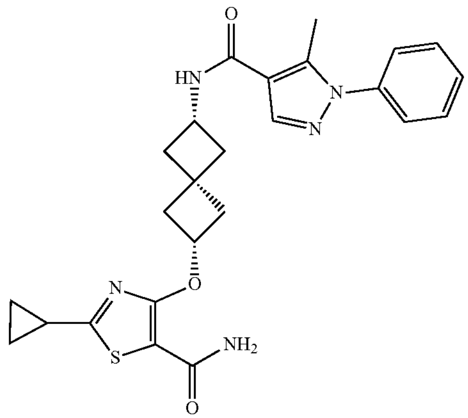 | 2-cyclopropyl-4-{[(aR)-6-(5-methyl-1-phenyl-1H-pyrazole-4-amido)spiro[3.3]heptan-2-yl]oxy}-1,3-thiazole-5-carboxamide | 478.3 | A: 1.69 B: 1.68 | (500 MHz, DMSO-d6) δ 8.24 (br s, 1H), 8.08 (s, 1H), 7.58-7.50 (m, 2H), 7.47 (br d, J = 5.4 Hz, 3H), 5.05 (quin, J = 6.8 Hz, 1H), 4.34-4.23 (m, 1H), 2.61-2.56 (m, 1H), 2.45 (s, 3H), 2.43-2.35 (m, 2H), 2.34-2.16 (m, 4H), 2.15-2.06 (m, 2H), 1.28-1.19 (m, 1H), 1.19-1.11 (m, 2H), 0.95 (br s, 2H) |
| 69 | 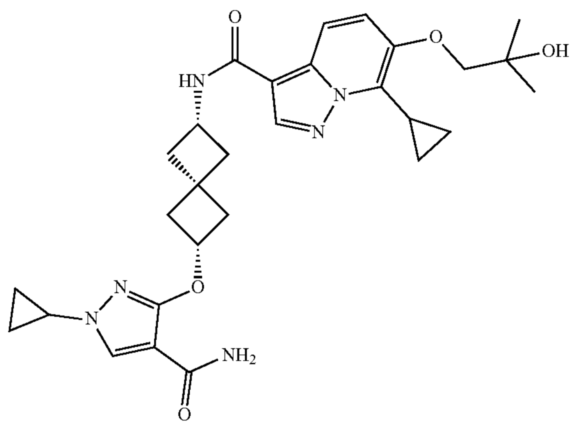 | 1-cyclopropyl-3-{[(aR)-6-[7-cyclopropyl-6-(2-hydroxy-2-methylpropoxy)pyrazolo[1,5-a]pyridine-3-amido]spiro[3.3]heptan-2-yl]oxy}-1H-pyrazole-4-carboxamide | 549.3 | C: 7.58 D: 6.20 | (500 MHz, METHANOL-d4) δ 8.46 (s, 1H), 8.10 (d, J = 9.6 Hz, 1H), 7.91 (s, 1H), 7.46 (d, J = 9.6 Hz, 1H), 5.05-4.94 (m, 1H), 4.48 (t, J = 8.0 Hz, 1H), 3.90 (s, 2H), 3.56 (dt, J = 7.3, 3.5 Hz, 1H), 2.83-2.68 (m, 1H), 2.62-2.53 (m, 2H), 2.51-2.40 (m, 2H), 2.35 -2.20 (m, 4H), 1.43-1.35 (m, 9H), 1.22-1.13 (m, 2H), 1.11-0.97 (m, 4H). |

TABLE 1-continued

| Example | Structure | Name | LCMS (M + H)+ | HPLC Method, RT (min.) | 1H NMR |
|---|---|---|---|---|---|
| 70 | 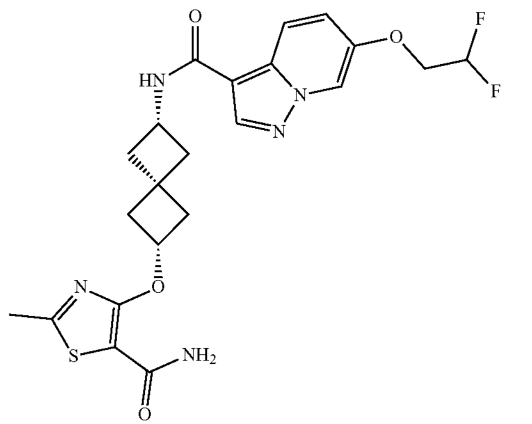 | 2-methyl-4-[((aR)-6-[6-(2,2-difluoroethoxy)pyrazolo[1,5-a]pyridine-3-amido]spiro[3.3]heptan-2-yl}oxy}-1,3-thiazole-5-carboxamide | 492.2 | A: 1.44 B: 1.51 | (500 MHz, DMSO-d6) δ 8.56 (br s, 1H), 8.45 (s, 1H), 8.35 (br d, J = 7.0 Hz, 1H), 8.10 (br d, J = 9.8 Hz, 1H), 7.48 (br s, 1H), 7.33 (br d, J = 9.8 Hz, 1H), 6.87 (br s, 1H), 6.59-6.22 (m, 1H), 5.11 (br t, J = 6.9 Hz, 1H), 4.49-4.23 (m, 3H), 2.61 (br d, J = 5.5 Hz, 1H), 2.57 (s, 3H), 2.48-2.07 (m, 6H) |
| 71 | 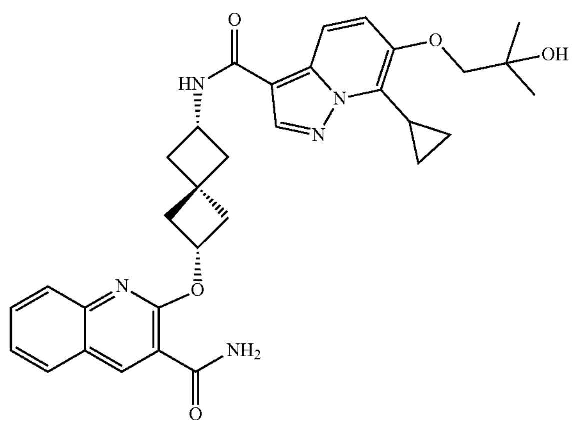 | 2-(((aR)6-(7-cyclopropyl-6-(2-hydroxy-2-methylpropoxy)pyrazolo[1,5-a]pyridine-3-carboxamido)spiro[3.3]heptan-2-yl)oxy)quinoline-3-carboxamide | 570.4 | A: 1.74 B: 1.74 | 1H NMR (500 MHz, DMSO-d6) δ 8.66 (s, 1H), 8.50 (s, 1H), 8.30 (br d, J = 7.6 Hz, 1H), 8.01 (dd, J = 18.6, 8.8 Hz, 2H), 7.94 (s, 1H), 7.83-7.70 (m, 4H), 7.51-7.42 (m, 2H), 5.36 (quin, J = 7.1 Hz, 1H), 4.45-4.33 (m, 1H), 3.79 (s, 2H), 2.80-2.74 (m, 1H), 2.63-2.56 (m, 2H), 2.42-2.11 (m, 5H), 1.46 (br d, J = 3.7 Hz, 2H), 1.24 (s, 6H), 1.06 (br dd, J = 8.5, 2.1 Hz, 2H) |

TABLE 1-continued

| Example | Structure | Name | LCMS (M + H)+ | HPLC Method, RT (min.) | 1H NMR |
|---|---|---|---|---|---|
| 72 | 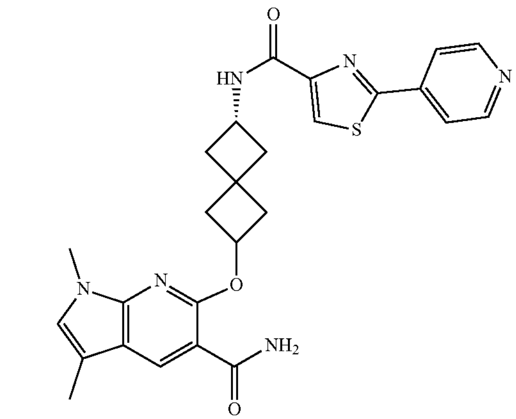 | N-[6-({5-carbamoyl-1,3-dimethyl-1H-pyrazolo[3,4-b]pyridin-6-yl}oxy)spiro[3.3]heptan-2-yl]-2-(pyridin-4-yl)-1,3-thiazole-4-carboxamide | 504.3 | A: 1.38 B: 1.05 | 1H NMR (400 MHz, DMSO-d6) 8.76 (d, J = 5.9 Hz, 2H), 8.71 (d, J = 8.3 Hz, 1H), 8.60 (s, 1H), 8.43 (s, 1H), 8.04 (d, J = 6.1 Hz, 2H), 7.58 (s, 1H), 7.60 (s, 1H), 5.29 (quin, J = 7.1 Hz, 1H), 4.49-4.36 (m, 1H), 3.88 (s, 3H), 2.83-2.75 (m, 1H), 2.60 (dt, J = 11.5, 6.0 Hz, 1H), 2.45 (s, 3H), 2.37-2.26 (m, 6H) |
| 73 | 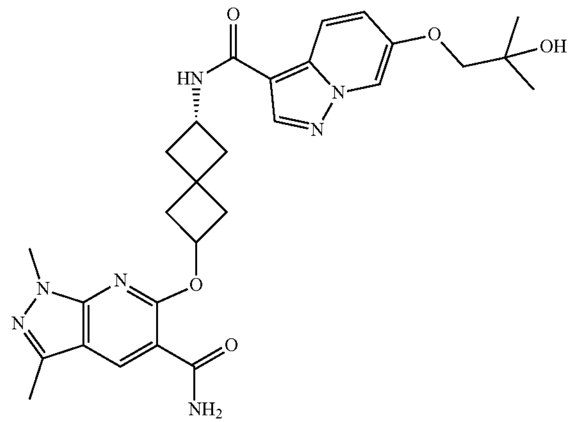 | 6-({6-[(2-hydroxy-2-methylpropoxy)pyrazolo[1,5-a]pyridine-3-amido]spiro[3.3]heptan-2-yl}oxy)-1,3-dimethyl-1H-pyrazolo[3,4-b]pyridine-5-carboxamide | 548.0 | A: 1.32 B: 1.33 | 1H NMR (400 MHz, DMSO-d6) 8.59 (s, 1H), 8.49-8.35 (m, 2H), 8.26 (d, J = 8.0 Hz, 1H), 8.08 (d, J = 9.5 Hz, 1H), 7.57 (s, 1H), 7.60 (s, 1H), 7.27 (dd, J = 9.5, 2.0 Hz, 1H), 5.28 (quin, J = 7.3 Hz, 1H), 4.71 (s, 1H), 4.49-4.36 (m, 1H), 3.95-3.84 (m, 3H), 3.83-3.72 (m, 2H), 2.84-2.73 (m, 1H), 2.59 (dt, J = 11.9, 5.8 Hz, 1H), 2.44 (s, 3H), 2.39-2.25 (m, 4H), 2.23-2.12 (m, 2H), 1.22 (s, 6H) |

TABLE 1-continued

| Example | Structure | Name | LCMS (M + H)+ | HPLC Method, RT (min.) | 1H NMR |
|---|---|---|---|---|---|
| 74 | 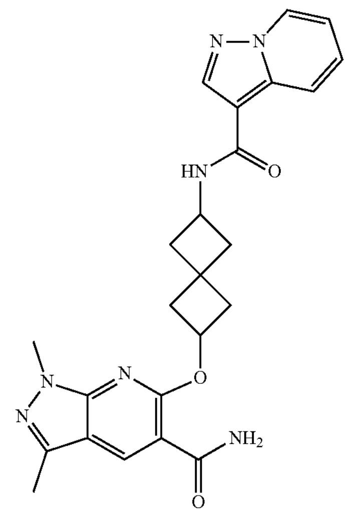 [SMILES: Cc1nn(C)c2nc(OC3CC4(CC(NC(=O)c5cnn6ccccc56)C4)C3)c(C(N)=O)cc12] | 1,3-dimethyl-6-[(6-{pyrazolo[1,5-a]pyridine-3-amido}spiro[3.3]heptan-2-yl)oxy]-1H-pyrazolo[3,4-b]pyridine-5-carboxamide | 460.0 | A: 1.27 B: 1.28 | 1H NMR (400 MHz, DMSO-d6) 8.74 (d, J = 6.8 Hz, 1H), 8.60 (s, 1H), 8.55 (s, 1H), 8.31 (d, J = 7.3 Hz, 1H), 8.18 (d, J = 9.0 Hz, 1H), 7.58 (s, 1H), 7.60 (s, 1H), 7.48-7.33 (m, 1H), 7.04 (t, J = 6.6 Hz, 1H), 5.29 (quin, J = 7.2 Hz, 1H), 4.45-4.34 (m, 1H), 3.88 (s, 3H), 2.82-2.73 (m, 1H), 2.64-2.55 (m, 1H), 2.45 (s, 3H), 2.39-2.27 (m, 4H), 2.24-2.12 (m, 2H) |
| 75 | 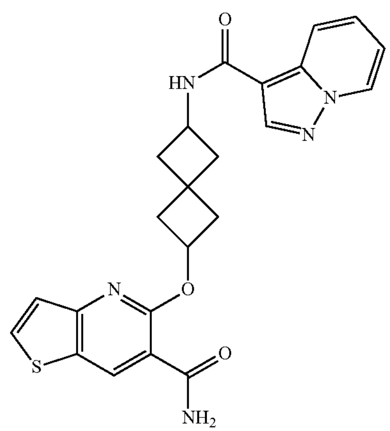 [SMILES: NC(=O)c1cc2sccc2nc1OC1CC2(CC(NC(=O)c3cnn4ccccc34)C2)C1] | 5-[(6-{pyrazolo[1,5-a]pyridine-3-amido}spiro[3.3]heptan-2-yl)oxy]thieno[3,2-b]pyridine-6-carboxamide | 448.2 | A: 1.38 B: 1.39 | 1H NMR (400 MHz, DMSO-d6) 8.80 (s, 1H), 8.72 (d, J = 6.8 Hz, 1H), 8.58-8.49 (m, 1H), 8.34 (d, J = 7.8 Hz, 1H), 8.23-8.06 (m, 2H), 7.70 (d, J = 8.3 Hz, 2H), 7.52-7.35 (m, 2H), 7.04 (t, J = 6.4 Hz, 1H), 5.12 (quin, J = 7.2 Hz, 1H), 4.42-4.35 (m, 1H), 2.72 (dd, J = 11.2, 7.1 Hz, 1H), 2.56 (d, J = 5.6 Hz, 1H), 2.38-2.15 (m, 6H) |

TABLE 1-continued

| Example | Structure | Name | LCMS (M + H)+ | HPLC Method, RT (min.) | 1H NMR |
|---|---|---|---|---|---|
| 76 | 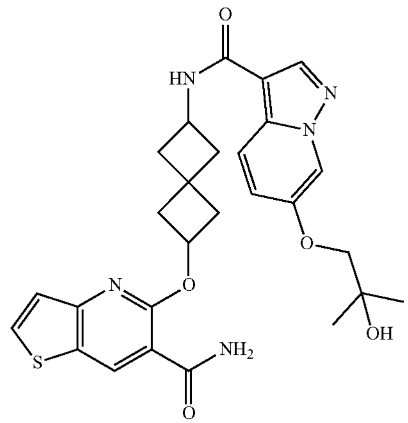 [SMILES: CC(C)(O)COc1ccc2c(C(=O)NC3CC4(C3)CC(Oc3nc5ccsc5cc3C(N)=O)C4)cnn2c1] | 5-({6-[6-(2-hydroxy-2-methylpropoxy)pyrazolo[1,5-a]pyridine-3-amido]spiro[3.3]heptan-2-yl}oxy)thieno[3,2-b]pyridine-6-carboxamide | 536.2 | A: 1.43 B: 1.44 | 1H NMR (400 MHz, DMSO-d6) 8.80 (s, 1H), 8.43 (s, 1H), 8.40 (s, 1H), 8.29 (d, J = 7.1 Hz, 1H), 8.20 (d, J = 5.4 Hz, 1H), 8.07 (d, J = 9.8 Hz, 1H), 7.70 (br s, 2H), 7.44 (d, J = 5.4 Hz, 1H), 7.27 (dd, J = 9.7, 1.8 Hz, 1H), 5.22 (quin, J = 7.2 Hz, 1H), 4.78 (s, 1H), 4.42-4.33 (m, 1H), 3.78 (s, 2H), 2.74-2.67 (m, 1H), 2.60-2.54 (m, 1H), 2.49-2.35 (m, 2H), 2.38-2.15 (m, 4H), 1.21 (s, 6H) |
| 77 | 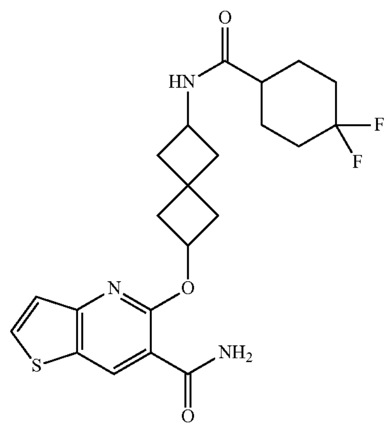 [SMILES: NC(=O)c1cc2sccc2nc1OC1CC2(CC(NC(=O)C3CCC(F)(F)CC3)C2)C1] | 5-{[6-(4,4-difluorocyclohexaneamido)spiro[3.3]heptan-2-yl]oxy}thieno[3,2-b]pyridine-6-carboxamide | 450.2 | A: 1.53 B: 1.54 | 1H NMR (400 MHz, DMSO-d6) 8.81 (d, J = 0.5 Hz, 1H), 8.21 (d, J = 5.6 Hz, 1H), 8.04 (d, J = 7.6 Hz, 1H), 7.71 (br s, 1H), 7.66 (br s, 1H), 7.43 (d, J = 5.6 Hz, 1H), 5.22 (quin, J = 7.2 Hz, 1H), 4.78 (s, 1H), 4.42-4.33 (m, 1H), 2.67-2.62 (m, 1H), 2.39 (br s, 1H), 2.30-2.14 (m, 4H), 2.09-1.89 (m, 4H), 1.87-1.67 (m, 4H), 1.64-1.51 (m, 2H) |

| Example | Structure | Name | LCMS (M + H)⁺ | HPLC Method, RT (min.) | ¹H NMR |
|---|---|---|---|---|---|
| 78 | 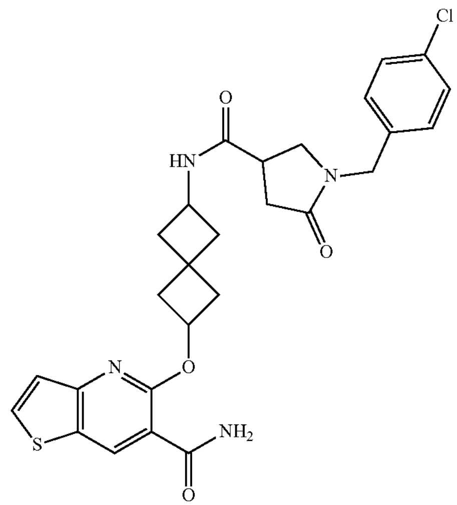 [SMILES: NC(=O)c1cc2sccc2nc1OC1CC2(CC(NC(=O)C3CC(=O)N(Cc4ccc(Cl)cc4)C3)C2)C1] | N-[6-({6-carbamoylthieno[3,2-b]pyridin-5-yl]oxy}spiro[3.3]heptan-2-yl]-1-[(4-chlorophenyl)methyl]-5-oxopyrrolidine-3-carboxamide (diastereomer 1) | 540.2 | A: 1.54 B: 1.55 | ¹H NMR (400 MHz, DMSO-d₆) 8.81 (s, 1H), 8.21 (d, J = 5.4 Hz, 2H), 7.66 (s, 1H), 7.70 (s, 1H), 7.47-7.37 (m, 3H), 7.25 (d, J = 8.1 Hz, 2H), 5.25 (quin, J = 7.2 Hz, 1H), 4.41-4.26 (m, 3H), 4.12-4.03 (m, 1H), 3.22-3.15 (m, 2H), 3.03 (t, J = 6.7 Hz, 1H), 2.67 (s, 1H), 2.47-2.39 (m, 4H), 2.30-2.17 (m, 4H) |
| 79 | 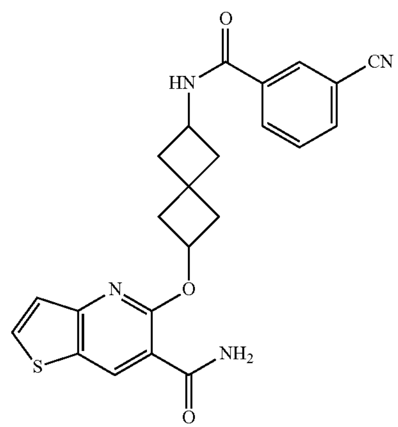 [SMILES: N#Cc1cccc(C(=O)NC2CC3(C2)CC(Oc2nc4ccsc4cc2C(N)=O)C3)c1] | 5-{[6-(3-cyanobenzamido)spiro[3.3]heptan-2-yl]oxy}thieno[3,2-b]pyridine-6-carboxamide | 433.2 | A: 1.50 B: no ionization | ¹H NMR (400 MHz, DMSO-d₆) 8.82 (d, J = 6.8 Hz, 1H), 8.80 (s, 1H), 8.25 (s, 1H), 8.20 (d, J = 5.4 Hz, 1H), 8.13 (d, J = 7.8 Hz, 1H), 7.98 (d, J = 7.8 Hz, 1H), 7.77-7.61 (m, 3H), 7.43 (d, J = 5.4 Hz, 1H), 5.24 (quin, J = 7.2 Hz, 1H), 4.40-4.31 (m, 1H), 2.76-2.69 (m, 1H), 2.60-2.53 (m, 1H), 2.40-2.18 (m, 6H) |

TABLE 1-continued

| Example | Structure | Name | LCMS (M + H)+ | HPLC Method, RT (min.) | 1H NMR |
|---|---|---|---|---|---|
| 80 | 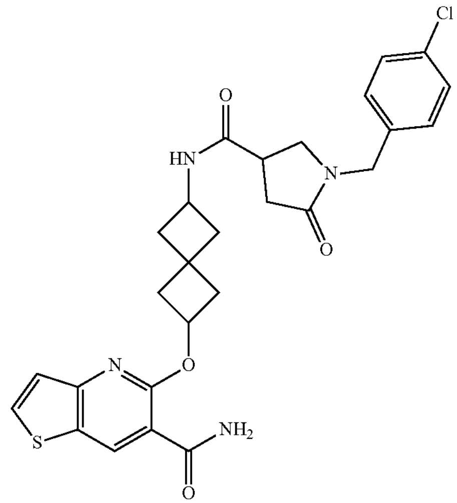 [SMILES: NC(=O)c1cc2sccc2nc1OC1CC2(CC(NC(=O)C3CC(=O)N(Cc4ccc(Cl)cc4)C3)C2)C1] | N-[6-({6-carbamoylthieno[3,2-b]pyridin-5-yl}oxy)spiro[3.3]heptan-2-yl]-1-[(4-chlorophenyl)methyl]-5-oxopyrrolidine-3-carboxamide (diastereomer 2) | 540.2 | A: 1.62 B: 1.62 | 1H NMR (400 MHz, DMSO-d6) 8.81 (s, 1H), 8.24-8.20 (m, 2H), 7.66 (s, 1H), 7.70 (s, 1H), 7.47-7.37 (m, 3H), 7.25 (d, J = 8.1 Hz, 2H), 5.24 (quin, J = 7.2 Hz, 1H), 4.41-4.26 (m, 3H), 4.12-4.03 (m, 1H), 3.22-3.15 (m, 2H), 3.03 (t, J = 6.7 Hz, 1H), 2.67 (s, 1H), 2.47-2.39 (m, 4H), 2.30-2.17 (m, 4H) |
| 81 | 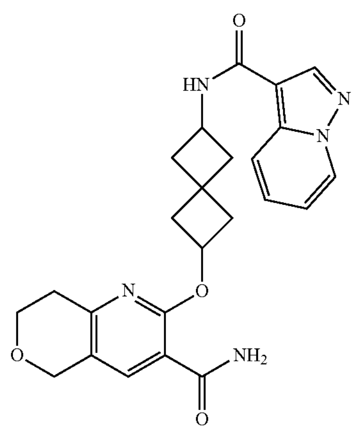 [SMILES: NC(=O)c1cc2c(nc1OC1CC3(CC(NC(=O)c4cnn5ccccc45)C3)C1)CCOC2] | 2-[(6-{pyrazolo[1,5-a]pyridine-3-amido}spiro[3.3]heptan-2-yl)oxy]-5H,7H,8H-pyrano[4,3-b]pyridine-3-carboxamide | 448.2 | A: 1.30 B: 1.29 | 1H NMR (400 MHz, DMSO-d6) 8.74 (d, J = 7.1 Hz, 1H), 8.55 (s, 1H), 8.31 (d, J = 7.3 Hz, 1H), 8.19 (d, J = 8.8 Hz, 1H), 7.91 (s, 1H), 7.63 (br s, 1H), 7.56 (br s, 1H), 7.50-7.39 (m, 1H), 7.13-6.96 (m, 1H), 5.24 (quin, J = 7.2 Hz, 1H), 4.66 (s, 2H), 4.43-4.31 (m, 1H), 3.18 (d, J = 5.4 Hz, 2H), 2.81 (t, J = 5.5 Hz, 2H), 2.70-2.66 (m, 1H), 2.48-2.42 (m, 1H), 2.39-2.32 (m, 2H), 2.30-2.11 (m, 4H) |

TABLE 1-continued

| Example | Structure | Name | LCMS (M + H)+ | HPLC Method, RT (min.) | 1H NMR |
|---|---|---|---|---|---|
| 82 | 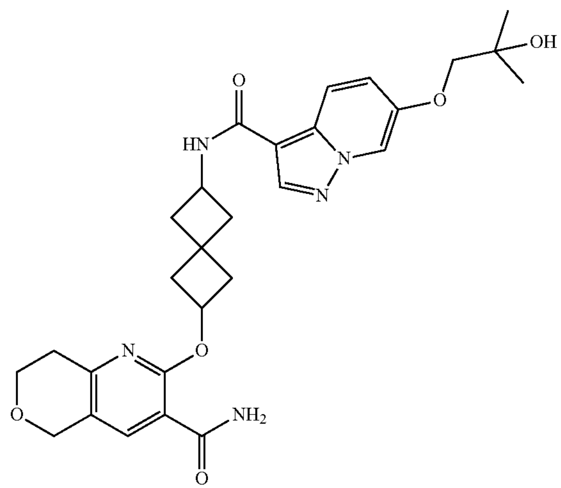 [SMILES: CC(C)(O)COc1ccc2c(C(=O)NC3CC4(C3)CC(Oc3nc5c(cc3C(N)=O)COCC5)C4)cnn2c1] | N-[6-({3-carbamoyl-5H,7H,8H-pyrano[4,3-b]pyridin-2-yl}oxy)spiro[3.3]heptan-2-yl]-6-(2-hydroxy-2-methylpropoxy)pyrazolo[1,5-a]pyridine-3-carboxamide | 536.3 | A: 1.37 B: 1.37 | 1H NMR (400 MHz, DMSO-d6) 8.49-8.36 (m, 2H), 8.27 (d, J = 7.3 Hz, 1H), 8.14-8.02 (m, 1H), 7.91 (s, 1H), 7.63 (br s, 1H), 7.56 (br s, 1H), 7.34-7.23 (m, 2H), 7.15 (s, 1H), 7.02 (s, 1H), 5.24 (quin, J = 12 Hz, 1H), 4.72 (br s, 1H), 4.66 (s, 2H), 4.42-4.30 (m, 1H), 3.95 (t, J = 5.7 Hz, 2H), 3.80 (s, 2H), 2.80 (t, J = 5.7 Hz, 2H), 2.71-2.64 (m, 1H), 2.45 (br s, 1H), 2.38-2.30 (m, 2H), 2.29-2.03 (m, 4H), 1.22 (s, 6H) |
| 83 | 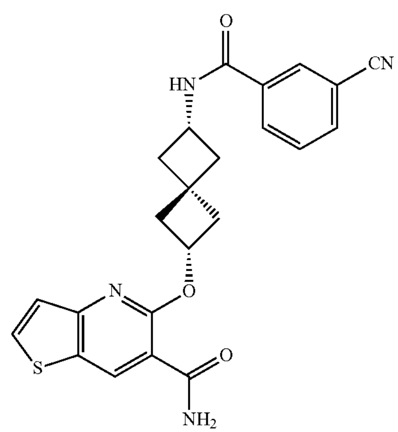 | 5-{[(aR)-6-(3-cyanobenzamido)spiro[3.3]heptan-2-yl]oxy}thieno[3,2-b]pyridine-6-carboxamide | 433.0 | A: 1.58 B: 1.58 | 1H NMR (400 MHz, DMSO-d6) 8.84 (d, J = 7.6 Hz, 1H), 8.80 (d, J = 0.5 Hz, 1H), 8.25 (s, 1H), 8.20 (d, J = 5.6 Hz, 1H), 8.13 (d, J = 8.3 Hz, 1H), 7.98 (d, J = 7.8 Hz, 1H), 7.80-7.60 (m, 3H), 7.48-7.37 (m, 1H), 5.24 (quin, J = 7.2 Hz, 1H), 4.39-4.30 (m, 1H), 2.75-2.69 (m, 1H), 2.59-2.55 (m, 1H), 2.41-2.17 (m, 6H) |

| Example | Structure | Name | LCMS (M + H)+ | HPLC Method, RT (min.) | 1H NMR |
|---|---|---|---|---|---|
| 84 | 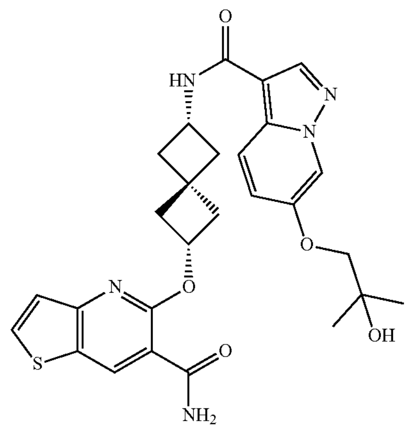 | 6-(2-hydroxy-2-methylpropoxy)-N-[(aR)-6-({6-carbamoylthieno[3,2-b]pyridin-5-yl}oxy)spiro[3.3]heptan-2-yl]pyrazolo[1,5-a]pyridine-3-carboxamide | 536.2 | A: 1.50 B: 1.51 | 1H NMR (400 MHz, DMSO-d6) 8.83 (s, 1H), 8.49-8.38 (m, 2H), 8.27 (d, J = 7.3 Hz, 1H), 8.22 (d, J = 5.4 Hz, 1H), 8.09 (d, J = 9.5 Hz, 1H), 7.71 (d, J = 8.8 Hz, 2H), 7.46 (d, J = 5.6 Hz, 1H), 7.28 (dd, J = 9.8, 2.2 Hz, 1H), 5.21 (quin, J = 7.2 Hz, 1H), 4.72 (br s, 1H), 4.44-4.35 (m, 2H), 3.80 (s, 2H), 2.78-2.72 (m, 1H), 2.60-2.54 (m, 1H), 2.47 (s, 1H), 2.39-2.16 (m, 5H), 1.23 (s, 6H) |
| 85 | 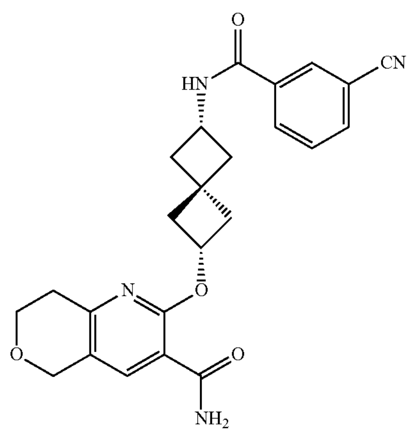 | 2-[[(aR)-6-(3-cyanobenzamido)spiro[3.3]heptan-2-yl]oxy]-5H,7H,8H-pyrano[4,3-b]pyridine-3-carboxamide | 433.2 | A: 1.42 B: 1.42 | 1H NMR (400 MHz, DMSO-d6) 8.80 (d, J = 7.1 Hz, 1H), 8.31-8.20 (m, 1H), 8.14 (dt, J = 8.3, 1.3 Hz, 1H), 8.05-7.96 (m, 1H), 7.91 (s, 1H), 7.69 (t, J = 7.8 Hz, 1H), 7.63 (br s, 1H), 7.55 (br. s., 1H), 5.21 (quin, J = 7.2 Hz, 1H), 4.71-4.60 (m, 2H), 4.41-4.30 (m, 1H), 3.95 (t, J = 5.7 Hz, 2H), 3.90 (s, 1H), 2.80 (t, J = 5.7 Hz, 2H), 2.71-2.66 (m, 1H), 2.49-2.43 (m, 1H), 2.38-2.34 (m, 1H), 2.29-2.12 (m, 4H) |

| Example | Structure | Name | LCMS (M + H)+ | HPLC Method, RT (min.) | 1H NMR |
|---|---|---|---|---|---|
| 86 | 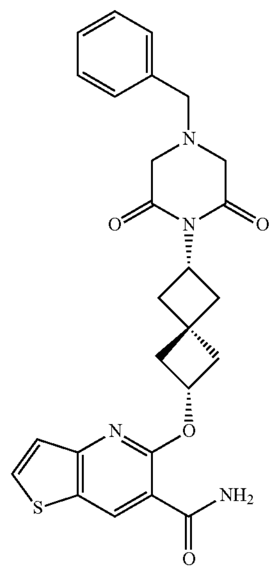 | 5-{[(aR)-6-(4-benzyl-2,6-dioxopiperazin-1-yl)spiro[3.3]heptan-2-yl]oxy}thieno[3,2-b]pyridine-6-carboxamide | 491.3 | A: 1.97 B: 1.92 | 1H NMR (400 MHz, DMSO-d6) δ 8.80 (s, 1H), 8.20 (d, J = 5.6 Hz, 1H), 7.69 (br s, 2H), 7.43 (d, J = 5.4 Hz, 1H), 7.40-7.23 (m, 5H), 5.26 (quin, J = 7.2 Hz, 1H), 4.77-4.57 (m, 1H), 3.62 (s, 2H), 3.37 (s, 4H), 2.74-2.55 (m, 4H), 2.44-2.37 (m, 1H), 2.32-2.18 (m, 3H) |
| 87 | 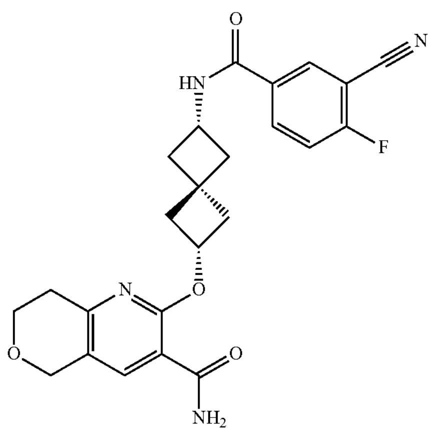 | 2-{[(aR)-6-(3-cyano-4-fluorobenzamido)spiro[3.3]heptan-2-yl]oxy}-5H,7H,8H-pyrano[4,3-b]pyridine-3-carboxamide | 451.2 | A: 1.39 B: 1.50 | 1H NMR (400 MHz, DMSO-d6) δ 8.79 (d, J = 7.3 Hz, 1H), 8.38 (d, J = 6.4 Hz, 1H), 8.28-8.17 (m, 1H), 7.91 (s, 1H), 7.73-7.59 (m, 2H), 7.53 (br s, 1H), 5.20 (quin, J = 7.2 Hz, 1H), 4.66 (s, 2H), 4.42-4.25 (m, 1H), 3.94 (t, J = 5.6 Hz, 2H), 2.79 (t, J = 5.5 Hz, 2H), 2.72-2.60 (m, 1H), 2.56-2.42 (m, 2H), 2.40-2.31 (m, 1H), 2.29-2.09 (m, 4H) |

TABLE 1-continued

| Example | Structure | Name | LCMS (M + H)+ | HPLC Method, RT (min.) | 1H NMR |
|---|---|---|---|---|---|
| 88 | 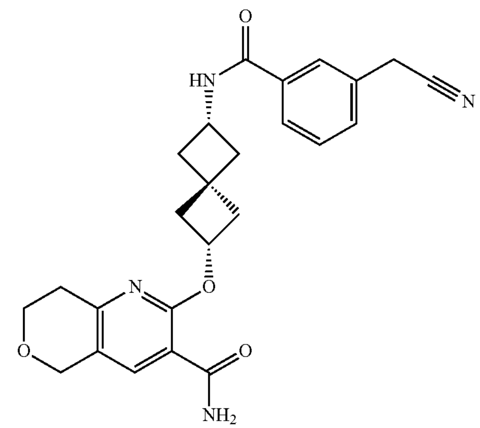 | 2-{[(aR)-6-[3-(cyanomethyl)benzamido]spiro[3.3]heptan-2-yl]oxy}-5H,7H,8H-pyrano[4,3-b]pyridine-3-carboxamide | 447.2 | A: 1.25 B: 1.37 | 1H NMR (400 MHz, DMSO-d6) δ 8.65 (d, J = 7.1 Hz, 1H), 7.91 (s, 1H), 7.84-7.74 (m, 2H), 7.66 (br s, 1H), 7.58-7.44 (m, 3H), 5.20 (quin, J = 7.3 Hz, 1H), 4.65 (s, 2H), 4.42-4.28 (m, 1H), 4.10 (s, 2H), 3.94 (t, J = 5.6 Hz, 2H), 2.81 (t, J = 5.6 Hz, 2H), 2.72-2.60 (m, 1H), 2.56-2.42 (m, 2H), 2.39-2.29 (an, 1H), 2.29-2.11 (m, 4H). |
| 89 | 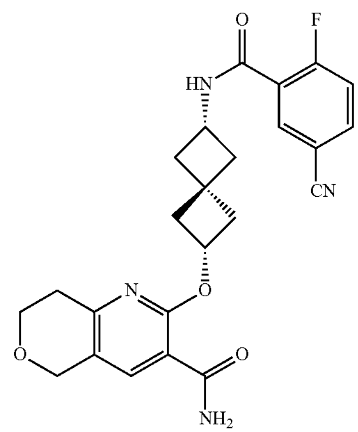 | 2-{[(aR)-6-(5-cyano-2-fluorobenzamido)spiro[3.3]heptan-2-yl]oxy}-5H,7H,8H-pyrano[4,3-b]pyridine-3-carboxamide | 451.2 | A: 1.31 B: 1.42 | 1H NMR (400 MHz, DMSO-d6) δ 8.76 (d, J = 7.6 Hz, 1H), 8.12-7.98 (m, 2H), 7.95-7.84 (m, 1H), 7.66 (br s, 1H), 7.54 (t, J = 9.2 Hz, 2H), 5.19 (quin, J = 7.2 Hz, 1H), 4.65 (s, 2H), 4.30 (dq, J = 15.7, 7.8 Hz, 1H), 3.94 (t, J = 5.7 Hz, 2H), 2.79 (t, J = 5.9 Hz, 2H), 2.65 (dd, J = 11.4, 6.5 Hz, 1H), 2.56-2.42 (m, 2H), 2.40-2.29 (m, 1H), 2.27-2.04 (m, 4H). |

TABLE 1-continued

| Example | Structure | Name | LCMS (M + H)+ | HPLC Method, RT (min.) | 1H NMR |
|---|---|---|---|---|---|
| 90 | 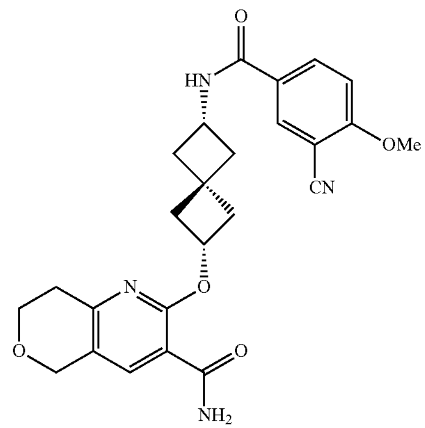 | 2-{[(aR)-6-(3-cyano-4-methoxybenzamido)spiro[3.3]heptan-2-yl]oxy}-5H,7H,8H-pyrano[4,3-b]pyridine-3-carboxamide | 463.2 | A: 1.34 B: 1.45 | 1H NMR (400 MHz, DMSO-d6) δ 8.62 (d, J = 7.3 Hz, 1H), 8.22 (s, 1H), 8.15 (d, J = 8.3 Hz, 1H), 7.91 (s, 1H), 7.66 (br s, 1H), 7.53 (br s, 1H), 7.33 (d, J = 9.0 Hz, 1H), 5.26-5.12 (m, 1H), 4.65 (s, 2H), 4.33 (dd, J = 15.5, 7.9 Hz, 1H), 4.01 (s, 3H), 3.96 (t, J = 5.6 Hz, 2H), 2.79 (t, J = 5.7 Hz, 2H), 2.66 (d, J = 9.8 Hz, 1H), 2.56-2.42 (m, 2H), 2.33 (br s, 1H), 2.28-2.07 (m, 4H) |
| 91 | 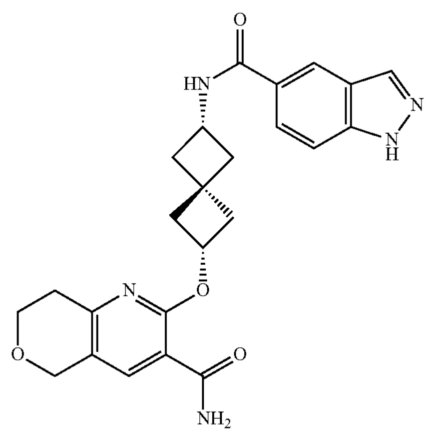 | N-[(aR)-6-({3-carbamoyl-5H,7H,8H-pyrano[4,3-b]pyridin-2-yl}oxy)spiro[3.3]heptan-2-yl]-1H-indazole-5-carboxamide | 448.2 | A: 1.07 B: 1.19 | 1H NMR (400 MHz, DMSO-d6) δ 13.25 (br s, 1H), 8.66 (d, J = 7.8 Hz, 1H), 8.58 (d, J = 7.6 Hz, 1H), 8.33 (s, 1H), 8.23-8.14 (m, 1H), 7.92 (s, 1H), 7.85 (d, J = 8.8 Hz, 1H), 7.73-7.61 (m, 1H), 7.59-7.49 (m, 2H), 5.27-5.15 (m, 1H), 4.66 (s, 2H), 4.45-4.31 (m, 1H), 3.94 (t, J = 5.5 Hz, 2H), 2.80 (t, J = 5.4 Hz, 2H), 2.67 (t, J = 10.8 Hz, 1H), 2.56-2.42 (m, 2H), 2.40-2.30 (m, 1H), 2.29-2.14 (m, 4H) |

TABLE 1-continued

| Example | Structure | Name | LCMS (M + H)+ | HPLC Method, RT (min.) | ¹H NMR |
|---|---|---|---|---|---|
| 92 | 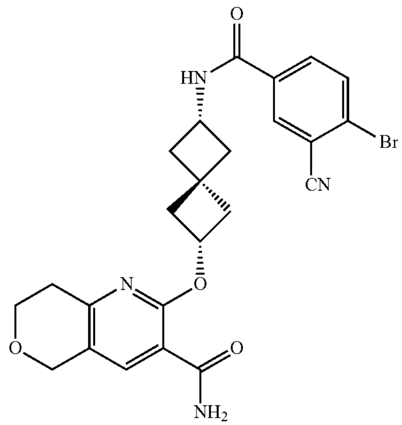 | 2-{[(aR)-6-(4-bromo-3-cyanobenzamido)spiro[3.3]heptan-2-yl]oxy}-5H,7H,8H-pyrano[4,3-b]pyridine-3-carboxamide | 511.1 | A: 1.52 B: 1.63 | ¹H NMR (400 MHz, DMSO-$d_6$) δ 8.83 (d, J = 7.1 Hz, 1H), 8.36 (s, 1H), 8.08-7.96 (m, 2H), 7.91 (s, 1H), 7.66 (br s, 1H), 7.53 (br s, 1H), 5.20 (quin, J = 7.0 Hz, 1H), 4.65 (s, 2H), 4.43-4.24 (m, 1H), 3.94 (t, J = 5.6 Hz, 2H), 2.86-2.73 (m, 2H), 2.72-2.57 (m, 1H), 2.56-2.42 (m, 2H), 2.41-2.30 (m, 1H), 2.29-2.08 (m, 4H) |
| 93 | 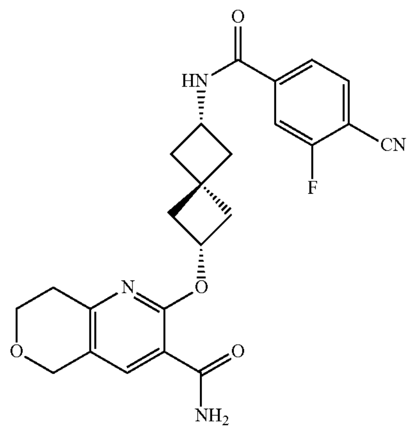 | 2-{[(aR)-6-(4-cyano-3-fluorobenzamido)spiro[3.3]heptan-2-yl]oxy}-5H,7H,8H-pyrano[4,3-b]pyridine-3-carboxamide | 451.2 | A: 1.40 B: 1.51 | ¹H NMR (400 MHz, DMSO-$d_6$) δ 8.91 (d, J = 7.1 Hz, 1H), 8.06 (t, J = 7.6 Hz, 1H), 7.95-7.79 (m, 3H), 7.66 (br s, 1H), 7.53 (br s, 1H), 5.20 (quin, J = 7.0 Hz, 1H), 4.65 (s, 2H), 4.40-4.27 (m, 1H), 3.94 (t, J = 5.6 Hz, 2H), 2.79 (t, J = 5.4 Hz, 2H), 2.71-2.60 (m, 1H), 2.56-2.43 (m, 2H), 2.41-2.30 (m, 1H), 2.30-2.11 (m, 4H) |

TABLE 1-continued

| Example | Structure | Name | LCMS (M + H)+ | HPLC Method, RT (min.) | 1H NMR |
|---|---|---|---|---|---|
| 94 | 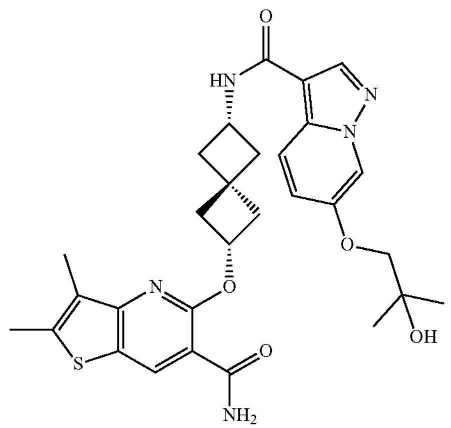 | 2,3-dimethyl-5-{[(aR)-6-[6-(2-hydroxy-2-methylpropoxy)pyrazolo[1,5-a]pyridine-3-amido]spiro[3.3]heptan-2-yl]oxy}thieno[3,2-b]pyridine-6-carboxamide | 564.0 | A: 1.82 B: 1.82 | 1H NMR (400 MHz, DMSO-d6) 8.69 (s, 1H), 8.48-8.36 (m, 2H), 8.27 (d, J = 7.8 Hz, 1H), 8.09 (d, J = 9.8 Hz, 1H), 7.66 (br s, 2H), 7.28 (dd, J = 9.7, 2.1 Hz, 1H), 5.34-5.23 (m, 1H), 4.74 (s, 1H), 4.46-4.37 (m, 1H), 3.80 (s, 2H), 2.82-2.73 (m, 1H), 2.62-2.56 (m, 1H), 2.53 (s, 3H), 2.40-2.14 (m, 9H), 1.23 (s, 6H) |
| 95 | 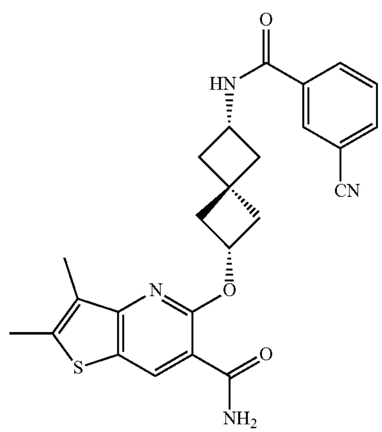 | 2,3-dimethyl-5-{[(aR)-6-(3-cyanobenzamido)spiro[3.3]heptan-2-yl]oxy}thieno[3,2-b]pyridine-6-carboxamide | 461.0 | A: 1.92 B: 1.94 | 1H NMR (400 MHz, DMSO-d6) 8.84 (d, J = 7.3 Hz, 1H), 8.64 (s, 1H), 8.23 (s, 1H), 8.12 (d, J = 7.3 Hz, 1H), 7.97 (d, J = 7.6 Hz, 1H), 7.74-7.54 (m, 3H), 5.26 (t, J = 7.0 Hz, 1H), 4.38-4.26 (m, 1H), 2.74 (d, J = 4.9 Hz, 1H), 2.46-2.37 (m, 2H), 2.61-2.54 (m, 1H), 2.39-2.16 (m, 10H) |

| Example | Structure | Name | LCMS (M + H)+ | HPLC Method, RT (min.) | 1H NMR |
|---|---|---|---|---|---|
| 96 | 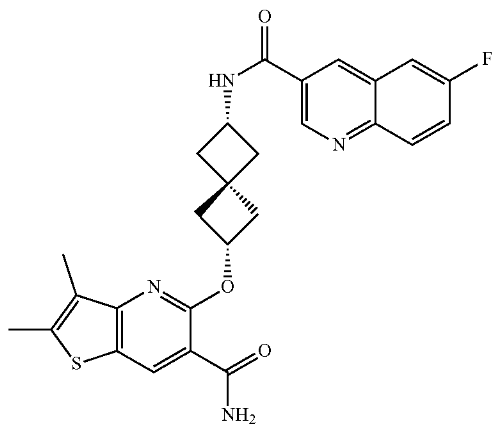 | 6-fluoro-N-[(aR)-6-({6-carbamoyl-2,3-dimethylthieno[3,2-b]pyridin-5-yl}oxy)spiro[3.3]heptan-2-yl]quinoline-3-carboxamide | 505.3 | A: 1.96 B: 1.90 | 1H NMR (400 MHz, DMSO-d6) 9.20 (s, 1H), 9.04 (d, J = 7.1 Hz, 1H), 8.75 (s, 1H), 8.65 (s, 1H), 8.13 (dd, J = 9.0, 5.4 Hz, 1H), 7.87 (d, J = 9.3 Hz, 1H), 7.76 (t, J = 9.2 Hz, 1H), 7.69 (br s, 1H), 7.64 (br s, 1H), 5.27 (quin, J = 7.0 Hz, 1H), 4.47-4.40 (m, 1H), 2.81-2.73 (m, 1H), 2.59 (dd, J = 12.1, 5.3 Hz, 2H), 2.39 (d, J = 4.4 Hz, 2H), 2.34-2.19 (m, 9H) |
| 97 | 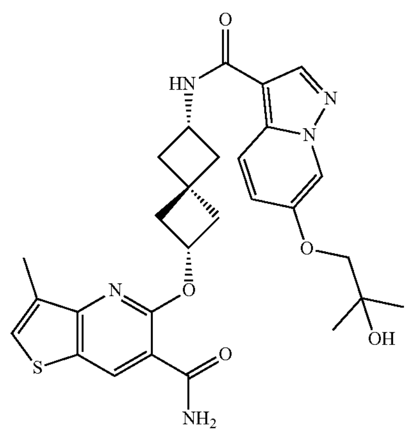 | 3-methyl-5-[(aR)-6-[6-(2-hydroxy-2-methylpropoxy)pyrazolo[1,5-a]pyridine-3-amido]spiro[3.3]heptan-2-yl]oxy]thieno[3,2-b]pyridine-6-carboxamide | 550.3 | A: 1.70 B: 1.71 | 1H NMR (400 MHz, DMSO-d6) 8.74 (s, 1H), 8.41 (s, 1H), 8.38 (s, 1H), 8.34 (d, J = 7.3 Hz, 1H), 8.06 (d, J = 9.8 Hz, 1H), 7.84 (s, 1H), 7.74 (br s, 1H), 7.67 (br s, 1H), 7.28 (d, J = 10.0 Hz, 1H), 5.29 (quin, J = 7.0 Hz, 1H), 4.89 (s, 1H), 4.40-4.31 (m, 1H), 3.77 (s, 2H), 2.79-2.72 (m, 1H), 2.58 (br s, 1H), 2.37 (s, 3H), 2.34-2.12 (m, 6H), 1.20 (s, 6H) |

TABLE 1-continued

| Example | Structure | Name | LCMS (M + H)+ | HPLC Method, RT (min.) | 1H NMR |
|---|---|---|---|---|---|
| 98 | 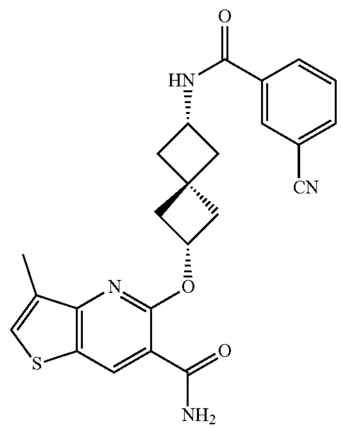 | 3-methyl-5-{[(aR)-6-(3-cyanobenzamido)spiro[3.3]heptan-2-yl]oxy}thieno[3,2-b]pyridine-6-carboxamide | 447.0 | A: 1.80 B: 1.81 | 1H NMR (400 MHz, DMSO-d6) 8.85 (d, J = 7.1 Hz, 1H), 8.74 (s, 1H), 8.22 (s, 1H), 8.11 (d, J = 8.1 Hz, 1H), 7.96 (d, J = 7.6 Hz, 1H), 7.84 (s, 1H), 7.73 (br s, 1H), 7.70-7.56 (m, 2H), 5.31 (quin, J = 7.0 Hz, 1H), 4.36-4.29 (m, 1H), 2.80-2.73 (m, 1H), 2.61-2.55 (m, 1H), 2.37 (s, 4H), 2.33-2.13 (m, 5H) |
| 99 | 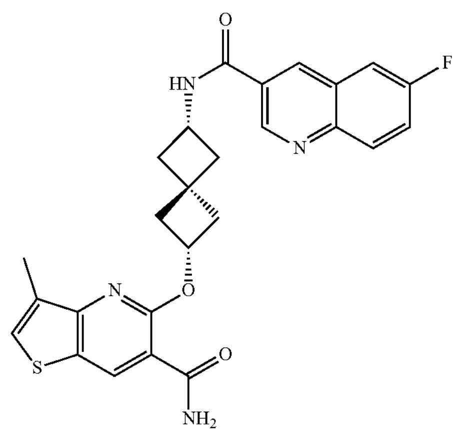 | 6-fluoro-N-[(aR)-6-({6-carbamoyl-3-methylthieno[3,2-b]pyridin-5-yl}oxy)spiro[3.3]heptan-2-yl]quinoline-3-carboxamide | 491.3 | A: 1.84 B: 1.78 | 1H NMR (400 MHz, DMSO-d6) 9.24 (d, J = 2.2 Hz, 1H), 9.03 (d, J = 7.1 Hz, 1H), 8.87-8.69 (m, 2H), 8.16 (dd, J = 9.4, 5.5 Hz, 1H), 7.97-7.84 (m, 2H), 7.78 (td, J = 8.9, 2.8 Hz, 1H), 7.71 (br s, 2H), 5.31 (quin, J = 7.0 Hz, 1H), 4.50-4.36 (m, 1H), 2.81 (dt, J = 11.6, 5.8 Hz, 1H), 2.66-2.55 (m, 1H), 2.46-2.37 (m, 5H), 2.35-2.23 (m, 4H), |

TABLE 1-continued

| Example | Structure | Name | LCMS (M + H)+ | HPLC Method, RT (min.) | 1H NMR |
|---|---|---|---|---|---|
| 100 | 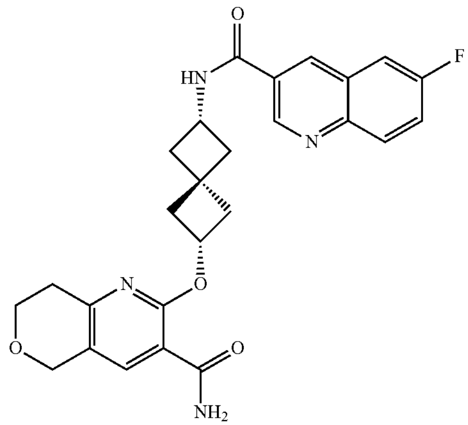 | 6-fluoro-N-[(aR)-6-({3-carbamoyl-5H,7H,8H-pyrano[4,3-b]pyridin-2-yl}oxy)spiro[3.3]heptan-2-yl]quinoline-3-carboxamide | 477.2 | A: 1.49 B: 1.40 | 1H NMR (400 MHz, DMSO-$d_6$) 9.23 (d, J = 2.0 Hz, 1H), 9.01 (d, J = 7.3 Hz, 1H), 8.77 (d, J = 1.7 Hz, 1H), 8.15 (dd, J = 9.3, 5.4 Hz, 1H), 7.98-7.82 (m, 2H), 7.77 (td, J = 8.9, 2.8 Hz, 1H), 7.64 (br. s., 1H), 7.57 (br s, 1H), 5.21 (quin, J = 7.1 Hz, 1H), 4.65 (s, 2H), 4.52-4.33 (m, 1H), 3.94 (t, J = 5.7 Hz, 2H), 2.79 (t, J = 5.7 Hz, 2H), 2.73-2.62 (m, 1H), 2.44-2.35 (m, 1H), 2.31-2.10 (m, 6H) |
| 101 | 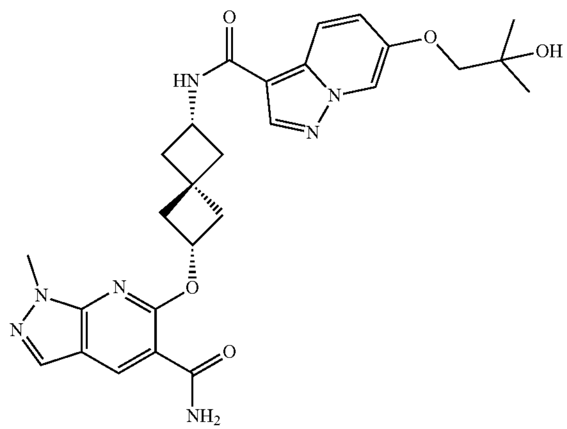 | 1-methyl-6-[(aR)-6-[6-(2-hydroxy-2-methylpropoxy)pyrazolo[1,5-a]pyridine-3-amido]spiro[3.3]heptan-2-yl]oxy}-1H-pyrazolo[3,4-b]pyridine-5-carboxamide | 534.0 | A: 1.34 B: 1.35 | 1H NMR (400 MHz, DMSO-$d_6$) 8.62 (s, 1H), 8.44 (s, 1H), 8.41 (d, J = 1.7 Hz, 1H), 8.31 (d, J = 7.6 Hz, 1H), 8.15-8.02 (m, 2H), 7.62 (d, J = 7.1 Hz, 2H), 7.29 (dd, J = 9.5, 2.2 Hz, 1H), 5.29 (quin, J = 7.2 Hz, 2H), 4.80 (s, 1H), 4.45-4.33 (m, 1H), 4.03-3.93 (m, 2H), 3.83-3.78 (m, 3H), 2.80 (dt, J = 11.3, 5.7 Hz, 1H), 2.61 (dt, J = 12.0, 5.7 Hz, 1H), 2.39-2.28 (m, 4H), 2.24-2.13 (m, 2H), 1.33-1.16 (m, 6H) |

TABLE 1-continued

| Example | Structure | Name | LCMS (M + H)+ | HPLC Method, RT (min.) | 1H NMR |
|---|---|---|---|---|---|
| 102 | 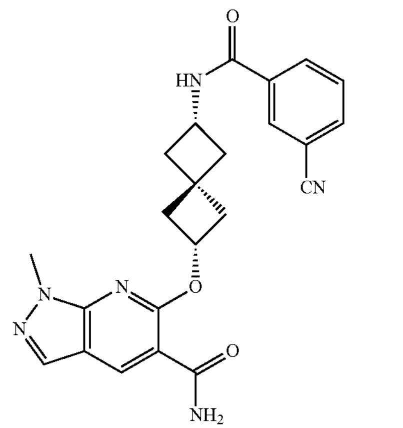 | 1-methyl-6-{[(aR)-6-(3-cyanobenzamido)spiro[3.3]heptan-2-yl]oxy}-1H-pyrazolo[3,4-b]pyridine-5-carboxamide | 431.0 | A: 1.38 B: 1.40 | 1H NMR (400 MHz, DMSO-d6) δ 8.83 (d, J = 7.3 Hz, 1H), 8.62 (s, 1H), 8.28-8.23 (m, 1H), 8.21-8.12 (m, 1H), 8.09 (s, 1H), 8.04-7.91 (m, 1H), 7.69 (t, J = 7.8 Hz, 1H), 7.61 (s, 2H), 5.29 (quin, J = 7.0 Hz, 1H), 4.47-4.31 (m, 1H), 3.97 (s, 3H), 2.80 (dt, J = 11.4, 5.8 Hz, 1H), 2.66-2.58 (m, 1H), 2.42-2.16 (m, 6H) |
| 103 | 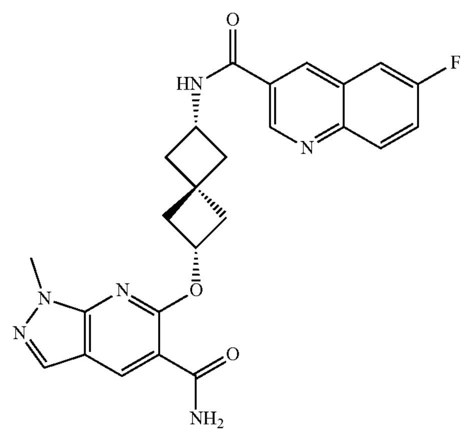 | 6-fluoro-N-[(aR)-6-({5-carbamoyl-1-methyl-1H-pyrazolo[3,4-b]pyridin-6-yl}oxy)spiro[3.3]heptan-2-yl]quinoline-3-carboxamide | 475.0 | A: 1.45 B: 1.38 | 1H NMR (400 MHz, DMSO-d6) δ 9.24 (d, J = 2.0 Hz, 1H), 9.03 (d, J = 7.1 Hz, 1H), 8.79 (d, J = 2.0 Hz, 1H), 8.62 (s, 1H), 8.16 (dd, J = 9.0, 5.4 Hz, 1H), 8.10 (s, 1H), 7.91 (dd, J = 9.3, 2.9 Hz, 1H), 7.78 (td, J = 8.9, 2.9 Hz, 1H), 7.62 (s, 2H), 5.29 (quin, J = 7.0 Hz, 1H), 4.51-4.40 (m, 1H), 3.98 (s, 3H), 2.88-2.78 (m, 1H), 2.70-2.57 (m, 1H), 2.46-2.21 (m, 6H) |

TABLE 1-continued
| Example | Name | LCMS (M + H)+ | HPLC Method, RT (min.) | 1H NMR |
|---|---|---|---|---|
| 104 | 1-cyclopropyl-3-{[(aR)-6-(4-benzyl-2,5-dioxoimidazolidin-1-yl)spiro[3.3]heptan-2-yl]oxy}-1H-pyrazole-4-carboxamide | 450.3 | C: 7.97 D: 6.33 | (500 MHz, METHANOL-$d_4$) δ 7.89 (s, 1H), 7.39-7.05 (m, 5H), 4.93 (t, J = 6.9 Hz, 1H), 4.36-4.24 (m, 1H), 4.23 (s, 1H), 3.60-3.47 (m, 1H), 3.12-2.98 (m, 2H), 2.80-2.58 (m, 3H), 2.58-2.45 (m, 1H), 2.31-1.99 (m, 4H), 1.11-0.94 (m, 4H) |
Structure:
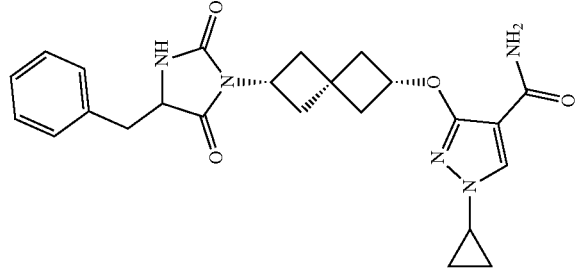

TABLE 1-continued

| Example | Structure | Name | LCMS (M + H)+ | HPLC Method, RT (min.) | 1H NMR |
|---|---|---|---|---|---|
| 105 | 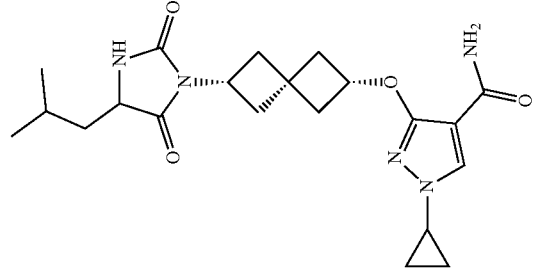 | 1-cyclopropyl-3-{[(aR)-6-[4-(2-methylpropyl)-2,5-dioxoimidazolidin-1-yl]spiro[3.3]heptan-2-yl]oxy}-1H-pyrazole-4-carboxamide | 416.3 | C: 8.01 D: 6.49 | (500 MHz, METHANOL-d4) δ 7.90 (s, 1H), 4.98 (t, J = 7.0 Hz, 1H), 4.47 (t, J = 8.5 Hz, 1H), 4.02 (dd, J = 9.1, 4.4 Hz, 1H), 3.56 (dt, J = 7.2, 3.6 Hz, 1H), 3.09-2.87 (m, 2H), 2.74 (dt, J = 11.6, 5.9 Hz, 1H), 2.60 (dt, J = 11.9, 6.0 Hz, 1H), 2.44-2.32 (m, 1H), 2.31-2.20 (m, 3H), 1.92-1.76 (m, 1H), 1.66 (ddd, J = 13.6, 8.9, 4.4 Hz, 1H), 1.50 (ddd, J = 14.0, 8.9, 5.5 Hz, 1H), 1.12-0.85 (m, 10H) |
| 106 | 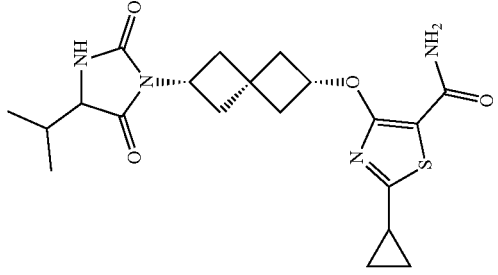 | 2-cyclopropyl-4-{[(aR)-6-[2,5-dioxo-4-(propan-2-yl)imidazolidin-1-yl]spiro[3.3]heptan-2-yl]oxy}-1,3-thiazole-5-carboxamide | 419.2 | C: 8.76 D: 7.34 | (500 MHz, METHANOL-d4) δ 5.16 (t, J = 7.2 Hz, 1H), 4.47 (t, J = 8.8 Hz, 1H), 3.90 (d, J = 3.6 Hz, 1H), 3.07-2.85 (m, 2H), 2.76-2.66 (m, 1H), 2.58 (dt, J = 12.2, 6.0 Hz, 1H), 2.42-2.22 (m, 5H), 2.15 (td, J = 6.8, 3.4 Hz, 1H), 1.26-1.16 (m, 2H), 1.13-1.06 (m, 2H), 1.04 (d, J = 7.2 Hz, 3H), 0.88 (d, J = 6.9 Hz, 3H) |

TABLE 1-continued

| Example | Structure | Name | LCMS (M + H)+ | HPLC Method, RT (min.) | ¹H NMR |
|---|---|---|---|---|---|
| 107 | 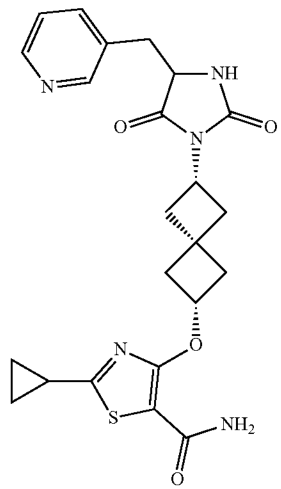 | 2-cyclopropyl-4-{[(aR)-6-{2,5-dioxo-4-[(pyridin-3-yl)methyl]imidazolidin-1-yl]spiro[3.3]heptan-2-yl]oxy}-1,3-thiazole-5-carboxamide | 468.2 | C: 8.46 D: 7.01 | (500 MHz, METHANOL-$d_4$) δ 8.81 (d, J = 5.5 Hz, 1H), 8.76 (s, 1H), 8.52 (d, J = 8.3 Hz, 1H), 8.06 (t, J = 6.9 Hz, 1H), 5.13 (t, J = 7.0 Hz, 1H), 4.46 (t, J = 5.6 Hz, 1H), 4.35 (t, J = 8.8 Hz, 1H), 2.91-2.75 (m, 2H), 2.67 (dt, J = 11.6, 5.9 Hz, 1H), 2.59-2.50 (m, 1H), 2.35-2.12 (m, 5H), 1.25-1.18 (m, 2H), 1.12-1.04 (m, 2H) |
| 108 | 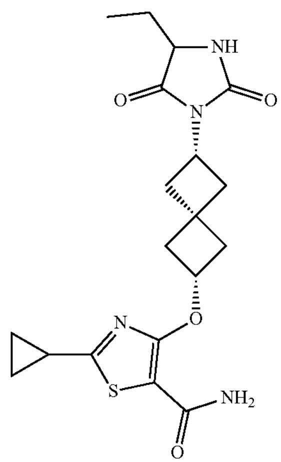 | 2-cyclopropyl-4-{[(aR)-6-(4-ethyl-2,5-dioxoimidazolidin-1-yl)spiro[3.3]heptan-2-yl]oxy}-1,3-thiazole-5-carboxamide | 405.2 | C: 6.50 D: 4.10 | (500 MHz, DMSO-$d_6$) δ 8.21 (s, 1H), 7.50 (br s, 1H), 6.77 (br s, 1H), 5.22-4.81 (m, 1H), 4.53-4.12 (m, 1H), 4.00-3.72 (m, 1H), 2.90-2.70 (m, 2H), 2.68-2.55 (m, 1H), 2.44 (dt, J = 11.8, 5.9 Hz, 1H), 2.38-2.13 (m, 5H), 2.08 (s, 1H), 2.02-1.91 (m, 1H), 1.75-1.63 (m, 1H), 1.18-1.12 (m, 2H), 1.01-0.94 (m, 2H), 0.84 (t, J = 7.4 Hz, 2H) |

TABLE 1-continued

| Example | Structure | Name | LCMS (M + H)+ | HPLC Method, RT (min.) | 1H NMR |
|---|---|---|---|---|---|
| 109 | 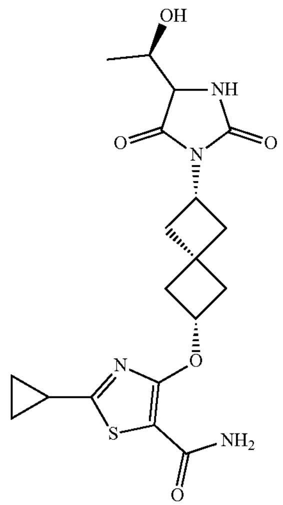 | 2-cyclopropyl-4-{[(aR)-6-{4-[(1R)-1-hydroxyethyl]-2,5-dioxoimidazolidin-1-yl}spiro[3.3]heptan-2-yl]oxy}-1,3-thiazole-5-carboxamide | 403.2 | C: 8.23 D: 6.71 | (500 MHz, METHANOL-$d_4$) δ 5.81 (d, J = 7.4 Hz, 1H), 5.16 (t, J = 7.2 Hz, 1H), 4.53 (t, J = 8.8 Hz, 1H), 2.98 (br d, J = 10.7 Hz, 2H), 2.72 (br d, J = 5.5 Hz, 1H), 2.59 (dt, J = 11.9, 6.0 Hz, 1H), 2.44-2.22 (m, 6H), 1.83 (d, J = 7.4 Hz, 3H), 1.20 (dd, J = 8.0, 3.0 Hz, 2H), 1.14-1.03 (m, 2H) |
| 110 | 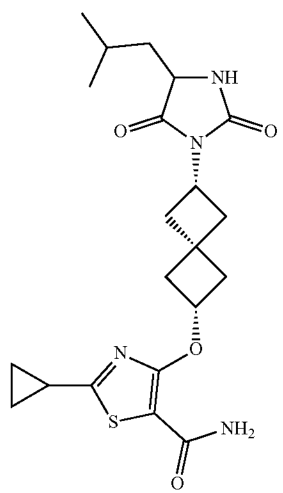 | 2-cyclopropyl-4-{[(aR)-6-[4-(2-methylpropyl)-2,5-dioxoimidazolidin-1-yl]spiro[3.3]heptan-2-yl]oxy}-1,3-thiazole-5-carboxamide, diastereomer 1 | 433.2 | E: 2.41 | (500 MHz, METHANOL-$d_4$) δ 5.16 (t, J = 7.0 Hz, 1H), 4.47 (t, J = 8.8 Hz, 1H), 4.02 (dd, J = 8.8, 4.4 Hz, 1H), 3.05-2.89 (m, 2H), 2.78-2.65 (m, 1H), 2.58 (dt, J = 11.8, 6.1 Hz, 1H), 2.43-2.22 (m, 5H), 1.90-1.75 (m, 1H), 1.66 (ddd, J = 13.8, 9.0, 4.4 Hz, 1H), 1.56-1.42 (m, 1H), 1.23-1.13 (m, 4H), 1.11-1.04 (m, 2H), 0.98 (d, J = 6.6 Hz, 6H) |

TABLE 1-continued

| Example | Structure | Name | LCMS (M + H)+ | HPLC Method, RT (min.) | 1H NMR |
|---|---|---|---|---|---|
| 111 | (structure) | 2-cyclopropyl-4-{[(αR)-6-[4-(2-methylpropyl)-2,5-dioxoimidazolidin-1-yl]spiro[3.3]heptan-2-yl]oxy}-1,3-thiazole-5-carboxamide, diastereomer 2 | 433.2 | E: 2.40 | (500 MHz, METHANOL-d₄) δ 5.16 (t, J = 7.0 Hz, 1H), 4.47 (s, 1H), 4.02 (dd, J = 9.1, 4.4 Hz, 1H), 2.97 (td, J = 10.1, 3.7 Hz, 2H), 2.77-2.67 (m, 1H), 2.63-2.53 (m, 1H), 2.42-2.20 (m, 5H), 1.90-1.75 (m, 1H), 1.66 (ddd, J = 13.6, 8.9, 4.4 Hz, 1H), 1.56-1.44 (m, 1H), 1.24-1.14 (m, 4H), 1.12-1.06 (m, 2H), 0.98 (d, J = 6.3 Hz, 6H) |

Example 112: 4-(((2S,4s,6)-6-(1-(4-cyanophenyl)-5-methyl-1H-pyrazole-4-carboxamido)spiro[3.3]heptan-2-yl)oxy)-2-methoxythiazole-5-carboxamide

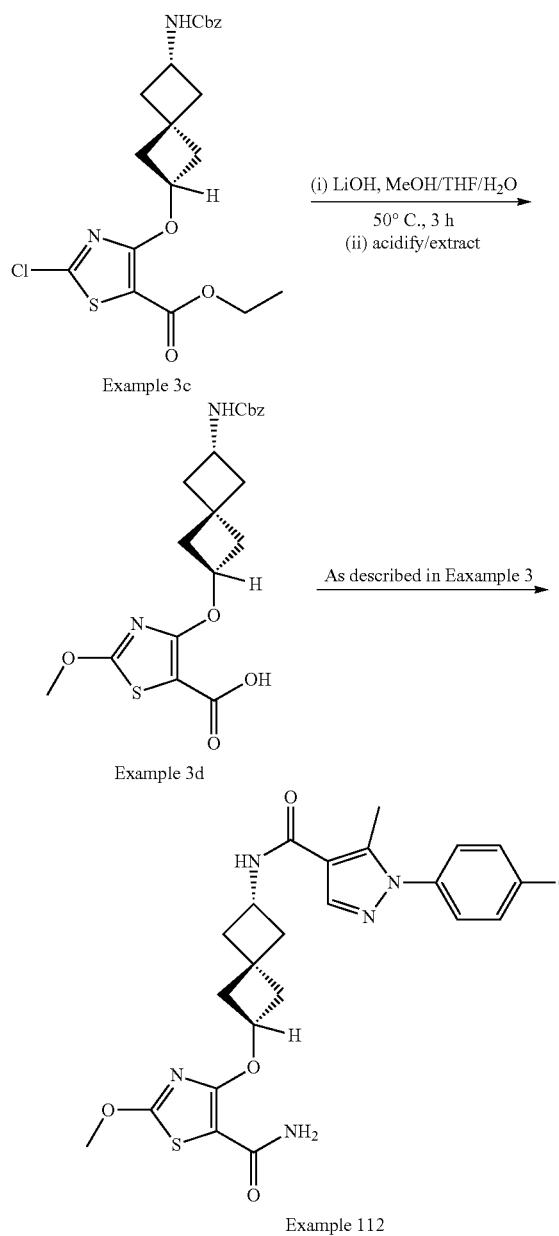

Example 3 (500 mg, 1.11 mmol) was dissolved in MeOH (3 mL)/THF (3.00 mL) and was treated with LiOH (1 M aq.) (3.33 mL, 3.33 mmol). The reaction mixture was stirred at 50° C. for 3 h. Solvent was removed under reduced pressure and the residue was suspended in water (10 mL). EtOAc (10 mL) was added, and the reaction mixture was slowly acidified by the addition of HCl (1 M aq.)(3.33 mL, 3.33 mmol)(pH ~3.0). The organic phase was separated. The aq. phase was extracted with EtOAc (2×15 mL). The combined organic fractions were washed with brine (1×50 mL), dried (Na$_2$SO$_4$) and filtered. EtOAc was removed under reduced pressure to afford Example 3c, which was used without further purification in subsequent step as described in Example 3, to afford Example 112 (3.9 mg, 23%). MS (ESI) m/z: 493.2. $^1$H NMR (500 MHz, DMSO-d6) δ 8.27 (br d, J=7.6 Hz, 1H), 8.20 (s, 1H1), 8.05 (br d, J=8.2 Hz, 2H), 7.79 (br d, J=8.2 Hz, 2H), 7.45 (br s, 1H), 6.71 (br s, 1H), 5.04 (quin, J=7.0 Hz, 1H), 4.46-4.25 (m, 1H), 4.04 (s, 3H), 3.40-3.32 (m, 1H), 2.67-2.59 (m, 1H), 2.48-2.22 (m, 5H), 2.22-2.07 (m, 2H)

Examples 113 to 117 were prepared as described for Example 112.

Examples 118 to 138 were made as described for Example 6.

Example 139: 2-(((2S,4s,6S)-6-(4-isobutyl-2,5-dioxoimidazolidin-1-yl)spiro[3.3]heptan-2-yl)oxy)pyrazolo[1,5-a]pyridine-3-carboxamide

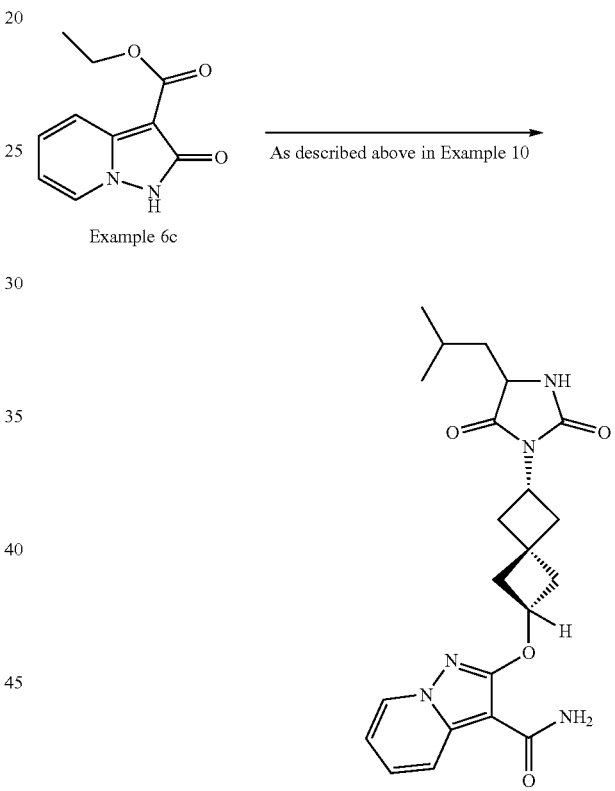

Example 139 was prepared from Example 6C as described in Example 10 above. (4.6 mg, 19%). MS (ESI) m/z: 426.3. $^1$H NMR (500 MHz, METHANOL-d4) δ 8.44 (d, J=6.9 Hz, 1H), 8.09 (d, J=8.8 Hz, 1H), 7.45 (t, J=7.8 Hz, 1H), 6.97 (td, J=6.9, 1.1 Hz, 1H), 5.19 (t, J=7.0 Hz, 1H), 4.49 (t, J=8.8 Hz, 1H), 4.03 (dd, J=8.9, 4.5 Hz, 1H), 3.00 (dt, J=10.2, 5.1 Hz, 2H), 2.83 (dt, J=11.6, 5.9 Hz, 1H), 2.69 (dt, J=12.0, 6.1 Hz, 1H), 2.50-2.21 (m, 4H), 1.90-1.73 (m, 1H), 1.67 (ddd, J=13.6, 8.9, 4.4 Hz, 1H), 1.50 (ddd, J=14.0, 8.9, 5.5 Hz, 1H), 0.98 (d, J=6.6 Hz, 6H)

Examples 140 to 141 were prepared as described for Example 124.

Examples 142 to 145 were prepared as described for Example 12.

Example 146: 1-methyl-6-(((2S,4s,6S)-6-(5-methyl-1-(4-(trifluoromethyl)phenyl)-1H-pyrazole-4-carboxamido)spiro[3.3]heptan-2-yl)oxy)-1H-pyrazolo[3,4-b]pyridine-5-carboxamide

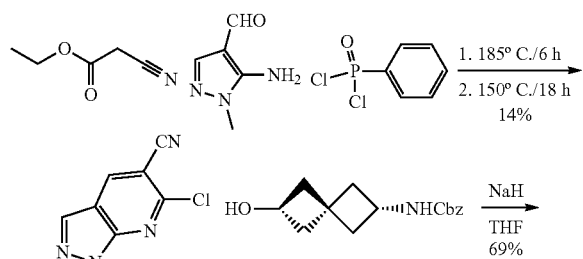

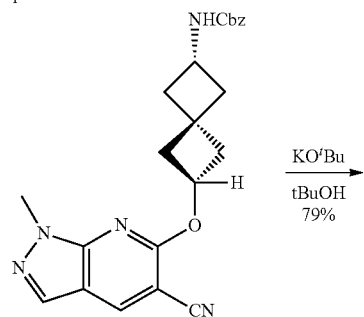

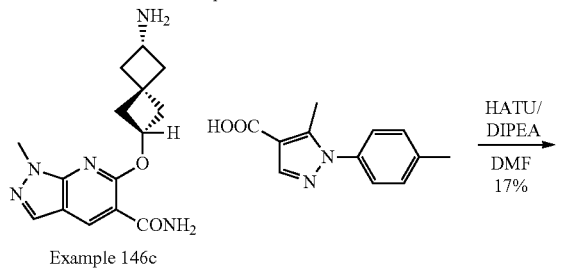

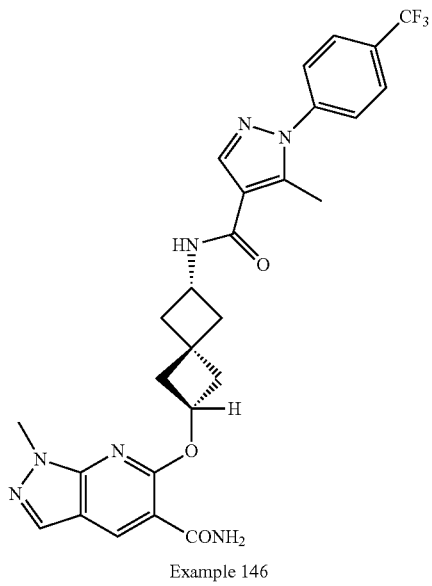

Example 146

Example 146a: 6-hydroxy-1-methyl-1H-pyrazolo[3,4-b]pyridine-5-carbonitrile

A solution of 5-amino-1-methyl-1H-pyrazole-4-carbaldehyde (2.5 g, 20 mmol) in ethyl cyanoacetate (4.52 g, 40.0 mmol) was heated to 185° C. for 6 h. After allowing to cool to room temperature, the reaction mixture was triturated with ethyl acetate (50 mL) to afford a brown solid which was combined with phenylphosphonic dichloride (24.36 ml, 172 mmol) and heated at 150° C. for 18 h. After allowing to cool to room temperature, the residue was partitioned between water (100 mL) and ethyl acetate (150 mL). The organic layer was separated, dried over sodium sulphate and concentrated under reduced pressure to afford t 6-chloro-1-methyl-1H-pyrazolo[3,4-b]pyridine-5-carbonitrile (500 mg, 2.47 mmol, 14.3% yield) as yellow solid.

Example 146b: benzyl ((2S,4s,6S)-6-((5-cyano-1-methyl-1H-pyrazolo[3,4-b]pyridin-6-yl)oxy)spiro[3.3]heptan-2-yl)carbamate To stirred solution of benzyl (6-hydroxyspiro[3.3]heptan-2-yl)carbamate (1080 mg, 4.15 mmol) in THF (15 mL) cooled at 0° C., was added NaH (415 mg, 10.4 mmol) portion-wise over 10 min. After 10 minutes. Example 146a (800 mg, 4.15 mmol) was added and the reaction mixture stirred at room temperature for 12 h. The reaction mixture was cooled to 0° C. and treated with MeOH (5 mL) dropwise over 10 min. After 5 minutes, the reaction mixture was evaporated to dryness under reduced pressure and water (100 mL) was added. The precipitated solid was filtered and dried under vacuum for 16 hours to afford Example 14b (1.2 g, 69% yield).

Example 146: 1-methyl-6-(((2S,4s,6S)-6-(5-methyl-1-(4-(trifluoromethyl)phenyl)-1H-pyrazole-4-carboxamido)spiro[3.3]heptan-2-yl)oxy)-1H-pyrazolo[3,4-b]pyridine-5-carboxamide To the stirred solution of Example 146c (30 mg, 0.10 mmol) and 5-methyl-1-(4-(trifluoromethyl)phenyl)-1H-pyrazole-4-carboxylic acid (26.9 mg, 0.100 mmol) in DMF (1 mL), HATU (37.9 mg, 0.100 mmol) was added followed by DIPEA (0.052 mL, 0.30 mmol). The reaction mixture was stirred at RT for 2 h. The reaction mixture was diluted with MeOH, and purified by prep HPLC to afford example 146 MS (ESI) m/z: 554.3. $^1$H MS (ESI) m/z: 426.3. $^1$H NMR (500 MHz, METHANOL-d4) δ 8.44 (d, J=6.9 Hz, 1H), 8.09 (d, J=8.8 Hz, 1H), 7.45 (t, J=7.8 Hz, 1H), 6.97 (td, J=6.9, 1.1 Hz, 1H), 5.19 (t, J=7.0 Hz, 1H), 4.49 (t, J=8.8 Hz, 1H), 4.03 (dd, J=8.9, 4.5 Hz, 1), 3.00 (dt, J=10.2, 5.1 Hz, 2H), 2.83 (dt, J=11.6, 5.9 Hz, 1H), 2.69 (dt, J=12.0, 6.1 Hz, 1H), 2.50-2.21 (m, 4H), 1.90-1.73 (m, 1H), 1.67 (ddd, J=13.6, 8.9, 4.4 Hz, 1H), 1.50 (ddd, J=14.0, 8.9, 5.5 Hz, 1H), 0.98 (d, J=6.6 Hz, 6H)

Examples 147 to 180 were prepared as described for Example 146.

Examples 181 to 182 were prepared as described for Example 95.

| Example | Structure | Name | LCMS (M + H)+ | HPLC Method RT (min) | 1H NMR |
|---|---|---|---|---|---|
| 113 | 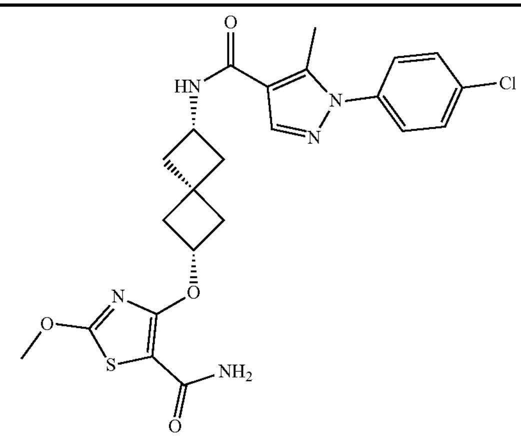 | 2-methoxy-4-{[(4s)-6-[1-(4-chlorophenyl)-5-methyl-1H-pyrazole-4-amido]spiro[3.3]heptan-2-yl]oxy}-1,3-thiazole-5-carboxamide | 502 | A: 1.91 B: 1.79 | B: NMR (500 MHz, DMSO-d6) δ 8.23 (br d, J = 7.6 Hz, 1H), 8.12 (s, 1H), 7.67-7.58 (m, 2H), 7.57-7.52 (m, 2H), 7.42 (br s, 1H), 6.71 (br s, 1H), 5.04 (br t, J = 7.0 Hz, 1H), 4.43-4.23 (m, 1H), 4.03 (s, 3H), 2.67-2.58 (m, 1H), 2.50 (s, 3H), 2.42 (qd, J = 11.2, 6.4 Hz, 2H), 2.35-2.23 (m, 3H), 2.20-2.09 (m, 2H) |
| 114 | 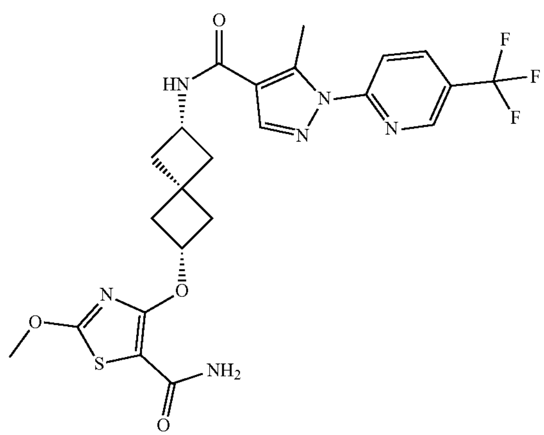 | 2-methoxy-4-{[(4s)-6-{5-methyl-1-[5-(trifluoromethyl)pyridin-2-yl]-1H-pyrazole-4-amido}spiro[3.3]heptan-2-yl]oxy}-1,3-thiazole-5-carboxamide | 537.3 | A: 1.99 B: 1.89 | B: NMR (500 MHz, DMSO-d6) δ 8.91 (br s, 1H), 8.39 (br d, J = 8.5 Hz, 1H), 8.27-8.13 (m, 2H), 8.06 (br d, J = 8.6 Hz, 1H), 5.04 (br t, J = 6.9 Hz, 1H), 4.44-4.16 (m, 1H), 4.03 (s, 3H), 2.86 (br s, 3H), 2.69-2.57 (m, 1H), 2.48-2.04 (m, 7H) |

| Example | Structure | Name | LCMS (M+H)+ | HPLC Method RT (min) | ¹H NMR |
|---|---|---|---|---|---|
| 115 | 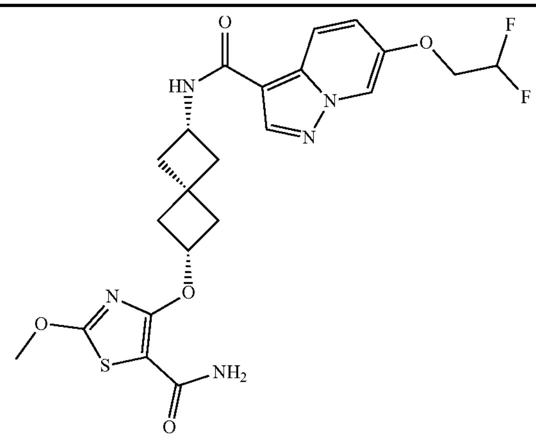 | 2-methoxy-4-{[(4s)-6-[6-(2,2-difluoroethoxy)pyrazolo[1,5-a]pyridine-3-amido]spiro[3.3]heptan-2-yl]oxy}-1,3-thiazole-5-carboxamide | 508.2 | A: 1.48 B: 1.48 | B: NMR (500 MHz, DMSO-d6) δ 8.56 (s, 1H), 8.45 (s, 1H), 8.34 (br d, J = 7.3 Hz, 1H), 8.10 (d, J = 9.8 Hz, 1H), 7.32 (br d, J = 9.8 Hz, 2H), 6.73 (br s, 1H), 6.55-6.26 (m, 1H), 5.03 (br t, J = 7.0 Hz, 1H), 4.49-4.26 (m, 3H), 4.02 (s, 3H), 2.62 (dt, J = 11.4, 5.9 Hz, 1H), 2.48-2.07 (m, 7H) |
| 116 | 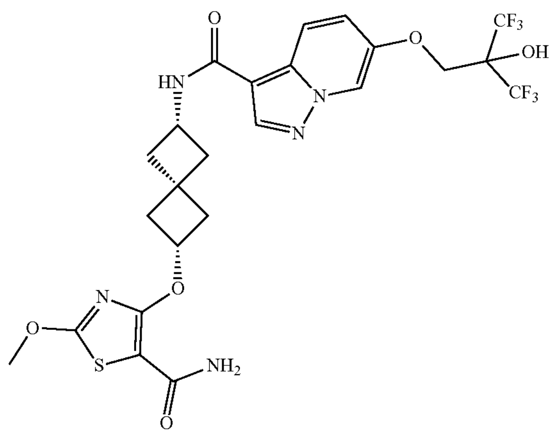 | 2-methoxy-4-{[(4s)-6-[6-[3,3,3-trifluoro-2-hydroxy-2-(trifluoromethyl)propoxy]pyrazolo[1,5-a]pyridine-3-amido]spiro[3.3]heptan-2-yl]oxy}-1,3-thiazole-5-carboxamide | 624.3 | A: 1.73 B: 1.80 | B: NMR (500 MHz, DMSO-d6) δ 8.64 (s, 1H), 8.46 (s, 1H), 8.18 (br d, J = 7.3 Hz, 1H), 8.12 (d, J = 9.7 Hz, 1H), 7.28 (br d, J = 9.7 Hz, 1H), 5.05 (br t, J = 6.9 Hz, 1H), 4.37 (br d, J = 8.0 Hz, 1H), 4.04 (s, 3H), 3.33 (br d, J = 6.9 Hz, 2H), 2.64 (dt, J = 11.3, 5.8 Hz, 1H), 2.48-2.10 (m, 7H) |

| Example | Structure | Name | LCMS (M + H)+ | HPLC Method RT (min) | ¹H NMR |
|---|---|---|---|---|---|
| 117 | 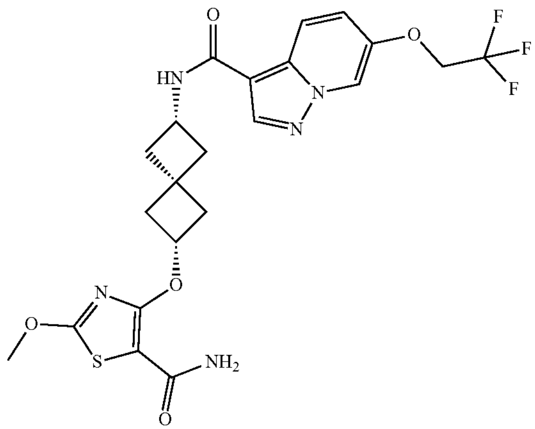 | 2-methoxy-4-{[(4s)-6-[6-(2,2,2-trifluoroethoxy)pyrazolo[1,5-a]pyridine-3-amido]spiro[3.3]heptan-2-yl]oxy}-1,3-thiazole-5-carboxamide | 526 | A: 1.61 B: 1.61 | B: NMR (500 MHz, DMSO-d6) δ 8.66 (s, 1H), 8.49 (s, 1H), 8.36 (br d, J = 7.3 Hz, 1H), 8.13 (d, J = 9.8 Hz, 1H), 7.46-7.31 (m, 2H), 6.72 (br s, 1H), 5.10-4.95 (m, 1H), 4.85 (q, J = 8.6 Hz, 2H), 4.46-4.26 (m, 1H), 4.03 (s, 3H), 2.62 (br dd, J = 11.3, 5.8 Hz, 1H), 2.48-2.07 (m, 7H) |
| 118 | 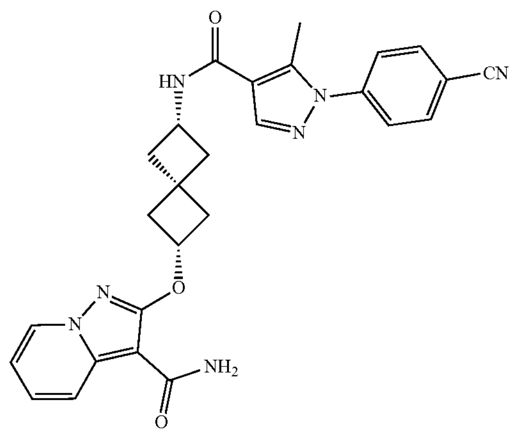 | 1-(4-cyanophenyl)-5-methyl-N-[(4s)-6-({3-carbamoylpyrazolo[1,5-a]pyridin-2-yl}oxy)spiro[3.3]heptan-2-yl]-1H-pyrazole-4-carboxamide | 496.2 | A: 1.45 B: 1.43 | B: NMR (500 MHz, DMSO-d6) δ 8.61 (br d, J = 6.7 Hz, 1H), 8.30 (br d, J = 7.3 Hz, 1H), 8.22 (s, 1H), 8.12-8.02 (m, 3H), 7.80 (br d, J = 8.2 Hz, 2H), 7.46 (br t, J = 7.9 Hz, 1H), 7.17 (br s, 1H), 6.99 (br t, J = 6.7 Hz, 1H), 6.61 (br s, 1H), 5.14 (br t, J = 6.9 Hz, 1H), 4.45-4.28 (m, 1H), 2.72 (br d, J = 4.9 Hz, 1H), 2.63-2.55 (m, 3H), 2.46 (br s, 1H), 2.41-2.28 (m, 3H), 2.19 (br s, 2H) |

| Example | Structure | Name | LCMS (M + H)+ | HPLC Method RT (min) | 1H NMR |
|---|---|---|---|---|---|
| 119 | 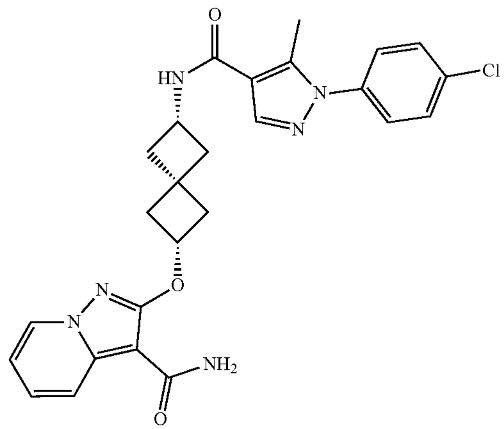 | 1-(4-chlorophenyl)-5-methyl-N-[(4s)-6-({3-carbamoylpyrazolo[1,5-a]pyridin-2-yl}oxy)spiro[3.3]heptan-2-yl]-1H-pyrazole-4-carboxamide | 505.3 | A: 1.68 B: 1.66 | B: NMR (500 MHz, DMSO-d6) δ 8.62 (br d, J = 6.7 Hz, 1H), 8.26 (br d, J = 7.6 Hz, 1H), 8.16 (s, 1H), 8.08 (br d, J = 8.9 Hz, 1H), 7.69-7.61 (m, 2H), 7.60-7.54 (m, 2H), 7.47 (br t, J = 7.9 Hz, 1H), 7.17 (br s, 1H), 6.99 (br t, J = 6.9 Hz, 1H), 6.62 (br s, 1H), 5.15 (br t, J = 6.9 Hz, 1H), 4.43-4.31 (m, 1H), 2.72 (br dd, J = 11.1, 5.6 Hz, 1H), 2.53 (br s, 4H), 2.50-2.25 (m, 4H), 2.25-2.13 (m, 2H) |
| 120 | 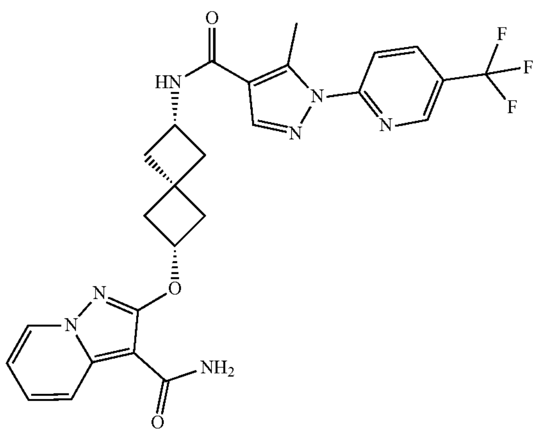 | 5-methyl-N-[(4s)-6-({3-carbamoylpyrazolo[1,5-a]pyridin-2-yl}oxy)spiro[3.3]heptan-2-yl]-1-[5-(trifluoromethyl)pyridin-2-yl]-1H-pyrazole-4-carboxamide | 540.1 | A: 1.82 B: 1.97 | B: 1H NMR (500 MHz, DMSO-d6) δ 8.91 (s, 1H), 8.54 (br d, J = 6.5 Hz, 1H), 8.38 (br d, J = 8.4 Hz, 1H), 8.27-8.13 (m, 2H), 8.10-7.99 (m, 2H), 7.43 (t, J = 7.9 Hz, 1H), 6.96 (t, J = 6.9 Hz, 1H), 5.13 (br t, J = 6.9 Hz, 1H), 4.44-4.24 (m, 1H), 3.41 (br s, 3H), 2.78-2.66 (m, 1H), 2.60-2.53 (m, 2H), 2.49-2.22 (m, 4H), 2.25-2.13 (m, 2H) |

| Example | Structure | Name | LCMS (M + H)+ | HPLC Method RT (min) | 1H NMR |
|---|---|---|---|---|---|
| 121 | 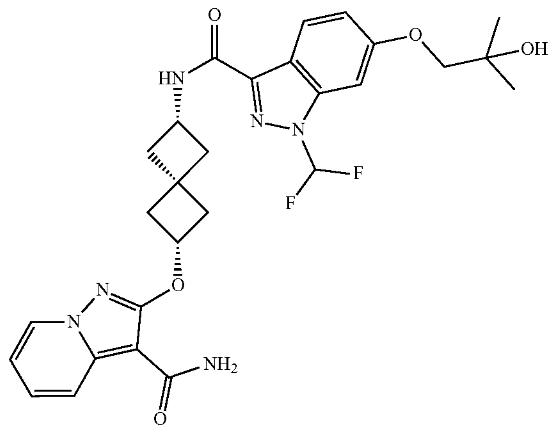 | 1-(difluoromethyl)-6-(2-hydroxy-2-methylpropoxy)-N-[(4s)-6-({3-carbamoylpyrazolo[1,5-a]pyridin-2-yl}oxy)spiro[3.3]heptan-2-yl]-1H-indazole-3-carboxamide | 569.3 | A: 1.81 B: 1.68 | B: NMR (500 MHz, DMSO-d6) δ 8.84 (br d, J = 7.9 Hz, 1H), 8.59 (br d, J = 6.7 Hz, 1H), 8.39-8.16 (m, 1H), 8.13-7.99 (m, 2H), 7.45 (br t, J = 7.8 Hz, 1H), 7.37 (s, 1H), 7.23-7.04 (m, 2H), 6.98 (br t, J = 6.7 Hz, 1H), 6.61 (br s, 1H), 5.12 (br t, J = 6.9 Hz, 1H), 4.54-4.32 (m, 1H), 3.85 (s, 2H), 2.72 (br dd, J = 11.3, 5.8 Hz, 1H), 2.43 (br d, J = 11.0 Hz, 1H), 2.38-2.22 (m, 5H), 1.29-1.22 (m, 6H) |
| 122 | 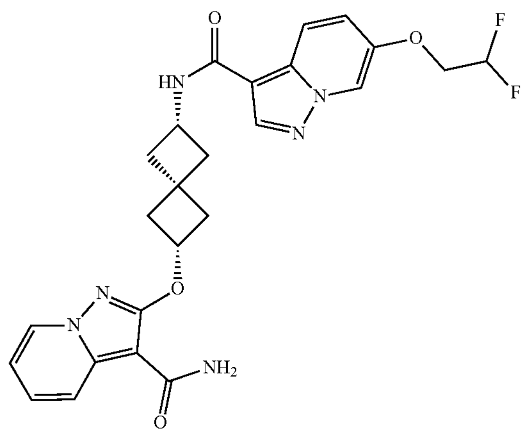 | 2-[[(4s)-6-[6-(2,2-difluoroethoxy)pyrazolo[1,5-a]pyridine-3-amido]spiro[3.3]heptan-2-yl]oxy]pyrazolo[1,5-a]pyridine-3-carboxamide | 511.1 | A: 1.49 B: 1.60 | B: NMR (500 MHz, DMSO-d6) δ 8.66-8.57 (m, 2H), 8.50 (s, 1H), 8.33 (br d, J = 7.3 Hz, 1H), 8.14 (d, J = 9.8 Hz, 1H), 8.08 (br d, J = 8.5 Hz, 1H), 7.46 (br t, J = 7.8 Hz, 1H), 7.35 (dd, J = 9.5, 1.8 Hz, 1H), 7.17 (br s, 1H), 6.99 (br t, J = 6.6 Hz, 1H), 6.62 (br s, 1H), 6.57-6.32 (m, 1H), 5.15 (br t, J = 7.0 Hz, 1H), 4.50-4.38 (m, 3H), 2.74 (dt, J = 11.2, 5.8 Hz, 1H), 2.50-2.44 (m, 1H), 2.44-2.30 (m, 3H), 2.26-2.14 (m, 2H) |

| Example | Structure | Name | LCMS (M + H)+ | HPLC Method RT (min) | ¹H NMR |
|---|---|---|---|---|---|
| 123 | 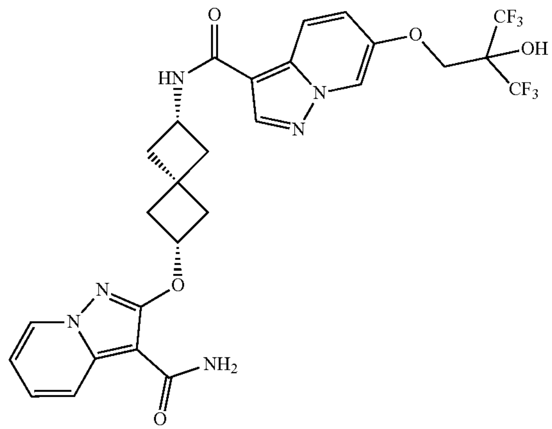 | 2-[[(4s)-6-{6-[3,3,3-trifluoro-2-hydroxy-2-(trifluoromethyl)propoxy]pyrazolo[1,5-a]pyridine-3-amido}spiro[3.3]heptan-2-yl]oxy}pyrazolo[1,5-a]pyridine-3-carboxamide | 627.1 | A: 1.65 B: 1.65 | NMR (500 MHz, DMSO-d6) δ 8.66 (s, 1H), 8.56 (br d, J = 6.7 Hz, 1H), 8.48 (s, 1H), 8.38 (br d, J = 7.3 Hz, 1H), 8.12 (d, J = 9.8 Hz, 1H), 8.04 (br d, J = 8.8 Hz, 1H), 7.46 (br t, J = 7.9 Hz, 1H), 7.29 (br d, J = 9.5 Hz, 1H), 7.08 (br s, 1H), 6.98 (br t, J = 6.7 Hz, 1H), 6.65 (br s, 1H), 5.12 (br t, J = 6.9 Hz, 1H), 4.51 (s, 2H), 4.45-4.30 (m, 1H), 3.65 (br s, 1H), 2.72 (dt, J = 11.1, 5.6 Hz, 1H), 2.50-2.41 (m, 1H), 2.40-2.26 (m, 3H), 2.24-2.12 (m, 2H) |
| 124 | 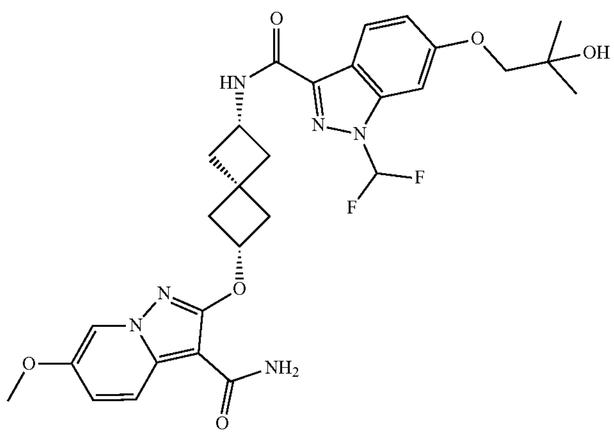 | 1-(difluoromethyl)-6-(2-hydroxy-2-methylpropoxy)-N-[(4s)-6-({3-carbamoyl-6-methoxypyrazolo[1,5-a]pyridin-2-yl}oxy)spiro[3.3]heptan-2-yl]-1H-indazole-3-carboxamide | 599.3 | A: 1.73 B: 1.73 | NMR (500 MHz, DMSO-d6) δ 8.83 (d, J = 7.9 Hz, 1H), 8.32 (d, J = 1.5 Hz, 1H), 8.09-8.02 (m, 1H), 7.94 (d, J = 9.8 Hz, 1H), 7.34 (s, 1H), 7.26 (dd, J = 9.8, 2.1 Hz, 1H), 7.14-6.97 (m, 2H), 6.57 (br s, 1H), 5.07 (t, J = 6.9 Hz, 1H), 4.42 (br d, J = 7.9 Hz, 1H), 3.80 (s, 2H), 3.62-3.52 (m, 1H), 2.69 (br d, J = 5.8 Hz, 1H), 2.46-2.18 (m, 6H), 1.24 (s, 6H) |

| Example | Structure | Name | LCMS (M+H)+ | HPLC Method RT (min) | 1H NMR |
|---|---|---|---|---|---|
| 125 | 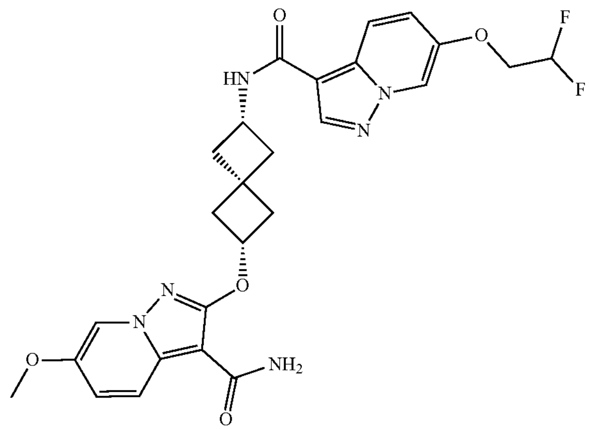 | 6-methoxy-2-[[(4s)-6-[6-(2,2-difluoroethoxy)pyrazolo[1,5-a]pyridine-3-amido]spiro[3.3]heptan-2-yl]oxy]pyrazolo[1,5-a]pyridine-3-carboxamide | 541.2 | A: 1.53 B: 1.61 | B: NMR (500 MHz, DMSO-d6) δ 8.57 (s, 1H), 8.46 (s, 1H), 8.30 (s, 1H), 8.19 (br d, J = 7.2 Hz, 1H), 8.12 (d, J = 9.7 Hz, 1H), 7.96 (d, J = 9.7 Hz, 1H), 7.34-7.29 (m, 1H), 7.25 (dd, J = 9.6, 1.9 Hz, 1H), 6.55-6.22 (m, 1H), 5.11 (br t, J = 6.9 Hz, 1H), 4.48-4.34 (m, 3H), 3.82 (s, 3H), 2.71 (dt, J = 11.4, 5.7 Hz, 1H), 2.49-2.26 (m, 4H), 2.24-2.13 (m, 2H) |
| 126 | 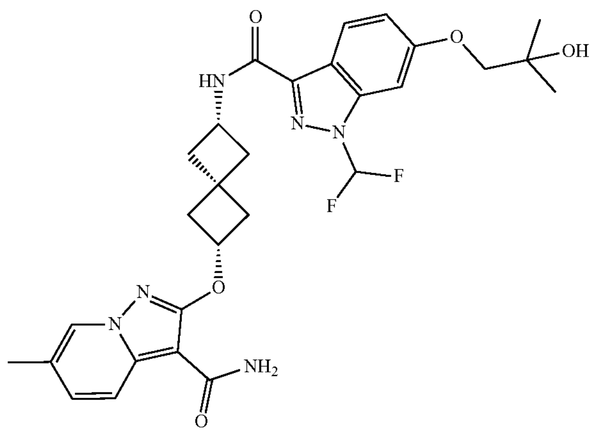 | 1-(difluoromethyl)-6-(2-hydroxy-2-methylpropoxy)-N-[(4s)-6-({3-carbamoyl-6-methylpyrazolo[1,5-a]pyridin-2-yl}oxy)spiro[3.3]heptan-2-yl]-1H-indazole-3-carboxamide | 583.4 | A: 1.84 B: 1.84 | NMR (500 MHz, DMSO-d6) δ 8.82 (br d, J = 7.9 Hz, 1H), 8.45 (s, 1H), 8.16-8.02 (m, 1H), 7.96 (d, J = 8.9 Hz, 1H), 7.42-7.26 (m, 2H), 7.08 (br d, J = 9.2 Hz, 2H), 6.55 (br s, 1H), 5.10 (br t, J = 6.9 Hz, 1H), 4.57-4.35 (m, 1H), 3.84 (s, 2H), 2.81-2.60 (m, 1H), 2.47-2.17 (m, 8H), 1.25 (s, 7H) |

| Example | Structure | Name | LCMS (M + H)+ | HPLC Method RT (min) | ¹H NMR |
|---|---|---|---|---|---|
| 127 | 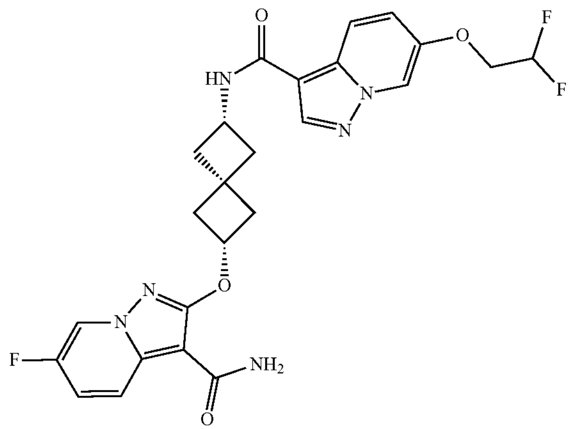 | 6-fluoro-2-{[(4s)-6-[6-(2,2-difluoroethoxy)pyrazolo[1,5-a]pyridine-3-amido]spiro[3.3]heptan-2-yl]oxy}pyrazolo[1,5-a]pyridine-3-carboxamide | 529.4 | A: 1.54 B: 1.53 | NMR (500 MHz, DMSO-d6) δ 8.90 (br d, J = 1.8 Hz, 1H), 8.56 (d, J = 1.5 Hz, 1H), 8.46 (s, 1H), 8.35 (br d, J = 7.3 Hz, 1H), 8.16-7.99 (m, 2H), 7.60-7.47 (m, 1H), 7.32 (dd, J = 9.8, 1.8 Hz, 1H), 7.15 (br s, 1H), 6.65 (br s, 1H), 6.55-6.20 (m, 1H), 5.10 (t, J = 7.0 Hz, 1H), 4.48-4.26 (m, 3H), 2.75-2.62 (m, 1H), 2.48-2.40 (m, 1H), 2.39-2.24 (m, 3H), 2.22-2.11 (m, 2H) |
| 128 | 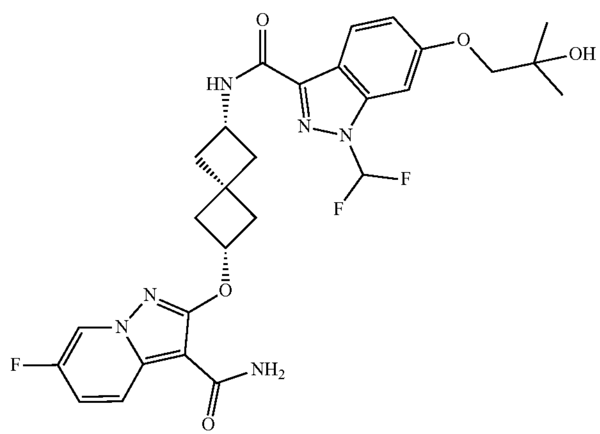 | 1-(difluoromethyl)-6-(2-hydroxy-2-methylpropoxy)-N-[(4s)-6-({3-carbamoyl-6-fluoropyrazolo[1,5-a]pyridin-2-yl}oxy)spiro[3.3]heptan-2-yl]-1H-indazole-3-carboxamide | 587.1 | A: 1.69 B: 1.71 | NMR (500 MHz, DMSO-d6) δ 8.91 (br d, J = 2.1 Hz, 1H), 8.83 (br d, J = 7.9 Hz, 1H), 8.10-8.02 (m, 2H), 7.60-7.51 (m, 1H), 7.33 (s, 1H), 7.16 (br s, 1H), 7.08 (dd, J = 8.9, 1.8 Hz, 1H), 6.64 (br s, 1H), 5.09 (br t, J = 6.9 Hz, 1H), 4.48-4.35 (m, 1H), 3.83 (s, 2H), 3.57 (br s, 2H), 2.70 (dt, J = 11.1, 5.7 Hz, 1H), 2.47-2.21 (m, 6H), 1.24 (s, 6H) |

| Example | Structure | Name | LCMS (M + H)+ | HPLC Method RT (min) | ¹H NMR |
|---|---|---|---|---|---|
| 129 | 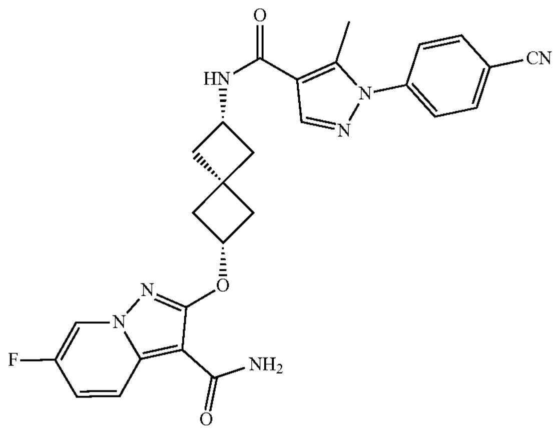 | 1-(4-cyanophenyl)-5-methyl-N-[(4s)-6-({3-carbamoyl-6-fluoropyrazolo[1,5-a]pyridin-2-yl}oxy)spiro[3.3]heptan-2-yl]-1H-pyrazole-4-carboxamide | 514.3 | A: 1.54 B: 1.52 | B: NMR (500 MHz, DMSO-d6) δ 8.85 (br s, 1H), 8.22-8.13 (m, 2H), 8.08 (dd, J = 9.7, 5.9 Hz, 1H), 8.00 (br d, J = 8.3 Hz, 2H), 7.75 (br d, J = 8.2 Hz, 2H), 7.53 (br t, J = 9.1 Hz, 1H), 5.12 (quin, J = 6.8 Hz, 1H), 4.41-4.27 (m, 1H), 3.68-3.51 (m, 2H), 2.76-2.63 (m, 1H), 2.48-2.24 (m, 4H), 2.23-2.11 (m, 2H) |
| 130 | 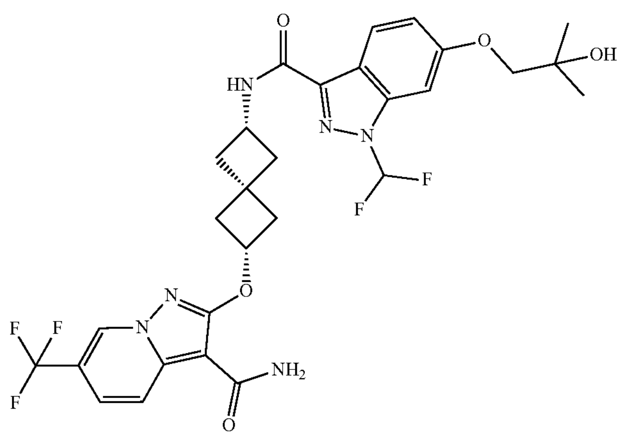 | 1-(difluoromethyl)-6-(2-hydroxy-2-methylpropoxy)-N-[(4s)-6-{[3-carbamoyl-6-(trifluoromethyl)pyrazolo[1,5-a]pyridin-2-yl]oxy}spiro[3.3]heptan-2-yl]-1H-indazole-3-carboxamide | 637.4 | A: 1.97 B: 1.97 | B: NMR (500 MHz, DMSO-d6) δ 9.18 (s, 1H), 8.65 (br d, J = 7.7 Hz, 1H), 8.32-8.12 (m, 2H), 8.11-8.01 (m, 1H), 7.66 (d, J = 9.2 Hz, 1H), 7.35 (s, 1H), 7.08 (dd, J = 8.9, 1.5 Hz, 1H), 5.16 (t, J = 6.9 Hz, 1H), 4.51-4.37 (m, 1H), 3.86 (s, 2H), 3.39-3.23 (m, 2H), 2.74 (dt, J = 11.4, 5.8 Hz, 1H), 2.49-2.26 (m, 6H), 1.25 (s, 6H) |

| Example | Structure | Name | LCMS (M + H)+ | HPLC Method RT (min) | 1H NMR |
|---|---|---|---|---|---|
| 131 | 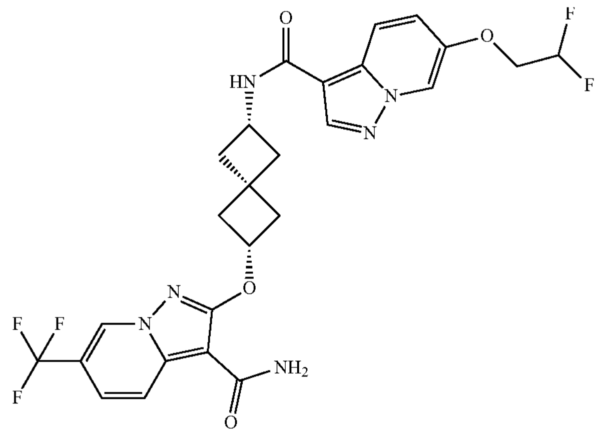 | 2-[[(4s)-6-[6-(2,2-difluoroethoxy)pyrazolo[1,5-a]pyridine-3-amido]spiro[3.3]heptan-2-yl]oxy]-6-(trifluoromethyl)pyrazolo[1,5-a]pyridine-3-carboxamide | 579.3 | A: 1.78 B: 1.74 | NMR (500 MHz, DMSO-d6) δ 9.26 (s, 1H), 8.60 (d, J = 1.5 Hz, 1H), 8.48 (s, 1H), 8.32 (br d, J = 7.6 Hz, 1H), 8.21 (d, J = 9.5 Hz, 1H), 8.11 (d, J = 9.5 Hz, 1H), 7.68 (br d, J = 9.5 Hz, 1H), 7.41-7.26 (m, 2H), 6.72 (br s, 1H), 6.60-6.19 (m, 1H), 5.15 (br t, J = 7.0 Hz, 1H), 4.53-4.24 (m, 3H), 2.72 (dt, J = 11.3, 5.6 Hz, 1H), 2.48-2.25 (m, 4H), 2.23-2.07 (m, 2H) |
| 132 | 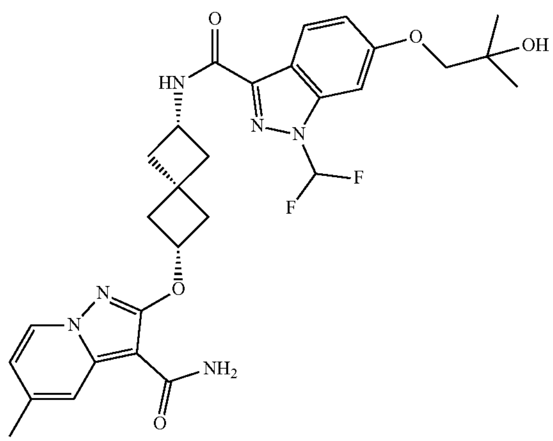 | 1-(difluoromethyl)-6-(2-hydroxy-2-methylpropoxy)-N-[(4s)-6-({3-carbamoyl-5-methylpyrazolo[1,5-a]pyridin-2-yl}oxy)spiro[3.3]heptan-2-yl]-1H-indazole-3-carboxamide | 583.4 | A: 1.84 B: 1.74 | NMR (500 MHz, DMSO-d6) δ 8.84 (br d, J = 7.6 Hz, 1H), 8.41 (d, J = 6.7 Hz, 1H), 8.29-7.95 (m, 2H), 7.81 (s, 1H), 7.30 (s, 1H), 7.15-7.02 (m, 1H), 6.97 (br s, 1H), 6.81 (d, J = 5.8 Hz, 1H), 6.61 (br s, 1H), 5.07 (br t, J = 7.0 Hz, 1H), 4.48-4.33 (m, 1H), 2.75-2.62 (m, 1H), 2.47-2.20 (m, 9H), 1.23 (s, 6H) |

| Example | Structure | Name | LCMS (M+H)+ | HPLC Method RT (min) | 1H NMR |
|---|---|---|---|---|---|
| 133 | 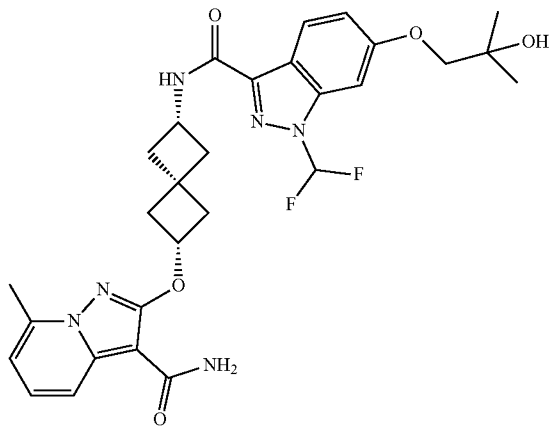 | 1-(difluoromethyl)-6-(2-hydroxy-2-methylpropoxy)-N-[(4s)-6-({3-carbamoyl-7-methylpyrazolo[1,5-a]pyridin-2-yl}-oxy)spiro[3.3]heptan-2-yl]-1H-indazole-3-carboxamide | 583.4 | A: 1.91 B: 1.92 | B: NMR (500 MHz, DMSO-d6) δ 8.83 (br d, J = 7.9 Hz, 1H), 8.10-8.00 (m, 1H), 7.95 (d, J = 8.5 Hz, 1H), 7.38 (t, J = 7.9 Hz, 1H), 7.34 (s, 1H), 7.15-7.01 (m, 2H), 6.89 (br d, J = 7.0 Hz, 1H), 6.63 (br s, 1H), 5.15 (br t, J = 7.0 Hz, 1H), 4.52-4.29 (m, 1H), 3.83 (s, 2H), 3.63-3.47 (m, 2H), 2.74 (dt, J = 10.9, 5.7 Hz, 1H), 2.62 (s, 3H), 2.48-2.40 (m, 1H), 2.39-2.23 (m, 5H), 1.24 (s, 6H) |
| 134 | 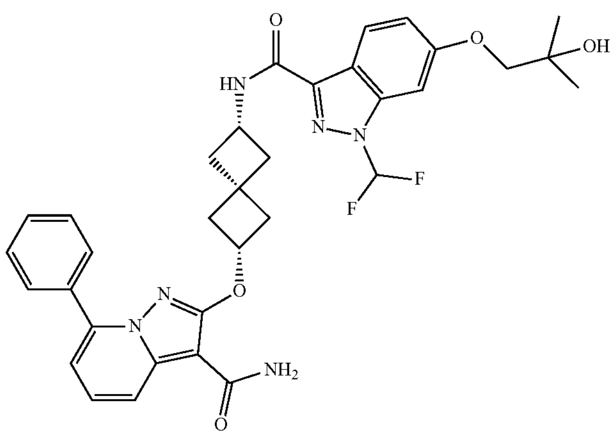 | 1-(difluoromethyl)-6-(2-hydroxy-2-methylpropoxy)-N-[(4s)-6-({3-carbamoyl-7-phenylpyrazolo[1,5-a]pyridin-2-yl}-oxy)spiro[3.3]heptan-2-yl]-1H-indazole-3-carboxamide | 645.4 | A: 2.11 B: 2.14 | B: NMR (500 MHz, DMSO-d6) δ 8.82 (br d, J = 7.9 Hz, 1H), 8.14-8.03 (m, 2H), 7.94 (br d, J = 6.7 Hz, 2H), 7.62-7.48 (m, 4H), 7.35 (s, 1H), 7.18-7.01 (m, 3H), 6.63 (br s, 1H), 4.96 (br t, J = 7.0 Hz, 1H), 4.50-4.32 (m, 1H), 3.84 (s, 2H), 3.56-3.41 (m, 2H), 2.74-2.59 (m, 1H), 2.47 (br d, J = 5.5 Hz, 1H), 2.41-2.19 (m, 6H), 1.24 (s, 6H) |

| Example | Structure | Name | LCMS (M+H)+ | HPLC Method RT (min) | 1H NMR |
|---|---|---|---|---|---|
| 135 | 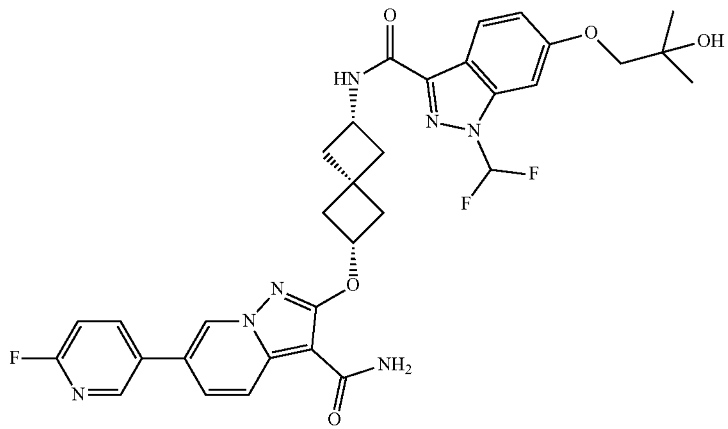 | 1-(difluoromethyl)-6-(2-hydroxy-2-methylpropoxy)-N-[(4s)-6-{[3-carbamoyl-6-(6-fluoropyridin-3-yl)pyrazolo[1,5-a]pyridin-2-yl]oxy}spiro[3.3]heptan-2-yl]-1H-indazole-3-carboxamide | 664.4 | A: 1.83 B: 1.88 | B: NMR (500 MHz, DMSO-d6) δ 9.06 (s, 1H), 8.69-8.57 (m, 2H), 8.43-8.32 (m, 1H), 8.15 (d, J = 9.0 Hz, 2H), 8.08 (d, J = 8.9 Hz, 1H), 7.83 (br d, J = 9.2 Hz, 1H), 7.36 (s, 1H), 7.29 (dd, J = 8.5, 2.4 Hz, 1H), 7.09 (br d, J = 8.9 Hz, 1H), 5.17 (br t, J = 6.9 Hz, 1H), 4.45 (br d, J = 8.1 Hz, 1H), 3.86 (s, 2H), 2.82-2.68 (m, 1H), 2.57 (br s, 2H), 2.49-2.25 (m, 6H), 1.26 (s, 6H) |
| 136 | 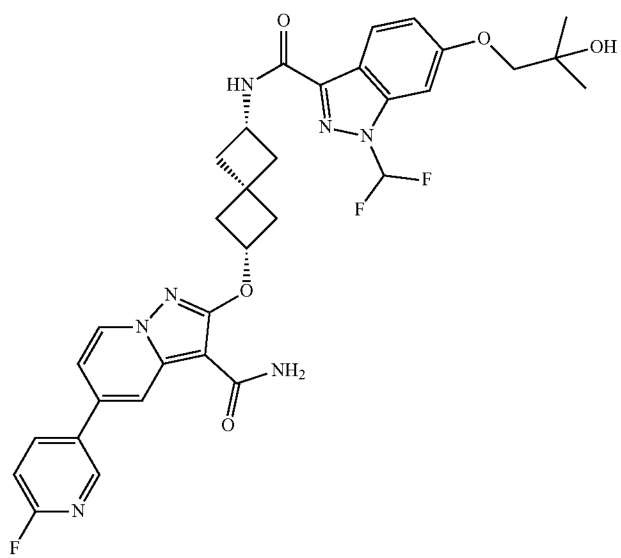 | 1-(difluoromethyl)-6-(2-hydroxy-2-methylpropoxy)-N-[(4s)-6-{[3-carbamoyl-5-(6-fluoropyridin-3-yl)pyrazolo[1,5-a]pyridin-2-yl]oxy}spiro[3.3]heptan-2-yl]-1H-indazole-3-carboxamide | 664.1 | A: 1.77 B: 1.73 | B: NMR (500 MHz, DMSO-d6) δ 8.84 (br d, J = 7.9 Hz, 1H), 8.70-8.59 (m, 2H), 8.44-8.30 (m, 1H), 8.29-8.23 (m, 1H), 8.09-8.00 (m, 1H), 7.39-7.27 (m, 3H), 7.17 (br s, 1H), 7.08 (br d, J = 10.4 Hz, 1H), 6.71 (br s, 1H), 5.12 (br t, J = 6.9 Hz, 1H), 4.41 (br d, J = 8.2 Hz, 1H), 3.75-3.64 (m, 4H), 2.80-2.65 (m, 1H), 2.48-2.18 (m, 6H), 1.23 (s, 6H) |

| Example | Structure | Name | LCMS (M + H)+ | HPLC Method RT (min) | ¹H NMR |
|---|---|---|---|---|---|
| 137 | 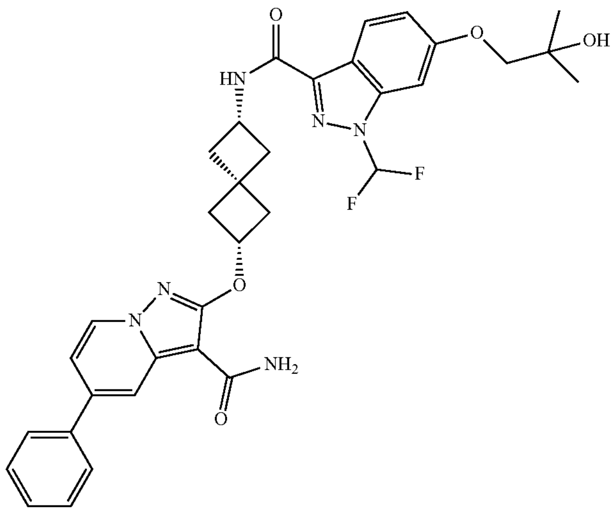 | 1-(difluoromethyl)-6-(2-hydroxy-2-methylpropoxy)-N-[(4s)-6-({3-carbamoyl-5-phenylpyrazolo[1,5-a]pyridin-2-yl}oxy)spiro[3.3]heptan-2-yl]-1H-indazole-3-carboxamide | 645.1 | A: 2.11 B: 2.01 | B: NMR (500 MHz, DMSO-d6) δ 8.84 (br d, J = 7.9 Hz, 1H), 8.62 (d, J = 7.0 Hz, 1H), 8.27 (s, 1H), 8.18-7.95 (m, 2H), 7.76 (br d, J = 7.3 Hz, 2H), 7.62-7.50 (m, 2H), 7.49-7.40 (m, 1H), 7.30 (br s, 2H), 7.16-7.03 (m, 2H), 6.69 (br s, 1H), 5.12 (br t, J = 6.9 Hz, 1H), 4.48-4.34 (m, 1H), 3.75-3.65 (m, 5H), 2.72 (dt, J = 11.2, 5.8 Hz, 1H), 2.48-2.21 (m, 6H), 1.23 (s, 6H) |
| 138 | 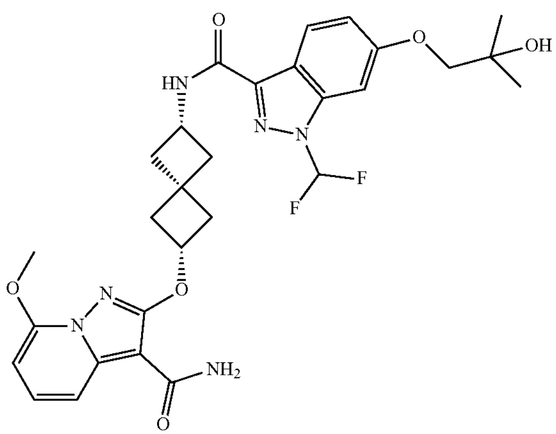 | 1-(difluoromethyl)-6-(2-hydroxy-2-methylpropoxy)-N-[(4s)-6-({3-carbamoyl-7-methoxypyrazolo[1,5-a]pyridin-2-yl}oxy)spiro[3.3]heptan-2-yl]-1H-indazole-3-carboxamide | 599.4 | A: 1.64 B: 1.65 | B: NMR (500 MHz, DMSO-d6) δ 8.83 (br d, J = 7.9 Hz, 1H), 8.10-8.02 (m, 1H), 7.66 (d, J = 8.9 Hz, 1H), 7.44 (t, J = 8.2 Hz, 1H), 7.34 (s, 1H), 7.11-7.00 (m, 2H), 6.62 (br s, 1H), 6.48 (d, J = 7.6 Hz, 1H), 5.15 (br t, J = 6.9 Hz, 1H), 4.53-4.29 (m, 1H), 4.09 (s, 3H), 3.65-3.43 (m, 3H), 2.71 (dt, J = 11.4, 5.6 Hz, 1H), 2.48-2.15 (m, 6H), 1.24 (s, 6H) |

| Example | Structure | Name | LCMS (M+H)+ | HPLC Method RT (min) | 1H NMR |
|---|---|---|---|---|---|
| 140 | 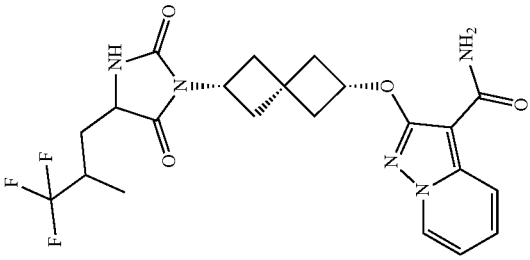 | 2-{[(4s)-6-[2,5-dioxo-4-(3,3,3-trifluoro-2-methylpropyl)imidazolidin-1-yl]spiro[3.3]heptan-2-yl]oxy}pyrazolo[1,5-a]pyridine-3-carboxamide | 480.2 | C: 2.30 | NMR (500 MHz, METHANOL-d4) δ 8.43 (d, J = 6.9 Hz, 1H), 8.10 (d, J = 8.8 Hz, 1H), 7.48-7.41 (m, 1H), 6.97 (td, J = 6.9, 1.2 Hz, 1H), 5.28-5.10 (m, 1H), 4.60-4.42 (m, 1H), 4.19-4.05 (m, 1H), 3.06-2.93 (m, 2H), 2.83 (dt, J = 11.7, 6.0 Hz, 1H), 2.75-2.60 (m, 2H), 2.57-2.26 (m, 5H), 1.86 (ddd, J = 8.8, 5.0, 3.3 Hz, 1H), 1.22-1.18 (m, 3H) |

| Example | Structure | Name | LCMS (M + H)+ | HPLC Method RT (min) | ¹H NMR |
|---|---|---|---|---|---|
| 141 | 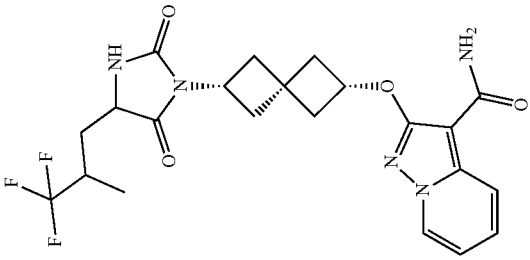 | 2-{[(4s)-6-[2,5-dioxo-4-(3,3,3-trifluoro-2-methylpropyl)imidazolidin-1-yl]spiro[3.3]heptan-2-yl]oxy}pyrazolo[1,5-a]pyridine-3-carboxamide | 480.1 | C: 230 | NMR (500 MHz, METHANOL-d4) δ 8.43 (d, J = 6.9 Hz, 1H), 8.10 (d, J = 8.8 Hz, 1H), 7.48-7.41 (m, 1H), 6.97 (td, J = 6.9, 1.2 Hz, 1H), 5.28-5.10 (m, 1H), 4.60-4.42 (m, 1H), 4.19-4.05 (m, 1H), 3.06-2.93 (m, 2H), 2.83 (dt, J = 11.7, 6.0 Hz, 1H), 2.75-2.60 (m, 2H), 2.57-2.26 (m, 5H), 1.86 (ddd, J = 8.8, 5.0, 3.3 Hz, 1H), 1.22-1.18 (m, 3H) |

| Example | Structure | Name | LCMS (M + H)+ | HPLC Method RT (min) | $^1$H NMR |
|---|---|---|---|---|---|
| 142 | 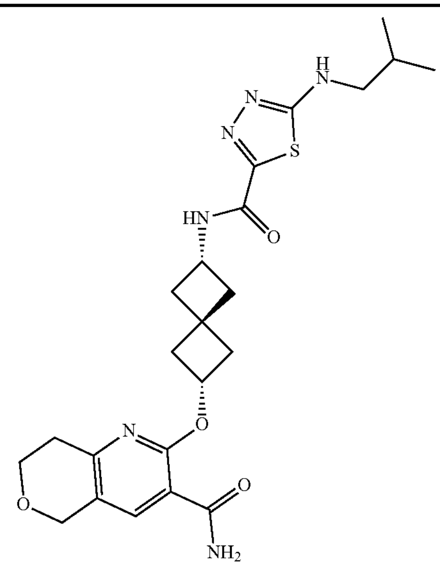 | 5-[(2-methylpropyl)amino]-N-[(4s)-6-({3-carbamoyl-5H,7H,8H-pyrano[4,3-b]pyridin-2-yl}oxy)spiro[3.3]heptan-2-yl]-1,3,4-thiadiazole-2-carboxamide | 487.3 | A: 1.58 B: 1.55 | B: NMR (400 MHz, DMSO-d6) d 8.96 (d, J = 8.3 Hz, 1H), 8.33-8.26 (m, 1H), 7.90 (s, 1H), 7.65 (br. s., 1H), 7.56 (s, 1H), 5.17 (t, J = 7.2 Hz, 1H), 4.65 (s, 2H), 4.31-4.20 (m, 1H), 3.94 (t, J = 5.7 Hz, 2H), 3.17 (d, J = 5.1 Hz, 1H), 3.15-3.09 (m, 2H), 2.79 (t, J = 5.7 Hz, 2H), 2.63 (s, 1H), 2.46-2.34 (m, 2H), 2.29-2.12 (m, 5H), 1.90-1.81 (m, 1H), 1.23 (s, 2H), 0.91 (d, J = 6.6 Hz, 6H) |

| Example | Structure | Name | LCMS (M + H)+ | HPLC Method RT (min) | ¹H NMR |
|---|---|---|---|---|---|
| 143 | 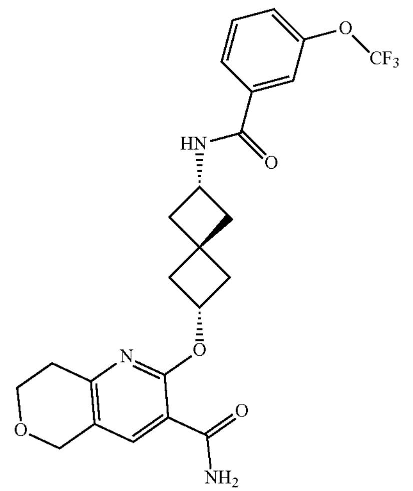 | 2-{[(4s)-6-[3-(trifluoromethoxy)benzamido]spiro[3.3]heptan-2-yl]oxy}-5H,7H,8H-pyrano[4,3-b]pyridine-3-carboxamide | 492.2 | A: 1.85 B: 1.83 | B: NMR (400 MHz, DMSO-d6) δ 8.80 (d, J = 7.3 Hz, 1H), 7.95-7.84 (m, 2H), 7.79 (s, 1H), 7.66 (br. s., 1H), 7.64-7.58 (m, 1H), 7.58-7.47 (m, 2H), 5.20 (t, J = 7.2 Hz, 1H), 4.65 (s, 2H), 4.38-4.30 (m, 1H), 3.94 (t, J = 5.7 Hz, 2H), 3.17 (d, J = 5.4 Hz, 1H), 2.80 (t, J = 5.6 Hz, 2H), 2.69-2.64 (m, 1H), 2.49-2.43 (m, 2H), 2.34 (d, J = 3.9 Hz, 1H), 2.28-2.16 (m, 4H), 2.07 (s, 1H) |
| 144 | 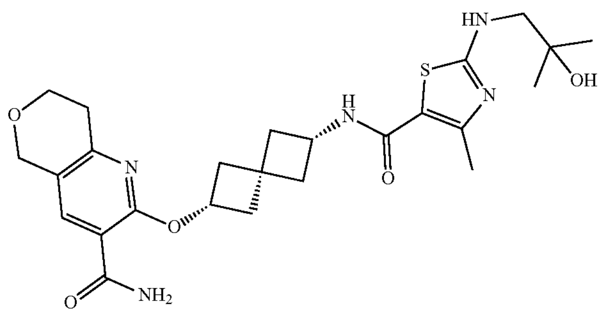 | 2-[(2-hydroxy-2-methylpropyl)amino]-4-methyl-N-[(4s)-6-({3-carbamoyl-5H,7H,8H-pyrano[4,3-b]pyridin-2-yl}oxy)spiro[3.3]heptan-2-yl]-1,3-thiazole-5-carboxamide | 516.2 | A: 1.07 B: 1.24 | B: NMR (400 MHz, DMSO-d6) δ ppm = 7.91 (s, 1H), 7.86 (t, J = 5.7 Hz, 1H), 7.74-7.59 (m, 2H), 7.54 (br. s., 1H), 5.18 (t, J = 7.0 Hz, 1H), 4.70-4.55 (m, 3H), 4.27-4.15 (m, 1H), 3.99-3.88 (m, 2H), 3.18 (d, J = 5.6 Hz, 2H), 2.64-2.59 (m, 1H), 2.43 (d, J = 5.1 Hz, 2H), 2.40-2.28 (m, 4H), 2.28-2.02 (m, 6H), 1.19-1.05 (m, 6H). |

-continued

| Example | Structure | Name | LCMS (M + H)+ | HPLC Method RT (min) | ¹H NMR |
|---|---|---|---|---|---|
| 145 | 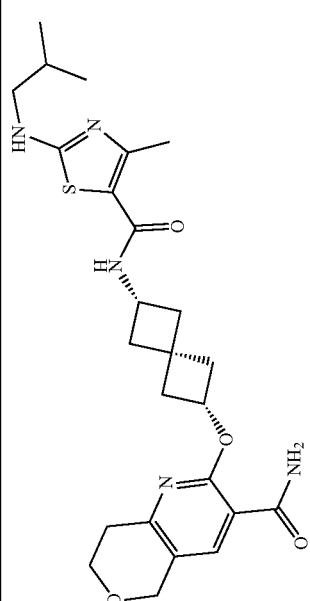 | 4-methyl-2-[(2-methylpropyl)amino]-N-[(4s)-6-({3-carbamoyl-5H,7H,8H-pyrano[4,3-b]pyridin-2-yl}oxy)spiro[3.3]heptan-2-yl]-1,3-thiazole-5-carboxamide | 500.2 | A: 1.59 B: 1.29 | B: NMR (400 MHz, DMSO-d6) δ ppm = 8.41 (br. s., 1H), 7.91 (s, 1H), 7.77 (d, J = 7.6 Hz, 1H), 7.67 (br. s., 1H), 7.54 (br. s., 1H), 5.18 (t, J = 7.1 Hz, 1H), 4.70-4.60 (m, 2H), 4.29-4.19 (m, 1H), 3.95 (t, J = 5.6 Hz, 2H), 3.04 (t, J = 6.0 Hz, 2H), 2.80 (t, J = 5.5 Hz, 2H), 2.62 (dd, J = 11.0, 5.6 Hz, 1H), 2.58-2.54 (m, 3H), 2.47-2.38 (m, 1H), 2.35-2.06 (m, 6H), 1.87 (dt, J = 13.3, 6.4 Hz, 1H), 0.91 (d, J = 6.8 Hz, 6H). |
| 147 | 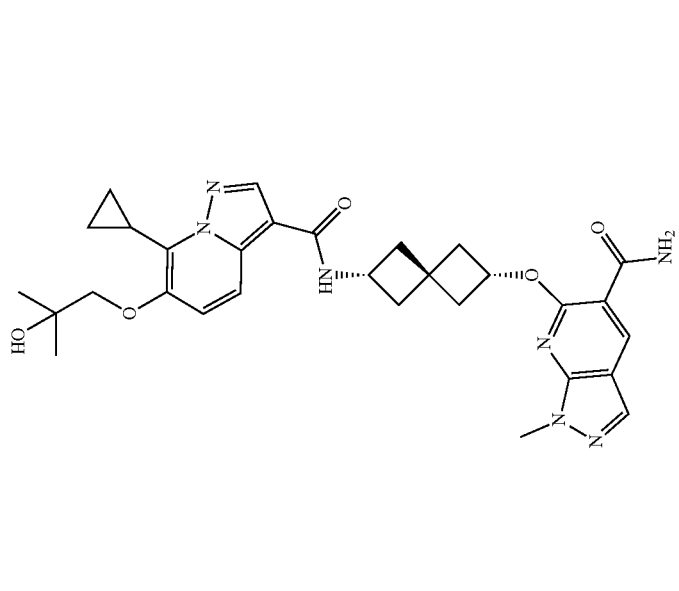 | 7-cyclopropyl-6-(2-hydroxy-2-methylpropoxy)-N-[(4s)-6-({5-carbamoyl-1-methyl-1H-pyrazolo[3,4-b]pyridin-6-yl}oxy)spiro[3.3]heptan-2-yl]pyrazolo[1,5-a]pyridine-3-carboxamide | 574.3 | A: 1.53 B: 1.54 | B: NMR (400 MHz, DMSO-d6) d 8.62 (s, 1H), 8.51 (s, 1H), 8.28 (d, J = 7.8 Hz, 1H), 8.10 (s, 1H), 8.04 (d, J = 9.8 Hz, 1H), 7.66 (br. s., 1H), 7.61 (br. s., 1H), 7.47 (d, J = 9.8 Hz, 1H), 5.30 (t, J = 7.2 Hz, 1H), 4.41 (d, J = 8.6 Hz, 1H), 3.98 (s, 3H), 3.80 (s, 2H), 2.84-2.78 (m, 1H), 2.65-2.57 (m, 3H), 2 |

| Example | Structure | Name | LCMS (M + H)+ | HPLC Method RT (min) | ¹H NMR |
|---|---|---|---|---|---|
| 148 | 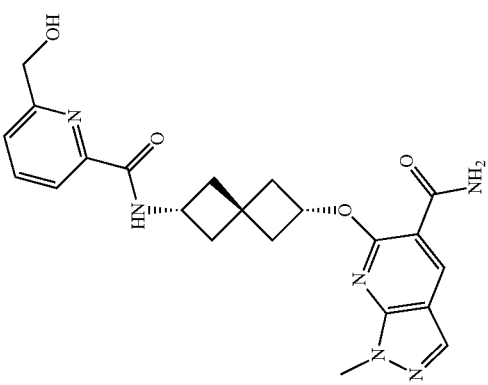 | 6-(hydroxymethyl)-N-[(4s)-6-({5-carbamoyl-1-methyl-1H-pyrazolo[3,4-b]pyridin-6-yl}oxy)spiro[3.3]heptan-2-yl]pyridine-2-carboxamide | 437.2 | A: 1.15 1.15 | A: NMR (400 MHz, DMSO-d6) d 8.86 (d, J = 8.6 Hz, 1H), 8.63 (s, 1H), 8.10 (s, 1H), 7.97 (t, J = 7.7 Hz, 1H), 7.88 (d, J = 7.1 Hz, 1H), 7.61 (d, J = 8.1 Hz, 3H), 5.48 (t, J = 6.0 Hz, 1H), 5.30 (t, J = 7.2 Hz, 1H), 4.67 (d, J = 5.9 Hz, 2H), 4.49-4.38 (m, 1H), 3.98 (s, 3H), 3.91 (s, 1H), 2.90 (s, 1H), 2.82 (dt, J = 11.6, 5.9 Hz, 1H), 2.74 (s, 1H), 2.65-2.59 (m, 1H), 2.39-2.27 (m, 5H) |

| Example | Structure | Name | LCMS (M + H)+ | HPLC Method RT (min) | 1H NMR |
|---|---|---|---|---|---|
| 149 | 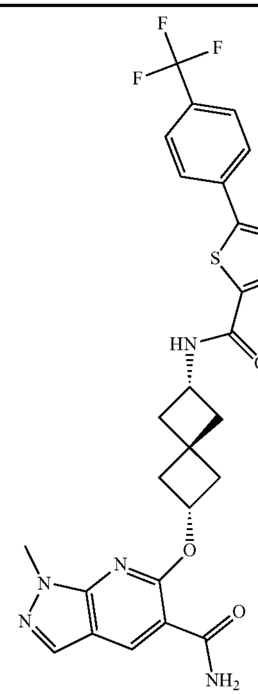 | N-[(4s)-6-({5-carbamoyl-1-methyl-1H-pyrazolo[3,4-b]pyridin-6-yl}oxy)spiro[3.3]heptan-2-yl]-5-[4-(trifluoromethyl)phenyl]-1,3,4-thiadiazole-2-carboxamide | 558.1 | A: 1.99 B: 1.99 | B: NMR (400 MHz, DMSO-d6) d 9.66 (d, J = 7.8 Hz, 1H), 8.62 (s, 1H), 8.36-8.21 (m, J = 8.1 Hz, 2H), 8.10 (s, 1H), 8.03-7.88 (m, J = 8.3 Hz, 2H), 7.66 (br. s., 1H), 7.60 (br. s., 2H), 5.29 (t, J = 7.2 Hz, 1H), 4.45-4.35 (m, 1H), 3.98 (s, 3H), 2.84-2.78 (m, 1H), 2.60 (dd, J = 10.9, 5.3 Hz, 1H), 2.44-2.21 (m, 7H) |

| Example | Structure | Name | LCMS (M + H)+ | HPLC Method RT (min) | $^1$H NMR |
|---|---|---|---|---|---|
| 150 | 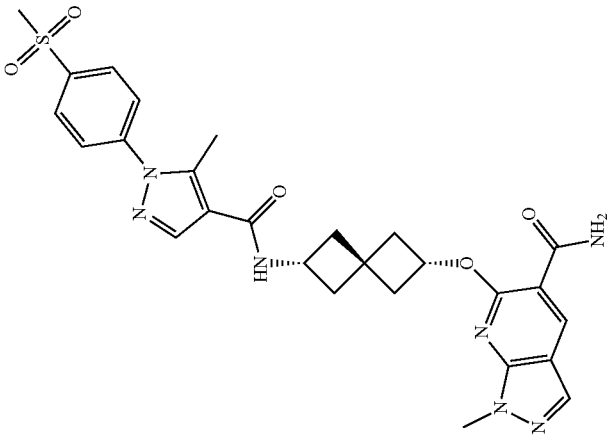 | 1-(4-methanesulfonylphenyl)-5-methyl-N-[(4s)-6-({5-carbamoyl-1-methyl-1H-pyrazolo[3,4-b]pyridin-6-yl}oxy)spiro[3.3]heptan-2-yl]-1H-pyrazole-4-carboxamide | 564.3 | A: 1.31 B: 1.32 | B: NMR (400 MHz, DMSO-d6) d 8.63 (s, 1H), 8.29 (d, J = 7.6 Hz, 1H), 8.21 (s, 1H), 8.17-8.00 (m, 3H), 7.85 (d, J = 8.6 Hz, 2H), 7.67 (br. s., 1H), 7.61 (br. s., 1H), 5.30 (t, J = 6.8 Hz, 1H), 4.44-4.32 (m, 1H), 3.99 (s, 3H), 3.32 (br. s., 3H), 2.80 (d, J = 4.4 Hz, 1H), 2.60 (s, 3H), 2.37-2.31 (m, 2H), 2.19 (d, J = 10.5 Hz, 1H) |

| Example | Structure | Name | LCMS (M + H)+ | HPLC Method RT (min) | 1H NMR |
|---|---|---|---|---|---|
| 151 | 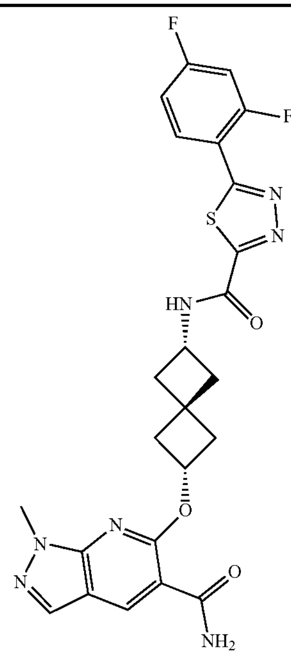 | 5-(2,4-difluorophenyl)-N-[(4s)-6-({5-carbamoyl-1-methyl-1H-pyrazolo[3,4-b]pyridin-6-yl}oxy)spiro[3.3]heptan-2-yl]-1,3,4-thiadiazole-2-carboxamide | 526.2 | A: 1.81 B: 1.79 | NMR (400 MHz, DMSO-d6) δ 9.62 (d, J = 7.8 Hz, 1H), 8.62 (s, 1H), 8.40 (d, J = 6.4 Hz, 1H), 8.10 (s, 1H), 7.71-7.62 (m, 2H), 7.59 (br. s., 1H), 7.41-7.35 (m, 1H), 5.29 (t, J = 7.0 Hz, 1H), 4.45-4.38 (m, 1H), 3.99 (s, 3H), 2.81 (s, 1H), 2.60 (d, J = 4.6 Hz, 1H), 2.41-2.32 (m, 6H), 1.25 (s, 1H) |

| Example | Structure | Name | LCMS (M + H)+ | HPLC Method RT (min) | ¹H NMR |
|---|---|---|---|---|---|
| 152 | 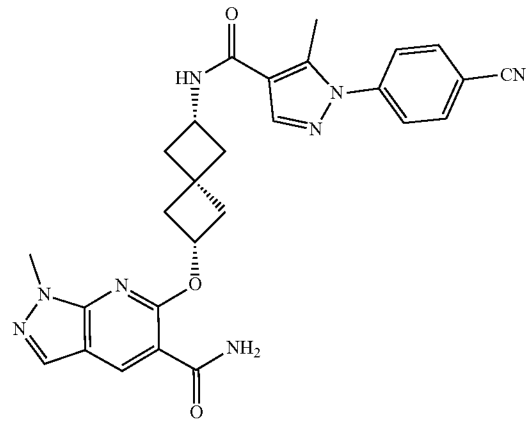 | 1-(4-cyanophenyl)-5-methyl-N-[(4s)-6-({5-carbamoyl-1-methyl-1H-pyrazolo[3,4-b]pyridin-6-yl}oxy)spiro[3.3]heptan-2-yl]-1H-pyrazole-4-carboxamide | 511.3 | A: 1.45 B: 1.47 | B: NMR (400 MHz, DMSO-d6) d 8.62 (s, 1H), 8.27 (d, J = 7.6 Hz, 1H), 8.19 (s, 1H), 8.09 (s, 1H), 8.07-7.95 (m, 2H), 7.84-7.73 (m, 2H), 7.60 (s, 1H), 7.63 (s, 1H), 5.29 (t, J = 7.2 Hz, 1H), 4.41-4.31 (m, 1H), 4.05-3.92 (m, 3H), 3.90 (s, 2H), 2.82-2.75 (m, 1H), 2.65-2.54 (m, 4H), 2.39-2.24 (m, 3H), 2.24-2.12 (m, 2H) |
| 153 | 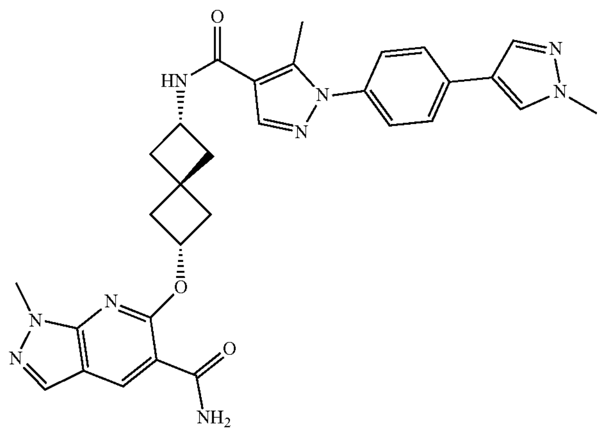 | 5-methyl-1-[4-(1-methyl-1H-pyrazol-4-yl)phenyl]-N-[(4s)-6-({5-carbamoyl-1-methyl-1H-pyrazolo[3,4-b]pyridin-6-yl}oxy)spiro[3.3]heptan-2-yl]-1H-pyrazole-4-carboxamide | 566.3 | A: 1.42 B: 1.43 | B: NMR (400 MHz, DMSO-d6) d 8.62 (s, 1H), 8.22 (s, 1H), 8.19 (d, J = 7.6 Hz, 1H), 8.11 (d, J = 8.3 Hz, 2H), 7.94 (s, 1H), 7.76-7.68 (m, J = 8.6 Hz, 2H), 7.59 (s, 1H), 7.63 (s, 1H), 7.51-7.39 (m, J = 8.6 Hz, 2H), 5.30 (t, J = 7.3 Hz, 1H), 4.41-4.34 (m, 1H), 3.98 (s, 3H), 3.93-3.83 (m, 3H), 2.79 (dd, J = 12.2, 5.9 Hz, 1H), 2.61 (dd, J = 12.2, 6.4 Hz, 1H), 2.39-2.25 (m, 3H), 2.24-2.16 (m, 2H), 1.24 (s, 1H) |

| Example | Structure | Name | LCMS (M + H)+ | HPLC Method RT (min) | 1H NMR |
|---|---|---|---|---|---|
| 154 | 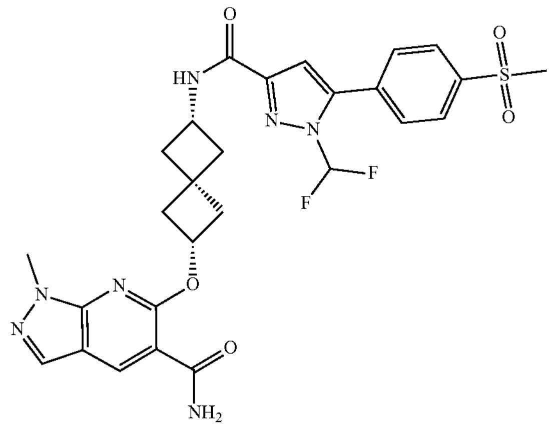 | 1-(difluoromethyl)-5-(4-methanesulfonyl)phenyl)-N-[(4s)-6-({5-carbamoyl-1-methyl-1H-pyrazolo[3,4-b]pyridin-6-yl}oxy)spiro[3.3]heptan-2-yl]-1H-pyrazole-3-carboxamide | 600.2 | A: 1.48 B: 1.49 | NMR (400 MHz, DMSO-d6) δ ppm = 8.73 (d, J = 7.8 Hz, 1H), 8.62 (s, 1H), 8.16-8.04 (m, 3H), 7.83 (d, J = 8.6 Hz, 2H), 7.70 (s, 1H), 7.63 (s, 1H), 7.59 (s, 1H), 7.12 (s, 1H), 5.29 (quin, J = 7.2 Hz, 1H), 4.45-4.35 (m, 1H), 3.98 (s, 3H), 3.91 (s, 3H), 2.85-2.75 (m, 1H), 2.64-2.56 (m, 1H), 2.46 (br. s., 1H), 2.38-2.20 (m, 5H). |
| 155 | 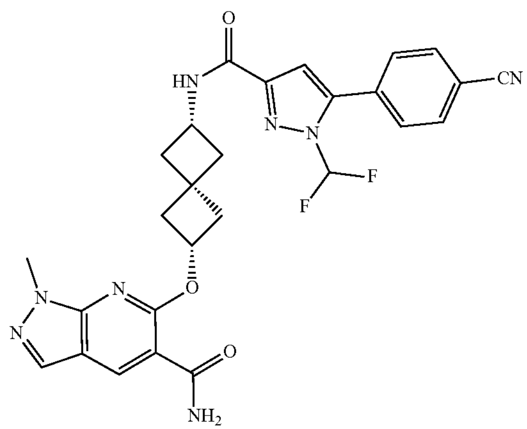 | 5-(4-cyanophenyl)-1-(difluoromethyl)-N-[(4s)-6-({5-carbamoyl-1-methyl-1H-pyrazolo[3,4-b]pyridin-6-yl}oxy)spiro[3.3]heptan-2-yl]-1H-pyrazole-3-carboxamide | 547.3 | A: 1.65 B: 1.66 | NMR (400 MHz, DMSO-d6) δ ppm = 8.72 (d, J = 8.1 Hz, 1H), 8.62 (s, 1H), 8.09 (s, 1H), 8.07-7.99 (m, 2H), 7.83 (s, 1H), 7.80-7.71 (m, 2H), 7.59 (s, 1H), 7.63 (s, 1H), 7.12 (s, 1H), 5.29 (t, J = 7.2 Hz, 1H), 4.46-4.32 (m, 1H), 3.98 (s, 3H), 2.86-2.76 (m, 1H), 2.63-2.57 (m, 1H), 2.49-2.44 (m, 1H), 2.39-2.18 (m, 5H). |

| Example | Structure | Name | LCMS (M + H)+ | HPLC Method RT (min) | ¹H NMR |
|---|---|---|---|---|---|
| 156 | 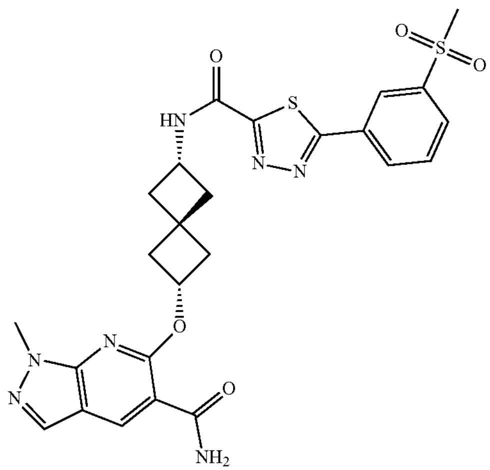 | 5-(3-methanesulfonylphenyl)-N-[(4s)-6-({5-carbamoyl-1-methyl-1H-pyrazolo[3,4-b]pyridin-6-yl}oxy)spiro[3.3]heptan-2-yl]-1,3,4-thiadiazole-2-carboxamide | 568.2 | A: 1.44 B: 1.46 | B: NMR (400 MHz, DMSO-d6) d 9.64 (d, J = 7.6 Hz, 1H), 8.62 (s, 1H), 8.55 (t, J = 1.6 Hz, 1H), 8.39 (dt, J = 8.1, 1.3 Hz, 1H), 8.21-8.13 (m, 1H), 8.09 (s, 1H), 7.88 (t, J = 7.9 Hz, 1H), 7.59 (s, 1H), 7.63 (s, 1H), 5.35-5.22 (m, 1H), 4.47-4.36 (m, 1H), 3.98 (s, 3H), 3.91 (s, 1H), 3.35 (s, 3H), 2.86-2.74 (m, 1H), 2.66-2.56 (m, 1H), 2.45-2.24 (m, 5H) |
| 157 | 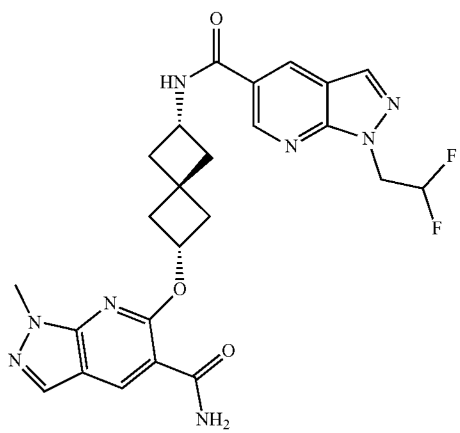 | 1-methyl-6-[[(4s)-6-[1-(2,2-difluoroethyl)-1H-pyrazolo[3,4-b]pyridine-5-amido]spiro[3.3]heptan-2-yl]oxy]-1H-pyrazolo[3,4-b]pyridine-5-carboxamide | 511.2 | A: 1.34 B: 1.35 | B: NMR (400 MHz, DMSO-d6) d 9.03 (d, J = 2.0 Hz, 1H), 8.89-8.80 (m, 1H), 8.76 (d, J = 2.2 Hz, 1H), 8.67-8.59 (m, 1H), 8.41 (s, 1H), 8.15-8.06 (m, 1H), 7.60 (s, 1H), 7.64 (s, 1H), 6.57-6.43 (m, 1H), 5.30 (t, J = 7.2 Hz, 1H), 4.96 (td, J = 15.2, 3.7 Hz, 2H), 4.48-4.39 (m, 1H), 4.03-3.93 (m, 3H), 2.85-2.77 (m, 1H), 2.65-2.53 (m, 3H), 2.43-2.19 (m, 5H) |

| Example | Structure | Name | LCMS (M + H)+ | HPLC Method RT (min) | 1H NMR |
|---|---|---|---|---|---|
| 158 | 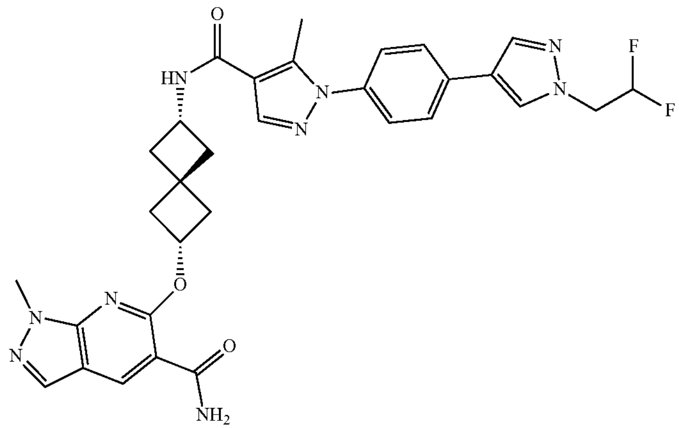 | 1-{4-[1-(2,2-difluoroethyl)-1H-pyrazol-4-yl]phenyl}-5-methyl-N-[(4s)-6-({5-carbamoyl-1-methyl-1H-pyrazolo[3,4-b]pyridin-6-yl}oxy)spiro[3.3]heptan-2-yl]-1H-pyrazole-4-carboxamide | 616.6 | A: 1.55 B: 1.54 | B: NMR (400 MHz, DMSO-d6) d 8.63 (s, 1H), 8.32 (s, 1H), 8.20 (d, J = 7.6 Hz, 1H), 8.13 (s, 1H), 8.10 (s, 1H), 8.07 (s, 1H), 7.80-7.68 (m, 2H), 7.59 (s, 1H), 7.64 (s, 1H), 7.54-7.45 (m, J = 8.6 Hz, 2H), 6.41 (t, J = 3.7 Hz, 1H), 5.30 (t, J = 7.2 Hz, 1H), 4.67 (td, J = 15.2, 3.7 Hz, 2H), 4.41-4.32 (m, 1H), 3.98 (s, 3H), 2.84-2.75 (m, 1H), 2.65-2.56 (m, 1H), 2.40-2.26 (m, 3H), 2.24-2.13 (m, 2H) |
| 159 | 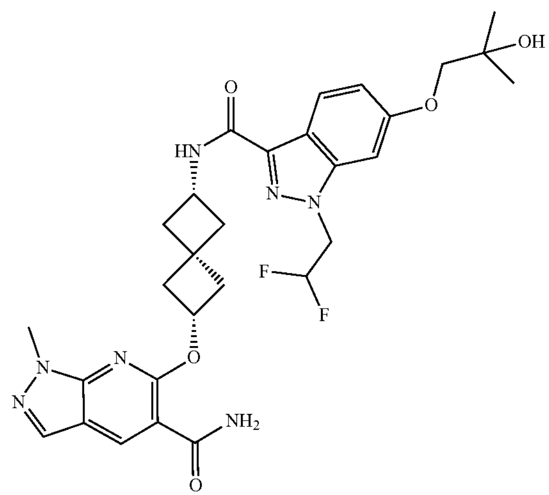 | 1-(2,2-difluoroethyl)-6-(2-hydroxy-2-methylpropoxy)-N-[(4s)-6-({5-carbamoyl-1-methyl-1H-pyrazolo[3,4-b]pyridin-6-yl}oxy)spiro[3.3]heptan-2-yl]-1H-indazole-3-carboxamide | 598.2 | A: 1.51 B: 1.50 | B: NMR (400 MHz, DMSO-d6) d 8.62 (s, 1H), 8.51-8.36 (m, 1H), 8.09 (s, 1H), 8.02-7.94 (m, 1H), 7.59 (s, 1H), 7.63 (s, 1H), 7.31 (s, 1H), 7.23-7.12 (m, 1H), 6.94 (dd, J = 8.8, 2.0 Hz, 1H), 6.49 (t, J = 3.5 Hz, 1H), 5.29 (quin, J = 7.1 Hz, 1H), 5.04-4.87 (m, 2H), 4.71 (s, 1H), 4.49-4.39 (m, 1H), 3.98 (s, 3H), 3.82 (s, 2H), 2.80 (dt, J = 11.6, 5.8 Hz, 1H), 2.64-2.56 (m, 1H), 2.46 (br. s., 1H), 2.39-2.19 (m, 5H), 1.34-1.21 (m, 6H) |

| Example | Structure | Name | LCMS (M + H)+ | HPLC Method RT (min) | 1H NMR |
|---|---|---|---|---|---|
| 160 | 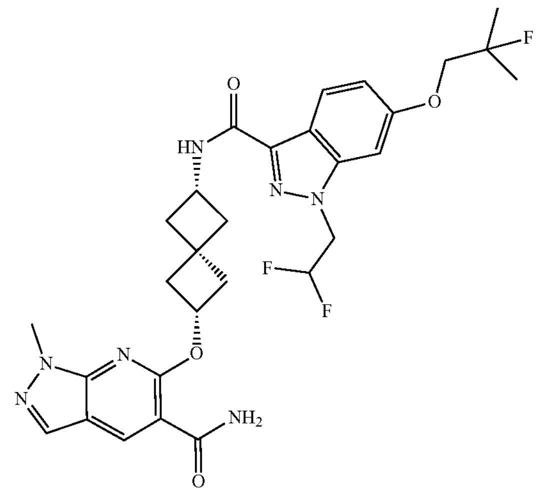 | 1-(2,2-difluoroethyl)-6-(2-fluoro-2-methylpropoxy)-N-[(4s)-6-({5-carbamoyl-1-methyl-1H-pyrazolo[3,4-b]pyridin-6-yl}oxy)spiro[3.3]heptan-2-yl]-1H-indazole-3-carboxamide | 600.3 | A: 1.80 B: 1.82 | B: NMR (400 MHz, DMSO-d6) d 8.62 (s, 1H), 8.48 (d, J = 7.8 Hz, 1H), 8.09 (s, 1H), 8.02 (d, J = 8.8 Hz, 1H), 7.59 (s, 1H), 7.63 (s, 1H), 7.38 (d, J = 1.7 Hz, 1H), 6.98 (dd, J = 8.9, 2.1 Hz, 1H), 6.50 (t, J = 3.8 Hz, 1H), 5.29 (t, J = 7.2 Hz, 1H), 4.96 (td, J = 14.9, 3.9 Hz, 2H), 4.49-4.40 (m, 1H), 4.11 (d, J = 19.8 Hz, 2H), 3.98 (s, 3H), 2.83-2.76 (m, 1H), 2.64-2.56 (m, 2H), 2.41-2.25 (m, 5H), 1.51 (s, 3H), 1.46 (s, 3H) |
| 161 | 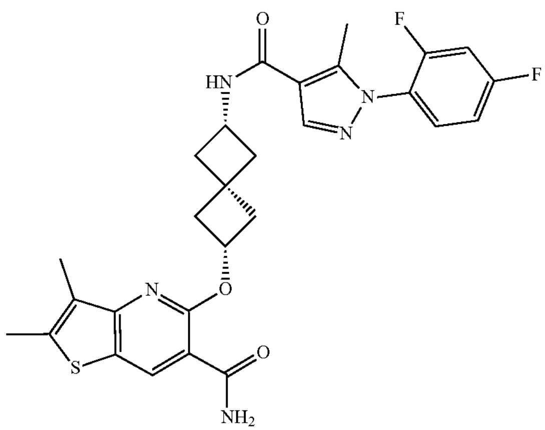 | 1-(2,4-difluorophenyl)-5-methyl-N-[(4s)-6-({6-carbamoyl-2,3-dimethylthieno[3,2-b]pyridin-5-yl}oxy)spiro[3.3]heptan-2-yl]-1H-pyrazole-4-carboxamide | 552.2 | A: 2.05 B: 2.06 | B: NMR (400 MHz, DMSO-d6) δ ppm = 8.76-8.65 (m, 1H), 8.25 (d, J = 7.6 Hz, 1H), 8.16 (s, 1H), 7.78-7.51 (m, 4H), 7.38-7.26 (m, 1H), 5.29 (quin, J = 7.2 Hz, 1H), 4.45-4.30 (m, 1H), 3.91 (s, 1H), 2.81-2.72 (m, 1H), 2.65-2.57 (m, 1H), 2.55-2.53 (m, 3H), 2.41-2.14 (m, 11H). |

| Example | Structure | Name | LCMS (M + H)+ | HPLC Method RT (min) | ¹H NMR |
|---|---|---|---|---|---|
| 162 | 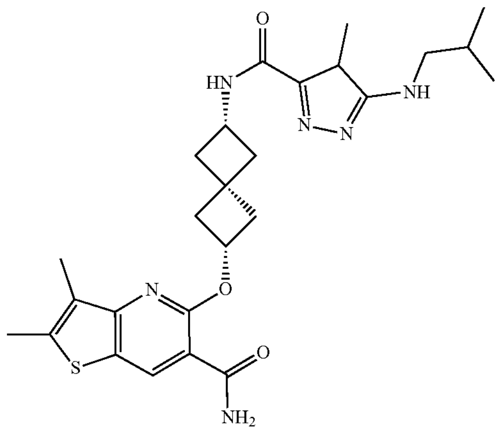 | 5-[(2-methylpropyl)amino]-N-[(4s)-6-({6-carbamoyl-2,3-dimethylthieno[3,2-b]pyridin-5-yl}oxy)spiro[3.3]heptan-2-yl]-1,3,4-thiadiazole-2-carboxamide | 515.2 | A: 2.05 B: 2.03 | B: NMR (400 MHz, DMSO-d6) δ ppm = 8.99 (d, J = 8.1 Hz, 1H), 8.69 (s, 1H), 8.29 (t, J = 5.4 Hz, 1H), 7.70 (br. s., 1H), 7.64 (br. s., 1H), 5.26 (t, J = 7.2 Hz, 1H), 4.40-4.25 (m, 1H), 3.22-3.10 (m, 2H), 2.80-2.71 (m, 1H), 2.60-2.53 (m, 4H), 2.43 (t, J = 7.5 Hz, 1H), 2.39-2.23 (m, 8H), 1.89 (dt, J = 13.3, 6.8 Hz, 1H), 0.92 (d, J = 6.6 Hz, 6H). |

What is claimed is:

1. A compound of Formula (I):

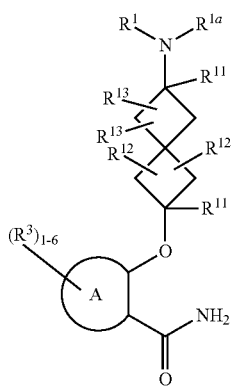

(I)

or a stereoisomer, an enantiomer, a diastereoisomer, a tautomer, a pharmaceutically-acceptable salt thereof, wherein:

Ring A is selected from a 5-membered heteroaryl comprising carbon atoms and 1-4 heteroatoms selected from N, O, and S, and a bicyclic heterocycle;

$R^1$ is selected from H and $C_{1-4}$ alkyl;

$R^{1a}$ is $C(O)R^4$; or $R^1$ and $R^{1a}$ are taken together with the nitrogen atom to which they are attached to form a ring of Formula (Ia);

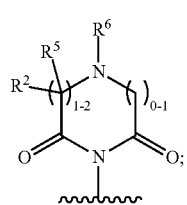

(Ia)

$R^2$ is selected from H, $C_{1-7}$ alkyl, $C_{2-7}$ alkenyl, $C_{2-7}$ alkynyl, $—(CR^{10}R^{10})_nC_{3-10}$ carbocycle and $—(CR^{10}R^{10})_n$-4- to 15-membered heterocycle comprising carbon atoms and 1-4 heteroatoms selected from N, $NR^8$, O, and $S(O)_p$, wherein said alkyl, alkenyl, alkynyl, carbocycle, and heterocycle are substituted with 1-4 $R^7$;

$R^3$, at each occurrence, is independently selected from H, halogen, $C_{1-6}$ alkyl, $C_{2-6}$ alkenyl, $C_{1-4}$ alkoxy, $C_{1-4}$ alkylthio, $C_{1-4}$ haloalkyl, $—CH_2OH$, $—OCH_2F$, $—OCHF_2$, $—OCF_3$, CN, $—NH_2$, $—NH(C_{1-4}$ alkyl), $—N(C_{1-4}$ alkyl)$_2$, $—CO_2H$, $—CH_2CO_2H$, $—CO_2(C_{1-4}$ alkyl), $—CO(C_{1-4}$ alkyl), $—CH_2NH_2$, $—CONH_2$, $—CONH(C_{1-4}$ alkyl), $—CON(C_{1-4}$ alkyl)$_2$, $—OCH_2CO_2H$, $—NHCO(C_{1-4}$ alkyl), $—NHCO_2(C_{1-4}$ alkyl), $—NHSO_2(C_{1-4}$ alkyl), $—SO_2NH_2$, $—C(=NH)NH_2$, a carbocycle, and a heterocycle, wherein said alkyl, alkenyl, alkoxy, alkylthio, haloalkyl, carbocycle, and heterocycle are substituted with 0-4 $R^9$;

$R^4$ is selected from $—(CR^{10}R^{10})_nC_{3-10}$ carbocycle and $—(CR^{10}R^{10})_n$-4- to 15-membered heterocycle comprising carbon atoms and 1-4 heteroatoms selected from N, $NR^8$, O, and $S(O)_p$; wherein said carbocycle, and heterocycle are substituted with 1-4 $R^7$;

$R^5$ is H; or $R^2$ and $R^5$ are taken together to form =O; or $R^2$ and $R^5$ are taken together with the carbon atom, to which they are both attached, to form a carbocycle or heterocycle wherein said carbocycle and heterocycle are substituted with 1-4 $R^7$;

$R^6$ is selected from H, $C_{1-4}$ alkyl, $—(CR^{10}R^{10})_nC_{3-10}$ carbocycle and $—(CR^{10}R^{10})_n$-4- to 15-membered heterocycle comprising carbon atoms and 1-4 heteroatoms selected from N, $NR^8$, O, and $S(O)_p$, wherein said alkyl, alkenyl, carbocycle, and heterocycle are substituted with 1-4 $R^7$; provided that $R^2$, $R^5$, and $R^6$ are not all H;

$R^7$, at each occurrence, is independently selected from H, =O, $NO_2$, halogen, $C_{1-7}$ alkyl, $C_{2-4}$ alkenyl, $C_{2-4}$ alkynyl, $C_{1-4}$ alkoxy, CN, OH, $CHF_2$, $CF_3$, $—(CH_2)_n—CO_2H$, $—(CH_2)_n—CO_2(C_{1-4}$ alkyl), $—(CH_2)_n—NR^8R^8$, $—NHCOH$, $—NHCO(C_{1-4}$ alkyl), $—NHCOCF_3$, $—NHCO_2(C_{1-4}$ alkyl), $—NHCO_2(CH_2)_2O(C_{1-4}$ alkyl), $—NHCO_2(CH_2)_3O(C_{1-4}$ alkyl), $—NHCO_2(CH_2)_2OH$, $—NHCO_2(CH_2)_2NH_2$, $—NHCO_2(CH_2)_2N(C_{1-4}$ alkyl)$_2$, $—NHCO_2CH_2CO_2H$, $—CH_2NHCO_2(C_{1-4}$ alkyl), $—NHC(O)NR^8R^8$, $—NHSO_2(C_{1-4}$ alkyl), $—S(O)_p(C_{1-4}$ alkyl), $—SO_2NH_2$, $—SO_2NH(C_{1-4}$ alkyl), $—SO_2N(C_{1-4}$ alkyl)$_2$, $—SO_2NH(CH_2)_2OH$, $—SO_2NH(CH_2)_2O(C_{1-4}$ alkyl), $—(CH_2)_n—CONR^8R^8$, $—O(CH_2)_n$-carbocycle, —O(CH$_2$)$_n$-heterocycle, —NHCO-carbocycle, —NHCO-heterocycle, —(CH$_2$)$_n$-carbocycle, and —(CH$_2$)$_n$-heterocycle comprising carbon atoms and 1-4 heteroatoms selected from N, NR$^8$, O, and S(O)$_p$, wherein said alkyl, alkenyl, alkynyl, alkoxy, carbocycle, and heterocycle are substituted with 0-4 R$^9$;

R$^8$, at each occurrence, is independently selected from H, C$_{1-6}$ alkyl, C$_{2-4}$ alkenyl, C$_{2-4}$ alkynyl, —(CH$_2$)$_n$—C(O)C$_{1-4}$alkyl, —(CH$_2$)$_n$—C(O)carbocycle, —(CH$_2$)$_n$—C(O)heterocycle, —(CH$_2$)$_n$—C(O)NR$^a$R$^a$, —(CH$_2$)$_n$—NR$^a$C(O) C$_{1-4}$alkyl, —(CH$_2$)$_n$—C(O)OC$_{1-4}$alkyl, —(CH$_2$)$_n$—C(O)C$_{1-4}$alkyl, —(CH$_2$)$_n$—C(O)O-carbocycle, —(CH$_2$)$_n$—C(O)O-heterocycle, —(CH$_2$)$_n$—SO$_2$alkyl, —(CH$_2$)$_n$ SO$_2$carbocycle, —(CH$_2$)$_n$—SO$_2$heterocycle, —(CH$_2$)$_n$—SO$_2$NR$^a$R$^a$, —(CH$_2$)$_n$-carbocycle, and —(CH$_2$)$_n$-heterocycle, wherein said alkyl, carbocycle, and heterocycle are substituted with 0-4 R$^9$;

alternatively, R$^8$ and R$^8$ are taken together with the nitrogen atom to which they are attached to form a 4- to 10-membered heterocycle substituted with 0-4 R$^9$;

R$^9$, at each occurrence, is independently selected from halogen, OH, =O, CN, NO$_2$, C$_{1-4}$ alkyl, C$_{1-4}$ alkoxy, CO(C$_{1-4}$ alkyl), CO$_2$H, CO$_2$(C$_{1-4}$ alkyl), —(CHR$^{10}$)$_n$NR$^a$R$^a$, S(O)$_p$(C$_{1-4}$ alkyl), —(CHR$^{10}$)$_n$CONR$^a$R$^a$, —(CHR$^{10}$)$_n$NR$^a$CO(C$_{1-4}$ alkyl), —(CHR$^{10}$)$_n$OCONR$^a$ (CH$_2$)$_n$CO$_2$R$^a$, S(O)$_p$C$_{1-4}$alkyl, S(O)$_p$NR$^a$R$^a$, —O(CHR$^{10}$)$_n$carbocycle, —O(CHR$^{10}$)$_n$heterocycle, —O(CHR$^{10}$)$_n$NR$^a$R$^a$, and —(CR$^{10}$R$^{10}$)$_n$-4- to 10-membered heterocycle, wherein said alkyl, alkoxy, carbocycle, and heterocycle are substituted with 0-4 R$^b$;

R$^{10}$, at each occurrence, is independently selected from H and C$_{1-4}$ alkyl;

R$^{11}$ is independently selected from H and C$_{1-3}$ alkyl optionally substituted with halogen, C$_{1-4}$ alkoxy, OH, CN, —CO$_2$H, —CO$_2$(C$_{1-4}$ alkyl), —CO(C$_{1-4}$ alkyl), —CONH$_2$, —CONH(C$_{1-4}$ alkyl), and —CON(C$_{1-4}$ alkyl)$_2$;

R$^{12}$ and R$^{13}$ are independently selected from H, OH, —OC$_{1-3}$ alkyl substituted with 0-4 R$^d$, C$_{1-3}$ alkyl with substituted with 0-4 R$^d$;

R$^a$, at each occurrence, is independently selected from H, C$_{1-4}$ alkyl, —(CH$_2$)$_n$OH, CO(C$_{1-4}$ alkyl), COCF$_3$, CO$_2$ (C$_{1-4}$ alkyl), —CONH$_2$, —CONH—C$_{1-4}$ alkylene-CO$_2$ (C$_{1-4}$ alkyl), C$_{1-4}$ alkylene-CO$_2$(C$_{1-4}$ alkyl), R$^c$, CO$_2$R$^c$, and CONHR$^c$; alternatively, R$^a$ and R$^a$ are taken together with the nitrogen atom to which they are attached to form a 4- to 10-membered heterocycle, wherein said alkyl, alkylene, and heterocycle are substituted with 0-4 R$^b$;

R$^b$, at each occurrence, is independently selected from =O, OH, halogen, C$_{1-4}$ alkyl, C$_{1-4}$ alkoxy, OCF$_3$, OC(O)C$_{1-4}$ alkyl, NH$_2$, NO$_2$, N(C$_{1-4}$ alkyl)$_2$, CO(C$_{1-4}$ alkyl), CO(C$_{1-4}$ haloalkyl), CO$_2$H, CO$_2$(C$_{1-4}$ alkyl), CONH$_2$, —CONH(C$_{1-4}$ alkyl), —CON(C$_{1-4}$ alkyl)$_2$, —CONH—C$_{1-4}$ alkylene-O(C$_{1-4}$ alkyl), —CONH—C$_{1-4}$ alkylene-NH(C$_{1-4}$ alkyl), —CONH—C$_{1-4}$ alkylene-N(C$_{1-4}$ alkyl)$_2$, —C$_{1-4}$ alkylene-O—P(O)(OH)$_2$, —NHCO$_2$(C$_{1-4}$ alkyl), —R$^c$, COR$^c$, CO$_2$R$^c$, and CONHR$^c$, wherein said alkyl and alkoxy are substituted with 0-2 R$^d$;

R$^c$, at each occurrence, is independently selected from —(CH$_2$)$_n$—C$_{3-6}$ cycloalkyl, —(CH$_2$)$_n$-phenyl, and —(CH$_2$)-5- to 6-membered heterocycle containing carbon atoms and 1-4 heteroatoms selected from the group consisting of: N, NH, N(C$_{1-4}$ alkyl), O, and S(O)$_p$; wherein each ring moiety is substituted with 0-2 R$^d$;

R$^d$, at each occurrence, is independently selected from =O, halogen, OH, C$_{1-4}$ alkyl, NH$_2$, NH(C$_{1-4}$ alkyl), N(C$_{1-4}$ alkyl)$_2$, C$_{1-4}$ alkoxy, and —NHCO(C$_{1-4}$ alkyl);

n, at each occurrence, is independently selected from 0, 1, 2, 3, and 4; and p, at each occurrence, is independently selected from 0, 1, and 2.

2. The compound of claim 1, having Formula (II):

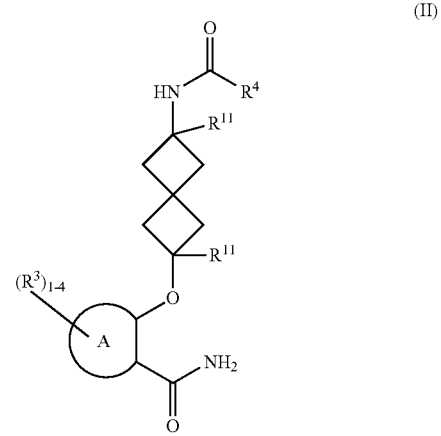

(II)

or a stereoisomer, an enantiomer, a diastereoisomer, a tautomer, a pharmaceutically-acceptable salt thereof, wherein

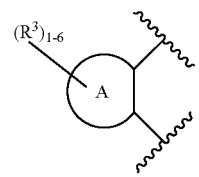

is selected from

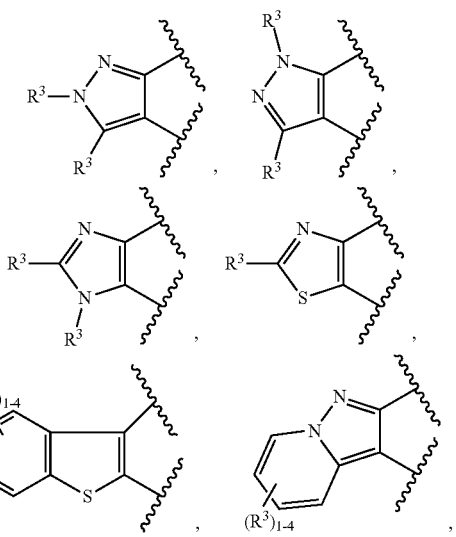

-continued

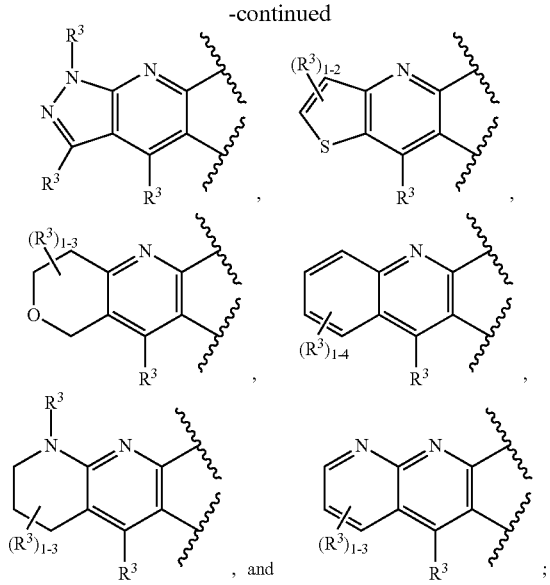

R³, at each occurrence, is independently selected from H, halogen, $C_{1-6}$ alkyl, $C_{2-6}$ alkenyl, $C_{1-4}$ alkoxy, $C_{1-4}$ alkylthio, $C_{1-4}$ haloalkyl, —$CH_2OH$, —$OCH_2F$, —$OCHF_2$, —$OCF_3$, CN, —$NH_2$, —NH($C_{1-4}$ alkyl), —N($C_{1-4}$ alkyl)$_2$, —$CO_2H$, —$CH_2CO_2H$, —$CO_2(C_{1-4}$ alkyl), —CO($C_{1-4}$ alkyl), —$CH_2NH_2$, —$CONH_2$, —CONH($C_{1-4}$ alkyl), —CON($C_{1-4}$ alkyl)$_2$, —$OCH_2CO_2H$, —NHCO($C_{1-4}$ alkyl), —$NHCO_2(C_{1-4}$ alkyl), —$NHSO_2(C_{1-4}$ alkyl), —$SO_2NH_2$, —C(=NH)$NH_2$, a carbocycle, and a heterocycle, wherein said alkyl, alkenyl, alkoxy, alkylthio, haloalkyl, carbocycle, and heterocycle are substituted with 0-4 $R^9$;

$R^4$ is selected from $C_{3-10}$ carbocycle and 4- to 15-membered heterocycle comprising carbon atoms and 1-4 heteroatoms selected from N, $NR^8$, O, and $S(O)_p$; wherein said carbocycle, and heterocycle are substituted with 1-4 $R^7$;

$R^7$, at each occurrence, is independently selected from H, =O, $NO_2$, halogen, $C_{1-7}$ alkyl, $C_{2-4}$ alkenyl, $C_{2-4}$ alkynyl, $C_{1-4}$ alkoxy, CN, OH, $CHF_2$, $CF_3$, —$(CH_2)_n$—$CO_2H$, —$(CH_2)_n$—$CO_2(C_{1-4}$ alkyl), —$(CH_2)_n$—$NR^8R^8$, —NHCOH, —NHCO($C_{1-4}$ alkyl), —$NHCOCF_3$, —$NHCO_2(C_{1-4}$ alkyl), —$NHCO_2(CH_2)_2O(C_{1-4}$ alkyl), —$NHCO_2(CH_2)_3O(C_{1-4}$ alkyl), —$NHCO_2(CH_2)_2OH$, —$NHCO_2(CH_2)_2NH_2$, —$NHCO_2(CH_2)_2N(C_{1-4}$ alkyl)$_2$, —$NHCO_2CH_2CO_2H$, —$CH_2NHCO_2(C_{1-4}$ alkyl), —NHC(O)$NR^8R^8$, —$NHSO_2(C_{1-4}$ alkyl), —$S(O)_p(C_{1-4}$ alkyl), —$SO_2NH_2$, —$SO_2NH(C_{1-4}$ alkyl), —$SO_2N(C_{1-4}$ alkyl)$_2$, —$SO_2NH(CH_2)_2OH$, —$SO_2NH(CH_2)_2O(C_{1-4}$ alkyl), —$(CH_2)_n$—$CONR^8R^8$, —$O(CH_2)_n$-carbocycle, —$O(CH_2)_n$-heterocycle, —NHCO-carbocycle, —NHCO-heterocycle, —$(CH_2)_n$-carbocycle, and —$(CH_2)_n$-heterocycle comprising carbon atoms and 1-4 heteroatoms selected from N, $NR^8$, O, and $S(O)_p$, wherein said alkyl, alkenyl, alkynyl, alkoxy, carbocycle, and heterocycle are substituted with 0-4 $R^9$;

$R^8$, at each occurrence, is independently selected from H, $C_{1-6}$ alkyl, $C_{2-4}$ alkenyl, $C_{2-4}$ alkynyl, —$(CH_2)_n$—C(O)$C_{1-4}$alkyl, —$(CH_2)_n$—C(O)carbocycle, —$(CH_2)_n$—C(O)heterocycle, —$(CH_2)_n$—C(O)$NR^aR^a$, —$(CH_2)_n$—$NR^aC(O)$ $C_{1-4}$alkyl, —$(CH_2)_n$—C(O)O$C_{1-4}$alkyl, —$(CH_2)_n$—C(O)$C_{1-4}$alkyl, —$(CH_2)_n$—C(O)O-carbocycle, —$(CH_2)_n$—C(O)O-heterocycle, —$(CH_2)_n$—$SO_2$alkyl, —$(CH_2)_n$ $SO_2$carbocycle, —$(CH_2)_n$—$SO_2$heterocycle, —$(CH_2)_n$—$SO_2NR^aR^a$, —$(CH_2)_n$-carbocycle, and —$(CH_2)_n$-heterocycle, wherein said alkyl, alkenyl, alkynyl, carbocycle, and heterocycle are substituted with 0-4 $R^9$;

alternatively, $R^8$ and $R^8$ are taken together with the nitrogen atom to which they are attached to form a 4- to 10-membered heterocycle substituted with 0-4 $R^9$;

$R^9$, at each occurrence, is independently selected from halogen, OH, =O, CN, $NO_2$, $C_{1-4}$ alkyl, $C_{1-4}$ alkoxy, CO($C_{1-4}$ alkyl), $CO_2H$, $CO_2(C_{1-4}$ alkyl), —$(CHR^{10})_nNR^aR^a$, $S(O)_p(C_{1-4}$ alkyl), —$(CHR^{10})_nCONR^aR^a$, —$(CHR^{10})_nNR^aCO(C_{1-4}$ alkyl), —$(CHR^{10})_nOCONR^a$ $(CH_2)_nCO_2R^a$, $S(O)_p$ $C_{1-4}$alkyl, $S(O)_pNR^aR^a$, —$O(CHR^{10})_n$carbocycle, —$O(CHR^{10})_n$heterocycle, —$O(CHR^{10})NR^aR^a$, and —$(CR^{10}R^{10})_n$-4- to 10-membered heterocycle, wherein said alkyl, alkoxy, carbocycle, and heterocycle are substituted with 0-4 $R^b$;

$R^{10}$, at each occurrence, is independently selected from H and $C_{1-4}$ alkyl;

$R^{11}$ is independently selected from H and $C_{1-3}$ alkyl optionally substituted with halogen, $C_{1-4}$ alkoxy, OH, and CN;

$R^a$, at each occurrence, is independently selected from H, $C_{1-4}$ alkyl, —$(CH_2)_nOH$, CO($C_{1-4}$ alkyl), $COCF_3$, $CO_2$($C_{1-4}$ alkyl), —$CONH_2$, —CONH—$C_{1-4}$ alkylene-$CO_2$ ($C_{1-4}$ alkyl), $C_{1-4}$ alkylene-$CO_2(C_{1-4}$ alkyl), $R^c$, $CO_2R^c$, and $CONHR^c$; alternatively, $R^a$ and $R^a$ are taken together with the nitrogen atom to which they are attached to form a 4- to 10-membered heterocycle, wherein said alkyl, alkylene, and heterocycle are substituted with 0-4 $R^b$;

$R^b$, at each occurrence, is independently selected from =O, OH, halogen, $C_{1-4}$ alkyl, $C_{1-4}$ alkoxy, $OCF_3$, $OC(O)C_{1-4}$ alkyl, $NH_2$, $NO_2$, $N(C_{1-4}$ alkyl)$_2$, $CO(C_{1-4}$alkyl), $CO(C_{1-4}$haloalkyl), $CO_2H$, $CO_2(C_{1-4}$alkyl), $CONH_2$, —CONH($C_{1-4}$ alkyl), —CON($C_{1-4}$ alkyl)$_2$, —CONH—$C_{1-4}$ alkylene-O($C_{1-4}$ alkyl), —CONH—$C_{1-4}$ alkylene-N($C_{1-4}$ alkyl)$_2$, —$NHCO_2(C_{1-4}$ alkyl), —$R^c$, $COR^c$, $CO_2R^c$, and $CONHR^c$, wherein said alkyl and alkoxy are substituted with 0-2 $R^d$;

$R^c$, at each occurrence, is independently selected from —$(CH_2)_n$—$C_{3-6}$ cycloalkyl, —$(CH_2)_n$-phenyl, and —$(CH_2)_n$-5- to 6-membered heterocycle containing carbon atoms and 1-4 heteroatoms selected from the group consisting of: N, NH, N($C_{1-4}$ alkyl), O, and $S(O)_p$; wherein each ring moiety is substituted with 0-2 $R^d$;

$R^d$, at each occurrence, is independently selected from =O, halogen, OH, $C_{1-4}$ alkyl, $NH_2$, NH($C_{1-4}$ alkyl), N($C_{1-4}$ alkyl)$_2$, $C_{1-4}$ alkoxy, and —NHCO($C_{1-4}$ alkyl);

n, at each occurrence, is independently selected from 0, 1, 2, 3, and 4; and p, at each occurrence, is independently selected from 0, 1, and 2.

3. The compound of claim 2, or a stereoisomer, an enantiomer, a diastereoisomer, a tautomer, a pharmaceutically-acceptable salt thereof, wherein:

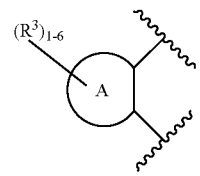

is selected from
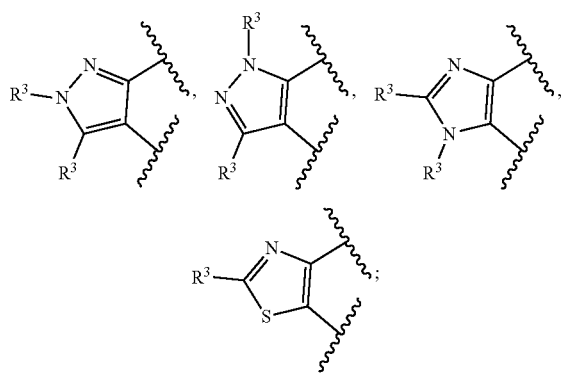
$R^3$, at each occurrence, is independently selected from H, $C_{1-4}$ alkyl, a carbocycle, and a heterocycle, wherein said alkyl, carbocycle, and heterocycle are substituted with 0-4 $R^9$;
$R^4$ is selected from
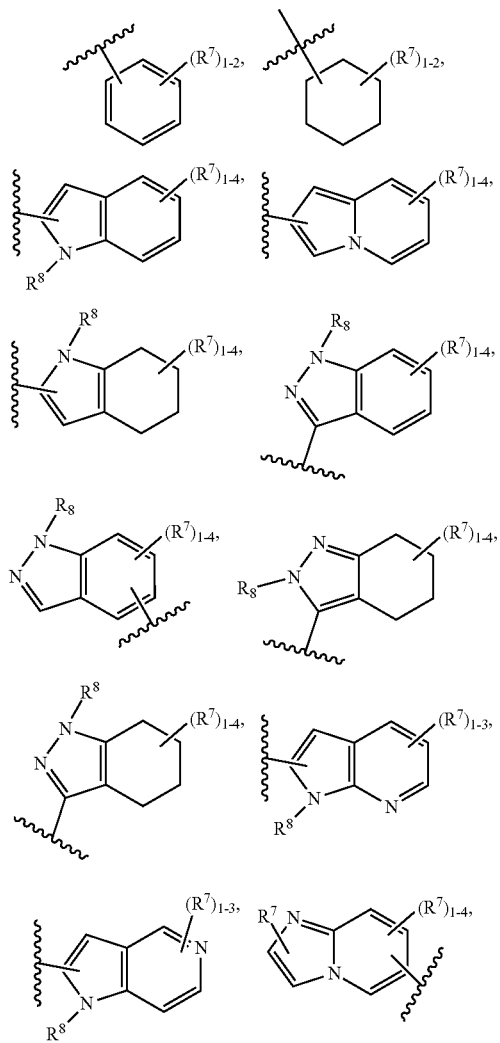
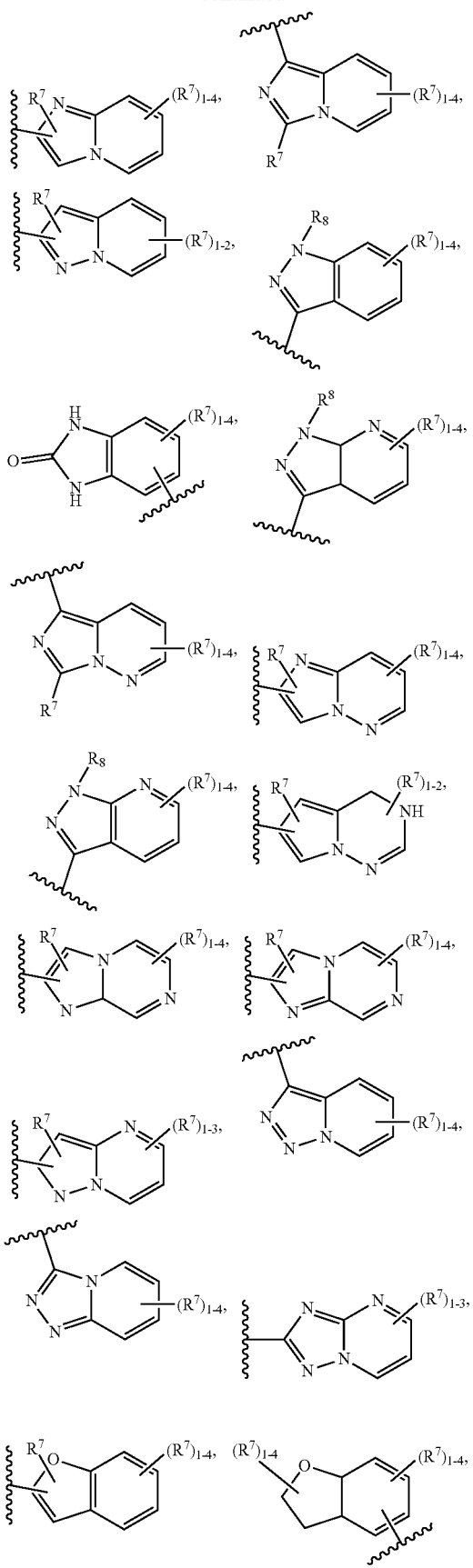

-continued

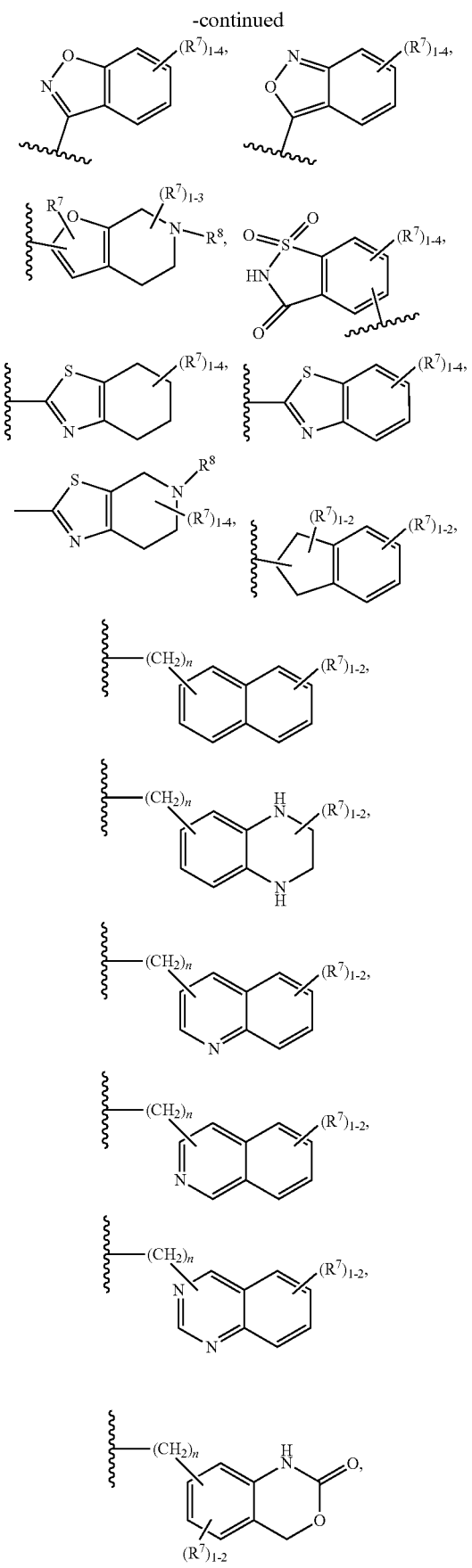

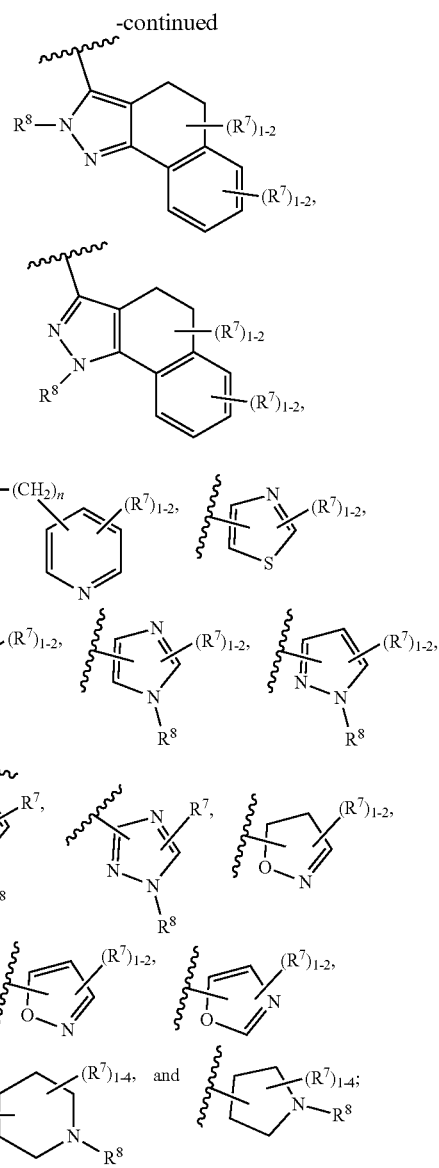

R[7], at each occurrence, is independently selected from H, =O, NO$_2$, halogen, C$_{1-4}$ alkyl, C$_{1-4}$ alkoxy, CN, OH, CF$_3$, —(CH$_2$)$_n$—CO$_2$H, —(CH$_2$)$_n$—CO$_2$(C$_{1-4}$ alkyl), —(CH$_2$)$_n$—NR[8]R[8], —NHCO(C$_{1-4}$ alkyl), —NHCOCF$_3$, —NHCO$_2$(C$_{1-4}$ alkyl), —NHCO$_2$(CH$_2$)$_2$O(C$_{1-4}$ alkyl), —NHCO$_2$(CH$_2$)$_3$O(C$_{1-4}$alkyl), —NHCO$_2$(CH$_2$)$_2$OH, —NHCO$_2$(CH$_2$)$_2$NH$_2$, —NHCO$_2$(CH$_2$)$_2$N(C$_{1-4}$ alkyl)$_2$, —NHCO$_2$CH$_2$CO$_2$H, —CH$_2$NHCO$_2$(C$_{1-4}$ alkyl), —NHC(O)NR[8]R[8], —NHSO$_2$(C$_{1-4}$ alkyl), —S(O)$_2$(C$_{1-4}$alkyl), —SO$_2$NH$_2$, —SO$_2$NH(C$_{1-4}$ alkyl), —SO$_2$N(C$_{1-4}$alkyl)$_2$, —SO$_2$NH (CH$_2$)$_2$OH, —SO$_2$NH(CH$_2$O(C$_1$ alkyl), —(CH$_2$)$_n$—CONR[8]R[8], —O(CH$_2$)$_n$-carbocycle, —O(CH$_2$)$_n$-heterocycle, —NHCO-carbocycle, —NHCO-heterocycle, —SO$_2$N(C$_{1-4}$alkyl)$_2$-carbocycle, —SO$_2$N(C$_{1-4}$alkyl)-heterocycle comprising carbon atoms and 1-4 heteroatoms selected from N, NR[8], O, and S(O)$_p$, (CH$_2$)$_n$-carbocycle, and —(CH$_2$)-heterocycle comprising carbon atoms and 1-4 heteroatoms selected from N, NR[8], O, and S(O)$_p$, wherein said alkyl, alkoxy, carbocycle, and heterocycle are substituted with 0-4 R[9];

283

R⁸, at each occurrence, is independently selected from H, $C_{1-4}$ alkyl, $C(O)C_{1-4}$alkyl, C(O)carbocycle, C(O)heterocycle, —$(CH_2)_n$—$C(O)NR^aR^a$, $C(O)OC_{1-4}$alkyl, C(O)O-carbocycle, C(O)O-heterocycle, $SO_2$alkyl, $SO_2$carbocycle, $SO_2$heterocycle, $SO_2NR^aR^a$, —$(CH_2)_n$-carbocycle, and —$(CH_2)_n$-heterocycle, wherein said alkyl, carbocycle, and heterocycle are substituted with 0-4 $R^9$;

alternatively, $R^8$ and $R^8$ are taken together with the nitrogen atom to which they are attached to form a 4- to 10-membered heterocycle substituted with 0-4 $R^9$;

$R^9$, at each occurrence, is independently selected from halogen, OH, =O, CN, $NO_2$, $CHF_2$, $CF_3$, $C_{1-4}$ alkyl, $C_{1-4}$ alkoxy, $CH_2OH$, $C_2H$, $CO_2(C_{1-4}$alkyl), $CONH_2$, —$(CH_2)_nNR^aR^a$, —$(CH_2)_nCONR^aR^a$, —$(CH_2)_nNHCO(C_{1-4}$ alkyl), —$S(O)_2(C_{1-4}$ alkyl), —$S(O)_2(C_{1-4}$ alkyl), —$O(CH_2)_n$heterocycle, —$O(CH_2)_{2-4}NR^aR^a$, and —$(CH_2)_n$-4- to 10-membered heterocycle, wherein said alkyl, alkoxy, carbocycle, and heterocycle are substituted with 0-4 $R^b$;

$R^a$, at each occurrence, is independently selected from H and $C_{1-4}$ alkyl; alternatively, $R^a$ and $R^a$ are taken together with the nitrogen atom to which they are attached to form a 4- to 10-membered heterocycle, wherein said alkyl, alkylene, and heterocycle are substituted with 0-4 $R^b$; and $R^b$, at each occurrence, is independently selected from =O, halogen, $C_{1-4}$ alkyl, $C_{1-4}$ alkoxy, $OCF_3$, $NH_2$, $NO_2$, $N(C_{1-4}$alkyl)$_2$, $CO(C_{1-4}$ alkyl), $CO(C_{1-4}$ haloalkyl), $CO_2(C_{1-4}$alkyl), $CONH_2$, —$CONH(C_{1-4}$ alkyl), —$CON(C_{1-4}$alkyl)$_2$, —CONH—$C_{1-4}$alkylene-$O(C_{1-4}$ alkyl), —CONH—$C_{1-4}$ alkylene-$N(C_{1-4}$alkyl)$_2$, and —$NHCO_2(C_{1-4}$ alkyl).

4. The compound of claim 3, or a stereoisomer, an enantiomer, a diastereoisomer, a tautomer, a pharmaceutically-acceptable salt thereof, wherein:

$R^3$, at each occurrence, is independently selected from H, $C_{1-4}$ alkyl, phenyl, $C_{3-6}$ cycloalkyl, and a heterocycle, wherein said alkyl, phenyl, cycloalkyl, and heterocycle are substituted with 0-4 $R^9$;

$R^4$ is selected from

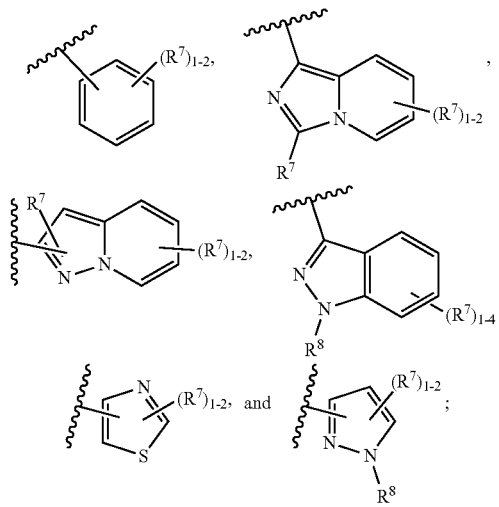

$R^7$, at each occurrence, is independently selected from H, halogen, $C_{1-7}$ alkyl, $C_{1-7}$ alkoxy, —$NR^8R^8$, $C_{3-6}$ cycloalkyl, phenyl, and —$(CH_2)_n$-heterocycle comprising carbon atoms and 1-4 heteroatoms selected from N, $NR^8$, O, and $S(O)_p$, wherein said alkyl, alkoxy, cycloalkyl phneyl, and heterocycle are substituted with 0-4 $R^9$;

$R^8$, at each occurrence, is independently selected from H, $C_{1-4}$ alkyl, —$(CH_2)_n$—$C_{3-6}$ cycloalkyl, —$(CH_2)_n$-phenyl, and —$(CH_2)_n$-heterocycle, wherein said alkyl, cycloalkyl, phenyl, and heterocycle are substituted with 0-4 $R^9$;

alternatively, $R^8$ and $R^8$ are taken together with the nitrogen atom to which they are attached to form a heterocycle selected from

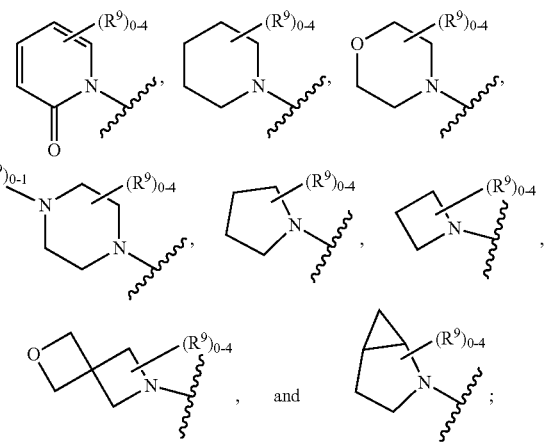

$R^9$, at each occurrence, is independently selected from F, Cl, OH, =O, CN, $C_{1-4}$ alkyl, $C_{1-4}$ alkoxy, —$(CH_2)_nNR^aR^a$, —$(CH_2)_nCONR^aR^a$, $C_{3-6}$ cycloalkyl, and a 4- to 10-membered heterocycle, wherein said alkyl, alkoxy, cycloalkyl, and heterocycle are substituted with 0-4 $R^b$;

$R^a$, at each occurrence, is independently selected from H, $C_{1-4}$ alkyl, —$(CH_2)_nOH$, $CO(C_{1-4}$ alkyl), $COCF_3$, $CO_2(C_{1-4}$ alkyl), —$CONH_2$, —CONH—$C_{1-4}$ alkylene-$CO_2(C_{1-4}$ alkyl), and $C_{1-4}$ alkylene-$CO_2(C_{1-4}$ alkyl); and $R^b$, at each occurrence, is independently selected from halogen, OH, $C_{1-4}$ alkyl, $C_{1-4}$ alkoxy, $OCF_3$, $NH_2$, $NO_2$, $N(C_{1-4}$ alkyl)$_2$, $CO(C_{1-4}$ alkyl), $CO(C_{1-4}$ haloalkyl), $CO_2(C_{1-4}$ alkyl), $CONH_2$, —$CONH(C_{1-4}$ alkyl), —$CON(C_{1-4}$ alkyl)$_2$, —CONH—$C_{1-4}$ alkylene-$O(C_{1-4}$ alkyl), —CONH—$C_{1-4}$ alkylene-$N(C_{1-4}$ alkyl)$_2$, and —$NHCO_2(C_{1-4}$ alkyl).

5. The compound of claim 4, or a stereoisomer, an enantiomer, a diastereoisomer, a tautomer, a pharmaceutically-acceptable salt thereof, wherein:

$R^3$, at each occurrence, is independently selected from H, $C_{1-4}$ alkyl, phenyl, $C_{3-6}$ cycloalkyl, and a heterocycle, wherein said alkyl, phenyl, cycloalkyl, and heterocycle are substituted with 0-4 $R^9$;

$R^4$ is selected from

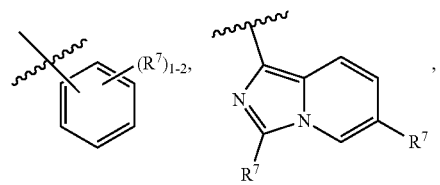

285
-continued

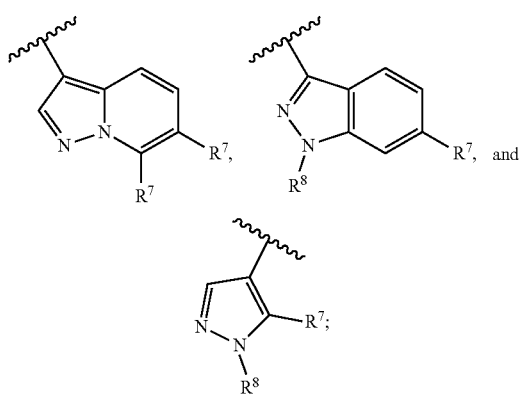

R⁷, at each occurrence, is independently selected from H, halogen, CN, $C_{1-7}$ alkyl, $C_{1-7}$ alkoxy, —NR⁸R⁸, $C_{3-6}$ cycloalkyl, phenyl, and —(CH₂)-heterocycle comprising carbon atoms and 1-4 heteroatoms selected from N, NR⁸, O, and $S(O)_p$, wherein said alkyl, alkoxy, cycloalkyl phneyl, and heterocycle are substituted with 0-4 R⁹;

R⁸, at each occurrence, is independently selected from H, $C_{1-4}$ alkyl, —$(CH_2)_n$—$C_{3-6}$ cycloalkyl, —$(CH_2)_n$-phenyl, and —$(CH_2)_n$-heterocycle, wherein said alkyl, cycloalkyl, phenyl, and heterocycle are substituted with 0-4 R⁹;

alternatively, R⁸ and R⁸ are taken together with the nitrogen atom to which they are attached to form a heterocycle selected from

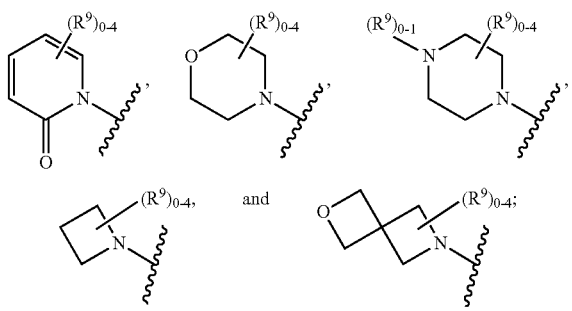

R⁹, at each occurrence, is independently selected from F, Cl, OH, =O, CN, $C_{1-4}$ alkyl, $C_{1-4}$ alkoxy, —$(CH_2)_n$NR^aR^a, —$(CH_2)_n$CONR^aR^a, $C_{3-6}$ cycloalkyl, and a 4- to 10-membered heterocycle, wherein said alkyl, alkoxy, cycloalkyl, and heterocycle are substituted with 0-4 R^b;

R^a, at each occurrence, is independently selected from H, $C_{1-4}$ alkyl, —$(CH_2)_n$OH, CO($C_{1-4}$ alkyl), COCF₃, CO₂($C_{1-4}$ alkyl), —CONH₂, —CONH—$C_{1-4}$ alkylene-CO₂($C_{1-4}$ alkyl), and $C_{1-4}$ alkylene-CO₂($C_{1-4}$ alkyl); and R^b, at each occurrence, is independently selected from halogen, OH, $C_{1-4}$ alkyl, $C_{1-4}$ alkoxy, OCF₃, NH₂, NO₂, N($C_{1-4}$ alkyl)₂, CO($C_{1-4}$ alkyl), CO($C_{1-4}$ haloalkyl), CO₂($C_{1-4}$ alkyl), CONH₂, —CONH($C_{1-4}$ alkyl), —CON($C_{1-4}$ alkyl)₂, —CONH—$C_{1-4}$ alkylene-O($C_{1-4}$ alkyl), —CONH—$C_{1-4}$ alkylene-N($C_{1-4}$ alkyl)₂, and —NHCO₂($C_{1-4}$ alkyl).

286

6. The compound of claim 2, or a stereoisomer, an enantiomer, a diastereoisomer, a tautomer, a pharmaceutically-acceptable salt thereof, wherein:

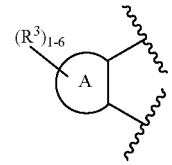

is selected from

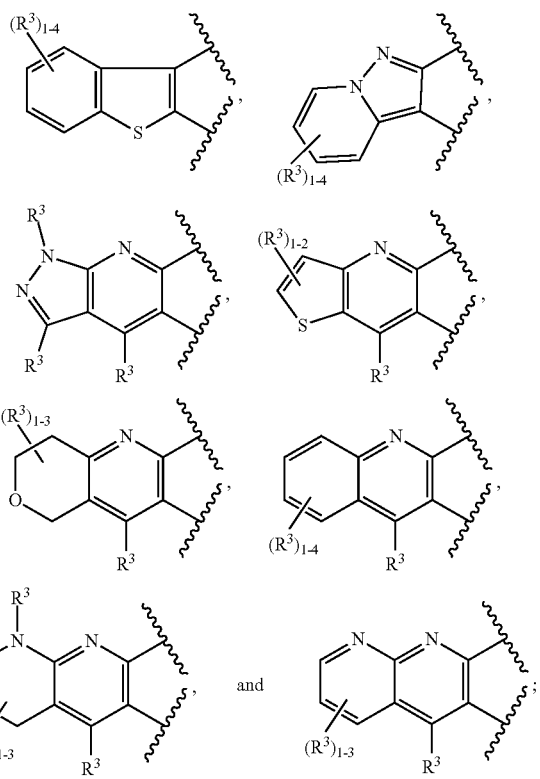

R³, at each occurrence, is independently selected from H and $C_{1-4}$ alkyl;

R⁴ is selected from

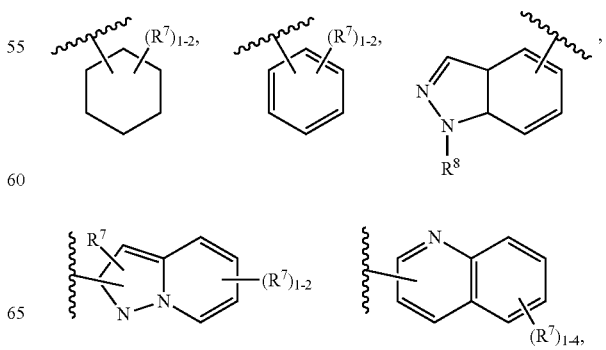

-continued

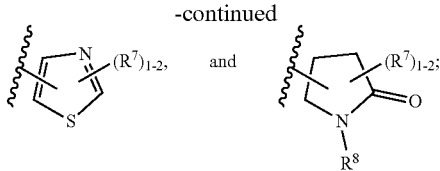

R⁷, at each occurrence, is independently selected from H, halogen, CN, $C_{1-4}$ alkyl, $C_{1-4}$ alkoxy, —NR⁸R⁸, $C_{3-6}$ cycloalkyl, phenyl, and —(CH₂)$_n$-heterocycle comprising carbon atoms and 1-4 heteroatoms selected from N, NR⁸, O, and S(O)$_p$, wherein said alkyl, alkoxy, cycloalkyl phneyl, and heterocycle are substituted with 0-4 R⁹;

R⁸, at each occurrence, is independently selected from H, $C_{1-4}$ alkyl, —(CH₂)$_n$-phenyl, and —(CH₂)$_n$-heterocycle, wherein said alkyl, phenyl, and heterocycle are substituted with 0-4 R⁹;

R⁹, at each occurrence, is independently selected from F, Cl, OH, =O, CN, $C_{1-4}$ alkyl, $C_{1-4}$ alkoxy, —(CH₂)$_n$NR$^a$R$^a$, —(CH₂)$_n$CONR$^a$R$^a$, $C_{3-6}$ cycloalkyl, and a 4- to 10-membered heterocycle, wherein said alkyl, alkoxy, cycloalkyl, and heterocycle are substituted with 0-4 R$^b$;

R$^a$, at each occurrence, is independently selected from H, $C_{1-4}$ alkyl, —(CH₂)$_n$OH, CO($C_{1-4}$ alkyl), COCF₃, CO₂($C_{1-4}$ alkyl), —CONH₂, —CONH—$C_{1-4}$ alkylene-CO₂($C_{1-4}$ alkyl), and $C_{1-4}$ alkylene-CO₂($C_{1-4}$ alkyl); and R$^b$, at each occurrence, is independently selected from halogen, $C_{1-4}$ alkyl, $C_{1-4}$ alkoxy, OCF₃, NH₂, NO₂, and N($C_{1-4}$ alkyl)₂.

7. The compound of claim 6, or a stereoisomer, an enantiomer, a diastereoisomer, a tautomer, a pharmaceutically-acceptable salt thereof, wherein:

R⁴ is selected from

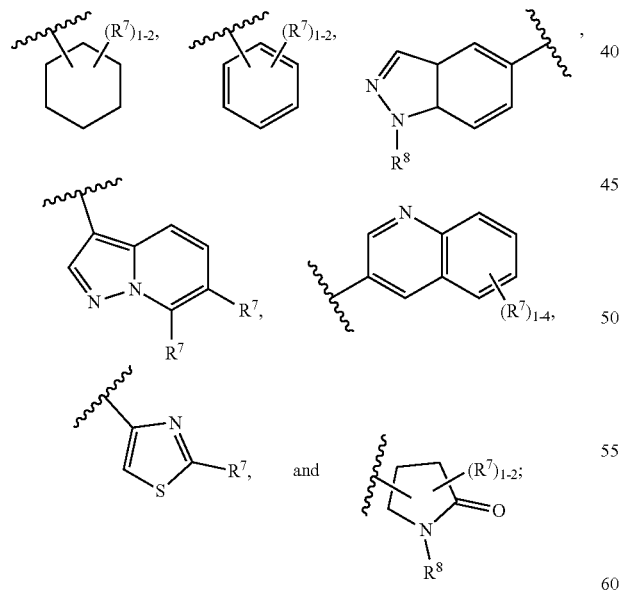

R⁷, at each occurrence, is independently selected from H, halogen, CN, $C_{1-4}$ alkyl, $C_{1-4}$ alkoxy, —NR⁸R⁸, $C_{3-6}$ cycloalkyl, phenyl, and —(CH₂)$_n$-heterocycle comprising carbon atoms and 1-4 heteroatoms selected from N, NR⁸, O, and S(O)$_p$, wherein said alkyl, alkoxy, cycloalkyl phneyl, and heterocycle are substituted with 0-4 R⁹;

R⁸, at each occurrence, is independently selected from H, $C_{1-4}$ alkyl, —(CH₂)$_n$—$C_{3-6}$ cycloalkyl, —(CH₂)$_n$-phenyl, and —(CH₂)$_n$-heterocycle, wherein said alkyl, cycloalkyl, phenyl, and heterocycle are substituted with 0-4 R⁹;

R⁹, at each occurrence, is independently selected from F, Cl, OH, =O, CN, $C_{1-4}$ alkyl, $C_{1-4}$ alkoxy, —(CH₂)$_n$NR$^a$R$^a$, —(CH₂)$_n$CONR$^a$R$^a$, $C_{3-6}$ cycloalkyl, and a 4- to 10-membered heterocycle, wherein said alkyl, alkoxy, cycloalkyl, and heterocycle are substituted with 0-4 R$^b$;

R$^a$, at each occurrence, is independently selected from H, $C_{1-4}$ alkyl, —(CH₂)$_n$OH, CO($C_{1-4}$ alkyl), COCF₃, CO₂($C_{1-4}$ alkyl), —CONH₂, —CONH—$C_{1-4}$ alkylene-CO₂($C_{1-4}$ alkyl), and $C_{1-4}$ alkylene-CO₂($C_{1-4}$ alkyl); and R$^b$, at each occurrence, is independently selected from halogen, $C_{1-4}$ alkyl, $C_{1-4}$ alkoxy, OCF₃, NH₂, NO₂, N($C_{1-4}$ alkyl)₂, CO($C_{1-4}$ alkyl), CO($C_{1-4}$ haloalkyl), CO₂($C_{1-4}$ alkyl), CONH₂, —CONH($C_{1-4}$ alkyl), —CON($C_{1-4}$ alkyl)₂, —CONH—$C_{1-4}$ alkylene-O($C_{1-4}$ alkyl), —CONH—$C_{1-4}$ alkylene-N($C_{1-4}$ alkyl)₂, and —NHCO₂($C_{1-4}$ alkyl).

8. The compound of claim 1, having Formula (III):

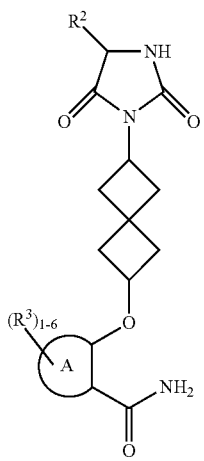

(III)

or a stereoisomer, an enantiomer, a diastereoisomer, a tautomer, a pharmaceutically-acceptable salt thereof, wherein:

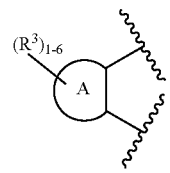

is selected from

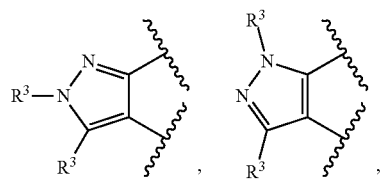

-continued

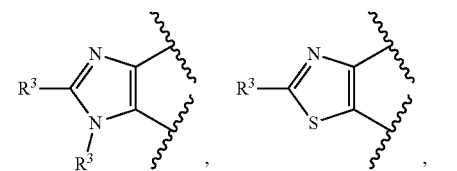

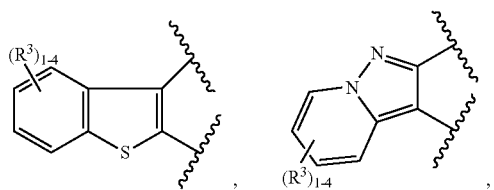

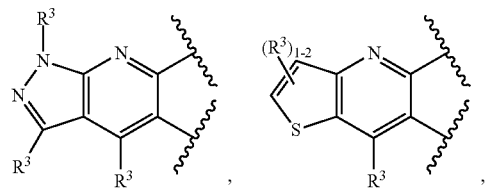

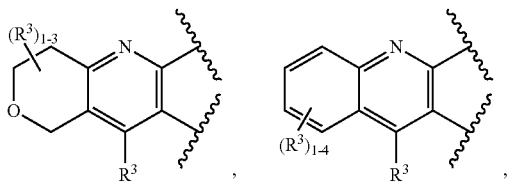

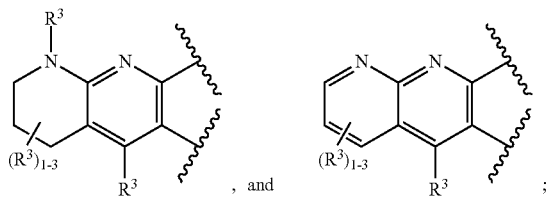

R² is selected from $C_{1-4}$ alkyl, —$(CH_2)_{0-1}$-phenyl and —$(CH_2)$ 4-6-membered heteroaryl comprising carbon atoms and 1-2 heteroatoms selected from N, O, and $S(O)_p$, wherein said alkyl, phenyl, and heteroaryl are substituted with 1-4 R⁷;

R³, at each occurrence, is independently selected from H, $C_{1-4}$ alkyl, and cyclopropyl; and R⁷, at each occurrence, is independently selected from H, $C_{1-4}$ alkyl, $_{1-4}$ alkoxy, CN, OH, $CHF_2$, and $CF_3$.

9. The compound of claim 1, having Formula (IV):

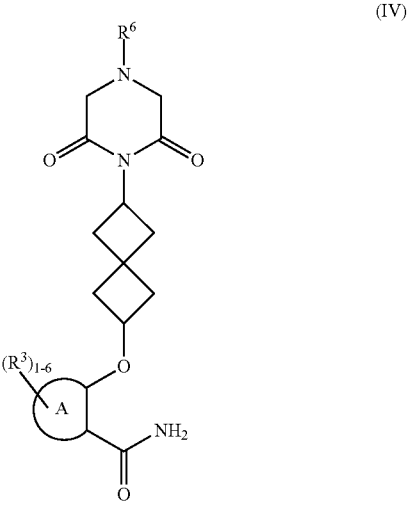

(IV)

or a stereoisomer, an enantiomer, a diastereoisomer, a tautomer, a pharmaceutically-acceptable salt thereof, wherein:

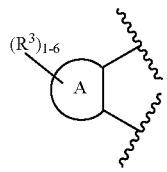

is selected from

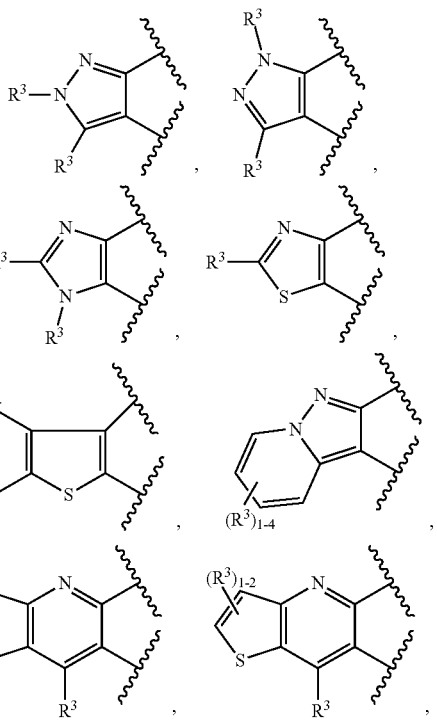

-continued

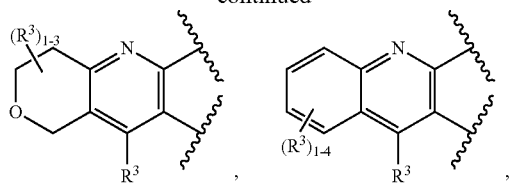

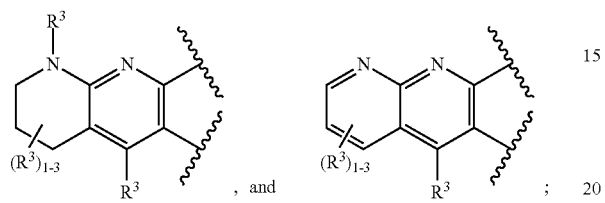, and

R³, at each occurrence, is independently selected from H, C₁₋₄ alkyl, and cyclopropyl; and R⁶ is selected from C₁₋₄ alkyl, —(CH₂)₀₋₁-phenyl and —(CH₂) 4-6-membered heteroaryl comprising carbon atoms and 1-2 heteroatoms selected from N, O, and S(O)$_p$.

10. The compound of claim 3, or a stereoisomer, an enantiomer, a diastereoisomer, a tautomer, a pharmaceutically-acceptable salt thereof, wherein:

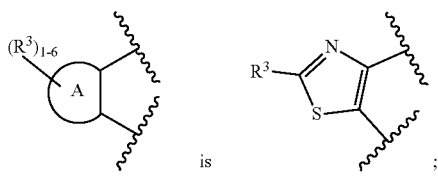 is

R³ is C₁₋₄ alkoxy;
R⁴ is selected from

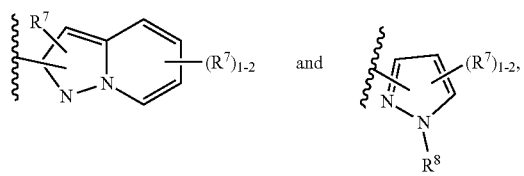

R⁷, at each occurrence, is independently selected from H, halogen, C₁₋₄ alkyl, C₁₋₄ alkoxy, CN, and OH, wherein said alkyl and alkoxy are substituted with 0-4 R⁹;

R⁸ is selected from 6-membered aryl and 6-membered heterocycle, wherein said aryl and heterocycle are substituted with 0-4 R⁹;

R⁹, at each occurrence, is independently selected from halogen, OH, CN, CHF₂, and CF₃.

11. The compound of claim 2, or a stereoisomer, an enantiomer, a diastereoisomer, a tautomer, a pharmaceutically-acceptable salt thereof, wherein:

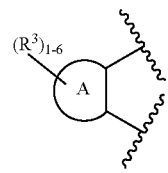

is selected from

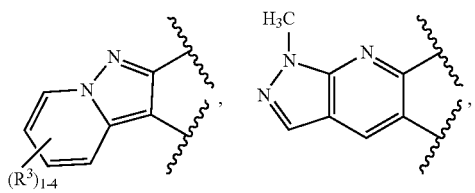

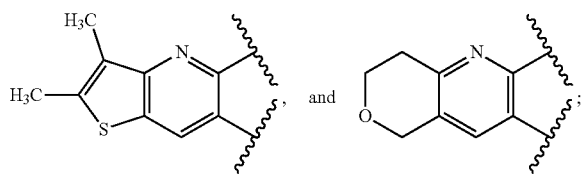

R³, at each occurrence, is independently selected from H, halogen, C₁₋₆ alkyl, C₁₋₄ alkoxy, a carbocycle, and a heterocycle, wherein said alkyl, alkoxy, carbocycle, and heterocycle are substituted with 0-4 R⁹;

R⁴ is selected from

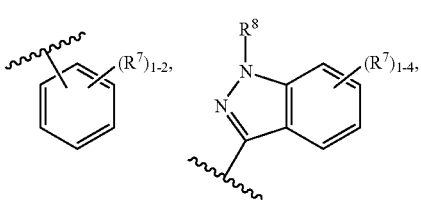

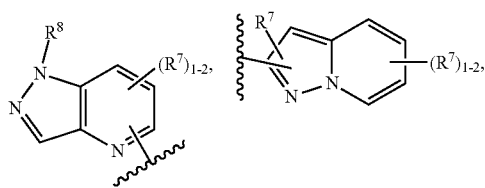

-continued

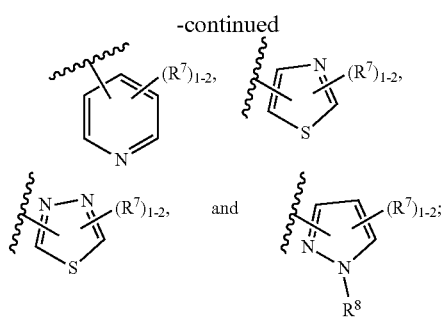

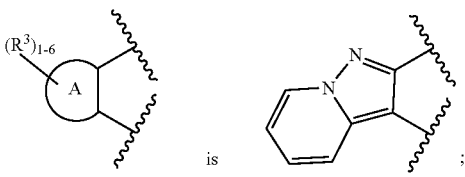

12. The compound of claim 8, or a stereoisomer, an enantiomer, a diastereoisomer, a tautomer, a pharmaceutically-acceptable salt thereof, wherein:

is $R^7$, at each occurrence, is independently selected from H, $C_{1-3}$ alkyl, $C_{1-4}$ alkoxy, $NHR^8$, and a carbocycle, wherein said alkyl, alkoxy, and carbocycle are substituted with 0-4 $R^9$;

$R^8$, at each occurrence, is independently selected from H, $C_{1-6}$ alkyl, a carbocycle, and a heterocycle, wherein said alkyl, carbocycle, and heterocycle are substituted with 0-4 $R^9$;

$R^9$, at each occurrence, is independently selected from halogen, OH, CN, $C_{1-4}$ alkyl, $S(O)_pC_{1-4}$alkyl, -4- to 10-membered heterocycle, wherein said alkyl and heterocycle are substituted with 0-4 $R^b$;

$R^a$, at each occurrence, is independently selected from H and $C_{1-4}$ alkyl substituted with 0-4 $R^b$;

$R^b$, at each occurrence, is independently selected from halogen and $C_{1-4}$ alkyl substituted with 0-2 $R^d$;

$R^d$ is halogen; and p, at each occurrence, is independently selected from 0, 1, and 2.

$R^2$ is $C_{1-4}$ alkyl substituted with 1-4 $R^7$;

$R^7$, at each occurrence, is independently selected from H, OH, $CHF_2$, and $CF_3$.

13. A pharmaceutical composition comprising one or more compounds according to claim 1 and a pharmaceutically acceptable carrier or diluent.

14. A method prophylaxis and/or treatment of a disorder associated with aberrant Rho kinase activity, comprising administrating to a patient in need thereof a therapeutically effective amount of a compound according to claim 1.

15. The method according to claim 14, wherein said disorder is selected from the group consisting of a cardiovascular disorder, a smooth muscle related disorder, a fibrotic disease, an inflammatory disease, neuropathic disorders, oncologic disorders, and an autoimmune disorder.

16. The method according to claim 15, wherein said cardiovascular disorder is selected from the group consisting of angina, atherosclerosis, stroke, cerebrovascular disease, heart failure, coronary artery disease, myocardial infarction, peripheral vascular disease, stenosis, vasospasm, hypertension and pulmonary hypertension.

* * * * *

UNITED STATES PATENT AND TRADEMARK OFFICE
CERTIFICATE OF CORRECTION

PATENT NO. : 11,078,197 B2
APPLICATION NO. : 16/629717
DATED : August 3, 2021
INVENTOR(S) : Peter Glunz et al.

It is certified that error appears in the above-identified patent and that said Letters Patent is hereby corrected as shown below:

On the Title Page

Item (57), Column 2 (Abstract), Line 3, Delete "thereof" and insert -- thereof, --, therefor.

In the Claims

In Claim 1, Column 273, Line 47, delete "heteocycle;" and insert -- heterocycle; --, therefor.

In Claim 1, Column 275, Line 10, delete "—$(CH_2)_n$—$C(O)NR^aR^a$," and insert -- —$(CH_2)_n$—$C(O)NR^aR^a$, --, therefor.

In Claim 1, Column 275, Line 14, delete "—$(CH_2)_nSO_2carbocycle$," and insert -- —$(CH_2)_n$—$SO_2carbocycle$, --, therefor.

In Claim 1, Column 275, Line 42, delete "alkyl with" and insert -- alkyl --, therefor.

In Claim 1, Column 275, Line 66, delete "—$(CH_2)$-5-" and insert -- —$(CH_2)_n$-5- --, therefor.

In Claim 2, Column 277, Line 45-46, delete "—$(CH_2)$—$NR^8R^8$," and insert -- —$(CH_2)_n$—$NR^8R^8$, --, therefor.

In Claim 2, Column 278, Line 2, delete "—$(CH_2)_nSO_2carbocycle$," and insert -- —$(CH_2)_n$—$SO_2carbocycle$, --, therefor.

In Claim 2, Column 278, Line 16, delete "—$O(CHR^{10})NR^aR^a$," and insert -- —$O(CHR^{10})_nNR^aR^a$, --, therefor.

In Claim 2, Column 278, Line 36, delete "$CO(C_{1-4}haloalkyl)$," and insert -- $CO(C_{1-4} haloalkyl)$, --, therefor.

Signed and Sealed this
Seventh Day of December, 2021

Drew Hirshfeld
*Performing the Functions and Duties of the*
*Under Secretary of Commerce for Intellectual Property and*
*Director of the United States Patent and Trademark Office*

In Claim 3, Column 280, Line 19-24 (Approx.), delete " 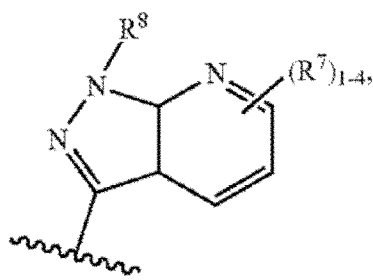 " and insert
-- 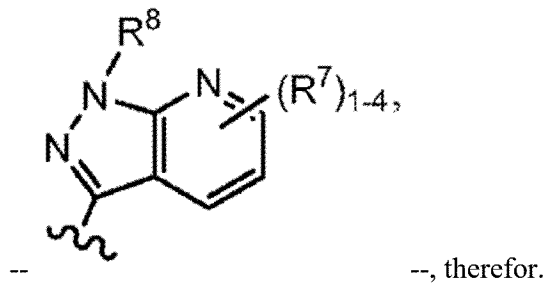 --, therefor.
In Claim 3, Column 280, Line 40-44, delete " 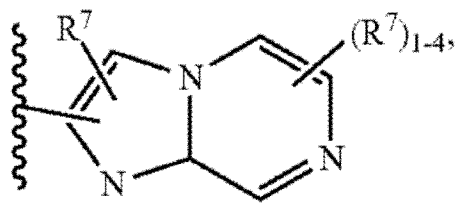 " and insert
-- 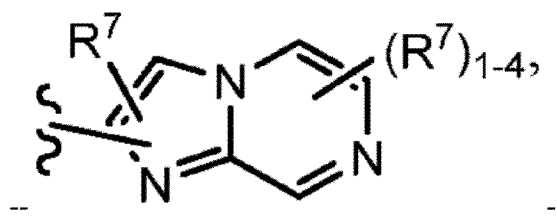 --, therefor.
In Claim 3, Column 280, Line 62-67, delete " 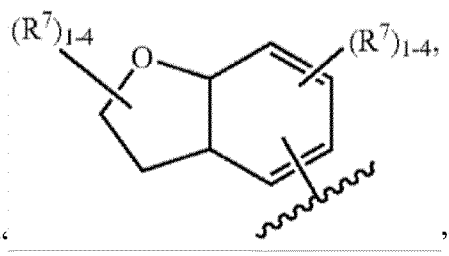 " and insert
-- 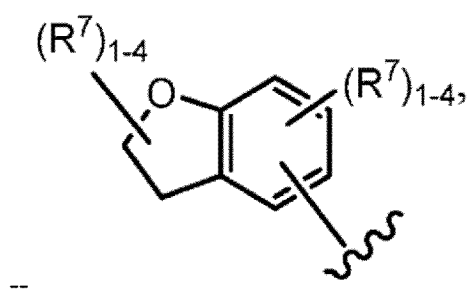 --, therefor.

CERTIFICATE OF CORRECTION (continued)
U.S. Pat. No. 11,078,197 B2

In Claim 3, Column 282, Line 58, delete "—SO$_2$NH(CH$_2$O(C$_1$ alkyl)," and insert -- —SO$_2$NH(CH$_2$)$_2$O(C$_{1-4}$ alkyl), --, therefor.

In Claim 3, Column 282, Line 64, delete "—(CH$_2$)-heterocycle" and insert -- —(CH$_2$)$_n$-heterocycle --, therefor.

In Claim 3, Column 283, Line 15, delete "C$_2$H," and insert -- CO$_2$H, --, therefor.

In Claim 3, Column 283, Line 18, delete "—O(CH$_2$)$_n$heterocycle," and insert -- —O(CH$_2$)n-heterocycle, --, therefor.

In Claim 3, Column 283, Line 31-32 (Approx.), delete "—CONH—C$_{1-4}$alkylene-O(C$_{1-4}$ alkyl)," and insert -- —CONH—C$_{1-4}$ alkylene-O(C$_{1-4}$ alkyl), --, therefor.

In Claim 4, Column 284, Line 3, delete "phneyl," and insert -- phenyl, --, therefor.

In Claim 5, Column 285, Line 21, delete "—(CH$_2$)-heterocycle" and insert -- —(CH$_2$)$_n$-heterocycle --, therefor.

In Claim 5, Column 285, Line 24, delete "phneyl," and insert -- phenyl, --, therefor.

In Claim 6, Column 287, Line 14, delete "phneyl," and insert -- phenyl, --, therefor.

In Claim 7, Column 287, Line 67, delete "phneyl," and insert -- phenyl, --, therefor.

In Claim 8, Column 289, Line 67, delete "$_{1-4}$ alkoxy," and insert -- C$_{1-4}$ alkoxy, --, therefor.

In Claim 10, Column 291, Line 63, delete "heterocyle" and insert -- heterocycle --, therefor.

In Claim 14, Column 294, Line 19, after "method" insert -- for the --.

SEQUENCE LISTING

```
<160> NUMBER OF SEQ ID NOS: 1

<210> SEQ ID NO 1
<211> LENGTH: 11
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<223> OTHER INFORMATION: FITC-AHA at N Terminus attached at A1 - A11
<220> FEATURE:
<221> NAME/KEY: MISC_FEATURE
<223> OTHER INFORMATION: OH at C Terminus attached at A1 - A11

<400> SEQUENCE: 1

Ala Lys Arg Arg Arg Leu Ser Ser Leu Arg Ala
1               5                   10
```